(12) United States Patent
Bernstein et al.

(10) Patent No.: US 12,189,872 B2
(45) Date of Patent: Jan. 7, 2025

(54) INTERACTING WITH AN ELECTRONIC DEVICE THROUGH PHYSICAL MOVEMENT

(71) Applicant: Apple Inc., Cupertino, CA (US)

(72) Inventors: Jeffrey Traer Bernstein, San Francisco, CA (US); Lukas Robert Tom Girling, Bristol (GB); Julian Missig, Burlingame, CA (US); Golnaz Abdollahian, San Francisco, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/511,778

(22) Filed: Nov. 16, 2023

(65) Prior Publication Data
US 2024/0085992 A1   Mar. 14, 2024

Related U.S. Application Data

(63) Continuation of application No. 17/950,943, filed on Sep. 22, 2022, now Pat. No. 11,861,077, which is a
(Continued)

(51) Int. Cl.
*G06F 3/0346* (2013.01)
*G04C 3/00* (2006.01)
(Continued)

(52) U.S. Cl.
CPC ........... *G06F 3/0346* (2013.01); *G04C 3/002* (2013.01); *G06F 1/1694* (2013.01); *G06F 3/011* (2013.01);
(Continued)

(58) Field of Classification Search
CPC ........ G06F 3/0346; G06F 3/011; G06F 3/016; G06F 3/017; G06F 3/0482;
(Continued)

(56) References Cited

U.S. PATENT DOCUMENTS 5,483,261 A   1/1996   Yasutake
5,488,204 A   1/1996   Mead et al.
(Continued)

FOREIGN PATENT DOCUMENTS

EP   2290583 A1   3/2011
EP   2565765 A1   3/2013
(Continued)

OTHER PUBLICATIONS

Accessibility by design: An Apple Watch for everyone, Available Online at: https://developer.apple.com/videos/play/wwdc2021/10308/, Jun. 10, 2021, 2 pages.
(Continued)

*Primary Examiner* — Brent D Castiaux
(74) *Attorney, Agent, or Firm* — DLA Piper LLP (US)

(57) ABSTRACT

The present disclosure generally relates to interacting with an electronic device without touching a display screen or other physical input mechanisms. In some examples, the electronic device performs an operation in response to a positioning of a user's hand and/or an orientation of the electronic device.

18 Claims, 92 Drawing Sheets

Related U.S. Application Data continuation of application No. 17/383,880, filed on Jul. 23, 2021, now Pat. No. 11,520,416, which is a continuation of application No. 16/773,536, filed on Jan. 27, 2020, now Pat. No. 11,073,918, which is a continuation of application No. 15/937,716, filed on Mar. 27, 2018, now Pat. No. 10,558,278.

(60) Provisional application No. 62/531,248, filed on Jul. 11, 2017.

(51) Int. Cl.

| | | |
|---|---|---|
| *G06F 1/16* | (2006.01) | |
| *G06F 3/01* | (2006.01) | |
| *G06F 3/0482* | (2013.01) | |
| *G06F 3/04842* | (2022.01) | |
| *G06F 3/04845* | (2022.01) | |
| *G06F 3/0485* | (2022.01) | |
| *G06F 3/0487* | (2013.01) | |
| *G06F 3/0488* | (2022.01) | |
| *H04M 1/72454* | (2021.01) | |
| *H04M 1/72469* | (2021.01) | |
| *A61B 5/024* | (2006.01) | |
| *A61B 5/1455* | (2006.01) | |

(52) U.S. Cl.
CPC ............. *G06F 3/016* (2013.01); *G06F 3/017* (2013.01); *G06F 3/0482* (2013.01); *G06F 3/04842* (2013.01); *G06F 3/04845* (2013.01); *G06F 3/0485* (2013.01); *G06F 3/0487* (2013.01); *G06F 3/0488* (2013.01); *H04M 1/72454* (2021.01); *H04M 1/72469* (2021.01); *A61B 5/02416* (2013.01); *A61B 5/14552* (2013.01); *H04M 2250/12* (2013.01)

(58) Field of Classification Search
CPC ............. G06F 3/04842; G06F 3/04845; G06F 3/0485; G06F 3/0487; G06F 3/0488; G06F 1/1694; G04C 3/002; H04M 1/72454; H04M 1/72469; H04M 2250/12; A61B 5/02416; A61B 5/14552
See application file for complete search history.

(56) References Cited

U.S. PATENT DOCUMENTS

| | | |
|---|---|---|
| 5,825,352 A | 10/1998 | Bisset et al. |
| 5,835,079 A | 11/1998 | Shieh |
| 5,880,411 A | 3/1999 | Gillespie et al. |
| 6,031,531 A | 2/2000 | Kimble |
| 6,128,010 A | 10/2000 | Baxter et al. |
| 6,188,391 B1 | 2/2001 | Seely et al. |
| 6,310,610 B1 | 10/2001 | Beaton et al. |
| 6,323,846 B1 | 11/2001 | Westerman et al. |
| 6,690,387 B2 | 2/2004 | Zimmerman et al. |
| 7,015,894 B2 | 3/2006 | Morohoshi |
| 7,184,064 B2 | 2/2007 | Zimmerman et al. |
| 7,616,110 B2 | 11/2009 | Crump et al. |
| 7,663,607 B2 | 2/2010 | Hotelling et al. |
| 8,170,656 B2 | 5/2012 | Tan et al. |
| 8,341,537 B2 | 12/2012 | Ray et al. |
| 8,378,811 B2 | 2/2013 | Crump et al. |
| 8,447,704 B2 | 5/2013 | Tan et al. |
| 8,479,122 B2 | 7/2013 | Hotelling et al. |
| 8,508,472 B1 | 8/2013 | Wieder |
| 8,618,930 B2 | 12/2013 | Papadopoulos et al. |
| 8,634,808 B1 | 1/2014 | Zhong et al. |
| 8,769,554 B2 | 7/2014 | Onda et al. |
| 8,872,760 B2 | 10/2014 | Tsurumi |
| 8,963,806 B1 | 2/2015 | Starner et al. |
| 9,195,219 B2 | 11/2015 | Hong et al. |
| 9,223,296 B2 | 12/2015 | Yang et al. |
| 9,389,694 B2 | 7/2016 | Ataee et al. |
| 9,414,115 B1 | 8/2016 | Mao et al. |
| 9,532,723 B2 | 1/2017 | Kim et al. |
| 9,668,676 B2 | 6/2017 | Culbert |
| 9,704,386 B2 | 7/2017 | Yoon et al. |
| 9,753,543 B2 | 9/2017 | Jeon et al. |
| 9,939,899 B2 | 4/2018 | Allec et al. |
| 9,977,566 B2 | 5/2018 | Jitkoff et al. |
| 10,001,817 B2 | 6/2018 | Zambetti et al. |
| 10,261,595 B1 | 4/2019 | Kin |
| 10,318,034 B1 | 6/2019 | Hauenstein et al. |
| 10,627,914 B2 | 4/2020 | Ang et al. |
| 10,656,720 B1 | 5/2020 | Holz |
| 10,671,174 B2 | 6/2020 | Ang et al. |
| 10,684,693 B2 | 6/2020 | Kletsov et al. |
| 10,802,598 B2 | 10/2020 | Ang et al. |
| 10,926,135 B1 | 2/2021 | Mckirdy |
| 10,936,067 B1 | 3/2021 | Chand et al. |
| 10,966,149 B2 | 3/2021 | Yoon et al. |
| 11,048,334 B2 | 6/2021 | Rothberg et al. |
| 11,099,647 B2 | 8/2021 | Ang et al. |
| 11,150,730 B1 | 10/2021 | Anderson et al. |
| 11,331,045 B1 | 5/2022 | Moschella et al. |
| 11,347,320 B1 | 5/2022 | Shin et al. |
| 11,543,887 B2 | 1/2023 | Ang et al. |
| 2002/0024500 A1 | 2/2002 | Howard |
| 2006/0010402 A1 | 1/2006 | Undasan |
| 2006/0107226 A1 | 5/2006 | Matthews et al. |
| 2006/0197753 A1 | 9/2006 | Hotelling |
| 2007/0236451 A1 | 10/2007 | Ofek et al. |
| 2008/0300055 A1 | 12/2008 | Lutnick et al. |
| 2008/0320394 A1 | 12/2008 | Womack |
| 2009/0176532 A1 | 7/2009 | Chae et al. |
| 2009/0251410 A1 | 10/2009 | Mori et al. |
| 2009/0306487 A1 | 12/2009 | Crowe et al. |
| 2010/0026626 A1 | 2/2010 | Macfarlane |
| 2010/0088182 A1 | 4/2010 | Ryder et al. |
| 2010/0182126 A1 | 7/2010 | Martis et al. |
| 2010/0199232 A1 | 8/2010 | Mistry et al. |
| 2010/0289740 A1 | 11/2010 | Kim et al. |
| 2010/0289772 A1 | 11/2010 | Miller |
| 2011/0054360 A1 | 3/2011 | Son et al. |
| 2011/0090407 A1 | 4/2011 | Friedman |
| 2011/0148568 A1 | 6/2011 | Lim et al. |
| 2011/0153435 A1 | 6/2011 | Pisaris-Henderson |
| 2011/0173204 A1 | 7/2011 | Murillo et al. |
| 2011/0210931 A1 | 9/2011 | Shai |
| 2011/0235926 A1 | 9/2011 | Yokono |
| 2012/0127070 A1 | 5/2012 | Ryoo et al. |
| 2012/0188158 A1 | 7/2012 | Tan et al. |
| 2012/0290965 A1 | 11/2012 | Ignor et al. |
| 2012/0306748 A1 | 12/2012 | Fleizach et al. |
| 2013/0135203 A1 | 5/2013 | Croughwell, III |
| 2013/0234926 A1 | 9/2013 | Rauber |
| 2013/0239046 A1 | 9/2013 | Platzer et al. |
| 2013/0300651 A1 | 11/2013 | Lim |
| 2014/0028546 A1 | 1/2014 | Jeon et al. |
| 2014/0031698 A1 | 1/2014 | Moon et al. |
| 2014/0068526 A1 | 3/2014 | Figelman et al. |
| 2014/0078318 A1 | 3/2014 | Alameh |
| 2014/0104180 A1 | 4/2014 | Schaffer |
| 2014/0135612 A1 | 5/2014 | Yuen et al. |
| 2014/0139454 A1 | 5/2014 | Mistry et al. |
| 2014/0139637 A1 | 5/2014 | Mistry et al. |
| 2014/0143784 A1 | 5/2014 | Mistry et al. |
| 2014/0155705 A1 | 6/2014 | Papadopoulos et al. |
| 2014/0160078 A1 | 6/2014 | Seo et al. |
| 2014/0282270 A1 | 9/2014 | Slonneger |
| 2014/0293755 A1 | 10/2014 | Geiser et al. |
| 2014/0320434 A1 | 10/2014 | Pantel |
| 2014/0328147 A1 | 11/2014 | Yang et al. |
| 2014/0359522 A1 | 12/2014 | Kim et al. |
| 2014/0365979 A1 | 12/2014 | Yoon et al. |
| 2014/0375985 A1 | 12/2014 | Deliwala |
| 2015/0019135 A1 | 1/2015 | Kacyvenski et al. |
| 2015/0026647 A1 | 1/2015 | Park et al. |
| 2015/0061842 A1 | 3/2015 | Yoon et al. |
| 2015/0084660 A1 | 3/2015 | Knierim et al. |

(56) References Cited

U.S. PATENT DOCUMENTS

| | | |
|---|---|---|
| 2015/0084860 A1 | 3/2015 | Aleem et al. |
| 2015/0156803 A1 | 6/2015 | Ballard et al. |
| 2015/0169171 A1 | 6/2015 | Fotland |
| 2015/0185877 A1 | 7/2015 | Watanabe et al. |
| 2015/0199780 A1 | 7/2015 | Beyk |
| 2015/0205358 A1 | 7/2015 | Lyren |
| 2015/0220149 A1 | 8/2015 | Plagemann et al. |
| 2015/0242083 A1 | 8/2015 | Rainisto |
| 2015/0248235 A1 | 9/2015 | Offenberg et al. |
| 2015/0261310 A1 | 9/2015 | Walmsley et al. |
| 2015/0268821 A1 | 9/2015 | Ramsby et al. |
| 2015/0286295 A1 | 10/2015 | Pepe |
| 2015/0324057 A1 | 11/2015 | Chaji et al. |
| 2015/0332031 A1 | 11/2015 | Mistry et al. |
| 2015/0370333 A1 | 12/2015 | Ataee et al. |
| 2016/0011724 A1 | 1/2016 | Wheeler et al. |
| 2016/0029899 A1 * | 2/2016 | Kim ................... H04W 68/005 455/414.1 |
| 2016/0041580 A1 | 2/2016 | Inoue et al. |
| 2016/0041680 A1 | 2/2016 | Chi et al. |
| 2016/0062582 A1 | 3/2016 | Wilson et al. |
| 2016/0085266 A1 | 3/2016 | Lee et al. |
| 2016/0091980 A1 | 3/2016 | Baranski et al. |
| 2016/0094698 A1 | 3/2016 | Lee et al. |
| 2016/0098137 A1 | 4/2016 | Kim et al. |
| 2016/0124514 A1 | 5/2016 | Cha et al. |
| 2016/0196692 A1 | 7/2016 | Kjallstrom et al. |
| 2016/0248899 A1 | 8/2016 | Lee et al. |
| 2016/0291768 A1 | 10/2016 | Cho et al. |
| 2016/0296142 A1 | 10/2016 | Culbert |
| 2016/0313798 A1 | 10/2016 | Connor |
| 2016/0328108 A1 | 11/2016 | Li |
| 2017/0031453 A1 | 2/2017 | Presura |
| 2017/0065184 A1 | 3/2017 | Barak |
| 2017/0090567 A1 | 3/2017 | Allec et al. |
| 2017/0123487 A1 | 5/2017 | Hazra et al. |
| 2017/0220224 A1 | 8/2017 | Kodali et al. |
| 2017/0308227 A1 | 10/2017 | Park |
| 2018/0036469 A1 | 2/2018 | Crnkovich et al. |
| 2018/0046788 A1 | 2/2018 | Ohtani et al. |
| 2018/0059894 A1 | 3/2018 | Kim |
| 2018/0062691 A1 | 3/2018 | Barnett, Jr. |
| 2018/0081453 A1 | 3/2018 | Ely |
| 2018/0101235 A1 | 4/2018 | Bodensteiner et al. |
| 2018/0153430 A1 | 6/2018 | Ang et al. |
| 2018/0181261 A1 | 6/2018 | Saurabh |
| 2018/0253151 A1 | 9/2018 | Kletsov et al. |
| 2018/0294844 A1 | 10/2018 | Choi et al. |
| 2019/0018506 A1 | 1/2019 | Bernstein et al. |
| 2019/0033964 A1 | 1/2019 | Kulkarni et al. |
| 2019/0113889 A1 | 4/2019 | Kumar et al. |
| 2019/0121522 A1 | 4/2019 | Davis et al. |
| 2019/0146219 A1 | 5/2019 | Rodriguez, II |
| 2019/0191208 A1 | 6/2019 | Coenen et al. |
| 2019/0196600 A1 | 6/2019 | Rothberg et al. |
| 2019/0220040 A1 | 7/2019 | Wu et al. |
| 2019/0268771 A1 | 8/2019 | Seo et al. |
| 2019/0281547 A1 | 9/2019 | Yoon et al. |
| 2019/0317608 A1 | 10/2019 | Ono et al. |
| 2019/0357787 A1 | 11/2019 | Barachant et al. |
| 2019/0370094 A1 | 12/2019 | Louch et al. |
| 2020/0042088 A1 | 2/2020 | Ang et al. |
| 2020/0042089 A1 | 2/2020 | Ang et al. |
| 2020/0042095 A1 | 2/2020 | Ang et al. |
| 2020/0042145 A1 | 2/2020 | Williams et al. |
| 2020/0073483 A1 | 3/2020 | Berenzweig et al. |
| 2020/0097081 A1 | 3/2020 | Stone et al. |
| 2020/0097082 A1 | 3/2020 | Berenzweig et al. |
| 2020/0111260 A1 | 4/2020 | Osborn et al. |
| 2020/0150772 A1 | 5/2020 | Quinn et al. |
| 2020/0159340 A1 | 5/2020 | Bernstein et al. |
| 2020/0249752 A1 | 8/2020 | Parshionikar |
| 2020/0301509 A1 | 9/2020 | Liu et al. |
| 2020/0310540 A1 | 10/2020 | Hussami et al. |
| 2020/0310541 A1 | 10/2020 | Reisman et al. |
| 2020/0379716 A1 | 12/2020 | Carrigan et al. |
| 2020/0401292 A1 | 12/2020 | Lorenz et al. |
| 2021/0064132 A1 | 3/2021 | Rubin et al. |
| 2021/0076091 A1 | 3/2021 | Shohara |
| 2021/0124417 A1 | 4/2021 | Ma |
| 2021/0232225 A1 | 7/2021 | Cipoletta et al. |
| 2021/0263702 A1 | 8/2021 | Carrigan |
| 2021/0349552 A1 | 11/2021 | Bernstein et al. |
| 2021/0405760 A1 | 12/2021 | Schoen |
| 2022/0019284 A1 | 1/2022 | Kaifosh et al. |
| 2022/0044309 A1 | 2/2022 | Jose |
| 2022/0050425 A1 | 2/2022 | Connor |
| 2022/0121344 A1 | 4/2022 | Pastrana Vicente et al. |
| 2022/0156353 A1 | 5/2022 | Duffy et al. |
| 2022/0253146 A1 | 8/2022 | Erivantcev et al. |
| 2022/0291753 A1 | 9/2022 | Erivantcev et al. |
| 2022/0326779 A1 | 10/2022 | Chung et al. |
| 2022/0374085 A1 | 11/2022 | Nguyen et al. |
| 2023/0024627 A1 | 1/2023 | Bernstein et al. |
| 2023/0072423 A1 | 3/2023 | Osborn et al. |
| 2023/0074476 A1 | 3/2023 | Bae et al. |
| 2023/0090410 A1 | 3/2023 | Sharma et al. |
| 2023/0113991 A1 | 4/2023 | Ang et al. |
| 2023/0177870 A1 | 6/2023 | Chao et al. |
| 2023/0195237 A1 | 6/2023 | Nguyen et al. |
| 2023/0252737 A1 | 8/2023 | Dreyer et al. |
| 2023/0259207 A1 | 8/2023 | Lam et al. |
| 2023/0270363 A1 | 8/2023 | Qazi et al. |
| 2023/0376193 A1 | 11/2023 | Han et al. |
| 2024/0094819 A1 | 3/2024 | Nie et al. |

FOREIGN PATENT DOCUMENTS

| | | |
|---|---|---|
| EP | 2698686 A2 | 2/2014 |
| EP | 2813921 A1 | 12/2014 |
| EP | 2980715 A1 | 2/2016 |
| EP | 2999208 A1 | 3/2016 |
| EP | 3001282 A1 | 3/2016 |
| EP | 3125097 A2 | 2/2017 |
| JP | 2000-163031 A | 6/2000 |
| JP | 2001-216069 A | 8/2001 |
| JP | 2002-342033 A | 11/2002 |
| JP | 2006-209563 A | 8/2006 |
| JP | 2018-536933 A | 12/2018 |
| WO | 2012/138663 A2 | 10/2012 |
| WO | 2014/117125 A1 | 7/2014 |
| WO | 2015/060856 A1 | 4/2015 |
| WO | 2015/119637 A1 | 8/2015 |
| WO | 2015/121100 A1 | 8/2015 |
| WO | 2016/053459 A1 | 4/2016 |
| WO | 2019/173136 A1 | 9/2019 |

OTHER PUBLICATIONS

Apple Previews Powerful Software Updates Designed for People with Disabilities, Available online at: https://www.apple.com/newsroom/2021/05/apple-previews-powerful-software-updates-designed-for-people-with-disabilities/, May 19, 2021, 10 pages.

Applicant Initiated Interview Summary received for U.S. Appl. No. 14/973,573, mailed on Jul. 10, 2017, 3 pages.

Applicant-Initiated Interview Summary received for U.S. Appl. No. 16/773,536, mailed on Mar. 26, 2021, 4 pages.

Applicant-Initiated Interview Summary received for U.S. Appl. No. 18/109,808, mailed on Sep. 25, 2023, 5 pages.

Corrected Notice of Allowance received for U.S. Appl. No. 17/950,943, mailed on Jul. 10, 2023, 2 pages.

Eisenstein et al., "Analysis of Clustering Techniques to Detect Hand Signs", Intelligent Multimedia, Video and Speech Processing, of 2001 International Symposium, Piscataway, NJ, USA, IEEE, 2001, 4 pages.

Final Office Action received for U.S. Appl. No. 14/616,573 mailed Mar. 10, 2017, 5 pages.

International Preliminary Report on Patentability received for PCT Patent Application No. PCT/US2018/038823, mailed on Jan. 23, 2020, 20 pages.

(56) References Cited

OTHER PUBLICATIONS

International Search Report and written opinion received for PCT Application No. PCT/US2016/048582 mailed on Sep. 13, 2016, 11 pages.
International Search Report and Written Opinion received for PCT Patent Application No. PCT/US2018/038823, mailed on Oct. 23, 2018, 30 pages.
International Search Report and Written Opinion received for PCT Patent Application No. PCT/US2022/030021, mailed on Nov. 9, 2022, 19 pages.
International Search Report received for PCT Application No. PCT/US2015/042976 mailed on Aug. 18, 2015, 22 pages.
Invitation to Pay Additional Fees and Partial International Search Report received for PCT Patent Application No. PCT/US2022/030021, mailed on Sep. 15, 2022, 13 pages.
Invitation to Pay Additional Fees received for PCT Patent Application No. PCT/US2018/038823, mailed on Sep. 5, 2018, 22 pages.
Lee et al., "A Multi-Touch Three-Dimensional Touch-Sensitive Tablet", CHI '85 Proceedings of the SIGCHI Conference on Human Factors in Computing Systems, Apr. 1985, pp. 21-25.
Nishiya et al., "Gesture Estimation Using Deep Learning from PPG Signal", Information Processing Society of Japan Kansai Branch Convention Proceedings [online], Japan, Information Processing Society of Japan, Available on: http: id.nii.ac.jp/1001/0020708, 2020, 4 pages.
Non-Final Office Action received for U.S. Appl. No. 14/616,573, mailed Jun. 16, 2016, 12 pages.
Non-Final Office Action received for U.S. Appl. No. 14/616,573, mailed on Jun. 14, 2017, 13 pages.
Non-Final Office Action received for U.S. Appl. No. 14/973,573, mailed on Apr. 20, 2017, 34 pages.
Non-Final Office Action received for U.S. Appl. No. 15/038,419, mailed Dec. 21, 2016, 13 pages.
Non-Final Office Action received for U.S. Appl. No. 15/937,716, mailed on Apr. 22, 2019, 28 pages.
Non-Final Office Action received for U.S. Appl. No. 16/773,536, mailed on Dec. 18, 2020, 19 pages.
Non-Final Office Action received for U.S. Appl. No. 18/109,808, mailed on Sep. 12, 2023, 49 pages.
Notice of Allowance received for U.S. Appl. No. 14/973,573, mailed on Nov. 30, 2017, 8 pages.
Notice of Allowance received for U.S. Appl. No. 15/038,419, mailed on Apr. 3, 2017, 10 pages.
Notice of Allowance received for U.S. Appl. No. 15/937,716, mailed on Oct. 23, 2019, 19 pages.
Notice of Allowance received for U.S. Appl. No. 16/773,536, mailed on Apr. 8, 2021, 16 pages.
Notice of Allowance received for U.S. Appl. No. 17/383,880, mailed on Aug. 29, 2022, 17 pages.
Notice of Allowance received for U.S. Appl. No. 17/383,880, mailed on Jun. 20, 2022, 17 pages.
Notice of Allowance received for U.S. Appl. No. 17/950,943, mailed on Jul. 5, 2023, 18 pages.
Notice of Allowance received for U.S. Appl. No. 17/950,943, mailed on Oct. 20, 2023, 18 pages.
Office Action received for European Patent Application No. 22729964.1, mailed on May 22, 2023, 9 pages.
Office Action received for Japanese Patent Application No. 2023-513867, mailed on Jul. 31, 2023, 11 pages.
Reuss et al., "Period Domain Analysis In Fetal Pulse Oximetry", Proceedings of t11e Second Joint EMBS/BMES Conference, Houston, TX, Oct. 23-26, 2002, 2 pages.
Rubine Dean, "Combining Gestures and Direct Manipulation", CHI '92, May 3-7, 1992, pp. 659-660.
Rubine Deanh, "The Automatic Recognition of Gestures", CMU-CS-91-202, Thesis Submitted in Partial Fulfillment of the Requirements for the Degree of Doctor of Philosophy in Computer Science at Carnegie Mellon University, Dec. 1991, 285 pages.
Westerman Wayne, "Hand Tracking, Finger Identification and Chordic Manipulation on a Multi-Touch Surface", Doctoral Dissertation, 1999, 363 Pages.
Zhang et al., "FinDroidHR: Smartwatch Gesture Input with Optical Heartrate Monitor", Proceedings of the ACM on Interactive Mobile, Wearable and Ubiquitous Technologies, Available Online at: https://dl.acm.org/doi/10.1145/3191788, vol. 2, No. 1, Mar. 2018, 42 pages.
Zhao et al., "Wireless Photoplethysmograph Knuckle Sensor System for Measuring Finger Motions", 2014 International Symposium on Optomechatronic Technologies, IEEE, 2014, pp. 205-209.
Zheng et al., "An Efficient User Verification System via Mouse Movements", Computer am1 Communications Security, ACM, New York, NY, USA, Dec. 17, 2011, pp. 139-150.
Advisory Action received for U.S. Appl. No. 17/747,613, mailed on Feb. 14, 2024, 3 pages.
Advisory Action received for U.S. Appl. No. 18/109,808, mailed on May 20, 2024, 6 pages.
Applicant-Initiated Interview Summary received for U.S. Appl. No. 18/109,808, mailed on Apr. 30, 2024, 5 pages.
Brief Communication Regarding Oral Proceedings received for European Patent Application No. 22729964.1. mailed on Mar. 21, 2024, 1 page.
Final Office Action received for U.S. Appl. No. 18/197,681, mailed on Jun. 27, 2024, 30 pages.
Intention to Grant received for European Patent Application No. 22729964.1, mailed on Apr. 24, 2024, 9 pages.
International Search Report and Written Opinion received for PCT Patent Application No. PCT/US2023/032794, mailed on Jan. 8, 2024, 19 pages.
Invitation to Pay Additional Fees and Partial International Search Report received for PCT Patent Application No. PCT/US2023/032794, mailed on Nov. 9, 2023, 12 pages.
Non-Final Office Action received for U.S. Appl. No. 18/109,808, mailed on Jul. 5, 2024, 53 pages.
Applicant-Initiated Interview Summary received for U.S. Appl. No. 17/747,613, mailed on Jan. 31, 2024, 3 pages.
Applicant-Initiated Interview Summary received for U.S. Appl. No. 18/109,808, mailed on Jan. 23, 2024, 5 pages.
Final Office Action received for U.S. Appl. No. 17/747,613, mailed on Jan. 11, 2024, 28 pages.
Non-Final Office Action received for U.S. Appl. No. 18/109,808, mailed on Jan. 4, 2024, 45 pages.
Non-Final Office Action received for U.S. Appl. No. 18/197,681, mailed on Jan. 30, 2024, 32 pages.
Applicant-Initiated Interview Summary received for U.S. Appl. No. 17/747,613, mailed on Dec. 14, 2023, 2 pages.
Applicant-Initiated Interview Summary received for U.S. Appl. No. 18/109,808, mailed on Nov. 22, 2023, 5 pages.
Final Office Action received for U.S. Appl. No. 18/109,808, mailed on Oct. 31, 2023, 54 pages.
International Preliminary Report on Patentability received for PCT Patent Application No. PCT/US2022/030021, mailed on Nov. 30, 2023, 14 pages.
International Search Report and Written Opinion received for PCT Patent Application No. PCT/US2023/012260, mailed on Aug. 2, 2023, 22 pages.
International Search Report and Written Opinion received for PCT Patent Application No. PCT/US2023/022410, mailed on Aug. 31, 2023, 21 pages.
Invitation to Pay Additional Fees and Partial International Search Report received for PCT Patent Application No. PCT/US2023/012260, mailed on Jun. 7, 2023, 11 pages.
Non-Final Office Action received for U.S. Appl. No. 17/747,613, mailed on Nov. 16, 2023, 28 pages.
Office Action received for Japanese Patent Application No. 2023-513867, mailed on Dec. 4, 2023, 6 pages (3 pages of English Translation and 3 pages of Official Copy).
Summons to Attend Oral Proceedings received for European Patent Application No. 22729964.1, mailed on Nov. 6, 2023, 7 pages.
Applicant-Initiated Interview Summary received for U.S. Appl. No. 18/197,681, mailed on Mar. 18, 2024, 4 pages.

(56) References Cited

OTHER PUBLICATIONS

Final Office Action received for U.S. Appl. No. 18/109,808, mailed on Mar. 5, 2024, 52 pages.

* cited by examiner

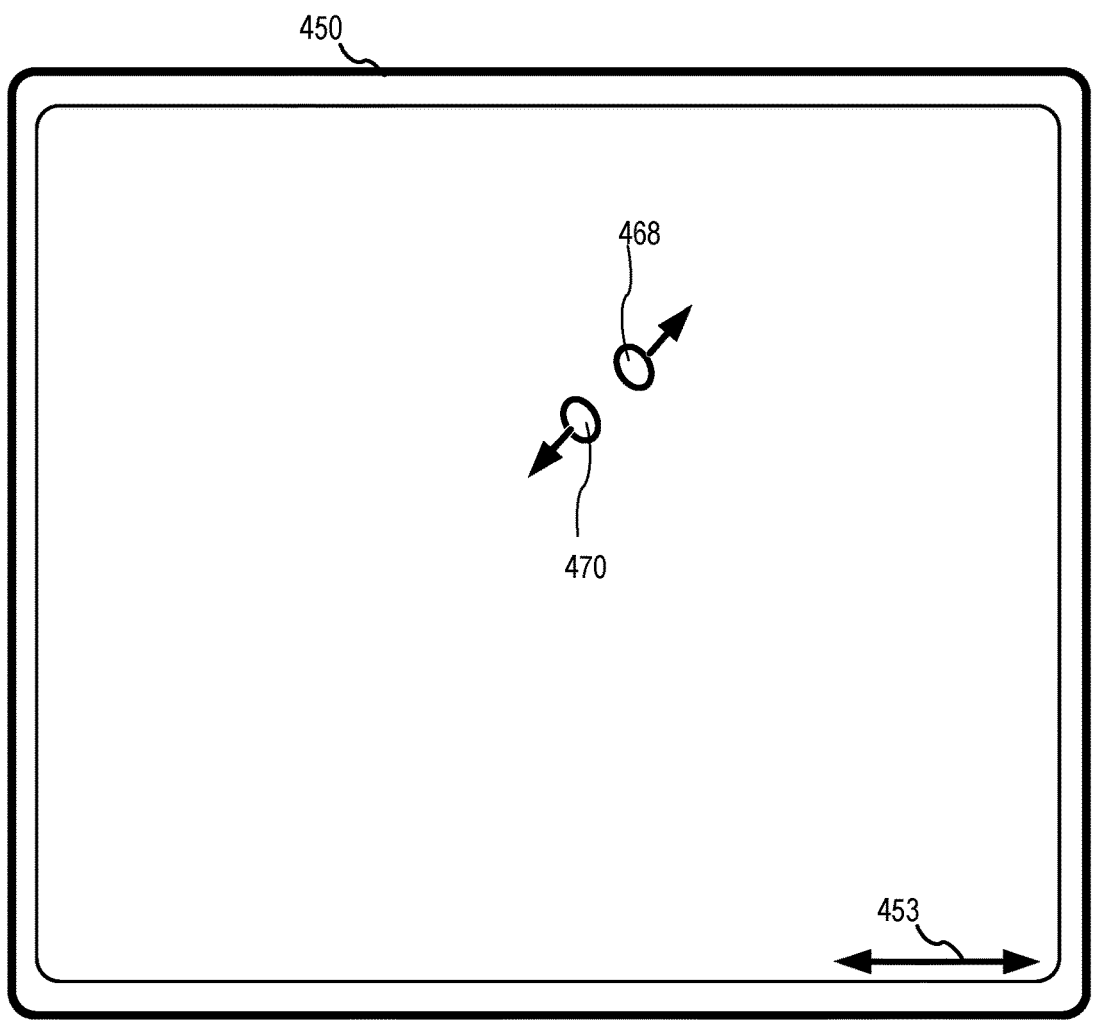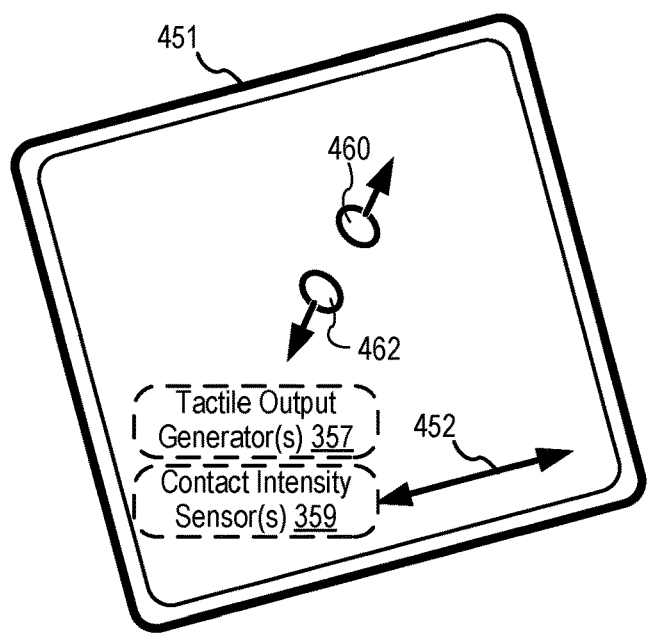
FIG. 4B

1300

1302
Display a first plurality of graphical elements indicating a predefined sequence of movements associated with an operation The first plurality of graphical elements comprise a first graphical element indicating a first movement and a second graphical element indicating a second movement The first movement comprises rotation of the electronic device in a first direction around a central axis from a neutral position to a first position and back toward the neutral position within a first predetermined time The second movement comprises a rotation of the electronic device in a second direction opposite the first direction around the central axis from the neutral position to a second position and back toward the neutral position within a second predetermined time

1304
Receive a plurality of tilt sensor inputs associated with movements of the electronic device

1310
While receiving the plurality of tilt sensor inputs, display a second plurality of graphical elements indicating movements of the electronic device

1312
While receiving the plurality of tilt sensor inputs, display an indicator that indicates the direction of rotation of the electronic device

1402
Display a first item at a first position on the display screen and a second item at a second position on the display screen, the first position and second position corresponding to positions along a line substantially perpendicular to an axis of rotation of the electronic device

1404
Receive a tilt sensor input associated with movement of the electronic device

1412
Display an indicator that indicates the direction of rotation of the electronic device In accordance with a determination that the tilt sensor input corresponds to a rotation of the electronic device in a first direction around the axis of rotation from a neutral position to a first position:

1406
Move the first item from the first position on the display screen to a third position along the line substantially perpendicular to the axis of rotation In accordance with a determination that the tilt sensor input corresponds to a rotation of the electronic device in a second direction opposite the first direction around the axis of rotation from the neutral position to a second position:

1408
Move the second item from the second position on the display screen to a fourth position along the line substantially perpendicular to the axis of rotation

1410
After moving the first or second item, and in accordance with a determination that no additional tilt sensor input above a threshold value is received within a predetermined time, selecting the moved item

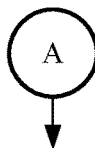

```
┌─────────────────────────────────────────────────────────────────────────┐
│  In accordance with a determination that the tilt sensor input corresponds to movement of a  │
│                                  second type:                                 │
│  ┌───────────────────────────────────────────────────────────────────┐  │
│  │                              1626                                 │  │
│  │   Determine the biological sensor input ceases to correspond to the predefined   │  │
│  │                             pattern                               │  │
│  └───────────────────────────────────────────────────────────────────┘  │
│  ┌───────────────────────────────────────────────────────────────────┐  │
│  │                              1612                                 │  │
│  │                      Perform the second operation                 │  │
│  └───────────────────────────────────────────────────────────────────┘  │
│  ┌───────────────────────────────────────────────────────────────────┐  │
│  │                              1616                                 │  │
│  │            Modify a visual appearance of the second graphical element            │  │
│  └───────────────────────────────────────────────────────────────────┘  │
└─────────────────────────────────────────────────────────────────────────┘
```

1618
Determine that the biological sensor input does not correspond to the predefined pattern for the predetermined time While the biological sensor input does not correspond to the predefined pattern:

1620
Receive the tilt sensor input associated with movement of the electronic device 1622
Forgo performing the first or second operations

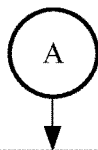

In response to the user input:

1714
In accordance with a determination that the electronic device satisfies a first operation criteria, the first operation criteria including a mode criterion that is satisfied when the electronic device is in the first mode, perform a first operation

1720
In accordance with the determination that the electronic device satisfies the first operation criteria, modify a visual appearance of the first graphical element

1718
In accordance with a determination that the electronic device satisfies a second operation criteria, the second operation criteria including a criterion that is satisfied when the electronic device is in the first mode, perform a second operation (e.g., decline call), wherein the second operation criteria is different than the first operation criteria and the second operation is different than the first operation

1722
In accordance with the determination that the electronic device satisfies the second operation criteria, modify a visual appearance of the second graphical element

1716
In accordance with a determination that the electronic device does not satisfy the first (or second) operation criteria, forgo performing the first operation

*FIG. 17B*

INTERACTING WITH AN ELECTRONIC DEVICE THROUGH PHYSICAL MOVEMENT

CROSS-REFERENCE TO RELATED APPLICATIONS

This application is a Continuation of U.S. Non-Provisional application Ser. No. 17/950,943, entitled "INTERACTING WITH AN ELECTRONIC DEVICE THROUGH PHYSICAL MOVEMENT," filed on Sep. 22, 2022, which is a Continuation of U.S. Non-Provisional application Ser. No. 17/383,880, now U.S. Pat. No. 11,520,416, entitled "INTERACTING WITH AN ELECTRONIC DEVICE THROUGH PHYSICAL MOVEMENT," filed on Jul. 23, 2021, which is a Continuation of U.S. Non-Provisional application Ser. No. 16/773,536, now U.S. Pat. No. 11,073,918, entitled "INTERACTING WITH AN ELECTRONIC DEVICE THROUGH PHYSICAL MOVEMENT," filed on Jan. 27, 2020, which is a Continuation of U.S. Non-Provisional application Ser. No. 15/937,716, now U.S. Pat. No. 10,558,278, entitled "INTERACTING WITH AN ELECTRONIC DEVICE THROUGH PHYSICAL MOVEMENT," filed on Mar. 27, 2018, which claims the benefit of U.S. Provisional Patent Application No. 62/531,248, entitled "INTERACTING WITH AN ELECTRONIC DEVICE THROUGH PHYSICAL MOVEMENT," filed on Jul. 11, 2017, which are hereby incorporated by reference in their entireties.

FIELD

The present disclosure relates generally to computer user interfaces, and more specifically to techniques for interacting with user interfaces.

BACKGROUND

Reduced-size electronic devices (e.g., devices that are smaller than typical cellular phones such as smart watches) that are configured to be worn by a user can allow a user to view and respond to various types of alerts, such as text messages, emails, voicemails, and calendar alerts. User interfaces that enable a reduced-size electronic device to be efficiently used for viewing and responding to alerts are desirable.

BRIEF SUMMARY

Some techniques for interacting with electronic devices, however, are generally cumbersome and inefficient. For example, some existing techniques use a complex and time-consuming user interface, which can include multiple button presses or finger touches. In the case of devices worn on a user's arm (e.g., a smart watch) operation of the device via a touchscreen interface effectively requires the use of both of the users hands, restricting their use for other purposes. Moreover, existing techniques require more time than necessary, wasting user time and device energy. This latter consideration is particularly important in battery-operated devices.

Accordingly, the present techniques provide electronic devices with faster, more efficient methods and interfaces for interacting with the devices without touching display screens or other physical input mechanisms. Such methods and interfaces optionally complement or replace other methods for interacting with the devices. Such methods and interfaces reduce the cognitive burden on a user and produce a more efficient human-machine interface. For battery-operated computing devices, such methods and interfaces conserve power and increase the time between battery charges.

Example methods are disclosed herein. An example method includes, at an electronic device with a display screen and a tilt sensor: displaying a first graphical element at a first location on the display screen; displaying a second graphical element at a second location on the display screen, the second graphical element being associated with a first operation; receiving a tilt sensor input associated with movement of the electronic device; in accordance with a determination that the tilt sensor input satisfies a first predefined tilt sensor condition: displaying the first graphical element proximate to the second location on the display screen; and performing the first operation associated with the second graphical element; and in accordance with a determination that the tilt sensor input fails to satisfy the first predefined tilt sensor condition, displaying the first graphical element at a third location on the display screen based on the tilt sensor input.

Another example method includes, at an electronic device with a display screen and a tilt sensor: displaying, on the display screen, a first plurality of graphical elements indicating a predefined sequence of movements associated with an operation, wherein: the first plurality of graphical elements comprise a first graphical element indicating a first movement and a second graphical element indicating a second movement, the first movement comprises rotation of the electronic device in a first direction around a central axis from a neutral position to a first position and back toward the neutral position within a first predetermined time, and the second movement comprises a rotation of the electronic device in a second direction opposite the first direction around the central axis from the neutral position to a second position and back toward the neutral position within a second predetermined time; receiving a plurality of tilt sensor inputs associated with movements of the electronic device; in accordance with a determination that the plurality of tilt sensor inputs corresponds to the predefined sequence of movements indicated by the first plurality of graphical elements: performing the operation associated with the predefined sequence of movements; in accordance with a determination that the plurality of tilt sensor inputs does not correspond to the predefined sequence of movements indicated by the first plurality of graphical elements: forgoing performing the operation associated with the predefined sequence of movements.

Another example method includes, at an electronic device with a display screen and a tilt sensor: displaying a first item at a first position on the display screen and a second item at a second position on the display screen, the first position and second position corresponding to positions along a line substantially perpendicular to an axis of rotation of the electronic device; receiving a tilt sensor input associated with movement of the electronic device; in accordance with a determination that the tilt sensor input corresponds to a rotation of the electronic device in a first direction around the axis of rotation from a neutral position to a first position: moving the first item from the first position on the display screen to a third position along the line substantially perpendicular to the axis of rotation; and in accordance with a determination that the tilt sensor input corresponds to a rotation of the electronic device in a second direction opposite the first direction around the axis of rotation from the neutral position to a second position: moving the second item from the second position on the display screen to a fourth position along the line substantially perpendicular to the axis of rotation.

Another example method includes, at an electronic device with a display screen and a biological sensor: displaying an affordance on the display screen; receiving biological sensor input associated with a positioning of a user's hand; in accordance with a determination that the biological sensor input corresponds to a predefined pattern for a predetermined time, the predefined pattern being associated with the positioning of the user's hand displaying an indication that the biological sensor input corresponds to the predefined pattern for the predetermined time; and performing an operation associated with the affordance; and in accordance with a determination that the sensor input does not correspond to the predefined pattern for the predetermined time: forgoing performing the operation associated with the affordance.

Another example method includes, at an electronic device with a display screen, a biological sensor, and a tilt sensor: displaying a user interface on the display screen, the user interface being responsive to at least a first operation and a second operation associated with movement of the electronic device; receiving biological sensor input associated with positioning of a user's hand; in accordance with a determination that the biological sensor input corresponds to a predefined pattern for a predetermined time, the predefined pattern being associated with the positioning of the user's hand: displaying an indication in the user interface that the sensor input corresponds to the predefined pattern; while the biological sensor input corresponds to the predefined pattern: receiving a tilt sensor input associated with movement of the electronic device; in accordance with a determination that the tilt sensor input corresponds to movement of a first type: performing the first operation; and in accordance with a determination that the tilt sensor input corresponds to movement of a second type: performing the second operation.

Another example method includes, at an electronic device with a display screen and a sensor: receiving, via the sensor, a sensor input; in response to receiving the sensor input, determining whether the electronic device satisfies a mode change criteria, the mode change criteria including an orientation criterion satisfied based on an orientation of the electronic device; in accordance with a determination that the mode change criteria is satisfied: transitioning the electronic device to a first mode; and modifying the user interface to indicate the electronic device is in the first mode; in accordance with a determination that the mode change criteria is not satisfied, forgoing transitioning the electronic device to the first mode; subsequent to receiving the sensor input, receiving a user input; and in response to the user input: in accordance with a determination that the electronic device satisfies a first operation criteria, the first operation criteria including a mode criterion that is satisfied when the electronic device is in the first mode, performing a first operation; and in accordance with a determination that the electronic device does not satisfy the first operation criteria, forgoing performing the first operation.

Exemplary devices are disclosed herein. An example electronic device includes a display screen; a tilt sensor; one or more processors; and memory storing one or more programs configured to be executed by the one or more processors, the one or more programs including instructions for: displaying a first graphical element at a first location on the display screen; displaying a second graphical element at a second location on the display screen, the second graphical element being associated with a first operation; receiving a tilt sensor input associated with movement of the electronic device; in accordance with a determination that the tilt sensor input satisfies a first predefined tilt sensor condition: displaying the first graphical element proximate to the second location on the display screen; and performing the first operation associated with the second graphical element; and in accordance with a determination that the tilt sensor input fails to satisfy the first predefined tilt sensor condition, displaying the first graphical element at a third location on the display screen based on the tilt sensor input.

Another example electronic device includes a display screen; a tilt sensor; one or more processors; and memory storing one or more programs configured to be executed by the one or more processors, the one or more programs including instructions for: displaying, on the display screen, a first plurality of graphical elements indicating a predefined sequence of movements associated with an operation, wherein: the first plurality of graphical elements comprise a first graphical element indicating a first movement and a second graphical element indicating a second movement, the first movement comprises rotation of the electronic device in a first direction around a central axis from a neutral position to a first position and back toward the neutral position within a first predetermined time, and the second movement comprises a rotation of the electronic device in a second direction opposite the first direction around the central axis from the neutral position to a second position and back toward the neutral position within a second predetermined time; receiving a plurality of tilt sensor inputs associated with movements of the electronic device; in accordance with a determination that the plurality of tilt sensor inputs corresponds to the predefined sequence of movements indicated by the first plurality of graphical elements: performing the operation associated with the predefined sequence of movements; in accordance with a determination that the plurality of tilt sensor inputs does not correspond to the predefined sequence of movements indicated by the first plurality of graphical elements: forgoing performing the operation associated with the predefined sequence of movements.

Another example electronic device includes a display screen; a tilt sensor; one or more processors; and memory storing one or more programs configured to be executed by the one or more processors, the one or more programs including instructions for: displaying a first item at a first position on the display screen and a second item at a second position on the display screen, the first position and second position corresponding to positions along a line substantially perpendicular to an axis of rotation of the electronic device; receiving a tilt sensor input associated with movement of the electronic device; in accordance with a determination that the tilt sensor input corresponds to a rotation of the electronic device in a first direction around the axis of rotation from a neutral position to a first position: moving the first item from the first position on the display screen to a third position along the line substantially perpendicular to the axis of rotation; and in accordance with a determination that the tilt sensor input corresponds to a rotation of the electronic device in a second direction opposite the first direction around the axis of rotation from the neutral position to a second position: moving the second item from the second position on the display screen to a fourth position along the line substantially perpendicular to the axis of rotation.

Another example electronic device includes a display screen; a biological sensor; one or more processors; and memory storing one or more programs configured to be executed by the one or more processors, the one or more programs including instructions for: displaying an affordance on the display screen; receiving biological sensor input associated with a positioning of a user's hand; in accordance with a determination that the biological sensor input corresponds to a predefined pattern for a predetermined time, the predefined pattern being associated with the positioning of the user's hand: displaying an indication that the biological sensor input corresponds to the predefined pattern for the predetermined time; and performing an operation associated with the affordance; and in accordance with a determination that the sensor input does not correspond to the predefined pattern for the predetermined time: forgoing performing the operation associated with the affordance.

Another example electronic device includes a display screen; a biological sensor; a tilt sensor; one or more processors; and memory storing one or more programs configured to be executed by the one or more processors, the one or more programs including instructions for: displaying a user interface on the display screen, the user interface being responsive to at least a first operation and a second operation associated with movement of the electronic device; receiving biological sensor input associated with positioning of a user's hand; in accordance with a determination that the biological sensor input corresponds to a predefined pattern for a predetermined time, the predefined pattern being associated with the positioning of the user's hand: displaying an indication in the user interface that the sensor input corresponds to the predefined pattern; while the biological sensor input corresponds to the predefined pattern: receiving a tilt sensor input associated with movement of the electronic device; in accordance with a determination that the tilt sensor input corresponds to movement of a first type: performing the first operation; and in accordance with a determination that the tilt sensor input corresponds to movement of a second type: performing the second operation.

Another example electronic device includes a display screen; a sensor; one or more processors; and memory storing one or more programs configured to be executed by the one or more processors, the one or more programs including instructions for: receiving, via the sensor, a sensor input; in response to receiving the sensor input, determining whether the electronic device satisfies a mode change criteria, the mode change criteria including an orientation criterion satisfied based on an orientation of the electronic device; in accordance with a determination that the mode change criteria is satisfied: transitioning the electronic device to a first mode; and modifying the user interface to indicate the electronic device is in the first mode; in accordance with a determination that the mode change criteria is not satisfied, forgoing transitioning the electronic device to the first mode; subsequent to receiving the sensor input, receiving a user input; and in response to the user input: in accordance with a determination that the electronic device satisfies a first operation criteria, the first operation criteria including a mode criterion that is satisfied when the electronic device is in the first mode, performing a first operation; and in accordance with a determination that the electronic device does not satisfy the first operation criteria, forgoing performing the first operation.

Example non-transitory computer readable storage media are disclosed herein. An example non-transitory computer readable storage medium stores one or more programs configured to be executed by one or more processors of an electronic device with a display screen and a tilt sensor, the one or more programs including instructions for: displaying a first graphical element at a first location on the display screen; displaying a second graphical element at a second location on the display screen, the second graphical element being associated with a first operation; receiving a tilt sensor input associated with movement of the electronic device; in accordance with a determination that the tilt sensor input satisfies a first predefined tilt sensor condition: displaying the first graphical element proximate to the second location on the display screen; and performing the first operation associated with the second graphical element; and in accordance with a determination that the tilt sensor input fails to satisfy the first predefined tilt sensor condition, displaying the first graphical element at a third location on the display screen based on the tilt sensor input.

Another example non-transitory computer readable storage medium stores one or more programs configured to be executed by one or more processors of an electronic device with a display screen and a tilt sensor, the one or more programs including instructions for: displaying, on the display screen, a first plurality of graphical elements indicating a predefined sequence of movements associated with an operation, wherein: the first plurality of graphical elements comprise a first graphical element indicating a first movement and a second graphical element indicating a second movement, the first movement comprises rotation of the electronic device in a first direction around a central axis from a neutral position to a first position and back toward the neutral position within a first predetermined time, and the second movement comprises a rotation of the electronic device in a second direction opposite the first direction around the central axis from the neutral position to a second position and back toward the neutral position within a second predetermined time; receiving a plurality of tilt sensor inputs associated with movements of the electronic device; in accordance with a determination that the plurality of tilt sensor inputs corresponds to the predefined sequence of movements indicated by the first plurality of graphical elements: performing the operation associated with the predefined sequence of movements; in accordance with a determination that the plurality of tilt sensor inputs does not correspond to the predefined sequence of movements indicated by the first plurality of graphical elements: forgoing performing the operation associated with the predefined sequence of movements.

Another example non-transitory computer readable storage medium stores one or more programs configured to be executed by one or more processors of an electronic device with a display screen and a tilt sensor, the one or more programs including instructions for: displaying a first item at a first position on the display screen and a second item at a second position on the display screen, the first position and second position corresponding to positions along a line substantially perpendicular to an axis of rotation of the electronic device; receiving a tilt sensor input associated with movement of the electronic device; in accordance with a determination that the tilt sensor input corresponds to a rotation of the electronic device in a first direction around the axis of rotation from a neutral position to a first position: moving the first item from the first position on the display screen to a third position along the line substantially perpendicular to the axis of rotation; and in accordance with a determination that the tilt sensor input corresponds to a rotation of the electronic device in a second direction opposite the first direction around the axis of rotation from the neutral position to a second position: moving the second item from the second position on the display screen to a fourth position along the line substantially perpendicular to the axis of rotation.

Another example non-transitory computer readable storage medium stores one or more programs configured to be executed by one or more processors of an electronic device with a display screen and a biological sensor, the one or more programs including instructions for: displaying an affordance on the display screen; receiving biological sensor input associated with a positioning of a user's hand; in accordance with a determination that the biological sensor input corresponds to a predefined pattern for a predetermined time, the predefined pattern being associated with the positioning of the user's hand displaying an indication that the biological sensor input corresponds to the predefined pattern for the predetermined time; and performing an operation associated with the affordance; and in accordance with a determination that the sensor input does not correspond to the predefined pattern for the predetermined time: forgoing performing the operation associated with the affordance.

Another example non-transitory computer readable storage medium stores one or more programs configured to be executed by one or more processors of an electronic device with a display screen, a tilt sensor, and a biological sensor, the one or more programs including instructions for: displaying a user interface on the display screen, the user interface being responsive to at least a first operation and a second operation associated with movement of the electronic device; receiving biological sensor input associated with positioning of a user's hand; in accordance with a determination that the biological sensor input corresponds to a predefined pattern for a predetermined time, the predefined pattern being associated with the positioning of the user's hand: displaying an indication in the user interface that the sensor input corresponds to the predefined pattern; while the biological sensor input corresponds to the predefined pattern: receiving a tilt sensor input associated with movement of the electronic device; in accordance with a determination that the tilt sensor input corresponds to movement of a first type: performing the first operation; and in accordance with a determination that the tilt sensor input corresponds to movement of a second type: performing the second operation.

Another example non-transitory computer readable storage medium stores one or more programs configured to be executed by one or more processors of an electronic device with a display screen and a sensor, the one or more programs including instructions for: receiving, via the sensor, a sensor input; in response to receiving the sensor input, determining whether the electronic device satisfies a mode change criteria, the mode change criteria including an orientation criterion satisfied based on an orientation of the electronic device; in accordance with a determination that the mode change criteria is satisfied: transitioning the electronic device to a first mode; and modifying the user interface to indicate the electronic device is in the first mode; in accordance with a determination that the mode change criteria is not satisfied, forgoing transitioning the electronic device to the first mode; subsequent to receiving the sensor input, receiving a user input; and in response to the user input: in accordance with a determination that the electronic device satisfies a first operation criteria, the first operation criteria including a mode criterion that is satisfied when the electronic device is in the first mode, performing a first operation; and in accordance with a determination that the electronic device does not satisfy the first operation criteria, forgoing performing the first operation.

Example transitory computer readable storage media are disclosed herein. An example transitory computer readable storage medium stores one or more programs configured to be executed by one or more processors of an electronic device with a display screen and a tilt sensor, the one or more programs including instructions for: displaying a first graphical element at a first location on the display screen; displaying a second graphical element at a second location on the display screen, the second graphical element being associated with a first operation; receiving a tilt sensor input associated with movement of the electronic device; in accordance with a determination that the tilt sensor input satisfies a first predefined tilt sensor condition: displaying the first graphical element proximate to the second location on the display screen; and performing the first operation associated with the second graphical element; and in accordance with a determination that the tilt sensor input fails to satisfy the first predefined tilt sensor condition, displaying the first graphical element at a third location on the display screen based on the tilt sensor input.

Another example transitory computer readable storage medium stores one or more programs configured to be executed by one or more processors of an electronic device with a display screen and a tilt sensor, the one or more programs including instructions for: displaying, on the display screen, a first plurality of graphical elements indicating a predefined sequence of movements associated with an operation, wherein: the first plurality of graphical elements comprise a first graphical element indicating a first movement and a second graphical element indicating a second movement, the first movement comprises rotation of the electronic device in a first direction around a central axis from a neutral position to a first position and back toward the neutral position within a first predetermined time, and the second movement comprises a rotation of the electronic device in a second direction opposite the first direction around the central axis from the neutral position to a second position and back toward the neutral position within a second predetermined time; receiving a plurality of tilt sensor inputs associated with movements of the electronic device; in accordance with a determination that the plurality of tilt sensor inputs corresponds to the predefined sequence of movements indicated by the first plurality of graphical elements: performing the operation associated with the predefined sequence of movements; in accordance with a determination that the plurality of tilt sensor inputs does not correspond to the predefined sequence of movements indicated by the first plurality of graphical elements: forgoing performing the operation associated with the predefined sequence of movements.

Another example transitory computer readable storage medium stores one or more programs configured to be executed by one or more processors of an electronic device with a display screen and a tilt sensor, the one or more programs including instructions for: displaying a first item at a first position on the display screen and a second item at a second position on the display screen, the first position and second position corresponding to positions along a line substantially perpendicular to an axis of rotation of the electronic device; receiving a tilt sensor input associated with movement of the electronic device; in accordance with a determination that the tilt sensor input corresponds to a rotation of the electronic device in a first direction around the axis of rotation from a neutral position to a first position: moving the first item from the first position on the display screen to a third position along the line substantially perpendicular to the axis of rotation; and in accordance with a determination that the tilt sensor input corresponds to a rotation of the electronic device in a second direction opposite the first direction around the axis of rotation from the neutral position to a second position: moving the second item from the second position on the display screen to a fourth position along the line substantially perpendicular to the axis of rotation.

Another example transitory computer readable storage medium stores one or more programs configured to be executed by one or more processors of an electronic device with a display screen and a biological sensor, the one or more programs including instructions for: displaying an affordance on the display screen; receiving biological sensor input associated with a positioning of a user's hand; in accordance with a determination that the biological sensor input corresponds to a predefined pattern for a predetermined time, the predefined pattern being associated with the positioning of the user's hand displaying an indication that the biological sensor input corresponds to the predefined pattern for the predetermined time; and performing an operation associated with the affordance; and in accordance with a determination that the sensor input does not correspond to the predefined pattern for the predetermined time: forgoing performing the operation associated with the affordance.

Another example transitory computer readable storage medium stores one or more programs configured to be executed by one or more processors of an electronic device with a display screen, a tilt sensor, and a biological sensor, the one or more programs including instructions for: displaying a user interface on the display screen, the user interface being responsive to at least a first operation and a second operation associated with movement of the electronic device; receiving biological sensor input associated with positioning of a user's hand; in accordance with a determination that the biological sensor input corresponds to a predefined pattern for a predetermined time, the predefined pattern being associated with the positioning of the user's hand: displaying an indication in the user interface that the sensor input corresponds to the predefined pattern; while the biological sensor input corresponds to the predefined pattern: receiving a tilt sensor input associated with movement of the electronic device; in accordance with a determination that the tilt sensor input corresponds to movement of a first type: performing the first operation; and in accordance with a determination that the tilt sensor input corresponds to movement of a second type: performing the second operation.

Another example transitory computer readable storage medium stores one or more programs configured to be executed by one or more processors of an electronic device with a display screen and a sensor, the one or more programs including instructions for: receiving, via the sensor, a sensor input; in response to receiving the sensor input, determining whether the electronic device satisfies a mode change criteria, the mode change criteria including an orientation criterion satisfied based on an orientation of the electronic device; in accordance with a determination that the mode change criteria is satisfied: transitioning the electronic device to a first mode; and modifying the user interface to indicate the electronic device is in the first mode; in accordance with a determination that the mode change criteria is not satisfied, forgoing transitioning the electronic device to the first mode; subsequent to receiving the sensor input, receiving a user input; and in response to the user input: in accordance with a determination that the electronic device satisfies a first operation criteria, the first operation criteria including a mode criterion that is satisfied when the electronic device is in the first mode, performing a first operation; and in accordance with a determination that the electronic device does not satisfy the first operation criteria, forgoing performing the first operation.

In accordance with some embodiments, an electronic device includes a display screen; a tilt sensor; means for displaying a first graphical element at a first location on the display screen; means for displaying a second graphical element at a second location on the display screen, the second graphical element being associated with a first operation; means for receiving a tilt sensor input associated with movement of the electronic device; means for, in accordance with a determination that the tilt sensor input satisfies a first predefined tilt sensor condition: displaying the first graphical element proximate to the second location on the display screen; and performing the first operation associated with the second graphical element; and means for, in accordance with a determination that the tilt sensor input fails to satisfy the first predefined tilt sensor condition: displaying the first graphical element at a third location on the display screen based on the tilt sensor input.

In accordance with some embodiments, an electronic device includes a display screen; a tilt sensor; means for displaying, on the display screen, a first plurality of graphical elements indicating a predefined sequence of movements associated with an operation, wherein: the first plurality of graphical elements comprise a first graphical element indicating a first movement and a second graphical element indicating a second movement, the first movement comprises rotation of the electronic device in a first direction around a central axis from a neutral position to a first position and back toward the neutral position within a first predetermined time, and the second movement comprises a rotation of the electronic device in a second direction opposite the first direction around the central axis from the neutral position to a second position and back toward the neutral position within a second predetermined time; means for receiving a plurality of tilt sensor inputs associated with movements of the electronic device; means for, in accordance with a determination that the plurality of tilt sensor inputs corresponds to the predefined sequence of movements indicated by the first plurality of graphical elements: performing the operation associated with the predefined sequence of movements; means for, in accordance with a determination that the plurality of tilt sensor inputs does not correspond to the predefined sequence of movements indicated by the first plurality of graphical elements: forgoing performing the operation associated with the predefined sequence of movements.

In accordance with some embodiments, an electronic device includes a display screen; a tilt sensor; means for displaying a first item at a first position on the display screen and a second item at a second position on the display screen, the first position and second position corresponding to positions along a line substantially perpendicular to an axis of rotation of the electronic device; means for receiving a tilt sensor input associated with movement of the electronic device; means for, in accordance with a determination that the tilt sensor input corresponds to a rotation of the electronic device in a first direction around the axis of rotation from a neutral position to a first position: moving the first item from the first position on the display screen to a third position along the line substantially perpendicular to the axis of rotation; and means for, in accordance with a determination that the tilt sensor input corresponds to a rotation of the electronic device in a second direction opposite the first direction around the axis of rotation from the neutral position to a second position: moving the second item from the second position on the display screen to a fourth position along the line substantially perpendicular to the axis of rotation.

In accordance with some embodiments, an electronic device includes a display screen; a biological sensor; means for displaying an affordance on the display screen; means for receiving biological sensor input associated with a positioning of a user's hand; means for, in accordance with a determination that the biological sensor input corresponds to a predefined pattern for a predetermined time, the predefined pattern being associated with the positioning of the user's hand: displaying an indication that the biological sensor input corresponds to the predefined pattern for the predetermined time; and performing an operation associated with the affordance; and means for, in accordance with a determination that the sensor input does not correspond to the predefined pattern for the predetermined time: forgoing performing the operation associated with the affordance.

In accordance with some embodiments, an electronic device includes a display screen; a biological sensor; a tilt sensor; means for displaying a user interface on the display screen, the user interface being responsive to at least a first operation and a second operation associated with movement of the electronic device; means for receiving biological sensor input associated with positioning of a user's hand; means for, in accordance with a determination that the biological sensor input corresponds to a predefined pattern for a predetermined time, the predefined pattern being associated with the positioning of the user's hand displaying an indication in the user interface that the sensor input corresponds to the predefined pattern; means for, while the biological sensor input corresponds to the predefined pattern: receiving a tilt sensor input associated with movement of the electronic device; means for, in accordance with a determination that the tilt sensor input corresponds to movement of a first type: performing the first operation; and means for, in accordance with a determination that the tilt sensor input corresponds to movement of a second type: performing the second operation.

In accordance with some embodiments, an electronic device includes a display screen; a sensor; means for receiving, via the sensor, a sensor input; means for, in response to receiving the sensor input, determining whether the electronic device satisfies a mode change criteria, the mode change criteria including an orientation criterion satisfied based on an orientation of the electronic device; means for, in accordance with a determination that the mode change criteria is satisfied: transitioning the electronic device to a first mode; and modifying the user interface to indicate the electronic device is in the first mode; means for, in accordance with a determination that the mode change criteria is not satisfied, forgoing transitioning the electronic device to the first mode; means for, subsequent to receiving the sensor input, receiving a user input; and in response to the user input: means for, in accordance with a determination that the electronic device satisfies a first operation criteria, the first operation criteria including a mode criterion that is satisfied when the electronic device is in the first mode, performing a first operation; and means for, in accordance with a determination that the electronic device does not satisfy the first operation criteria, forgoing performing the first operation.

In accordance with some embodiments, an electronic device comprises a display screen; one or more sensors; one or more processors; a memory; and one or more programs, wherein the one or more programs are stored in the memory and configured to be executed by the one or more processors, the one or more programs including instructions for performing any of the methods disclosed herein.

In accordance with some embodiments, a non-transitory computer readable storage medium stores one or more programs, the one or more programs comprising instructions, which when executed by one or more processors of an electronic device, cause the device to perform any of the methods disclosed herein.

Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for interacting with the devices without touching display screens or other physical input mechanisms, thereby increasing the effectiveness, efficiency, and user satisfaction with such devices. Such methods and interfaces may complement or replace other methods for interacting with the devices.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIG. 4B illustrates an exemplary user interface for a multifunction device with a touch-sensitive surface that is separate from the display in accordance with some embodiments.

FIGS. 13A-13B are flow diagrams illustrating a method for performing one or more operations with an electronic device, in accordance with some embodiments.

FIG. 14 is a flow diagram illustrating a method for performing one or more operations with an electronic device, in accordance with some embodiments.

FIGS. 16A-16B are flow diagrams illustrating a method 1600 for performing an operation with an electronic device, in accordance with some embodiments.

FIGS. 17A-17B are flow diagrams illustrating a method 1700 for performing an operation with an electronic device, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for interacting with the devices without touching display screens or other physical input mechanisms. Such techniques can reduce the cognitive burden on a user who interacts with the devices, thereby enhancing productivity. Further, such techniques can reduce processor and battery power by allowing operations to be performed more quickly and efficiently.

Figure 6A:
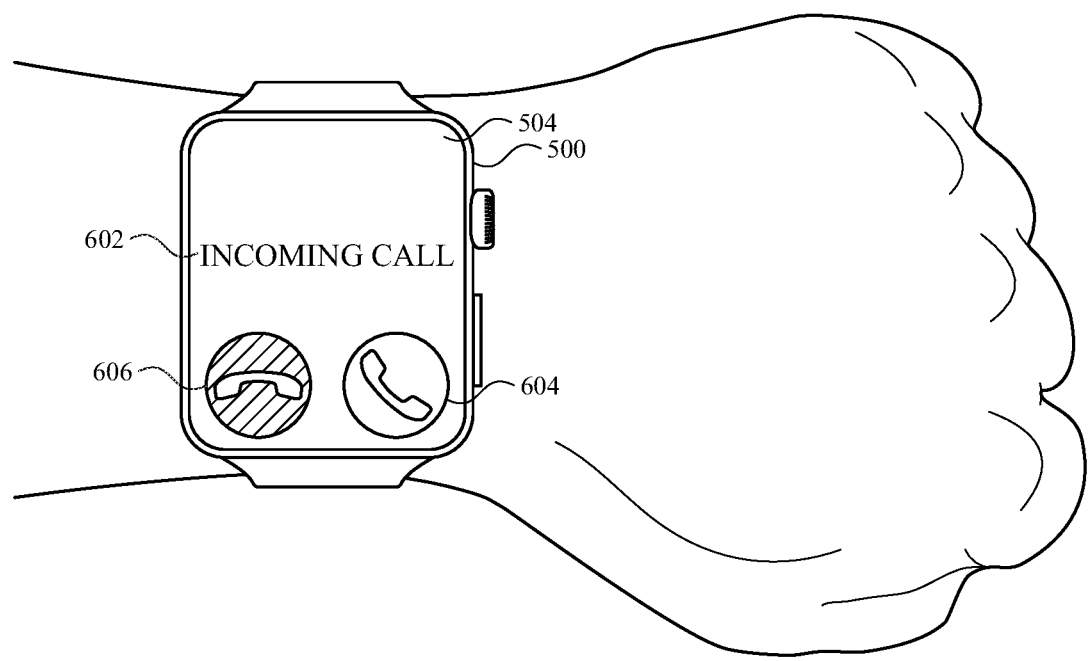
FIGS. 6A-6S illustrate exemplary user interfaces for interacting with an electronic device without touching a display screen or other physical input mechanism, in accordance with some embodiments.
Figure 6S:
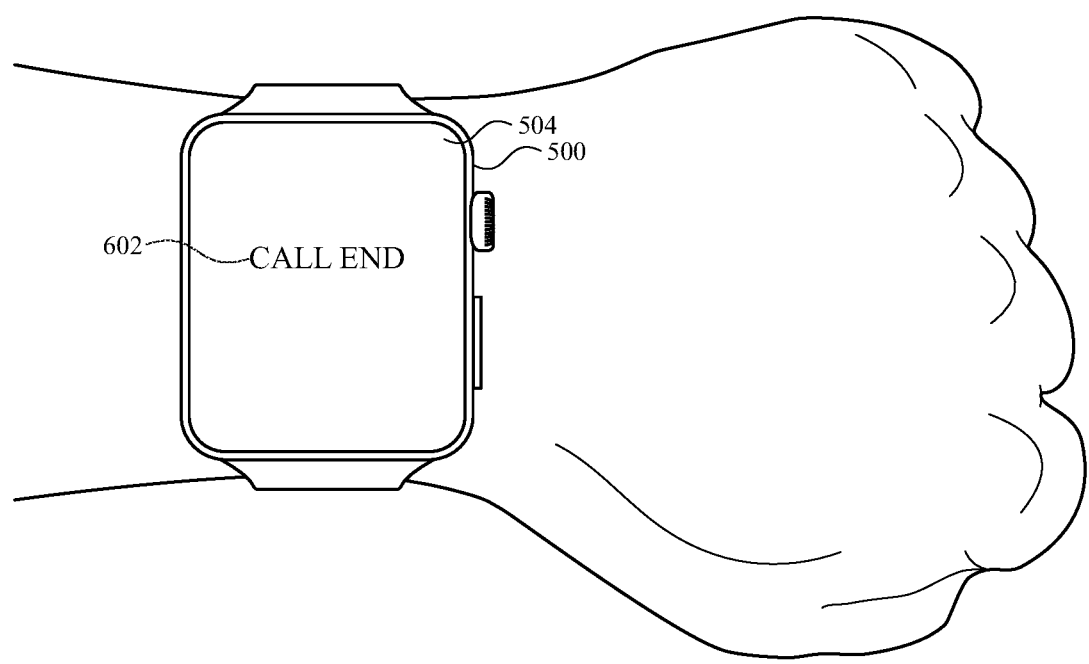
Figure 7A:
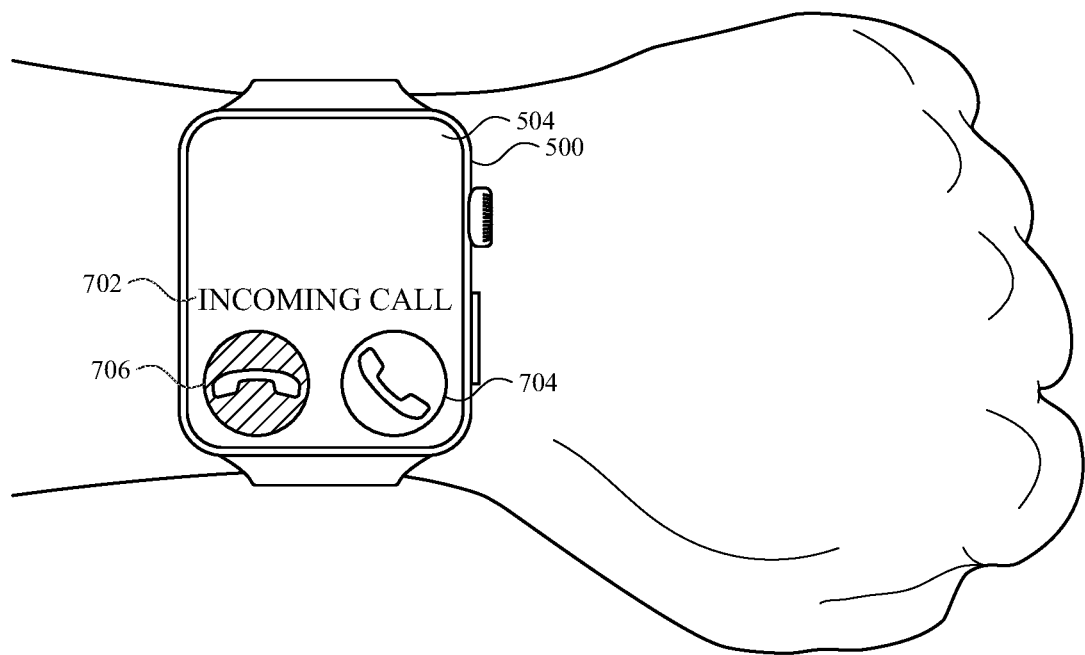
FIGS. 7A-7Q illustrate exemplary user interfaces for interacting with an electronic device without touching a display screen or other physical input mechanism, in accordance with some embodiments.
Figure 7B:
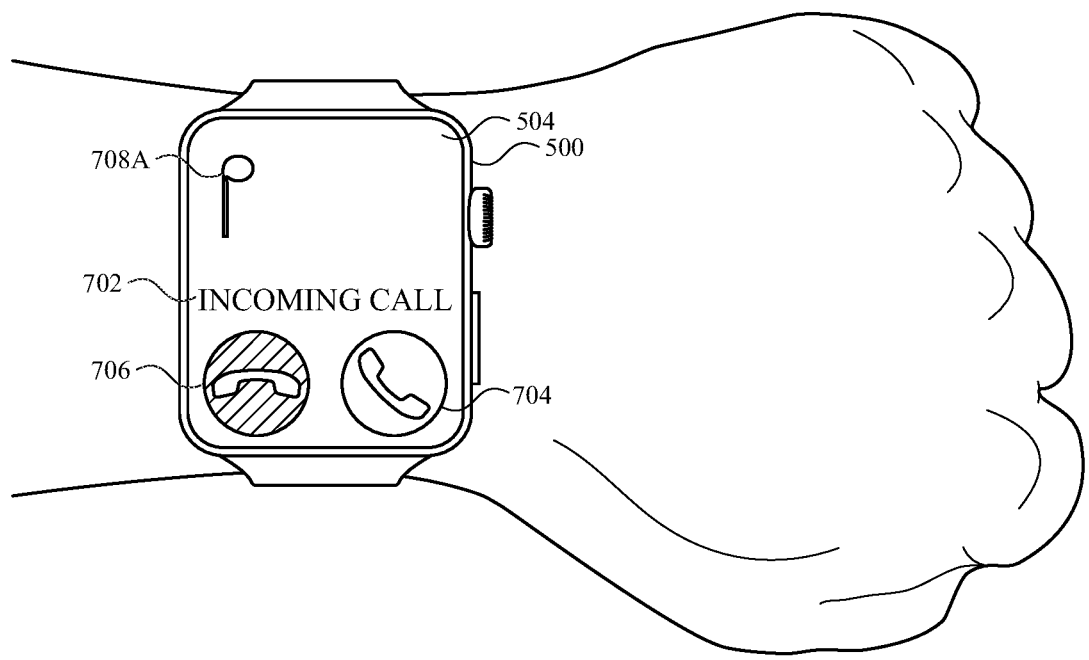
Figure 7C:
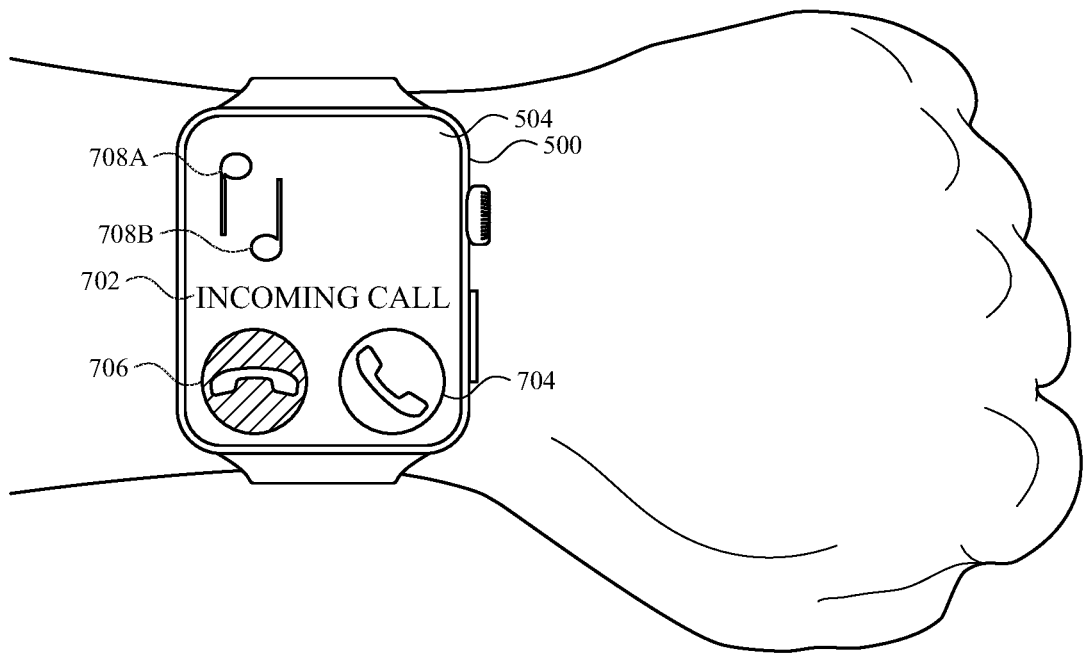
Figure 7D:
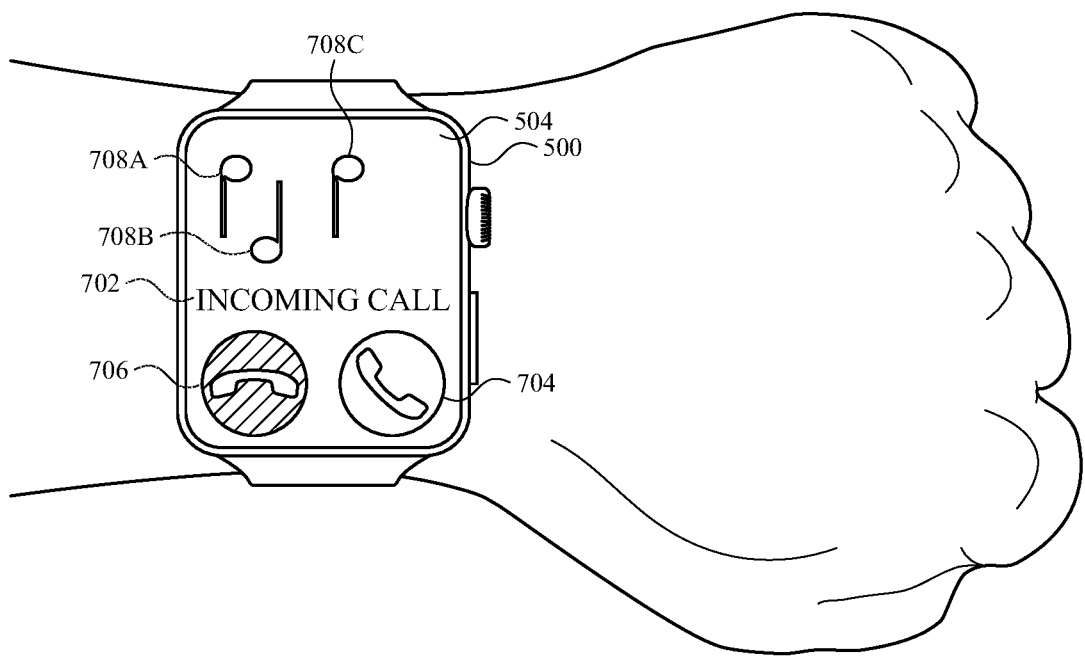
Figure 7Q:
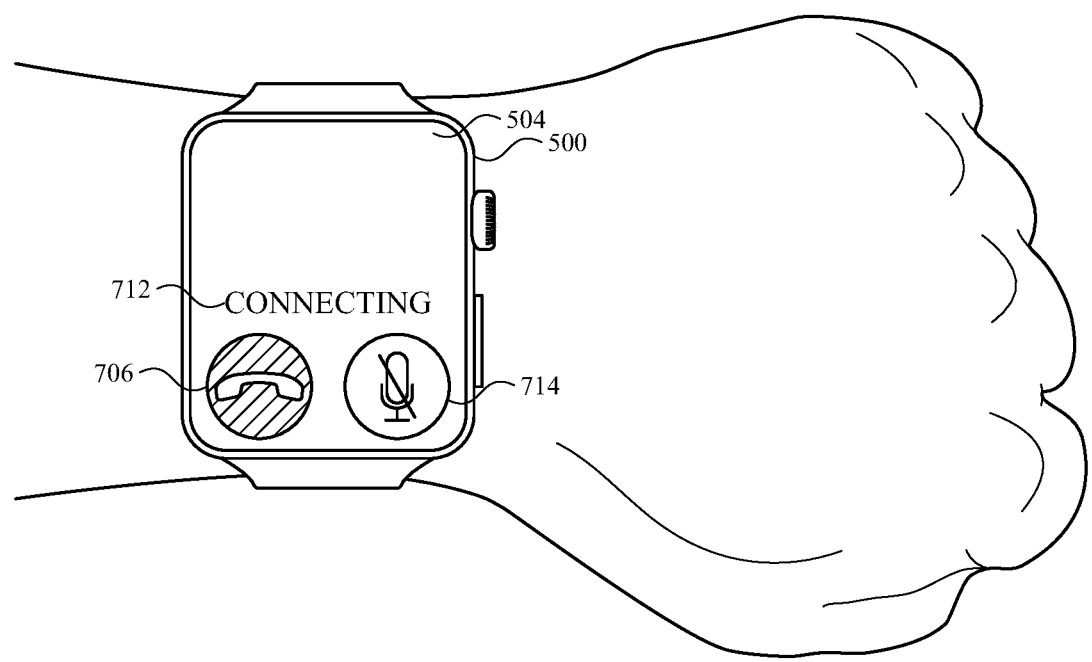
Figure 8A:
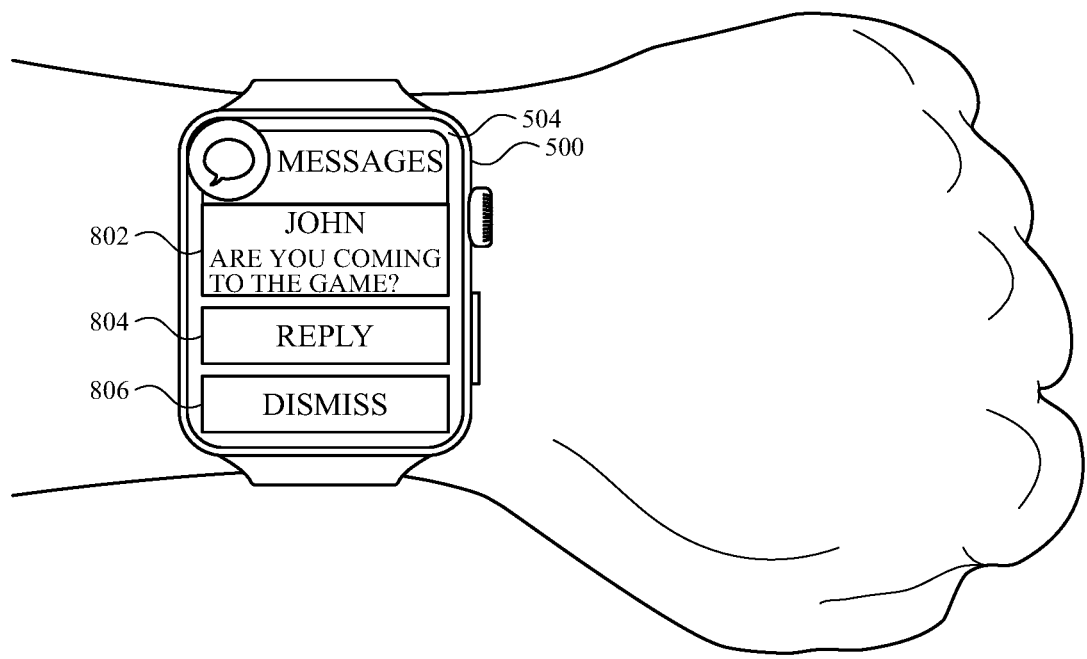
FIGS. 8A-8BI illustrate exemplary user interfaces for interacting with an electronic device without touching a display screen or other physical input mechanism, in accordance with some embodiments.
Figure 8B:
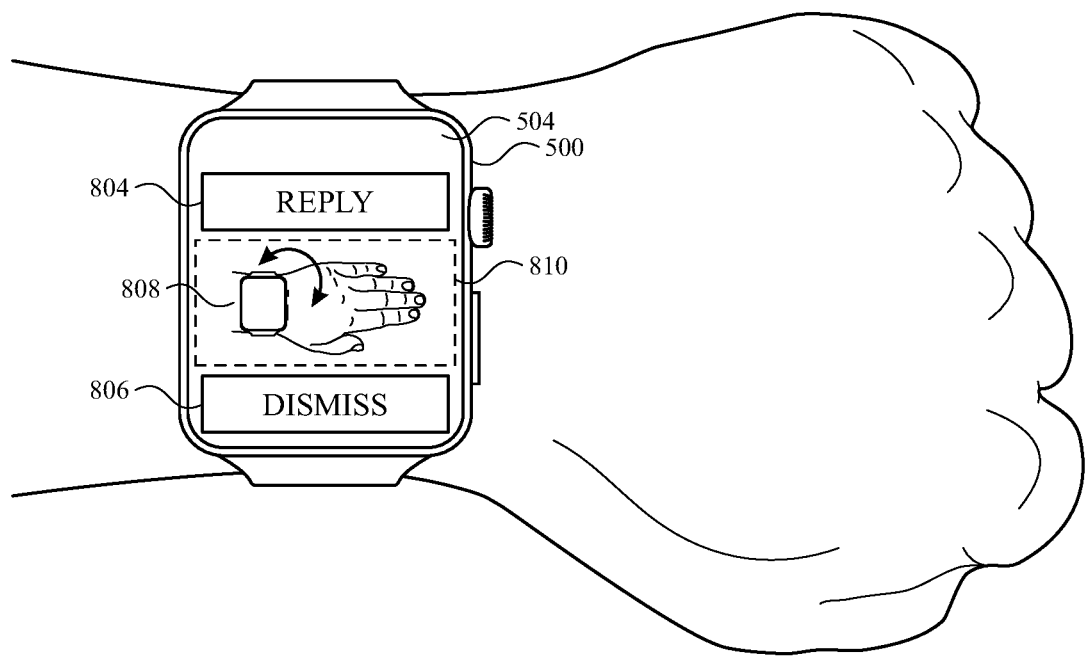
Figure 12A:
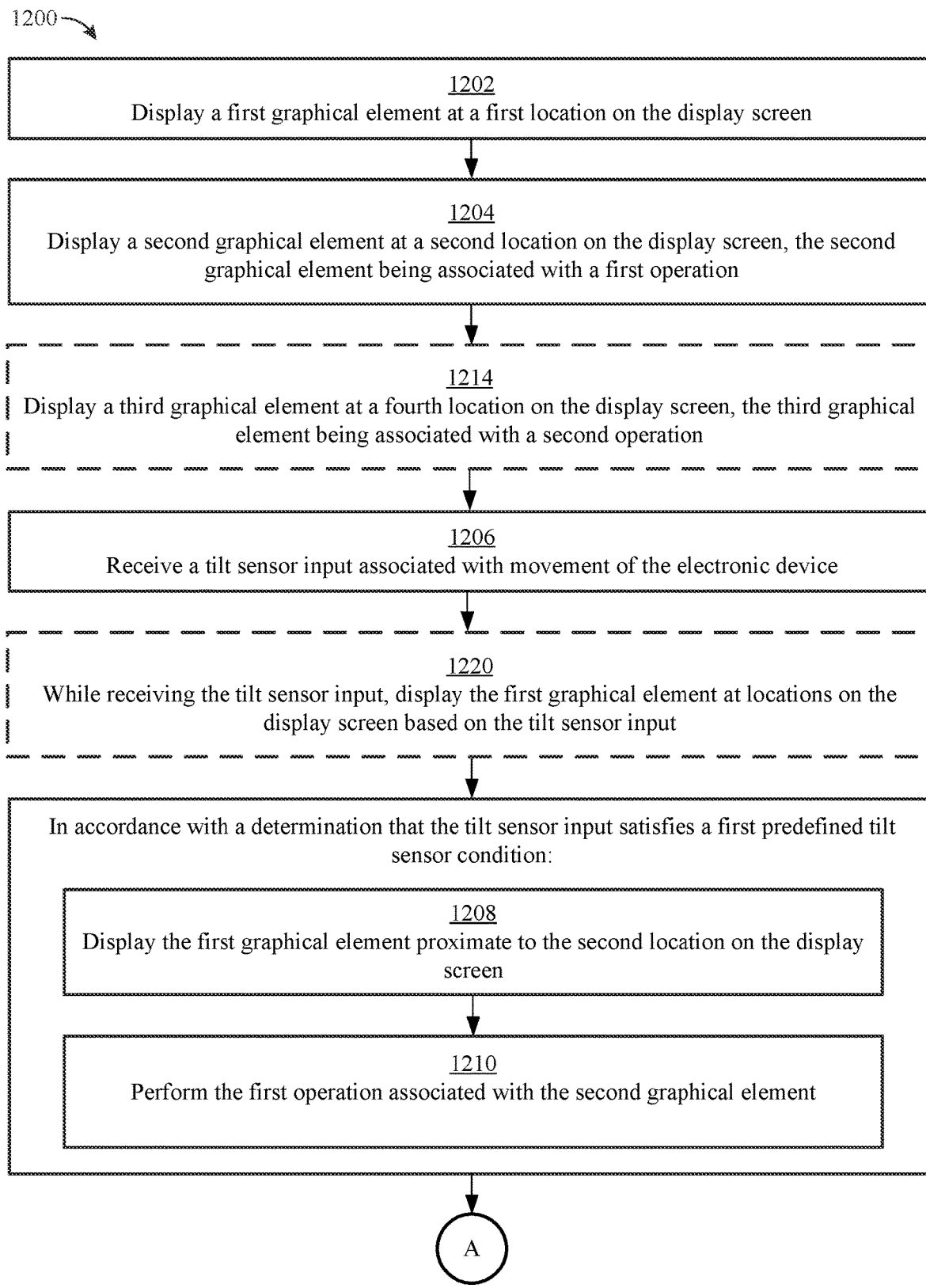
FIGS. 12A-12B are flow diagrams illustrating a method for performing one or more operations with an electronic device, in accordance with some embodiments.
Figure 12B:
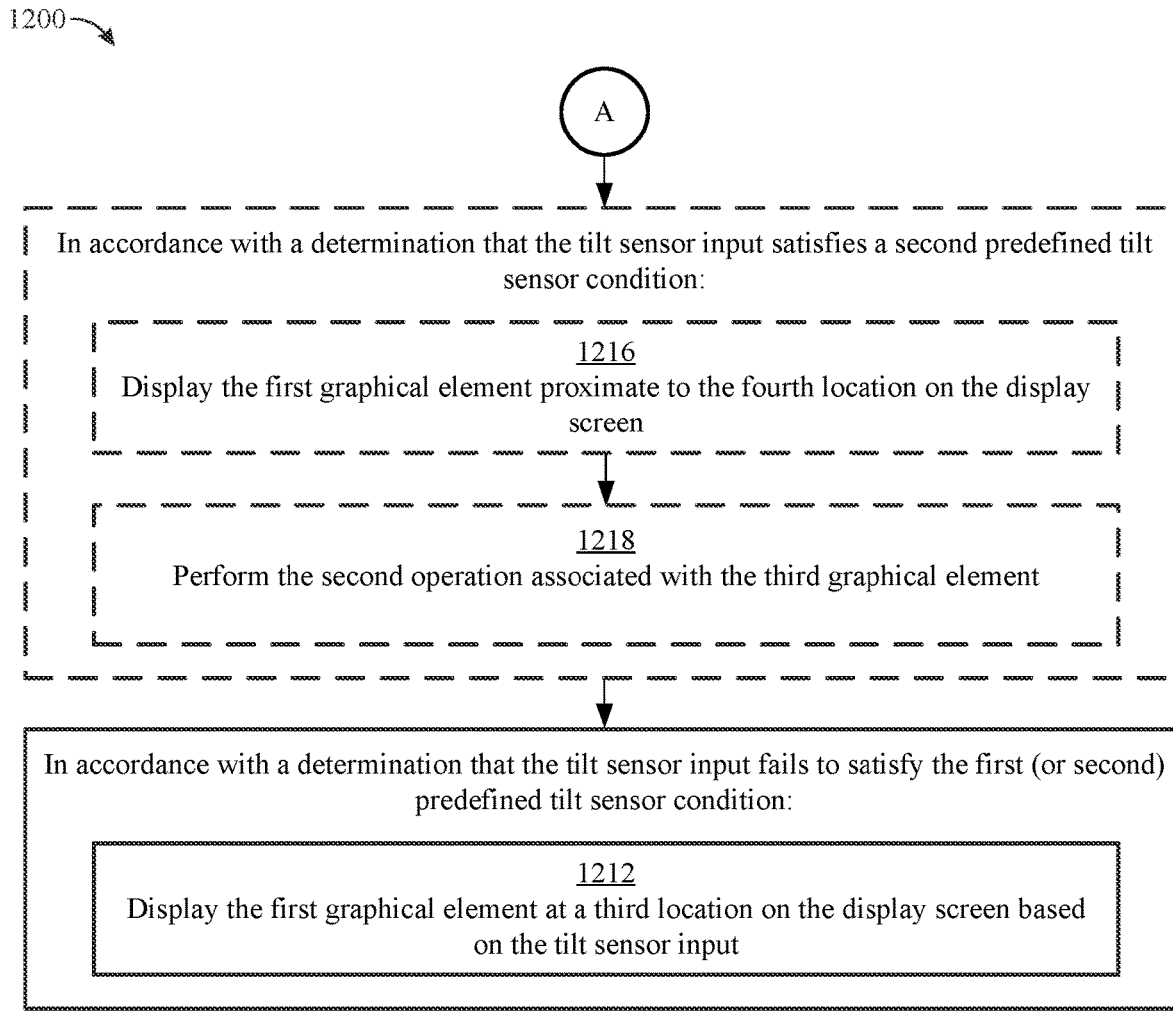
Figure 13B:
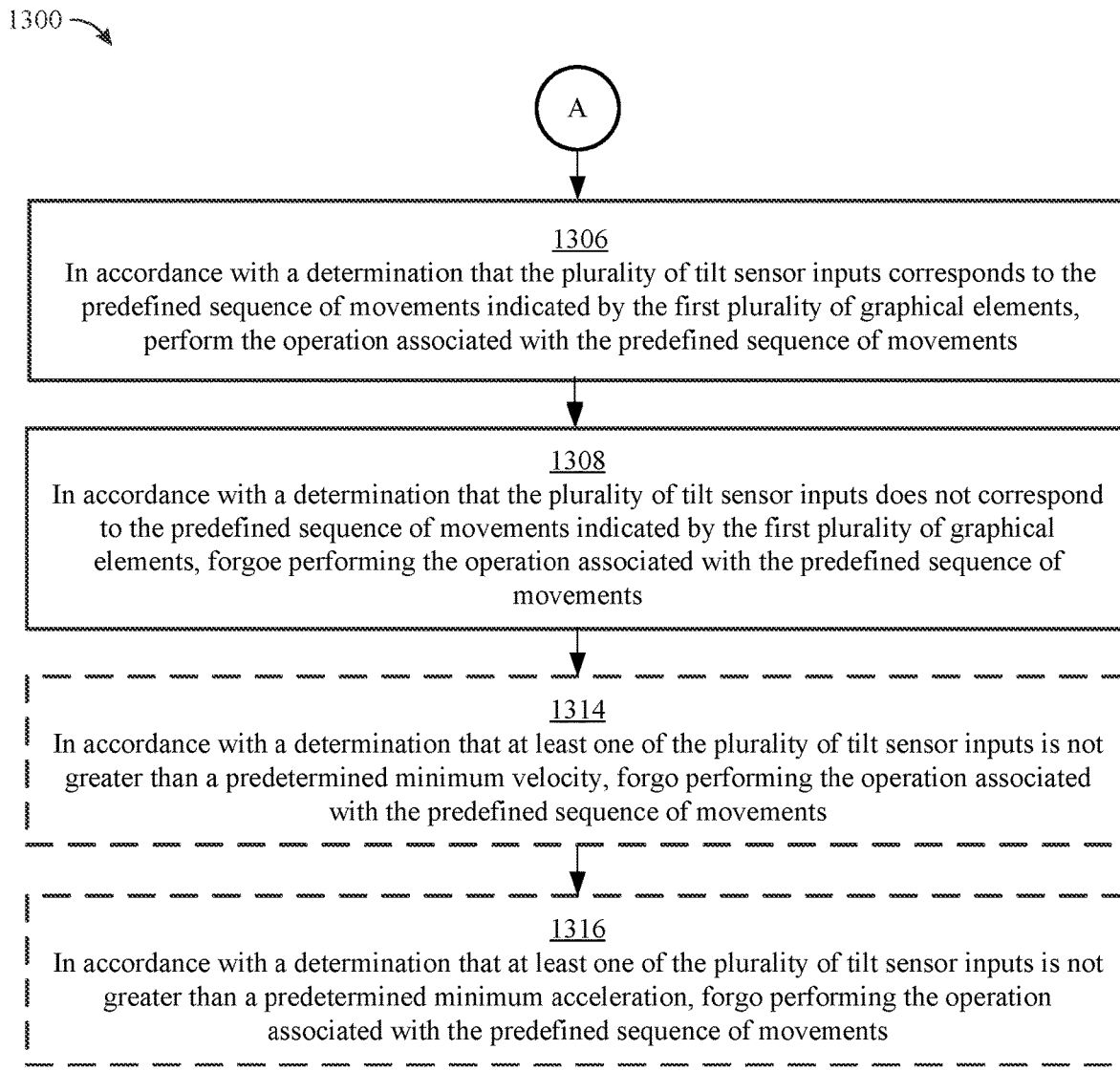
Figure 15:
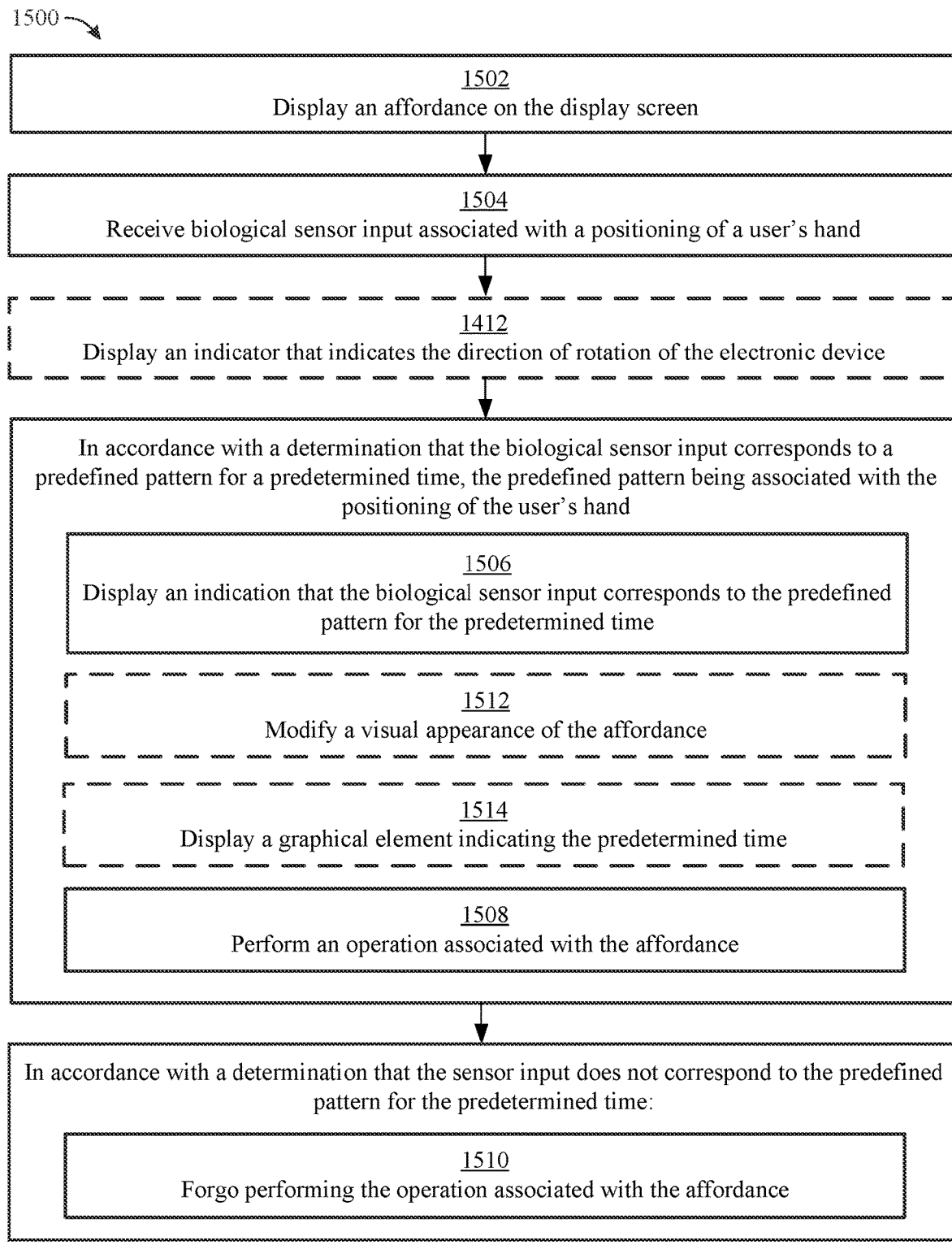
FIG. 15 is a flow diagram illustrating a method 1500 for performing an operation with an electronic device, in accordance with some embodiments.
Figure 16A:
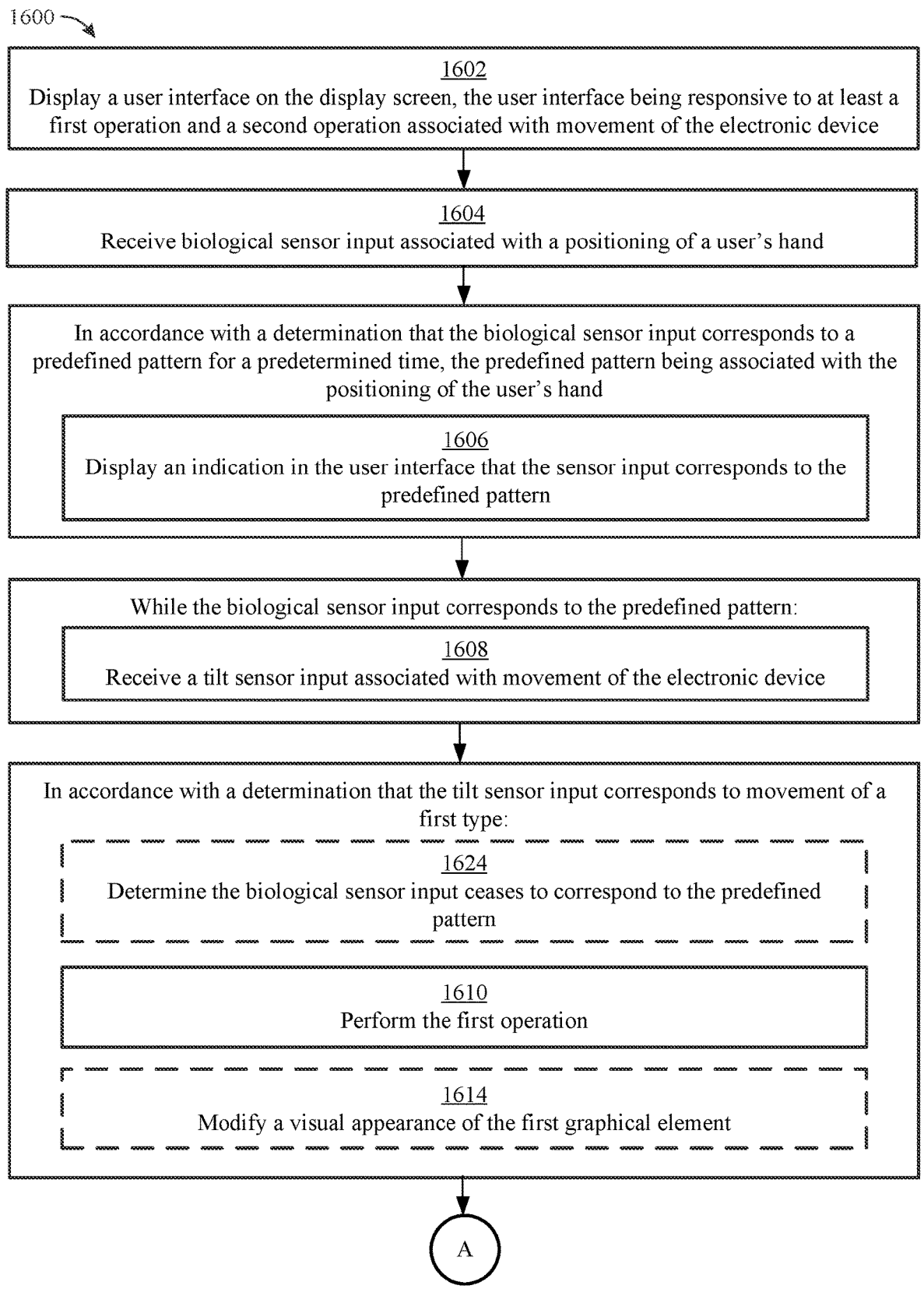
Figure 17A:
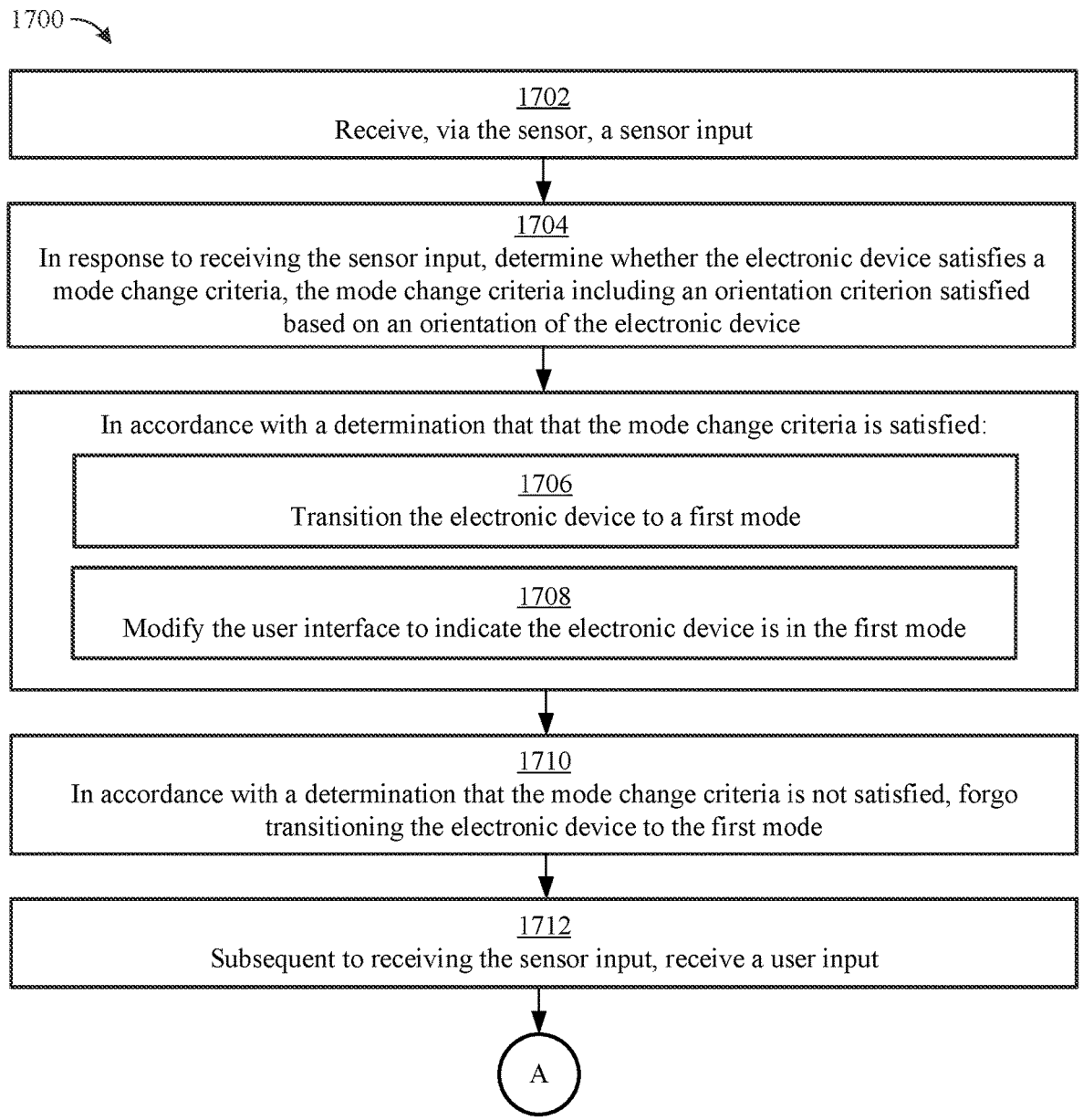

Below, FIGS. 1A-1B, 2, 3, 4A-4B, and 5A-5B provide a description of exemplary devices with which a user interacts. FIGS. 6A-6S illustrate exemplary user interfaces for interacting with the devices. FIGS. 12A-12B are flow diagrams illustrating methods of performing one or more operations with the devices, in accordance with some embodiments. The user interfaces in FIGS. 6A-6S are used to illustrate the processes described below, including the processes in FIGS. 12A-12B. FIGS. 7A-7Q illustrate exemplary user interfaces for interacting with the devices. FIGS. 13A-13B are flow diagrams illustrating methods of performing one or more operations with the devices, in accordance with some embodiments. The user interfaces in FIGS. 7A-7Q are used to illustrate the processes described below, including the processes in FIGS. 13A-13B. FIGS. 8A-8BI illustrate exemplary user interfaces for interacting with the devices. FIG. 14 is a flow diagram illustrating methods of performing one or more operations with the devices, in accordance with some embodiments. The user interfaces in FIGS. 8A-8BI are used to illustrate the processes described below, including the processes in FIG. 14. FIGS. 9B-9H illustrate exemplary user interfaces for interacting with the devices. FIG. 15 is a flow diagram illustrating methods of performing one or more operations with the devices, in accordance with some embodiments. The user interfaces in FIGS. 9B-9H are used to illustrate the processes described below, including the processes in FIG. 15. FIGS. 10A-10P illustrate exemplary user interfaces for interacting with the devices. FIGS. 16A-16B are flow diagrams illustrating methods of performing one or more operations with the devices, in accordance with some embodiments. The user interfaces in FIGS. 10A-10P are used to illustrate the processes described below, including the processes in FIGS. 16A-16B. FIGS. 11A-11D illustrate exemplary user interfaces for interacting with the devices. FIGS. 17A-17B are flow diagrams illustrating methods of performing one or more operations with the devices, in accordance with some embodiments. The user interfaces in FIGS. 11A-11D are used to illustrate the processes described below, including the processes in FIGS. 17A-17B.

Although the following description uses terms "first," "second," etc. to describe various elements, these elements should not be limited by the terms. These terms are only used to distinguish one element from another. For example, a first touch could be termed a second touch, and, similarly, a second touch could be termed a first touch, without departing from the scope of the various described embodiments. The first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad).

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
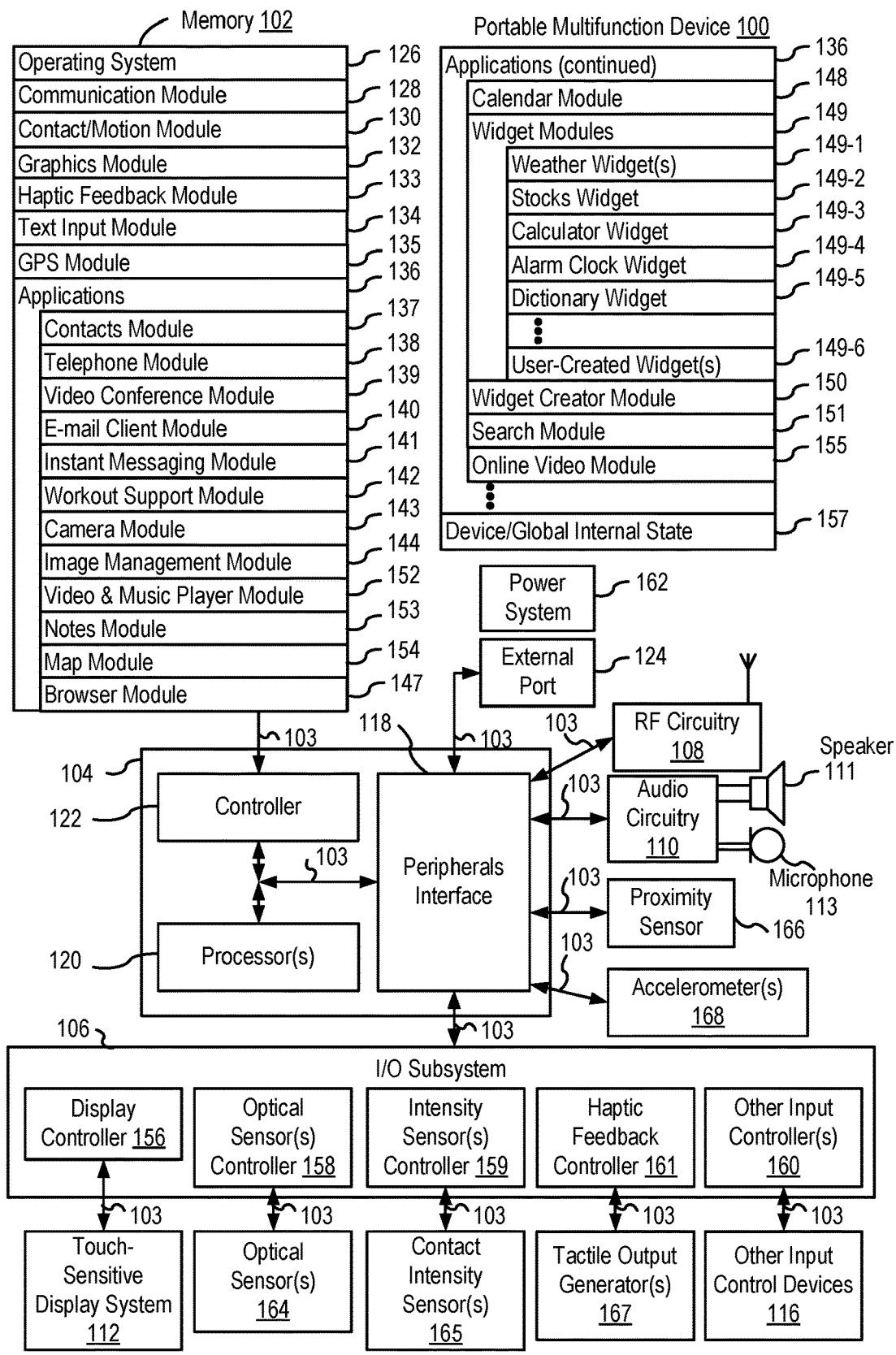
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some alternate embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6) U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad (not shown) for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer (not shown) and a GPS (or GLONASS or other global navigation system) receiver (not shown) for obtaining information concerning the location and orientation (e.g., portrait or landscape) of device 100.

Figure 3:
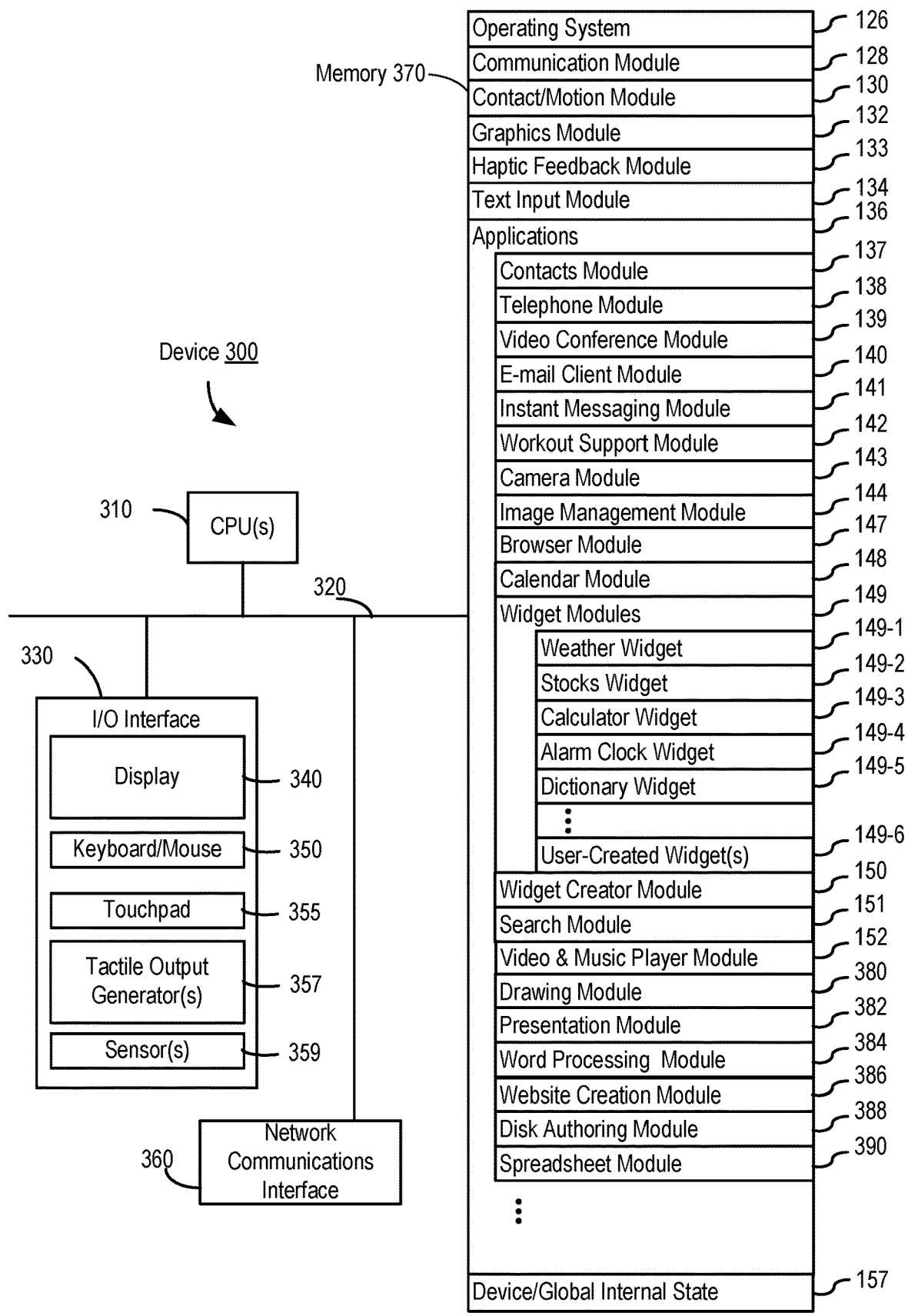
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts module 137, e-mail client module 140, instant messaging (IM) module 141, browser module 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:

Contacts module 137 (sometimes called an address book or contact list);
Telephone module 138;
Video conference module 139;
E-mail client module 140;
Instant messaging (IM) module 141;
Workout support module 142;
Camera module 143 for still and/or video images;
Image management module 144;
Video player module;
Music player module;
Browser module 147;
Calendar module 148;
Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
Widget creator module 150 for making user-created widgets 149-6;
Search module 151;
Video and music player module 152, which merges video player module and music player module;
Notes module 153;
Map module 154; and/or
Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone module 138, video conference module 139, e-mail client module 140, or IM module 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs, procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
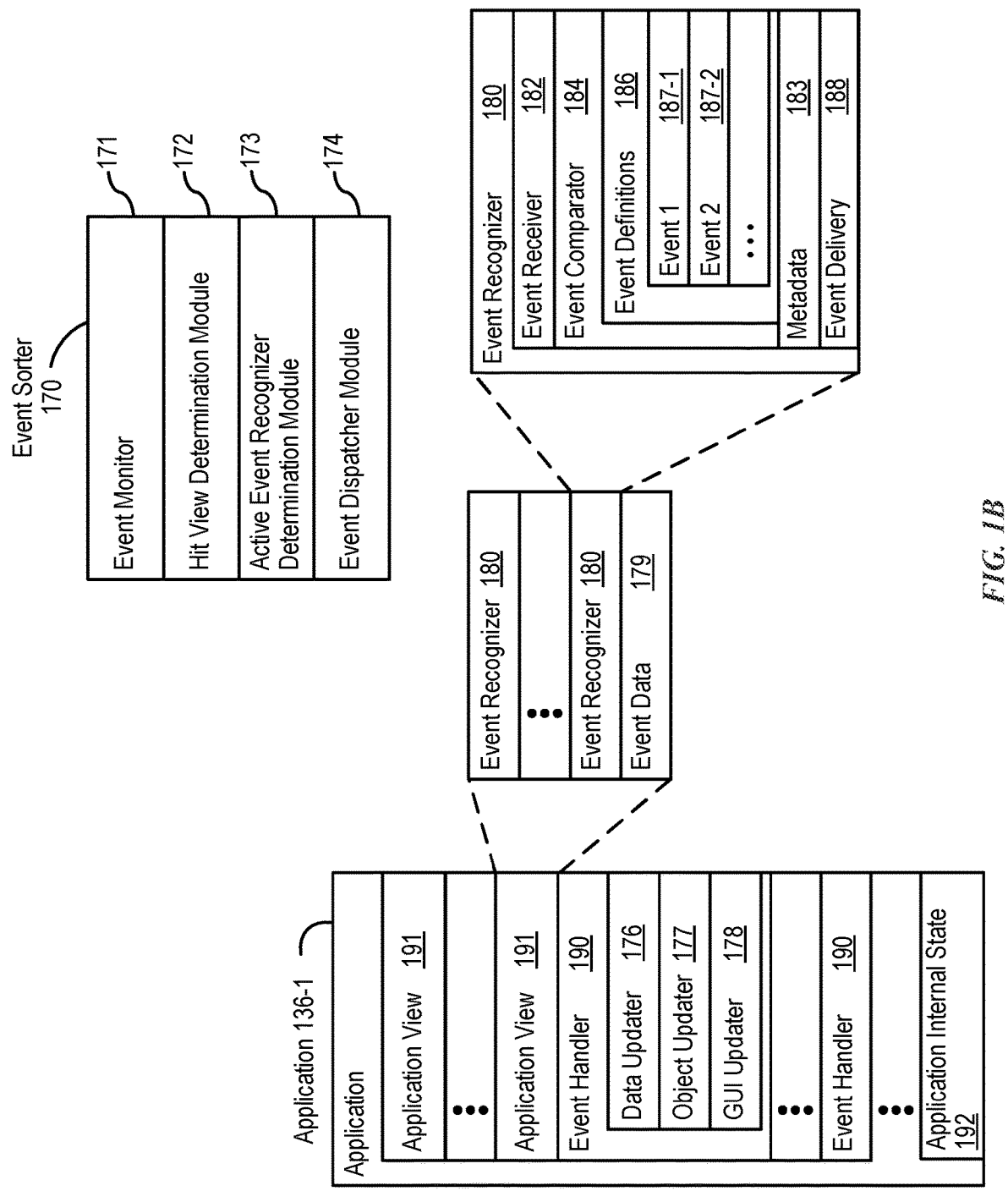
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit (not shown) or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (187) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definition 187 includes a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
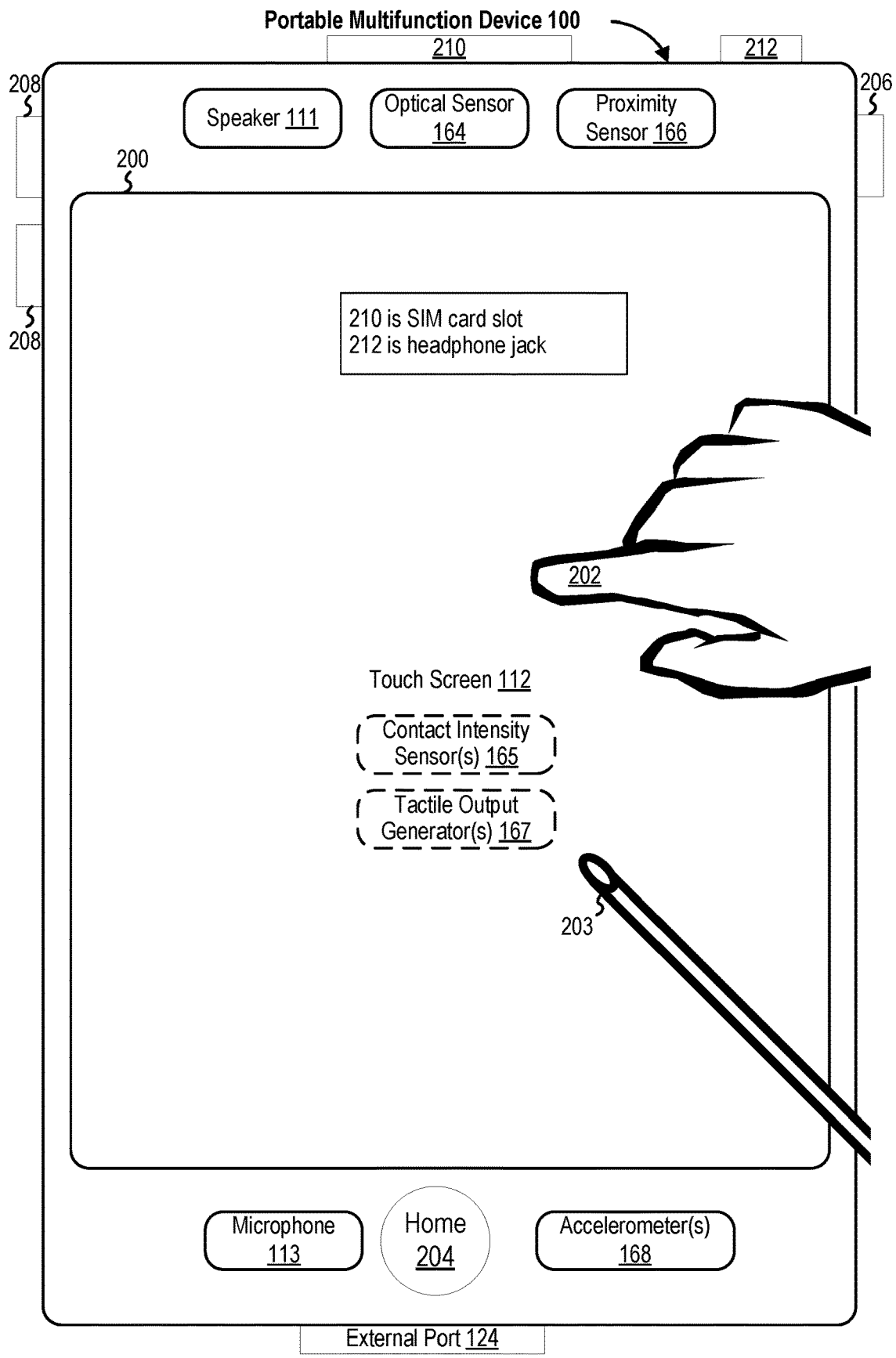
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or programs (e.g., sets of instructions) need not be implemented as separate software programs, procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
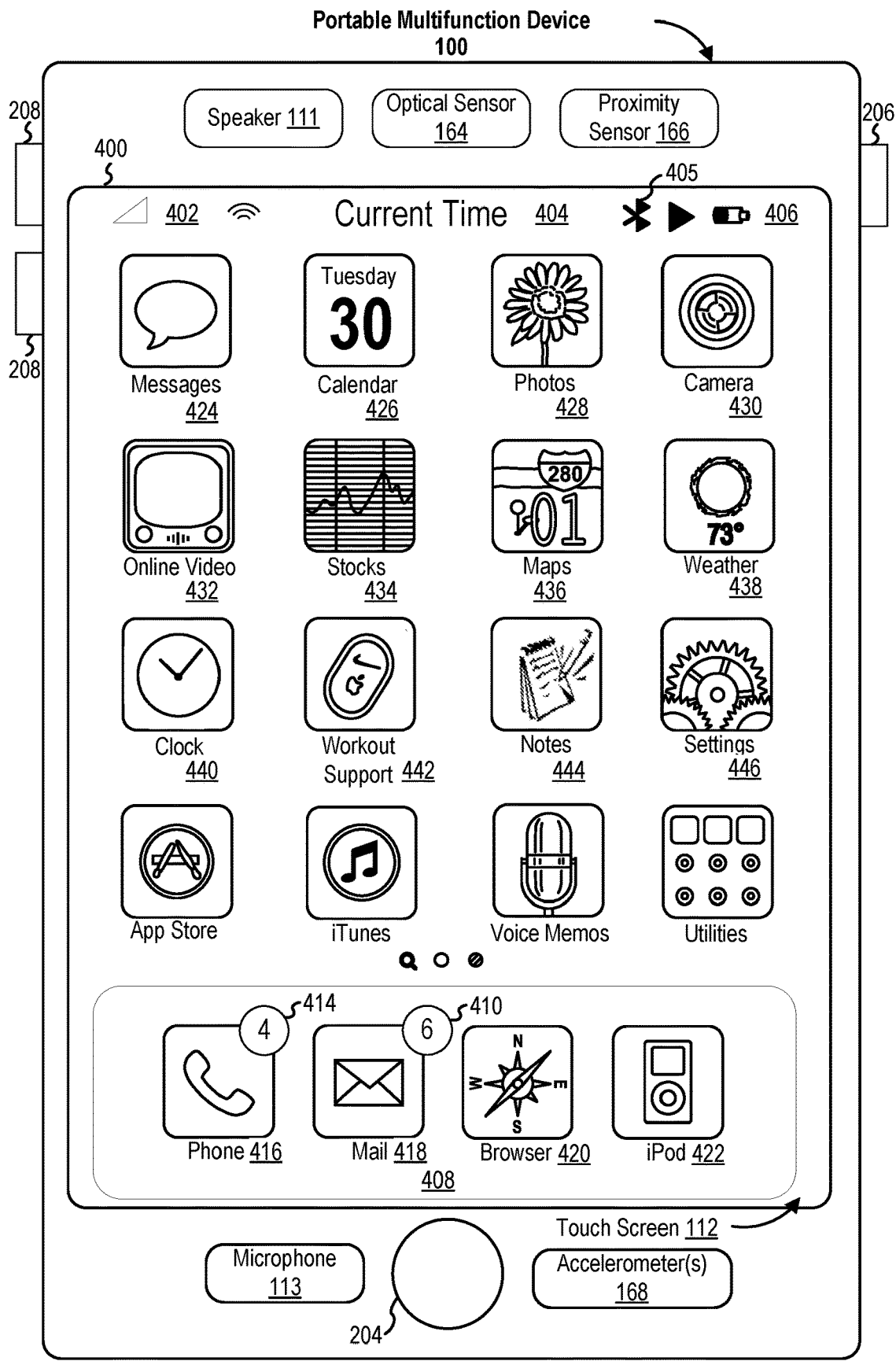
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;
Time 404;
Bluetooth indicator 405;
Battery status indicator 406;
Tray 408 with icons for frequently used applications, such as:
Icon 416 for telephone module 138, labeled "Phone," which optionally includes an indicator 414 of the number of missed calls or voicemail messages;
Icon 418 for e-mail client module 140, labeled "Mail," which optionally includes an indicator 410 of the number of unread e-mails;
Icon 420 for browser module 147, labeled "Browser;" and
Icon 422 for video and music player module 152, also referred to as iPod (trademark of Apple Inc.) module 152, labeled "iPod;" and
Icons for other applications, such as:
Icon 424 for IM module 141, labeled "Messages;"
Icon 426 for calendar module 148, labeled "Calendar;"
Icon 428 for image management module 144, labeled "Photos;"
Icon 430 for camera module 143, labeled "Camera;"
Icon 432 for online video module 155, labeled "Online Video;"
Icon 434 for stocks widget 149-2, labeled "Stocks;"
Icon 436 for map module 154, labeled "Maps;"
Icon 438 for weather widget 149-1, labeled "Weather;"
Icon 440 for alarm clock widget 149-4, labeled "Clock;"
Icon 442 for workout support module 142, labeled "Workout Support;"
Icon 444 for notes module 153, labeled "Notes;" and
Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
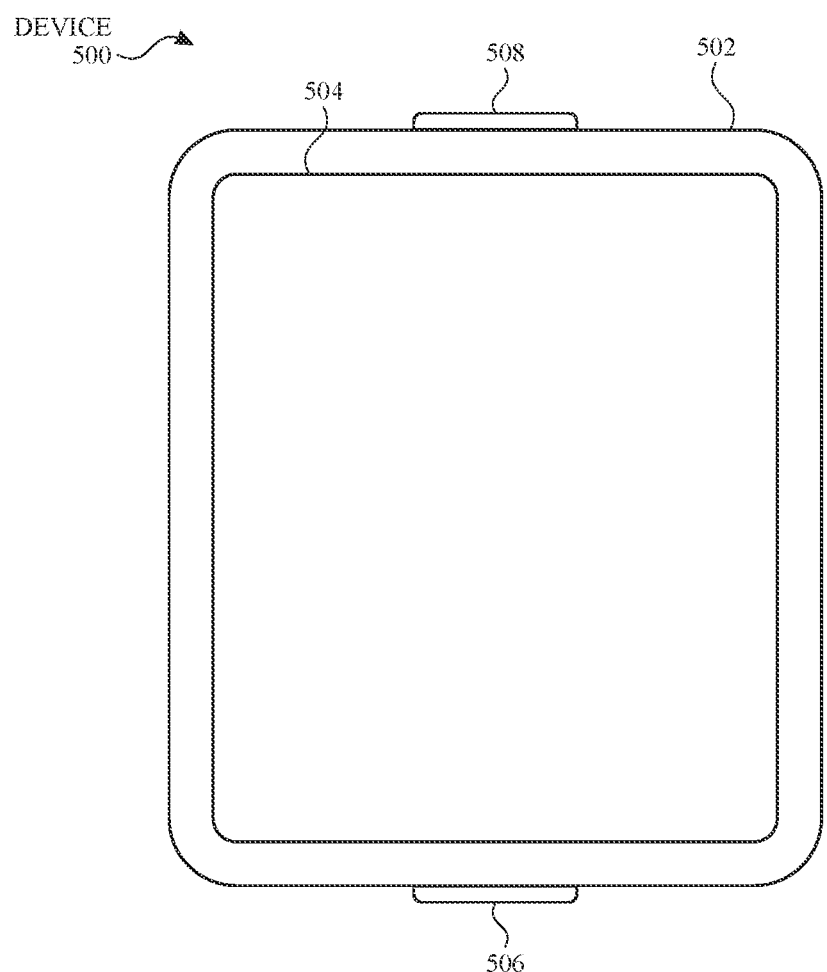
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
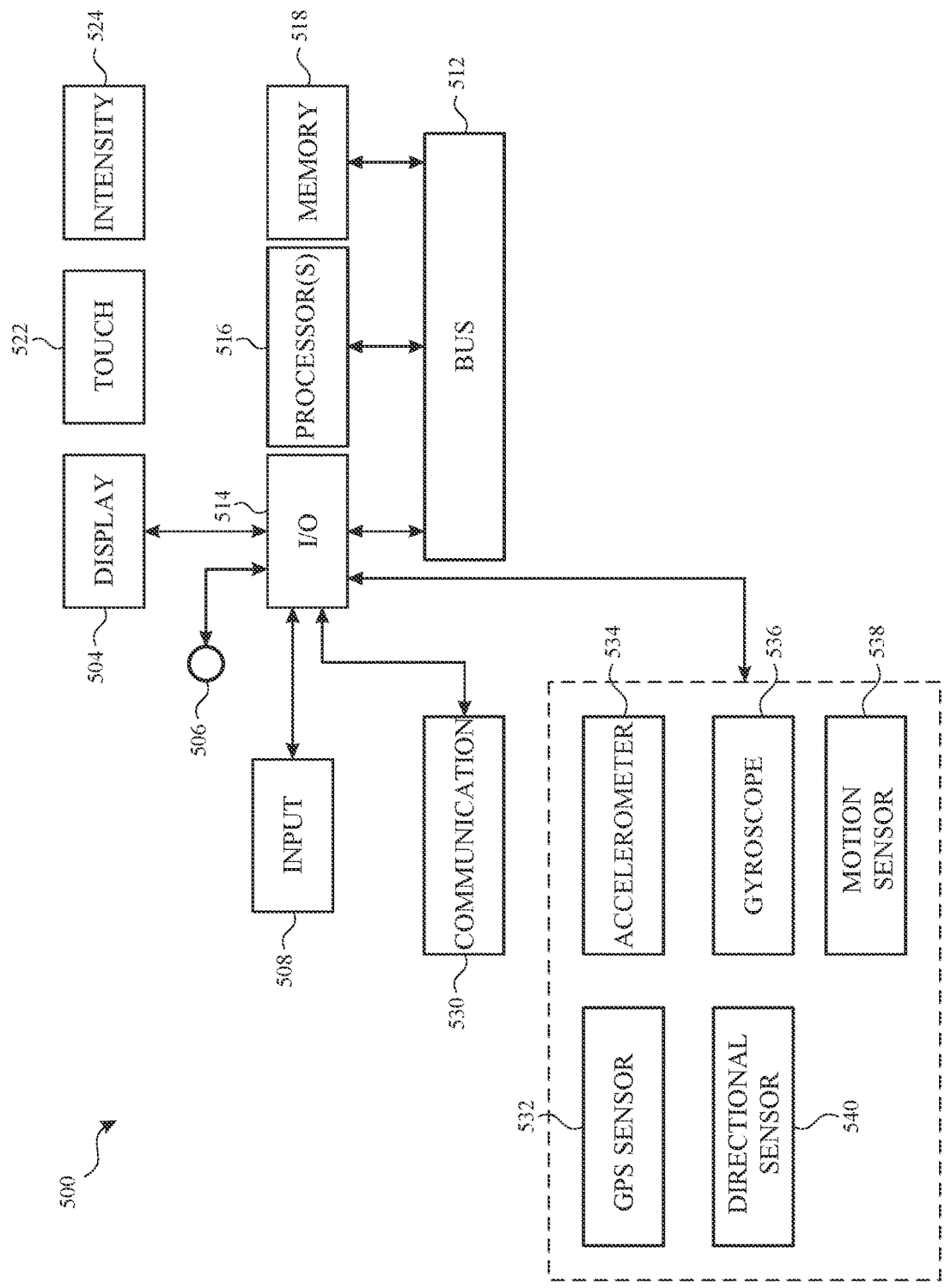
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 1200-1700 (FIGS. 12A-17B). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

In some embodiments, a portion of a gesture is identified for purposes of determining a characteristic intensity. For example, a touch-sensitive surface optionally receives a continuous swipe contact transitioning from a start location and reaching an end location, at which point the intensity of the contact increases. In this example, the characteristic intensity of the contact at the end location is, optionally, based on only a portion of the continuous swipe contact, and not the entire swipe contact (e.g., only the portion of the swipe contact at the end location). In some embodiments, a smoothing algorithm is, optionally, applied to the intensities of the swipe contact prior to determining the characteristic intensity of the contact. For example, the smoothing algorithm optionally includes one or more of: an unweighted sliding-average smoothing algorithm, a triangular smoothing algorithm, a median filter smoothing algorithm, and/or an exponential smoothing algorithm. In some circumstances, these smoothing algorithms eliminate narrow spikes or dips in the intensities of the swipe contact for purposes of determining a characteristic intensity.

The intensity of a contact on the touch-sensitive surface is, optionally, characterized relative to one or more intensity thresholds, such as a contact-detection intensity threshold, a light press intensity threshold, a deep press intensity threshold, and/or one or more other intensity thresholds. In some embodiments, the light press intensity threshold corresponds to an intensity at which the device will perform operations typically associated with clicking a button of a physical mouse or a trackpad. In some embodiments, the deep press intensity threshold corresponds to an intensity at which the device will perform operations that are different from operations typically associated with clicking a button of a physical mouse or a trackpad. In some embodiments, when a contact is detected with a characteristic intensity below the light press intensity threshold (e.g., and above a nominal contact-detection intensity threshold below which the contact is no longer detected), the device will move a focus selector in accordance with movement of the contact on the touch-sensitive surface without performing an operation associated with the light press intensity threshold or the deep press intensity threshold. Generally, unless otherwise stated, these intensity thresholds are consistent between different sets of user interface figures.

An increase of characteristic intensity of the contact from an intensity below the light press intensity threshold to an intensity between the light press intensity threshold and the deep press intensity threshold is sometimes referred to as a "light press" input. An increase of characteristic intensity of the contact from an intensity below the deep press intensity threshold to an intensity above the deep press intensity threshold is sometimes referred to as a "deep press" input. An increase of characteristic intensity of the contact from an intensity below the contact-detection intensity threshold to an intensity between the contact-detection intensity threshold and the light press intensity threshold is sometimes referred to as detecting the contact on the touch-surface. A decrease of characteristic intensity of the contact from an intensity above the contact-detection intensity threshold to an intensity below the contact-detection intensity threshold is sometimes referred to as detecting liftoff of the contact from the touch-surface. In some embodiments, the contact-detection intensity threshold is zero. In some embodiments, the contact-detection intensity threshold is greater than zero.

In some embodiments described herein, one or more operations are performed in response to detecting a gesture that includes a respective press input or in response to detecting the respective press input performed with a respective contact (or a plurality of contacts), where the respective press input is detected based at least in part on detecting an increase in intensity of the contact (or plurality of contacts) above a press-input intensity threshold. In some embodiments, the respective operation is performed in response to detecting the increase in intensity of the respective contact above the press-input intensity threshold (e.g., a "down stroke" of the respective press input). In some embodiments, the press input includes an increase in intensity of the respective contact above the press-input intensity threshold and a subsequent decrease in intensity of the contact below the press-input intensity threshold, and the respective operation is performed in response to detecting the subsequent decrease in intensity of the respective contact below the press-input threshold (e.g., an "up stroke" of the respective press input).

In some embodiments, the device employs intensity hysteresis to avoid accidental inputs sometimes termed "jitter," where the device defines or selects a hysteresis intensity threshold with a predefined relationship to the press-input intensity threshold (e.g., the hysteresis intensity threshold is X intensity units lower than the press-input intensity threshold or the hysteresis intensity threshold is 75%, 90%, or some reasonable proportion of the press-input intensity threshold). Thus, in some embodiments, the press input includes an increase in intensity of the respective contact above the press-input intensity threshold and a subsequent decrease in intensity of the contact below the hysteresis intensity threshold that corresponds to the press-input intensity threshold, and the respective operation is performed in response to detecting the subsequent decrease in intensity of the respective contact below the hysteresis intensity threshold (e.g., an "up stroke" of the respective press input). Similarly, in some embodiments, the press input is detected only when the device detects an increase in intensity of the contact from an intensity at or below the hysteresis intensity threshold to an intensity at or above the press-input intensity threshold and, optionally, a subsequent decrease in intensity of the contact to an intensity at or below the hysteresis intensity, and the respective operation is performed in response to detecting the press input (e.g., the increase in intensity of the contact or the decrease in intensity of the contact, depending on the circumstances).

For ease of explanation, the descriptions of operations performed in response to a press input associated with a press-input intensity threshold or in response to a gesture including the press input are, optionally, triggered in response to detecting either: an increase in intensity of a contact above the press-input intensity threshold, an increase in intensity of a contact from an intensity below the hysteresis intensity threshold to an intensity above the press-input intensity threshold, a decrease in intensity of the contact below the press-input intensity threshold, and/or a decrease in intensity of the contact below the hysteresis intensity threshold corresponding to the press-input intensity threshold. Additionally, in examples where an operation is described as being performed in response to detecting a decrease in intensity of a contact below the press-input intensity threshold, the operation is, optionally, performed in response to detecting a decrease in intensity of the contact below a hysteresis intensity threshold corresponding to, and lower than, the press-input intensity threshold.

Attention is now directed towards embodiments of user interfaces ("UI") and associated processes that are implemented on an electronic device, such as portable multifunction device 100, device 300, or device 500.

FIGS. 6A-6S illustrate exemplary user interfaces for interacting with an electronic device without touching a display screen or other physical input mechanism, in accordance with some embodiments. The user interfaces in these figures are used to illustrate the processes described below, including the processes in FIGS. 12A-12B.

In particular, FIGS. 6A-6S illustrate exemplary user interfaces for responding to an incoming telephone call with an electronic device 500. The electronic device 500 includes a display screen 504 and a tilt sensor, among other elements which can be found above and/or as discussed in reference to FIG. 5A. The display screen 504 can be a touch-sensitive display screen, and the tilt sensor can be an accelerometer 534, directional sensor 540 (e.g., compass), gyroscope 536, motion sensor 538, and/or a combination thereof. In the present example, device 500 is a wearable device on a user's wrist, such as a smart watch.

As shown in FIG. 6A, an incoming call notification 602 is initially displayed when the incoming telephone call is received. In addition, an answer call affordance 604 and a decline call affordance 606 are displayed. Throughout the sequence of interactions shown in FIGS. 6A-6G, the answer call affordance 604 or the decline call affordance 606 can be touched by the user to perform their respective operations with the electronic device 500 (e.g., answering the incoming call or declining the incoming telephone call, respectively). As shown in FIG. 6A, electronic device 500 is worn on the user's left wrist and is being held in a position such that display screen 504 is directly visible to the user's eyes (while being substantially perpendicular to the ground), such as is typical for users when they are checking the time.

Figure 6B:
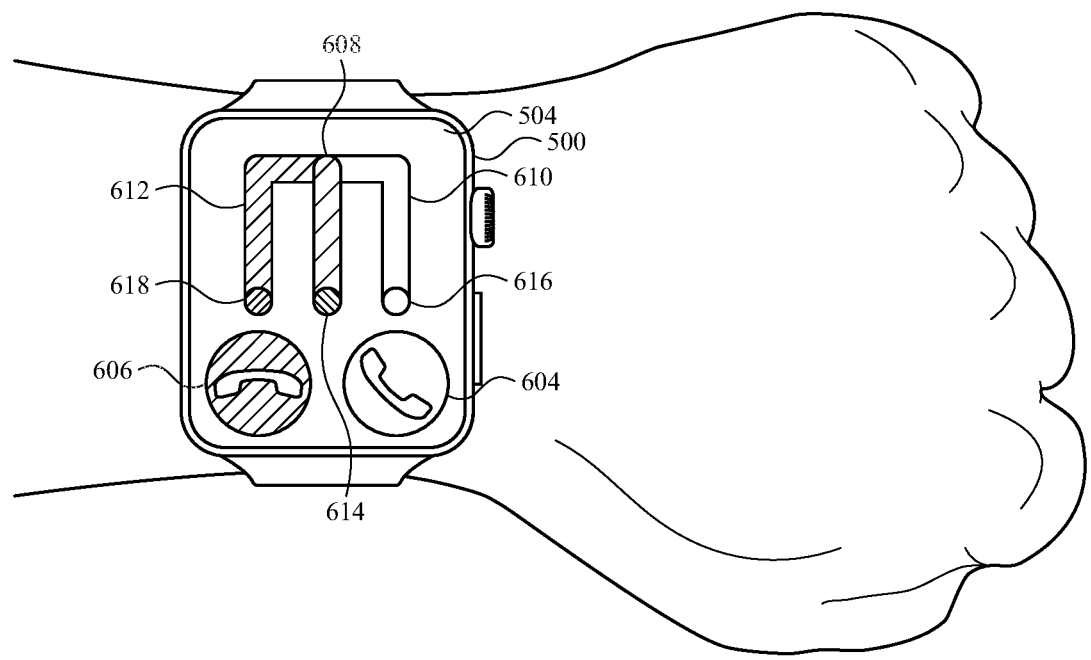

As shown in FIG. 6B, the incoming call notification 602 is replaced with an incoming call track 608. In some embodiments, the incoming call track 608 is displayed a predetermined time after initially receiving the incoming telephone call and/or in response to a user action. For instance, in some embodiments, the incoming call track 608 is displayed in response to the user lifting their arm into a raised position where the display screen 504 is visible to the user. The incoming call track 608 includes a right track segment 610 and a left track segment 612. The right and left track segments 610 and 612 share a center segment of the incoming call track 608. A graphical object 614 is displayed at an initial location on the center segment of the incoming call track 608. In some embodiments, the graphical object 614 is a virtual representation of a physical object (e.g., a ball). From the shared center segment of the incoming call track 608, the right track segment 610 leads to the answer call affordance 604, and the left track segment 612 leads to the decline call affordance 606. A first demarcation 616 is displayed at the end of the right track segment 610 proximate to the answer call affordance 604, and a second demarcation 618 is displayed at the end of the left track segment 612 proximate to the decline call affordance 606.

Figure 6C:
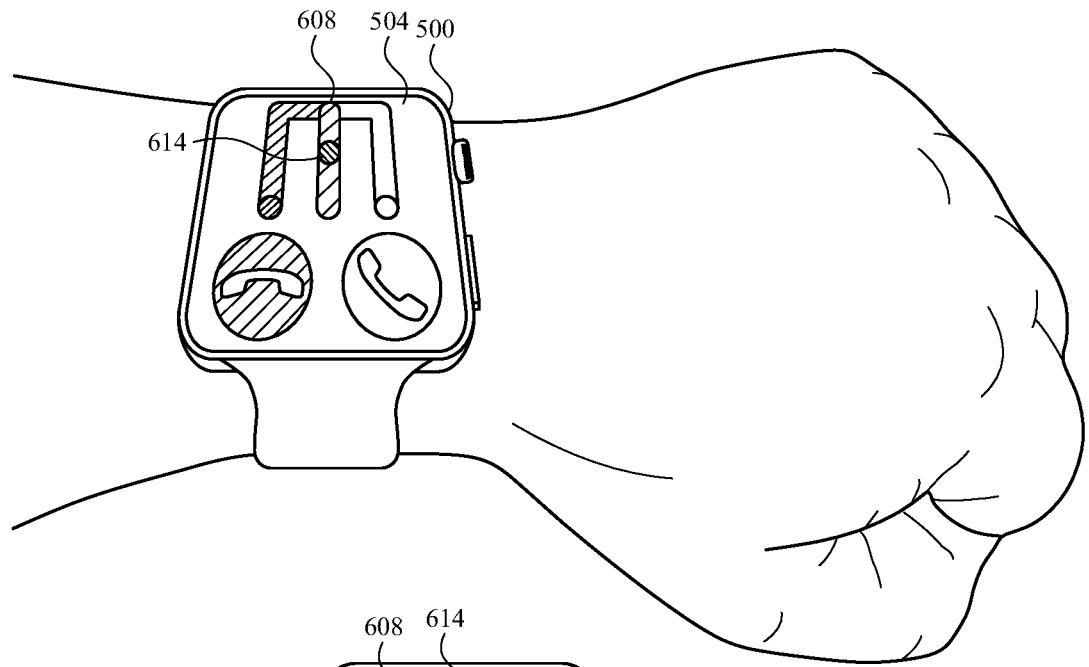

As shown in FIG. 6C, the orientation of the electronic device 500 is changed as a result of the user rotating their wrist away from their body (e.g., the electronic device 500 is tilted up such that the bottom of the display screen 504 is moved upward relative to the top of the display screen 504). In response to this change in orientation of the electronic device 500, the graphical object 614 moves along the center segment of the incoming call track 608 toward the top of the display screen 504. In some embodiments, the movement of the graphical object 614 between the different locations shown in FIGS. 6B-6G is animated. The animation corresponds to a simulated physical movement of the graphical object 614 rolling along the incoming call track 608. For instance, in some embodiments, the acceleration and velocity of the graphical object 614 as it moves along the incoming call track 608 is representative of how a physical ball would roll along a physical track being held in the same orientation as the electronic device 500.

While the graphical object 614 is displayed at the location shown in FIG. 6C, if the user rotates their wrist back toward their body (e.g., the electronic device 500 is tilted down such that the top of the display screen 504 is moved upward relative to the bottom of the display screen 504), then the graphical object 614 moves back toward its initial location on the center segment of the incoming call track 608 as shown in FIG. 6B. Alternatively, in some embodiments, the graphical object 614 remains at the furthest location it reached in the center segment of the incoming call track 608, such as shown in FIG. 6C (e.g., the graphical object 614 does not lose progress along the incoming call track 608). Furthermore, while the graphical object 614 is displayed at the location shown in FIG. 6C, if the user maintains the same orientation of the electronic device 500 or further rotates their wrist away from their body (e.g., the electronic device 500 is tilted up further such that the bottom of the display screen 504 is further moved upward relative to the top of the display screen 504), then the graphical object 614 continues to move toward the top of the display screen 504. In some embodiments, other orientations of the electronic device 500 (e.g., tilting to the left or right) do not have an effect on the movement of the graphical object 614.

Figure 6D:
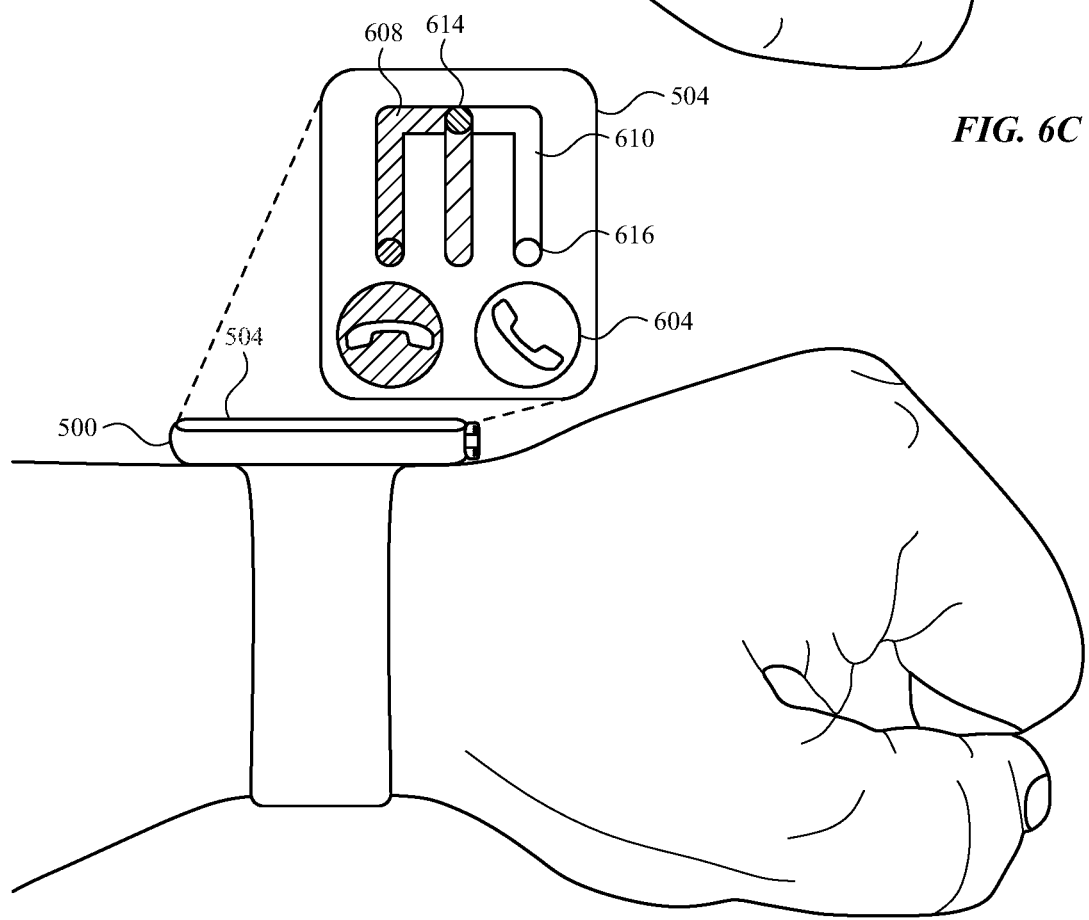

As shown in FIG. 6D, the orientation of the electronic device 500 is further changed as a result of the user further rotating their wrist away from their body (e.g., the electronic device 500 is tilted up further such that the bottom of the display screen 504 is further moved upward relative to the top of the display screen 504). In response to this orientation of the electronic device 500, the graphical object 614 continues to move toward the top of the display screen 504 until it encounters an upper edge of the incoming call track 608. From this upper edge location, the graphical object 614 cannot continue along the incoming call track 608 without the orientation of the electronic device 500 being changed to a different orientation (e.g., tilted to the left, right, or down).

While the graphical object 614 is displayed at the location shown in FIG. 6D, if the user rotates their wrist back toward their body (e.g., the electronic device 500 is tilted down such that the top of the display screen 504 is moved upward relative to the bottom of the display screen 504), then the graphical object 614 moves back toward its initial location on the center segment of the incoming call track 608 as shown in FIG. 6B. Alternatively, in some embodiments, the graphical object 614 remains at the upper edge of the incoming call track 608, as shown in FIG. 6D (e.g., the graphical object 614 does not lose progress along the incoming call track 608). Furthermore, while the graphical object 614 is displayed at the location shown in FIG. 6D, if the user then changes the angle of their arm/hand to tilt the electronic device 500 to the right (e.g., the left side of the display screen 504 is moved upward relative to the right side of the display screen 504), then the graphical object moves toward the right side of the display screen 504 along right track segment 610. In addition, if the user then changes the angle of their arm/hand to tilt the electronic device 500 to the left (e.g., the right side of the display screen 504 is moved upward relative to the left side of the display screen 504), then the graphical object moves toward the left side of the display screen 504 along left track segment 612. In some embodiments, other orientations of the electronic device 500 (e.g., tilting further up) do not have an effect on the movement of the graphical object 614.

Figure 6E:
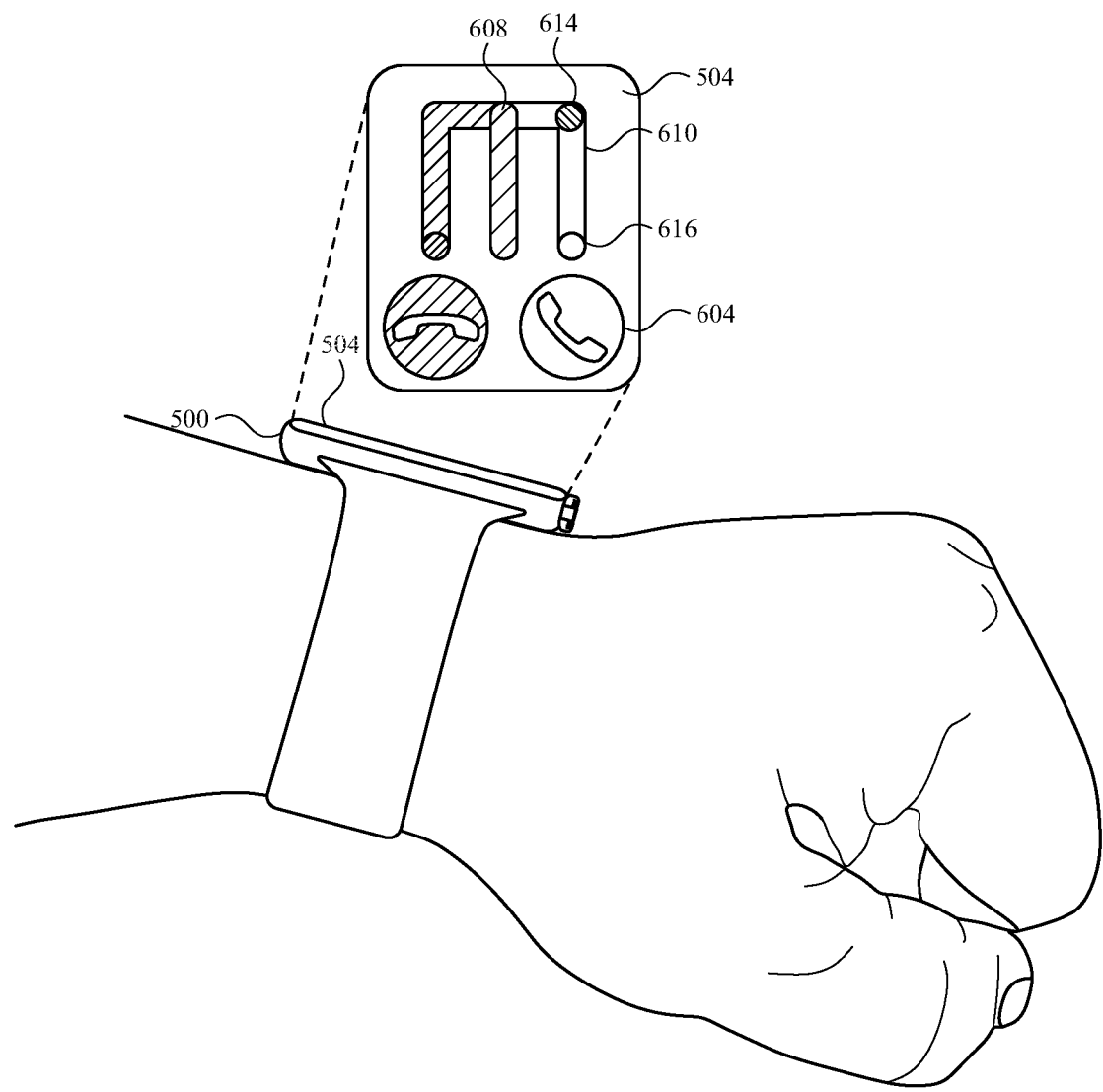

As shown in FIG. 6E, after the user rotates their wrist away from their body, the electronic device 500 is tilted to the right (e.g., the left side of the display screen 504 is moved upward relative to the right side of the display screen 504) as a result of the user changing the angle of their arm/hand In response to this orientation of the electronic device 500, the graphical object 614 moves toward the right side of the display screen 504 along right track segment 610, until the graphical object 614 encounters a right edge of the right track segment 610. From this right edge location, the graphical object 614 cannot continue along the right track segment 610 without the orientation of the electronic device 500 being changed to a different orientation (e.g., tilted to the left or down).

While the graphical object 614 is displayed at the location shown in FIG. 6E, if the user changes the angle of their arm/hand to tilt the electronic device 500 to the left (e.g., the right side of the display screen 504 is moved upward relative to the left side of the display screen 504), then the graphical object 614 moves back along the upper edge of the incoming call track 608 as shown in FIG. 6D. Alternatively, in some embodiments, the graphical object 614 remains at the right edge of the right track segment 610, as shown in FIG. 6E (e.g., the graphical object 614 does not lose progress along the incoming call track 608). Furthermore, while the graphical object 614 is displayed at the location shown in FIG. 6E, if the user then rotates their wrist toward their body (e.g., the electronic device 500 is tilted down such that the top of the display screen 504 is moved upward relative to the bottom of the display screen 504), then the graphical object 614 moves down the right track segment 610 toward the bottom of the display screen 504. In some embodiments, other orientations of the electronic device 500 (e.g., tilting further up or further to the right) do not have an effect on the movement of the graphical object 614.

Figure 6F:
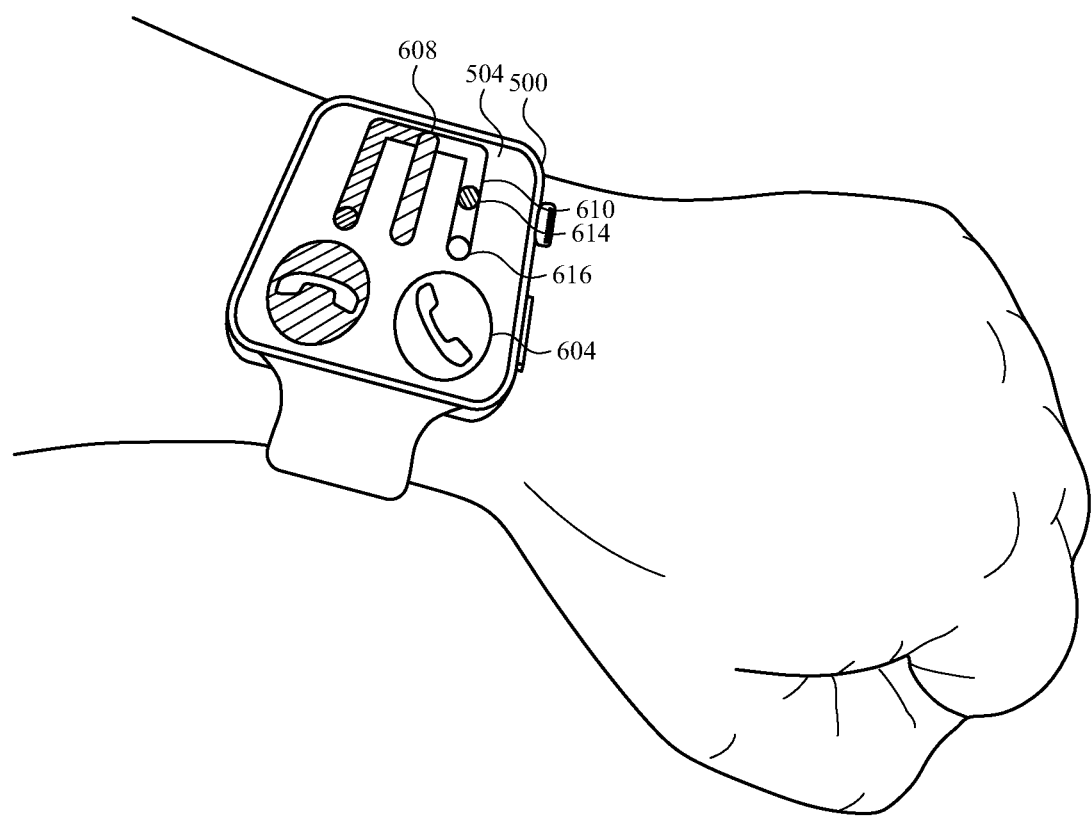

As shown in FIG. 6F, after tilting the electronic device 500 to the right, the orientation of the electronic device 500 is further changed as a result of the user rotating their wrist toward their body (e.g., the electronic device 500 is tilted down such that the top of the display screen 504 is moved upward relative to the bottom of the display screen 504). In response to this orientation of the electronic device 500, the graphical object 614 moves down the right track segment 610 toward the bottom of the display screen 504.

While the graphical object 614 is displayed at the location shown in FIG. 6F, if the user then rotates their wrist away from their body (e.g., the electronic device 500 is tilted up such that the bottom of the display screen 504 is moved upward relative to the top of the display screen 504), then the graphical object 614 moves back toward the upper edge of the incoming call track 608, as shown in FIG. 6E. Alternatively, in some embodiments, the graphical object 614 remains at the furthest location it reached in the right track segment 612, as shown in FIG. 6F (e.g., the graphical object 614 does not lose progress along the incoming call track 608). Furthermore, while the graphical object 614 is displayed at the location shown in FIG. 6F, if the user maintains the same orientation of the electronic device 500 or further rotates their wrist toward their body (e.g., the electronic device 500 is tilted down further such that the top of the display screen 504 is further moved upward relative to the bottom of the display screen 504), then the graphical object 614 continues to move down the right track segment 610 toward the bottom of the display screen 504. In some embodiments, other orientations of the electronic device 500 (e.g., tilting to the left or right) do not have an effect on the movement of the graphical object 614.

Figure 6G:
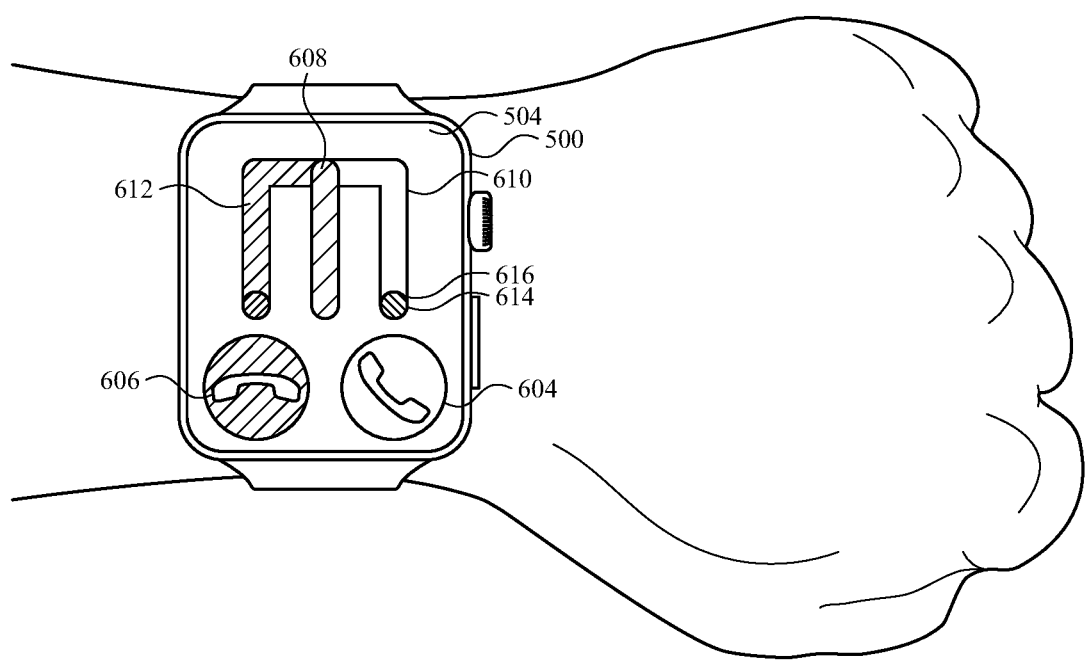

As shown in FIG. 6G, the orientation of the electronic device 500 is further changed as a result of the user further rotating their wrist toward their body. In response to this orientation of the electronic device 500, the graphical object 614 continues to move toward the bottom of the display screen 504 until it reaches the first demarcation 616 at the end of the right track segment 610. The graphical object 614 then stops moving and is displayed at the end of the right track segment 610 proximate to the answer call affordance 604. In some embodiments, the end of the right track segment 610 intersects the answer call affordance 604. In these embodiments, the graphical object 614 can be displayed adjacent to the answer call affordance 604, on top of the answer call affordance 604, behind the answer call affordance 604, or at other positions proximate to the answer call affordance 604.

Figure 6H:
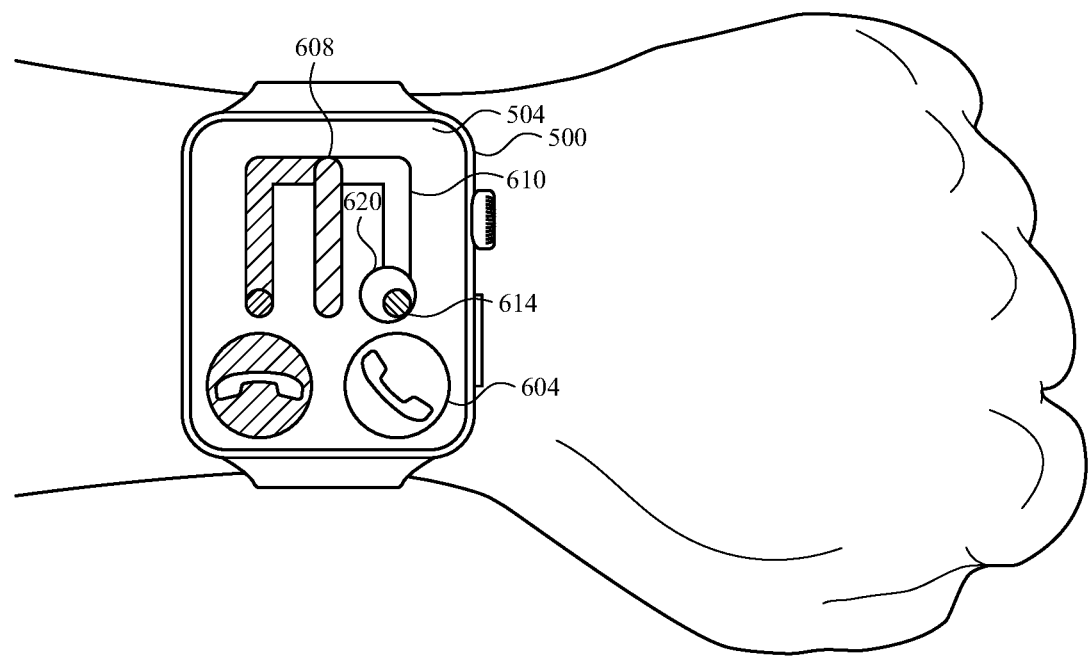
Figure 6I:
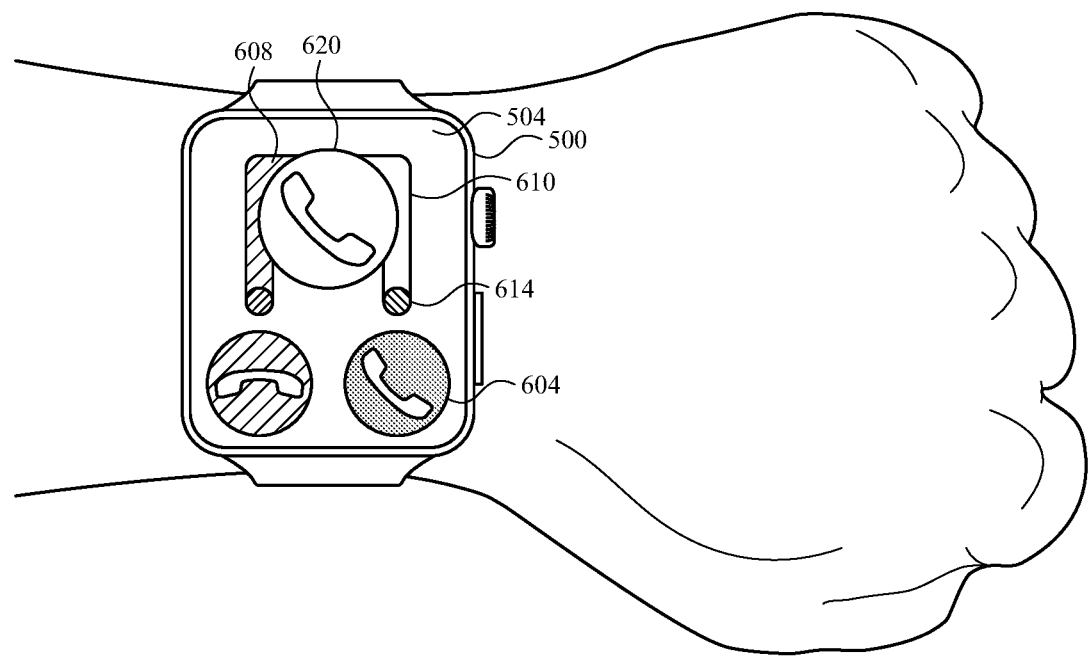
Figure 6J:
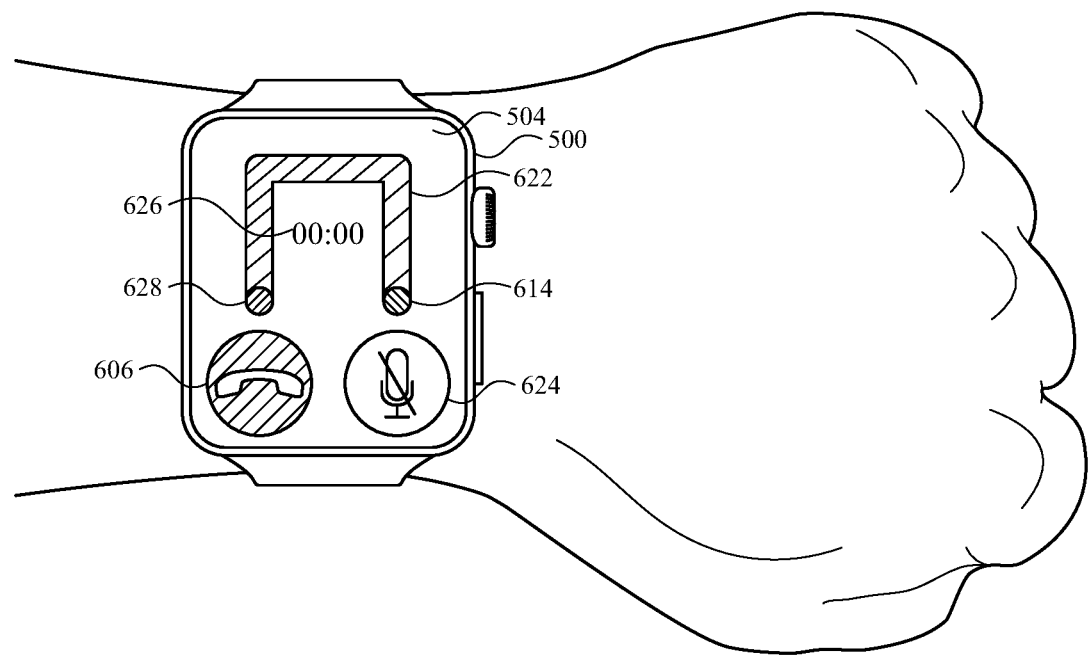
Figure 6K:
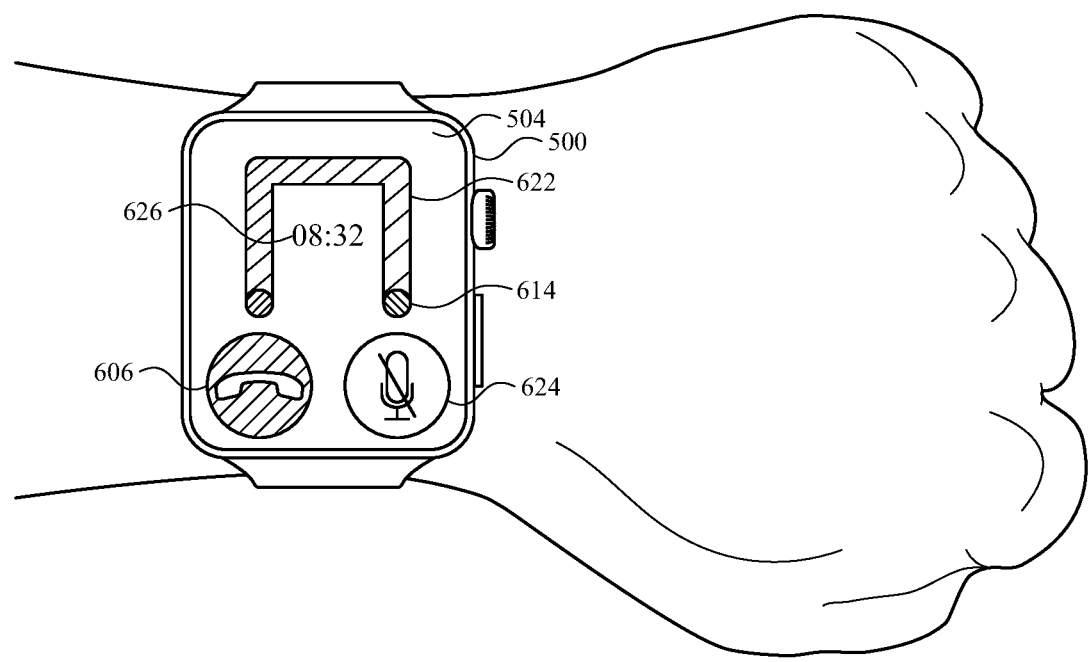
Figure 6L:
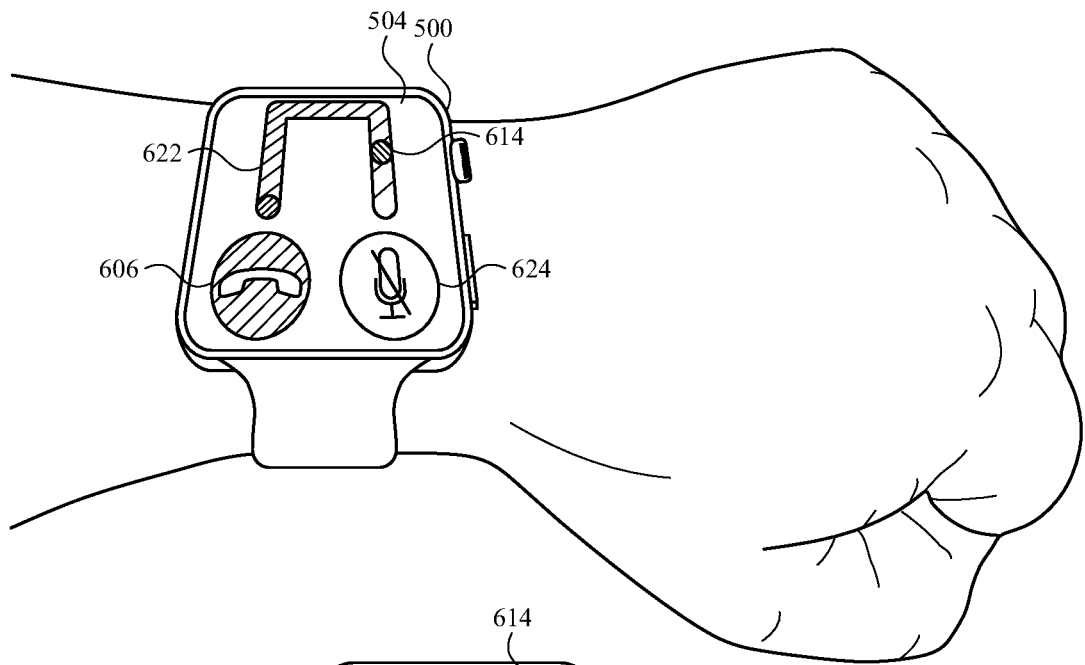
Figure 6M:
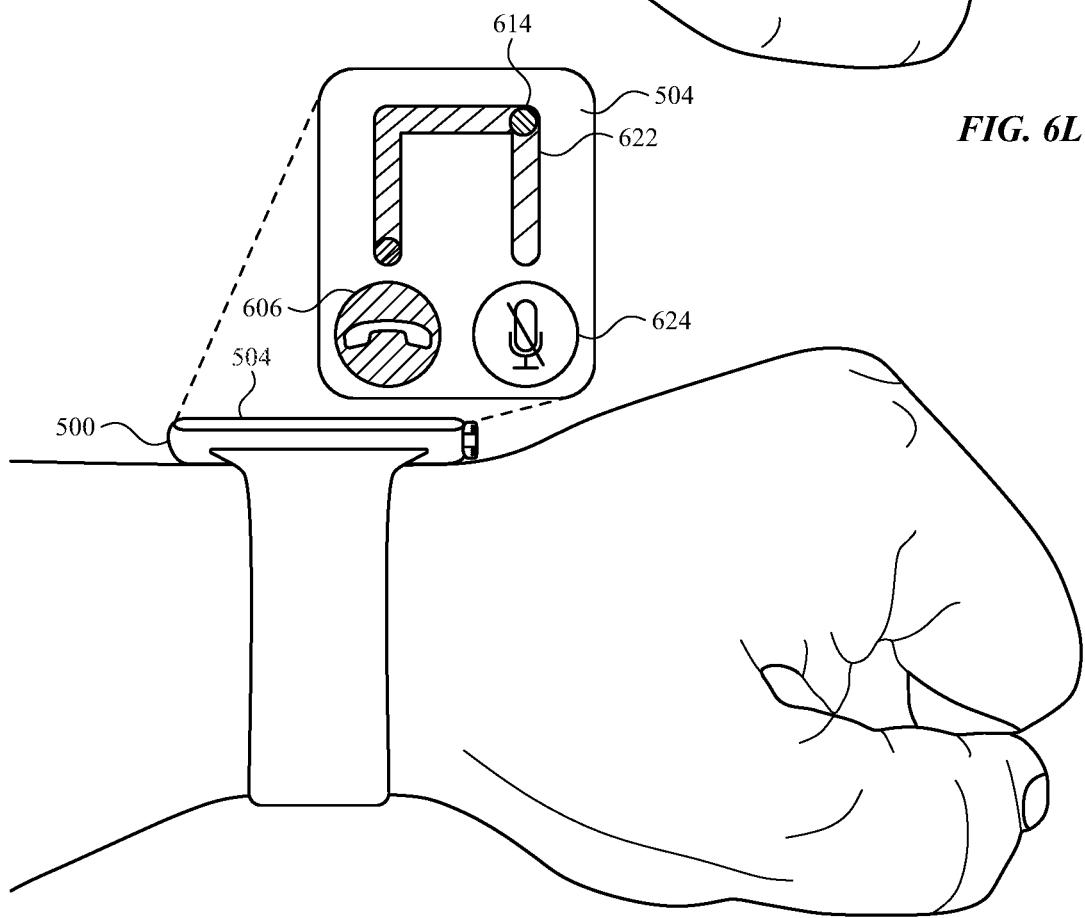
Figure 6N:
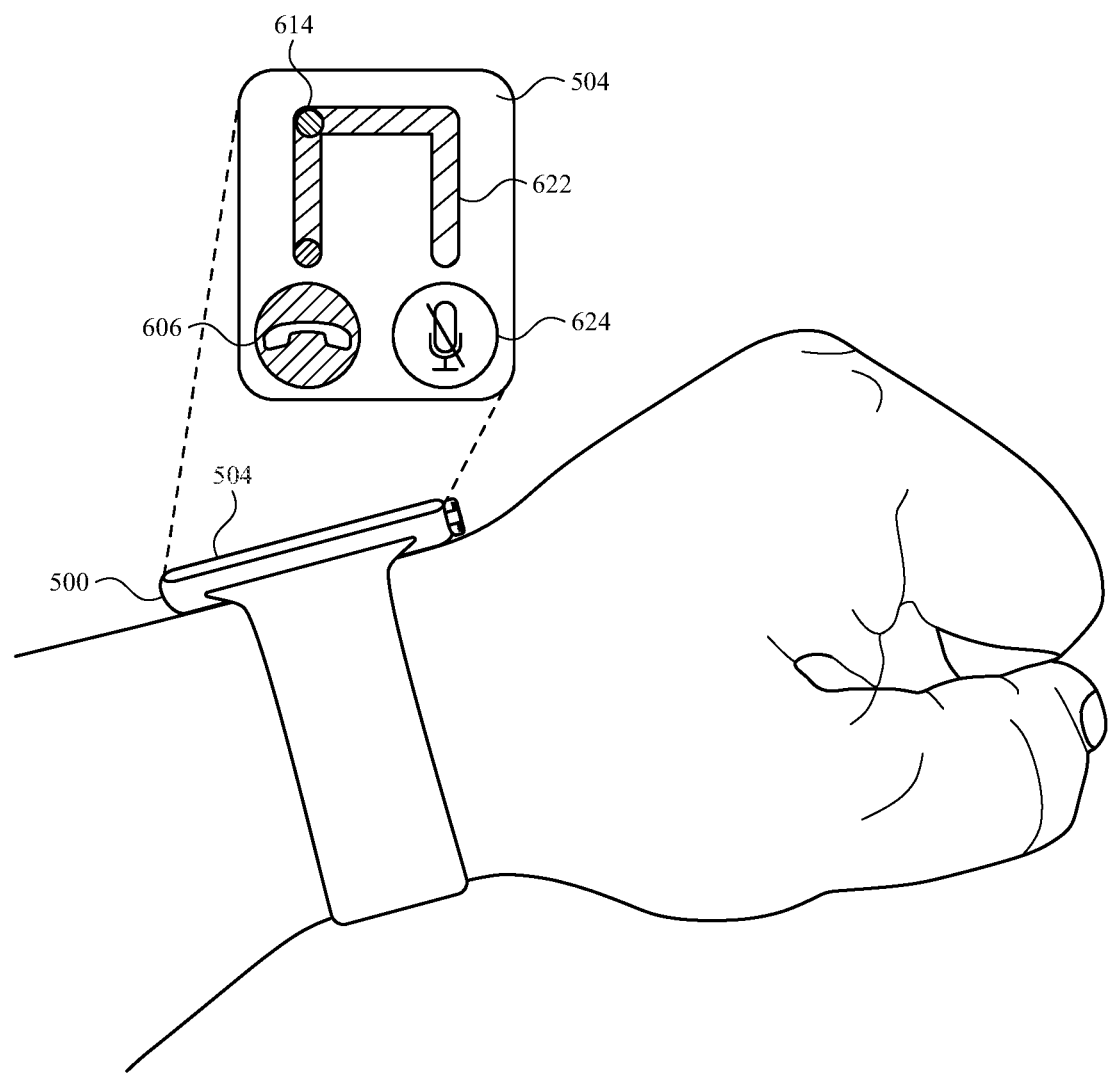
Figure 6O:
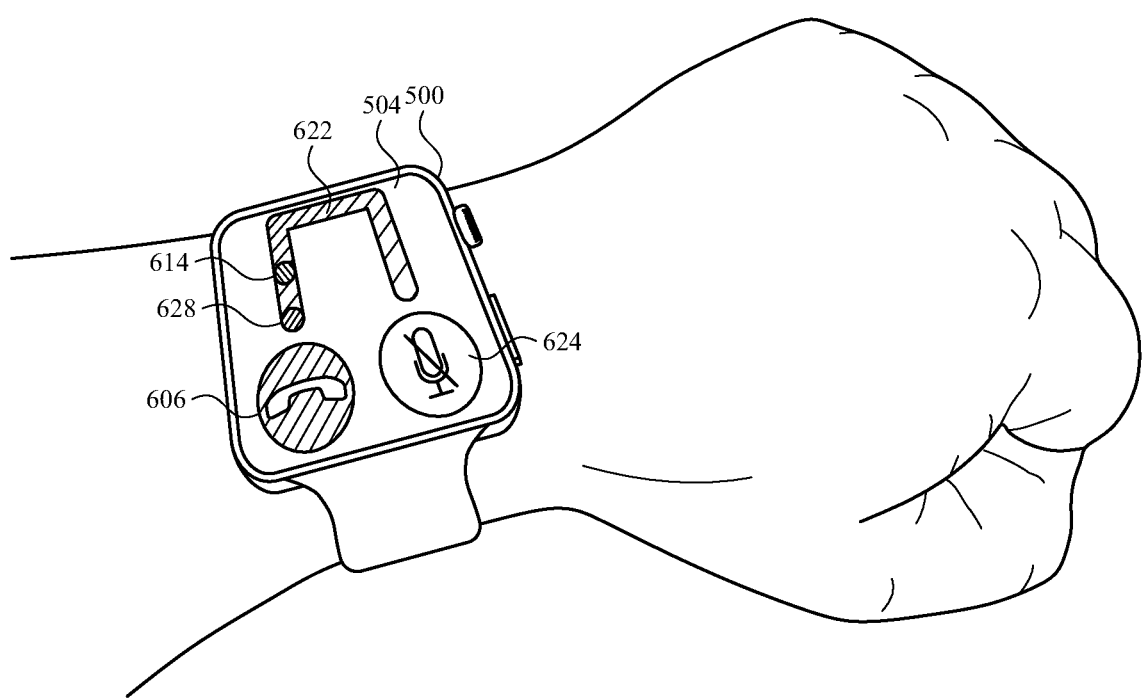
Figure 6P:
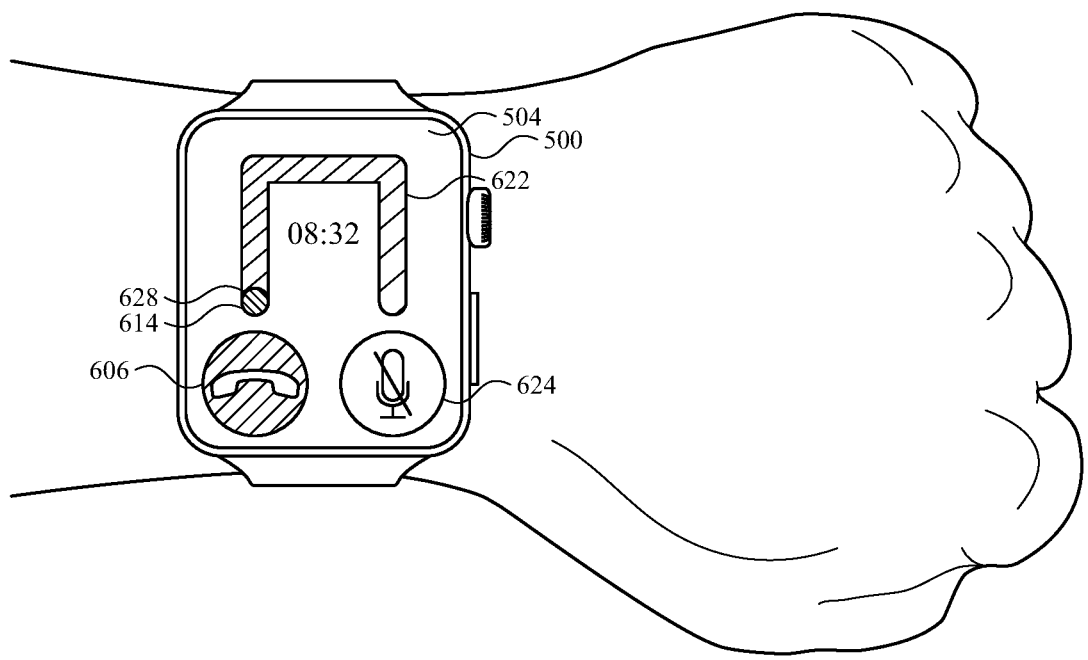

In response to the graphical element 614 being displayed at the end of the right track segment 610 proximate to the answer call affordance 604, a call answering notification 620 is initiated, as shown in FIG. 6H. The call answering notification 620 is an animated graphic that starts as a small circle proximate to the end of the right track segment 610 that then expands toward the center of the display screen 504 until it reaches a full-size. The full-size call answering notification 620 is shown in FIG. 6I. The call answering notification 620 indicates to the user that an answer call operation has been initiated by electronic device 500. In addition, in some embodiments, once the full-size call answering notification 620 is displayed, the answer call affordance 604 changes visual appearance to further indicate to the user that the answer call operation has been initiated. The answer call operation instructs the electronic device 500 or other associated device to answer the incoming telephone call.

A different sequence of interactions, related to those described in reference to FIGS. 6E-6I, can be carried out to decline an incoming telephone call with the electronic device 500. Instead of tilting the electronic device 500 to the right as shown in FIG. 6E, the electronic device is tilted to the left (e.g., the right side of the display screen 504 is moved upward relative to the left side of the display screen 504). In response to this orientation of the electronic device 500, the graphical object 614 moves toward the left side of the display screen 504 along left track segment 612, until the graphical object 614 encounters a left edge of the left track segment 612. The user then rotates their wrist toward their body (similar to as shown in FIGS. 6F-6G) to move the graphical object 614 down the left track segment 612 toward the bottom of the display screen 504. The graphical object 614 continues to move toward the bottom of the display screen 504 until it reaches the second demarcation 618 at the end of the left track segment 612. The graphical object 614 then stops moving and is displayed at the end of the left track segment 612 proximate to the decline call affordance 606. In some embodiments, the end of the left track segment 612 intersects the decline call affordance 606. In these embodiments, the graphical object 614 can be displayed adjacent to the decline call affordance 606, on top of the decline call affordance 606, behind the decline call affordance 606, or at other positions proximate to the decline call affordance 606.

Figure 6Q:
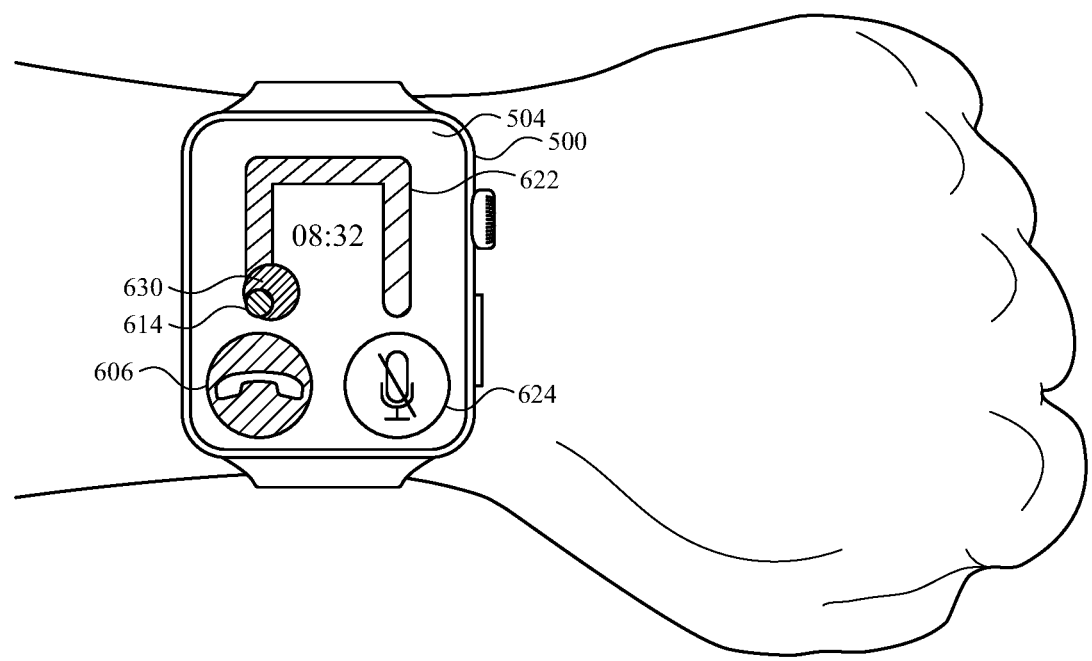

In response to the graphical element 614 being displayed at the end of the left track segment 612 proximate to the decline call affordance 606, a call ending notification is initiated (similar to the call ending notification 630 shown in FIG. 6Q). The call ending notification is an animated graphic that starts as a small circle proximate to the end of the left track segment 612 that then expands toward the center of the display screen 504 until it reaches a full-size. The call ending notification indicates to the user that a decline call operation has been initiated by electronic device 500. The decline call operation instructs the electronic device 500 or other associated device to decline the incoming telephone call.

Once in an active telephone call, the incoming call track 608 is replaced with an end call track 622 on the display screen 504, as shown in FIG. 6J. In addition, the answer call affordance 604 is replaced with a mute affordance 624. The decline call affordance 606 remains in the same location on the display screen as in FIGS. 6A-6I. Throughout the sequence of interactions shown in FIGS. 6J-6P, the decline call affordance 606 or mute affordance 624 can be touched by the user to perform their respective operation with the electronic device 500 (e.g., end the active telephone call or mute the microphone, respectively).

The graphical object 614 is displayed in the same location on the display screen 504 as in FIGS. 6G-6I (e.g., at the end of what was formerly the right track segment 610 of the incoming call track 608). The end call track 608 leads from this current location of the graphical object 614 to the decline call affordance 606 (e.g., from the end of what was formerly the right track segment 610 to the decline call affordance 606). A third demarcation 628 is displayed at the end of the end call track 622 proximate to the decline call affordance 606. In some embodiments, a call timer 626 is also displayed in a center region of the display screen 504. The time shown in the call timer 626 increases to indicate how long the telephone call is active, as shown in FIG. 6K.

As shown in FIG. 6L, the orientation of the electronic device 500 is changed as a result of the user rotating their wrist away from their body. In response to the new orientation of the electronic device 500, the graphical object 614 moves along the end call track 622 toward the top of the display screen 504. In some embodiments, the movement of the graphical object 614 between the different locations shown in FIGS. 6J-6P is animated in a similar manner as described in reference to FIGS. 6B-6G. The animation corresponds to a simulated physical movement of the graphical object 614 rolling along the end call track 622. For instance, in some embodiments, the acceleration and velocity of the graphical object 614 as it moves along the end call track 622 is representative of how a physical ball would roll along a physical track being held in the same orientation as the electronic device 500.

While the graphical object 614 is displayed at the location shown in FIG. 6L, if the user rotates their wrist back toward their body (e.g., the electronic device 500 is tilted down such that the top of the display screen 504 is moved upward relative to the bottom of the display screen 504), then the graphical object 614 moves back toward its initial location on the end call track 622 as shown in FIGS. 6J-6K. Alternatively, in some embodiments, the graphical object 614 remains at the furthest location it reached in the end call track 622, as shown in FIG. 6L (e.g., the graphical object 614 does not lose progress along the end call track 622). Furthermore, while the graphical object 614 is displayed at the location shown in FIG. 6L, if the user maintains the same orientation of the electronic device 500 or further rotates their wrist away from their body (e.g., the electronic device 500 is tilted up further such that the bottom of the display screen 504 is further moved upward relative to the top of the display screen 504), then the graphical object 614 continues to move toward the top of the display screen 504. In some embodiments, other orientations of the electronic device 500 (e.g., tilting to the left or right) do not have an effect on the movement of the graphical object 614.

As shown in FIG. 6M, the orientation of the electronic device 500 is further changed as a result of the user further rotating their wrist away from their body. In response to this orientation of the electronic device 500, the graphical object 614 continues to move toward the top of the display screen 504 until it encounters an upper edge of the end call track 622. From this upper edge location, the graphical object 614 cannot continue along the end call track 622 without the orientation of the electronic device 500 being changed to a different orientation (e.g., tilted to the left).

While the graphical object 614 is displayed at the location shown in FIG. 6M, if the user rotates their wrist back toward their body (e.g., the electronic device 500 is tilted down such that the top of the display screen 504 is moved upward relative to the bottom of the display screen 504), then the graphical object 614 moves back toward the bottom of the display screen 504. Alternatively, in some embodiments, the graphical object 614 remains at the upper edge of the end call track 608, as shown in FIG. 6M (e.g., the graphical object 614 does not lose progress along the end call track 608). Furthermore, while the graphical object 614 is displayed at the location shown in FIG. 6M, if the user then changes the angle of their arm/hand to tilt the electronic device 500 to the left (e.g., the right side of the display screen 504 is moved upward relative to the left side of the display screen 504), then the graphical object moves toward the left side of the display screen 504 along end call track 622. In some embodiments, other orientations of the electronic device 500 (e.g., tilting further up or to the right) do not have an effect on the movement of the graphical object 614.

As shown in FIG. 6N, after the user rotates their wrist away from their body, the electronic device 500 is tilted to the left (e.g., the right side of the display screen 504 is moved upward relative to the left side of the display screen 504) as a result of the user changing the angle of their arm/hand In response to this orientation of the electronic device 500, the graphical object 614 moves toward the left side of the display screen 504 along end call track 622, until the graphical object 614 encounters a left edge of the end call track 622. From this left edge location, the graphical object 614 cannot continue along the end call track 622 without the orientation of the electronic device 500 being changed to a different orientation (e.g., tilted to the right or down).

While the graphical object 614 is displayed at the location shown in FIG. 6N, if the user changes the angle of their arm/hand to tilt the electronic device 500 to the right (e.g., the left side of the display screen 504 is moved upward relative to the right side of the display screen 504), then the graphical object 614 moves back toward the right side of the display screen 504. Alternatively, in some embodiments, the graphical object 614 remains at the left edge of the end call track 622, as shown in FIG. 6N (e.g., the graphical object 614 does not lose progress along the end call track 622).

Furthermore, while the graphical object 614 is displayed at the location shown in FIG. 6N, if the user then rotates their wrist toward their body (e.g., the electronic device 500 is tilted down such that the top of the display screen 504 is moved upward relative to the bottom of the display screen 504), then the graphical object 614 moves down the end call track 622 toward the bottom of the display screen 504. In some embodiments, other orientations of the electronic device 500 (e.g., tilting further up or further to the left) do not have an effect on the movement of the graphical object 614.

As shown in FIG. 6O, after tilting the electronic device 500 to the left, the orientation of the electronic device 500 is further changed as a result of the user rotating their wrist toward their body. In response to this orientation of the electronic device 500, the graphical object 614 moves down the left side of the end call track 622 toward the bottom of the display screen 504.

While the graphical object 614 is displayed at the location shown in FIG. 6O, if the user then rotates their wrist away from their body (e.g., the electronic device 500 is tilted up such that the bottom of the display screen 504 is moved upward relative to the top of the display screen 504), then the graphical object 614 moves back toward the upper edge of the end call track 622, as shown in FIG. 6N. Alternatively, in some embodiments, the graphical object 614 remains at the furthest location it reached in the end call track 622, as shown in FIG. 6O (e.g., the graphical object 614 does not lose progress along the end call track 622). Furthermore, while the graphical object 614 is displayed at the location shown in FIG. 6O, if the user maintains the same orientation of the electronic device 500 or further rotates their wrist toward their body (e.g., the electronic device 500 is tilted down further such that the top of the display screen 504 is further moved upward relative to the bottom of the display screen 504), then the graphical object 614 continues to move down the end call track 622 toward the bottom of the display screen 504. In some embodiments, other orientations of the electronic device 500 (e.g., tilting to the left or right) do not have an effect on the movement of the graphical object 614.

As shown in FIG. 6P, the orientation of the electronic device 500 is further changed as a result of the user further rotating their wrist toward their body. In response to this orientation of the electronic device 500, the graphical object 614 continues to move toward the bottom of the display screen 504 until it reaches the third demarcation 628 at the end of the end call track 622. The graphical object 614 then stops moving and is displayed at the end of the end call track 622 proximate to the decline call affordance 606. In some embodiments, the end of the end call track intersects the decline call affordance 606. In these embodiments, the graphical object 614 can be displayed adjacent to the decline call affordance 606, on top of the decline call affordance 606, behind the decline call affordance 606, or at other positions proximate to the decline call affordance 606.

Figure 6R:
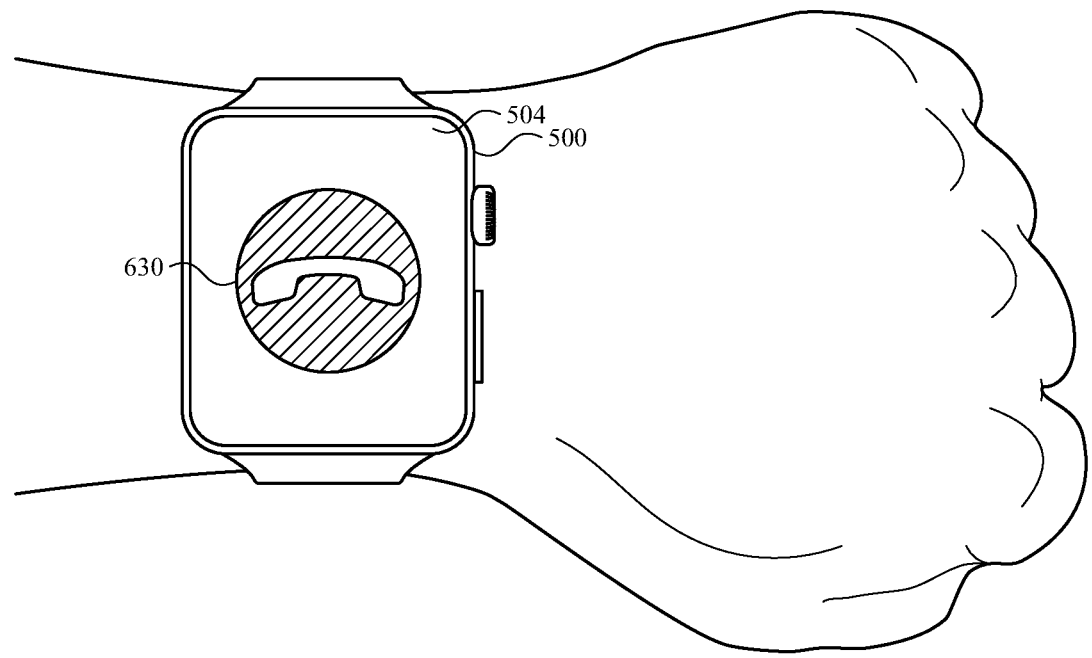

In response to the graphical element 614 being displayed at the end of the end call track 622 proximate to the decline call affordance 606, a call ending notification 630 is initiated, as shown in FIG. 6Q. The call ending notification 630 is an animated graphic that starts as a small circle proximate to the end of the end call track 622 that then expands toward the center of the display screen 504 until it reaches a full-size. The full-size call ending notification 630 is shown in FIG. 6R. The call ending notification 630 indicates to the user that an end call operation has been initiated by electronic device 500. Once the full-size call answering notification 620 is displayed, the other elements on the display screen 504 can be removed. The end call operation instructs the electronic device 500 or other associated device to end the active telephone call.

Once the active telephone call has ended, a call ended notification 632 is displayed on the display screen 504, as shown in FIG. 6S.

FIGS. 7A-7Q illustrate exemplary user interfaces for interacting with an electronic device without touching a display screen or other physical input mechanism, in accordance with some embodiments. The user interfaces in these figures are used to illustrate the processes described below, including the processes in FIGS. 13A-13B. As shown in FIG. 7A, electronic device 500 is worn on the user's left wrist and is being held in a position such that display screen 504 is directly visible to the user's eyes (while being substantially perpendicular to the ground), such as is typical for users when they are checking the time.

In particular, FIGS. 7A-7Q illustrate exemplary user interfaces for responding to an incoming telephone call with an electronic device 500. The electronic device 500 includes a display screen 504 and a tilt sensor, among other elements which can be found above and/or as discussed in reference to FIG. 5A. The display screen 504 can be a touch-sensitive display screen, and the tilt sensor can be an accelerometer 534, directional sensor 540 (e.g., compass), gyroscope 536, motion sensor 538, and/or a combination thereof. In the present example, device 500 is a wearable device on a user's wrist, such as a smart watch.

As shown in FIG. 7A, an incoming call notification 702 is initially displayed when the incoming telephone call is received. In addition, an answer call affordance 704 and a decline call affordance 706 are displayed. Throughout the sequence of interactions shown in FIGS. 7A-7P, the answer call affordance 704 or the decline call affordance 706 can be touched by the user to perform their respective operations with the electronic device 500 (e.g., answering the incoming call or declining the incoming telephone call, respectively).

As shown in FIGS. 7B-7E, a sequence of movement indicators 708a-708d (e.g., musical notes) are displayed in response to the incoming telephone call being received. In some embodiments, the first movement indicator 708a is displayed a predetermined time after initially receiving the incoming telephone call and/or in response to a user action. For instance, in some embodiments, the first movement indicator 708a is displayed in response to the user lifting their arm into a raised position where the display screen 504 is visible to the user. The second, third, and fourth movement indicators 708b-708d then appear in sequence after the first movement indicator 708a is displayed, where the second movement indicator 708b is displayed a predetermined time after the first movement indicator 708a is displayed, and so on. Alternatively, the entire sequence of movement indicators 708a-708d can be displayed approximately simultaneously in response to the incoming telephone call being received. The sequence of movement indicators 708a-708d indicates a sequence of movements that can be made with the electronic device 500 to respond to the incoming telephone call. For instance, the first movement indicator 708a (e.g., a "high" musical note) indicates that the first movement the user would make with the electronic device 500 is to rotate the display screen 504 away from their body (e.g., the user rotates their wrist to move the bottom of the display screen 504 upward relative to the top of the display screen 504). The second movement indicator 708b (e.g., a "low" musical note) indicates that the second movement the user would make with the electronic device 500 is to rotate the display screen 504 toward their body (e.g., the user rotates their wrist to move the top of the display screen 504 upward relative to the bottom of the display screen 504). The third and fourth movement indicators 708c-708d (e.g., high musical notes) indicate that the user would rotate the display screen 504 away from their body two more times. In some embodiments, each of the movements indicated by the sequence of movement indicators 708a-708d also include a rotation of the electronic device 500 back toward its original orientation within a predetermined time period (e.g., each movement is a "flicking" motion where the display screen 504 is quickly rotated away/toward the user and then is immediately rotated in the opposite direction). While four movement indicators 708a-708d are shown in FIGS. 7B-7E, the number of movement indicators can vary. For instance, a sequence of two, three, or five or more movement indicators can be displayed in response to the incoming telephone call being received. The direction of movement indicated by of the movement indicators can also vary. For instance, the sequence of movement indicators can indicate two rotations toward the user (e.g., two "low" musical notes) followed by two rotations away from the user (e.g., two "high" notes). The user can then input a sequence of movements corresponding to each of the displayed movement indicators, such as shown in FIGS. 7G-7N.

Figure 7E:
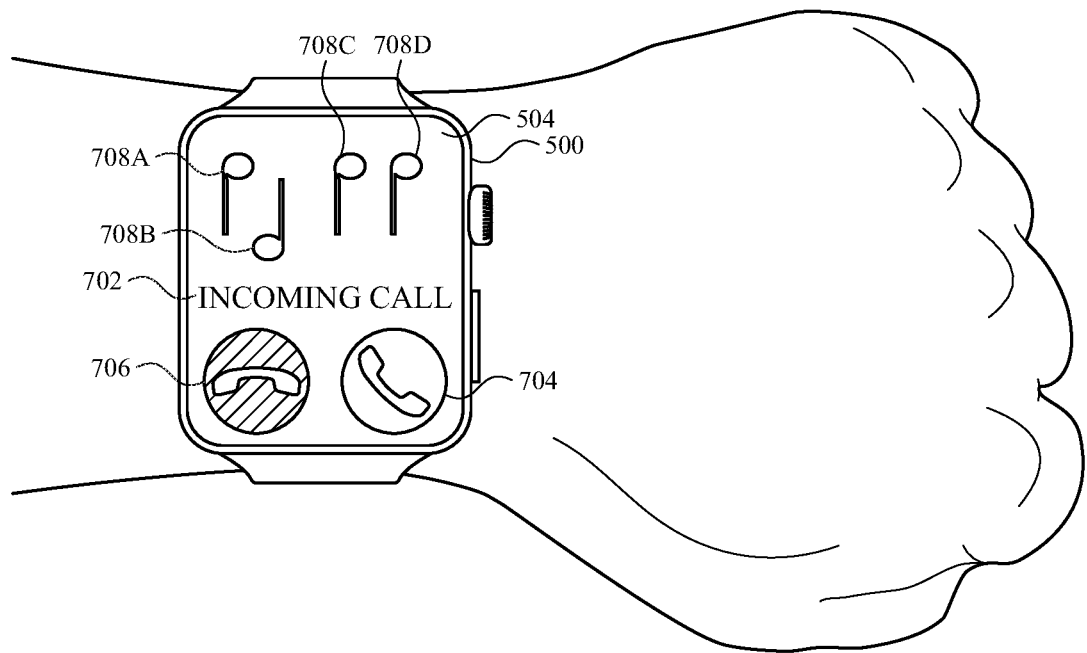
Figure 7F:
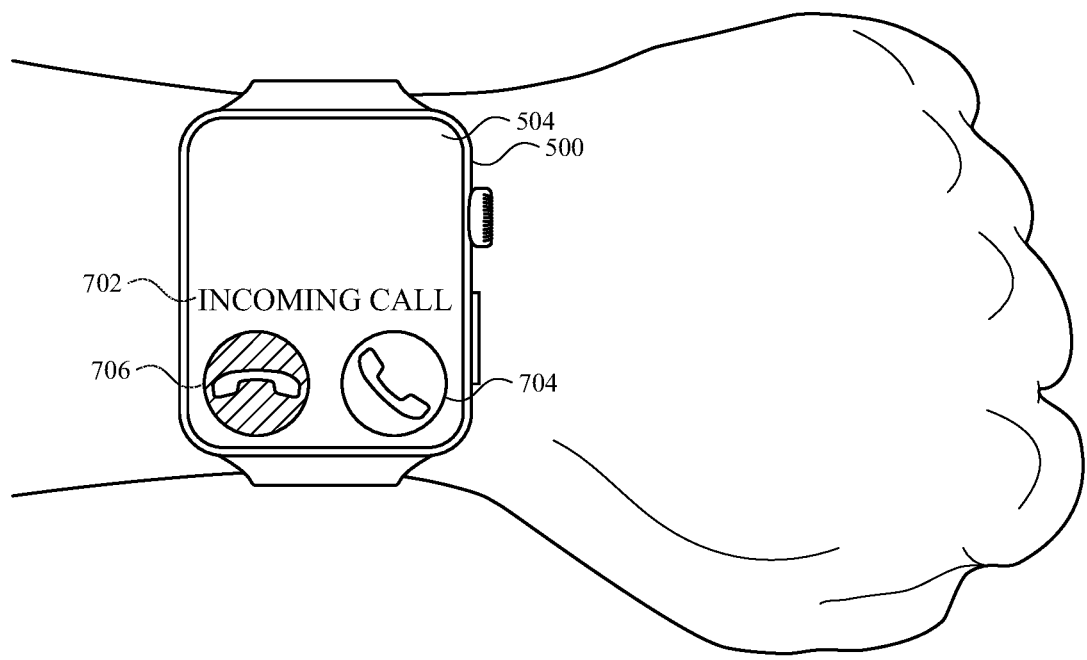

After all of movement indicators 708a-708d are displayed (as shown in FIG. 7E), the movement indicators 708a-708d are removed from the display screen 504, as shown in FIG. 7F. In some embodiments, the movement indicators 708a-708d are removed a predetermined time after the last movement indicator (e.g., 708d) is displayed. Each of the movement indicators 708a-708d are then displayed again, in sequence or approximately simultaneously, as shown in FIGS. 7B-7E. The display and removal of the movement indicators 708a-708d as shown in FIGS. 7B-7F can repeat until a user input is received, a predetermined time period has elapsed, or the incoming telephone call is no longer being received. In some embodiments, the display of each of the movement indicators 708a-708d corresponds to an audio notification of the incoming telephone call (e.g., a "ringtone"). For instance, the audio notification can include a repeating sequence of four tones (e.g., one high tone, one low tone, followed by two more high tones). In some embodiments, each of the movement indicators 708a-708d are displayed at approximately the same time as each of the tones of the audio notification.

Figure 7G:
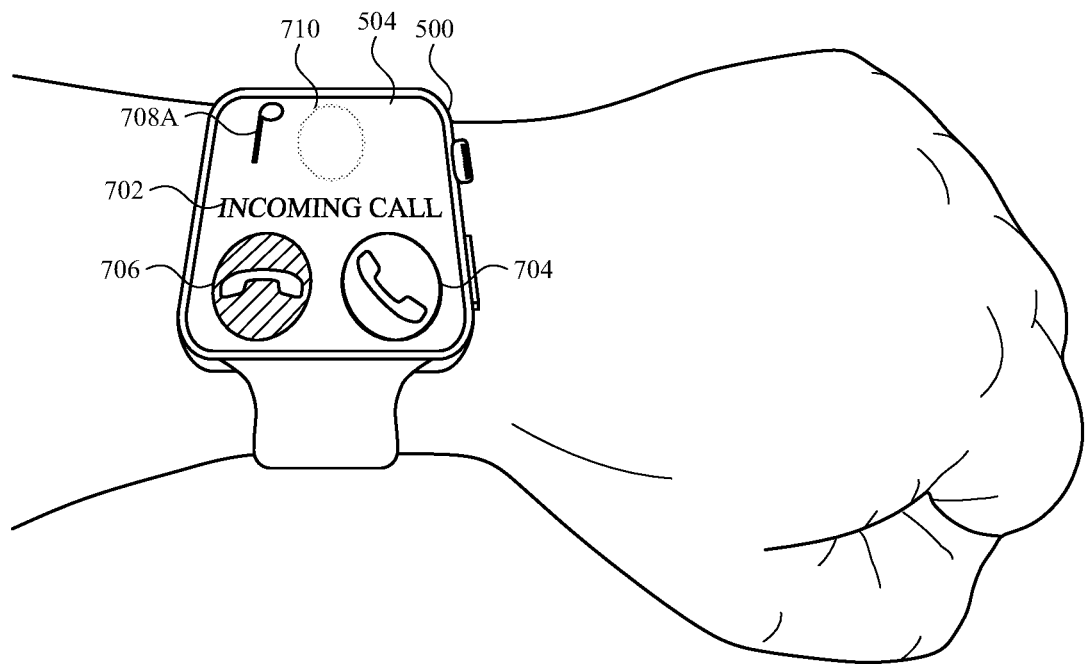
Figure 7H:
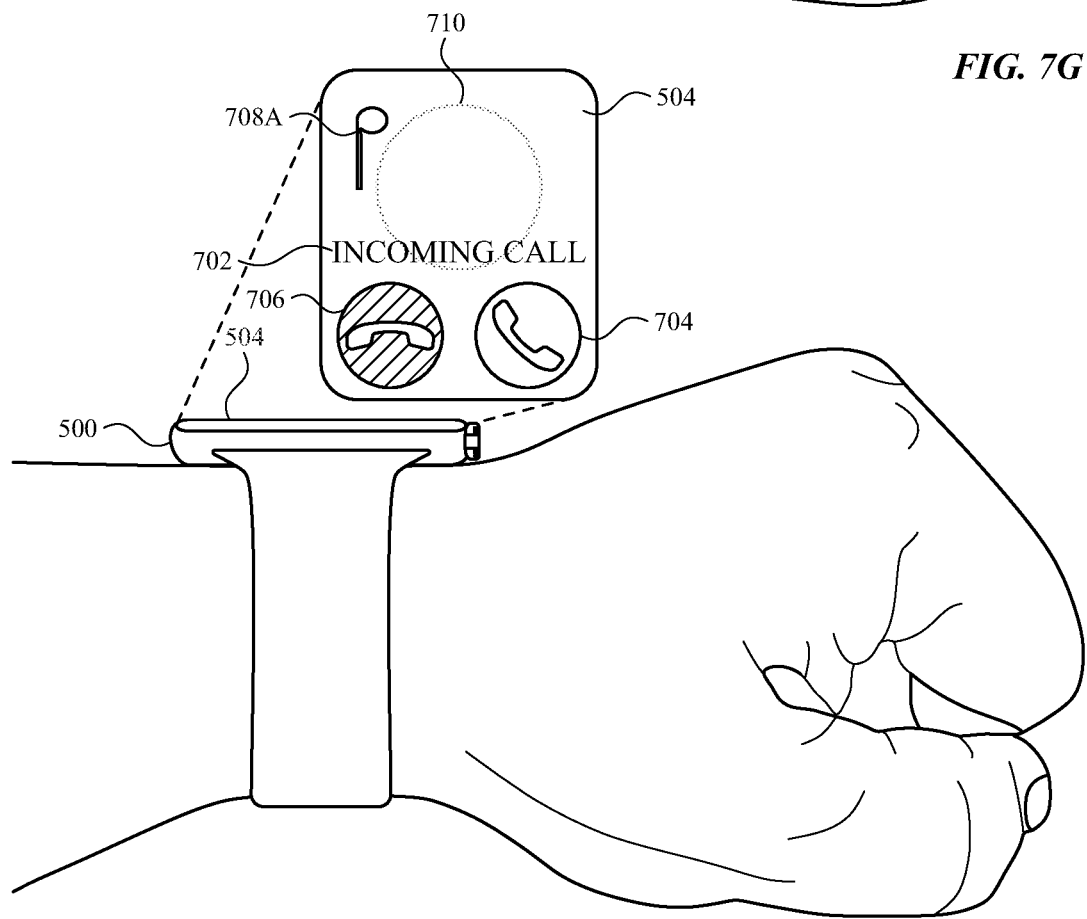

As shown in FIG. 7G, the orientation of the electronic device 500 is changed as a result of the user rotating their wrist away from their body (e.g., the electronic device 500 is tilted up such that the bottom of the display screen 504 is moved upward relative to the top of the display screen 504). This orientation corresponds to the movement indicated by the first movement indicator 708a. In response to the movement of the electronic device 500 to this orientation or a similar orientation, an input indicator 710 is displayed. The input indicator 710 is semi-transparent and is displayed overlapping the other elements on the display screen 504. In some embodiments, the input indicator 710 is displayed when the movement of the electronic device 500 meets a minimum velocity or acceleration threshold. If the minimum velocity or acceleration threshold is not met, then the input indicator 710 is not displayed. In some embodiments, the input indicator 710 is an animated graphic that moves in the direction of movement of the electronic device 504 (e.g., the input indicator 710 moves toward the top of the display screen 504 in response to the user rotating their wrist away from their body). The input indicator 710 can also be animated to enlarge in size during the movement of the electronic device 504, as shown in FIG. 7H. In some embodiments, the first movement indicator 708a is displayed in response to the corresponding movement of the electronic device 504 by the user.

As shown in FIG. 7H, the orientation of the electronic device 500 is further changed as a result of the user further rotating their wrist away from their body (e.g., the electronic device 500 is tilted up further such that the bottom of the display screen 504 is further moved upward relative to the top of the display screen 504). The input indicator 710 shown in FIG. 7H is displayed in an upper region of the display screen to indicate to the user the direction of rotation that was detected by the electronic device 500. In some embodiments, following the movement of the electronic device 500 into the orientation shown in FIG. 7H or a similar orientation, the electronic device 500 is rotated back toward its original orientation (e.g., the orientation shown in FIG. 7F) within a predetermined time period (e.g., the user makes a "flicking" motion with the electronic device 500, where the display screen 504 is quickly rotated away from the user and then is immediately rotated back toward the user).

Figure 7I:
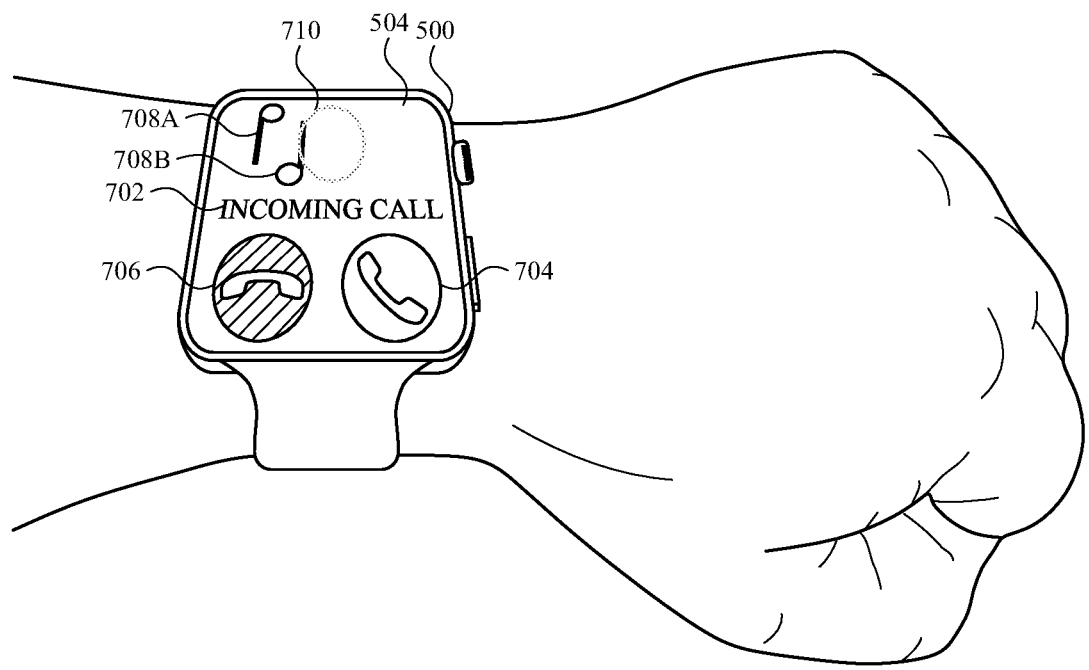
Figure 7J:
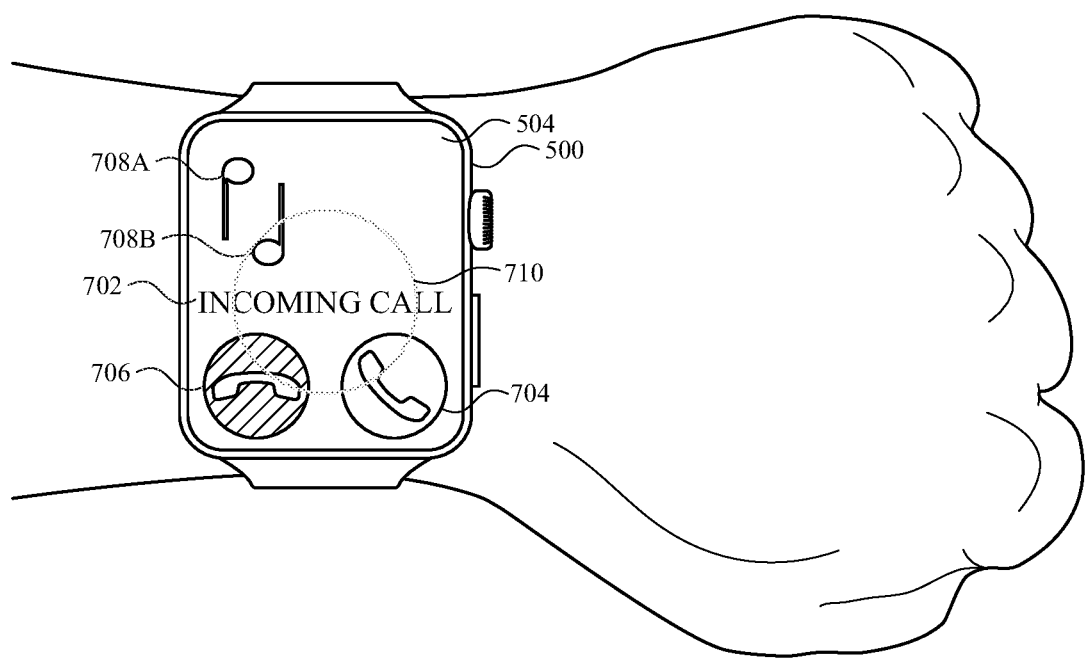

As shown in FIG. 7I, the orientation of the electronic device 500 is changed as a result of the user rotating their wrist toward their body (e.g., the electronic device 500 is tilted down such that the top of the display screen 504 is moved upward relative to the bottom of the display screen 504). This orientation corresponds to the movement indicated by the second movement indicator 708b. In response to the movement of the electronic device 500 to this orientation or a similar orientation, the input indicator 710 is displayed. The input indicator 710 is semi-transparent and is displayed overlapping the other elements on the display screen 504. In some embodiments, the input indicator 710 is displayed when the movement of the electronic device 500 meets a minimum velocity or acceleration threshold. If the minimum velocity or acceleration threshold is not met, then the input indicator 710 is not displayed. In some embodiments, the input indicator 710 is an animated graphic that moves in the direction of movement of the electronic device 504 (e.g., the input indicator 710 moves toward the bottom of the display screen 504 in response to the user rotating their wrist toward their body). The input indicator 710 can also be animated to enlarge in size during the movement of the electronic device 504, as shown in FIG. 7J. In some embodiments, the second movement indicator 708b is displayed in response to the corresponding movement of the electronic device 504 by the user.

As shown in FIG. 7J, the orientation of the electronic device 500 is further changed as a result of the user further rotating their wrist toward their body (e.g., the electronic device 500 is tilted down further such that the top of the display screen 504 is further moved upward relative to the bottom of the display screen 504). The input indicator 710 shown in FIG. 7J is displayed in a lower region of the display screen to indicate to the user the direction of rotation that was detected by the electronic device 500. In some embodiments, following the movement of the electronic device 500 into the orientation shown in FIG. 7J or a similar orientation, the electronic device 500 is rotated back toward its original orientation (e.g., the orientation shown in FIG. 7F) within a predetermined time period (e.g., the user makes a "flicking" motion with the electronic device 500, where the display screen 504 is quickly rotated toward the user and then is immediately rotated back away from the user).

Figure 7K:
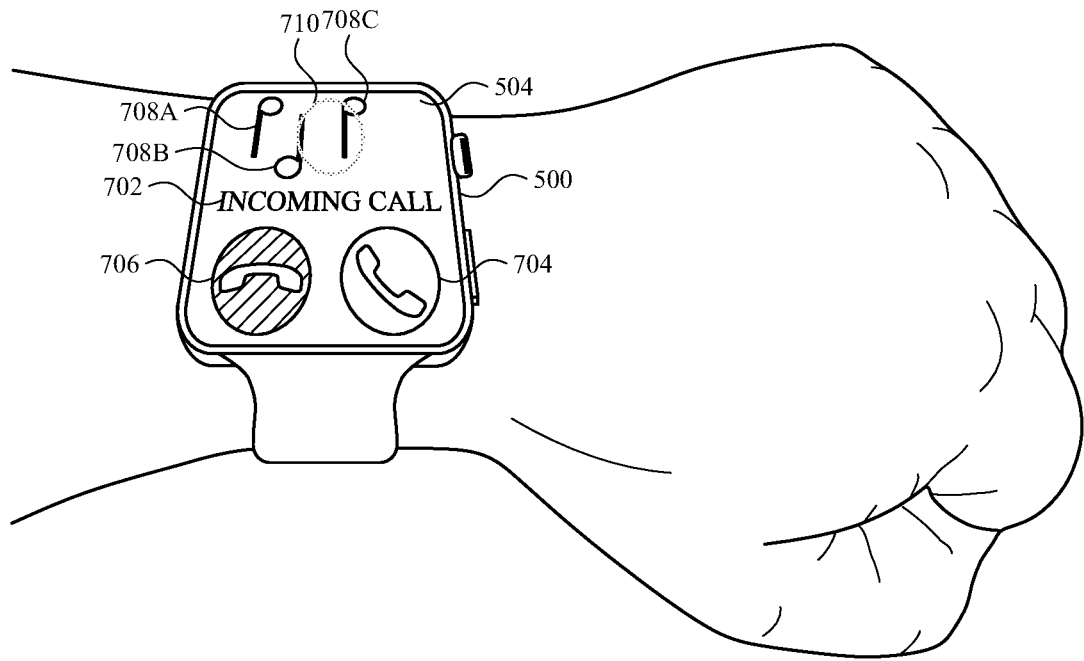
Figure 7L:
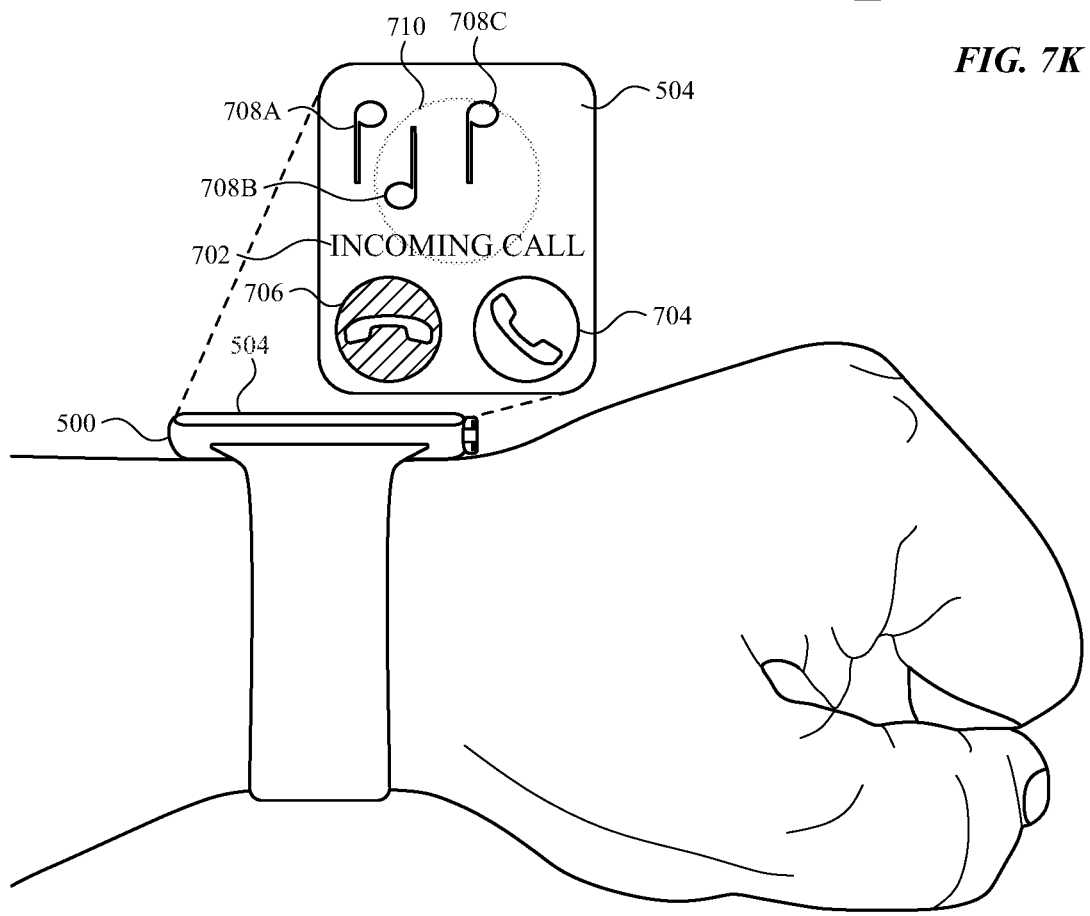

As shown in FIG. 7K, the orientation of the electronic device 500 is changed as a result of the user rotating their wrist away from their body a second time (e.g., the electronic device 500 is tilted up such that the bottom of the display screen 504 is moved upward relative to the top of the display screen 504). This orientation corresponds to the movement indicated by the third movement indicator 708*c*. In response to the movement of the electronic device 500 to this orientation or similar orientation, the input indicator 710 is displayed. The input indicator 710 is semi-transparent and is displayed overlapping the other elements on the display screen 504. In some embodiments, the input indicator 710 is displayed when the movement of the electronic device 500 meets a minimum velocity or acceleration threshold. If the minimum velocity or acceleration threshold is not met, then the input indicator 710 is not displayed. In some embodiments, the input indicator 710 is an animated graphic that moves in the direction of movement of the electronic device 504 (e.g., the input indicator 710 moves toward the top of the display screen 504 in response to the user rotating their wrist away from their body). The input indicator 710 can also be animated to enlarge in size during the movement of the electronic device 504, as shown in FIG. 7L. In some embodiments, the third movement indicator 708*c* is displayed in response to the corresponding movement of the electronic device 504 by the user.

As shown in FIG. 7L, the orientation of the electronic device 500 is further changed as a result of the user further rotating their wrist away from their body the second time (e.g., the electronic device 500 is tilted up further such that the bottom of the display screen 504 is further moved upward relative to the top of the display screen 504). The input indicator 710 shown in FIG. 7L is displayed in an upper region of the display screen to indicate to the user the direction of rotation that was detected by the electronic device 500. In some embodiments, following the movement of the electronic device 500 into the orientation shown in FIG. 7L or a similar orientation, the electronic device 500 is rotated back toward its original orientation (e.g., the orientation shown in FIG. 7F) within a predetermined time period (e.g., the user makes a "flicking" motion with the electronic device 500, where the display screen 504 is quickly rotated away from the user and then is immediately rotated back toward the user).

Figure 7M:
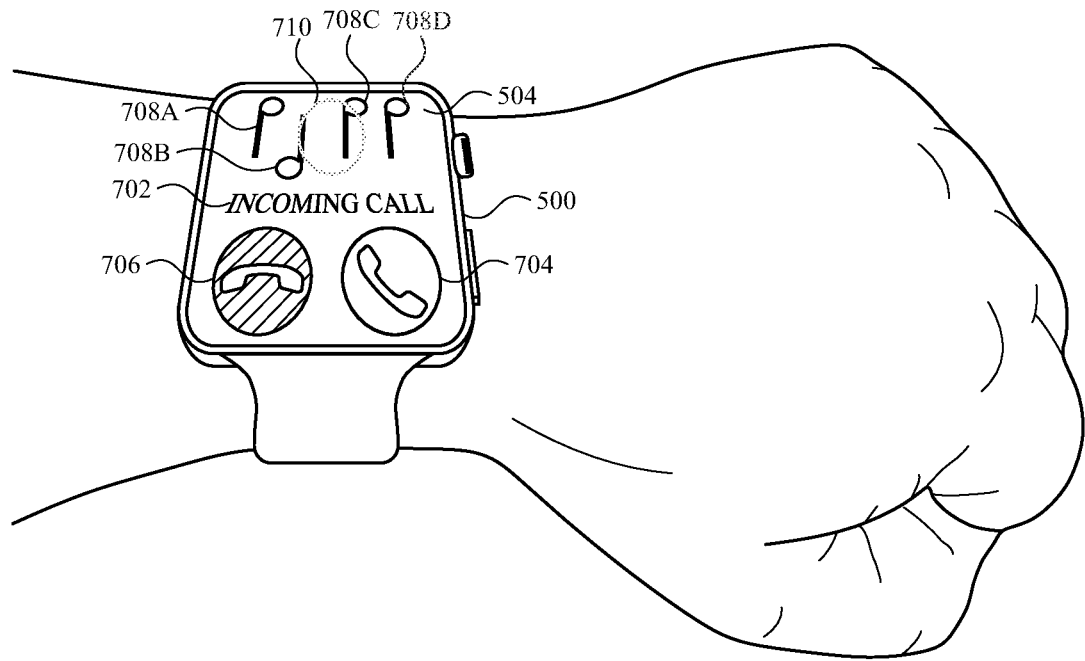
Figure 7N:
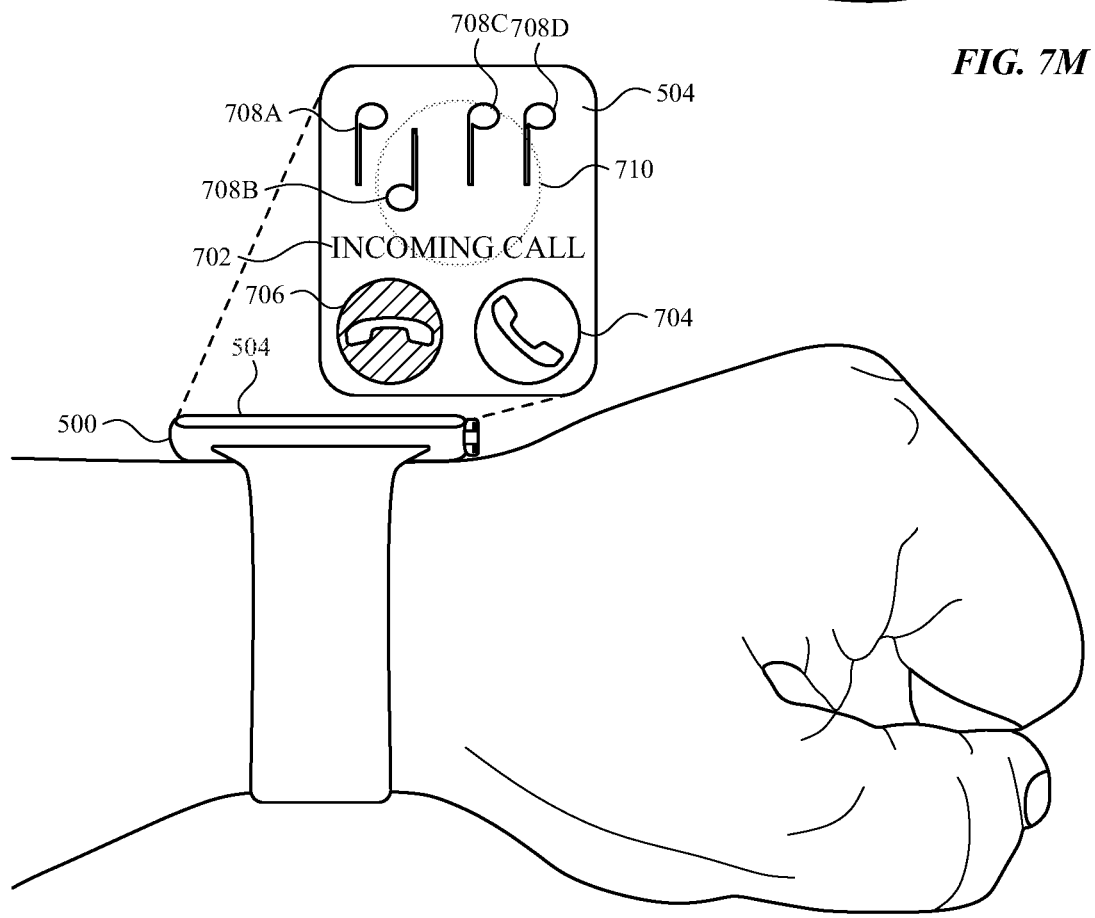

As shown in FIG. 7M, the orientation of the electronic device 500 is changed as a result of the user rotating their wrist away from their body a third time (e.g., the electronic device 500 is tilted up such that the bottom of the display screen 504 is moved upward relative to the top of the display screen 504). This orientation corresponds to the movement indicated by the fourth movement indicator 708*d*. In response to the movement of the electronic device 500 to this orientation or a similar orientation, the input indicator 710 is displayed. The input indicator 710 is semi-transparent and is displayed overlapping the other elements on the display screen 504. In some embodiments, the input indicator 710 is displayed when the movement of the electronic device 500 meets a minimum velocity or acceleration threshold. If the minimum velocity or acceleration threshold is not met, then the input indicator 710 is not displayed. In some embodiments, the input indicator 710 is an animated graphic that moves in the direction of movement of the electronic device 504 (e.g., the input indicator 710 moves toward the top of the display screen 504 in response to the user rotating their wrist away from their body). The input indicator 710 can also be animated to enlarge in size during the movement of the electronic device 504, as shown in FIG. 7N. In some embodiments, the fourth movement indicator 708*d* is displayed in response to the corresponding movement of the electronic device 504 by the user.

As shown in FIG. 7N, the orientation of the electronic device 500 is further changed as a result of the user further rotating their wrist away from their body the third time (e.g., the electronic device 500 is tilted up further such that the bottom of the display screen 504 is further moved upward relative to the top of the display screen 504). The input indicator 710 shown in FIG. 7N is displayed in an upper region of the display screen to indicate to the user the direction of rotation that was detected by the electronic device 500. In some embodiments, following the movement of the electronic device 500 into the orientation shown in FIG. 7N or similar orientation, the electronic device 500 is rotated back toward its original orientation (e.g., the orientation shown in FIG. 7F) within a predetermined time period (e.g., the user makes a "flicking" motion with the electronic device 500, where the display screen 504 is quickly rotated away from the user and then is immediately rotated back toward the user).

Figure 7O:
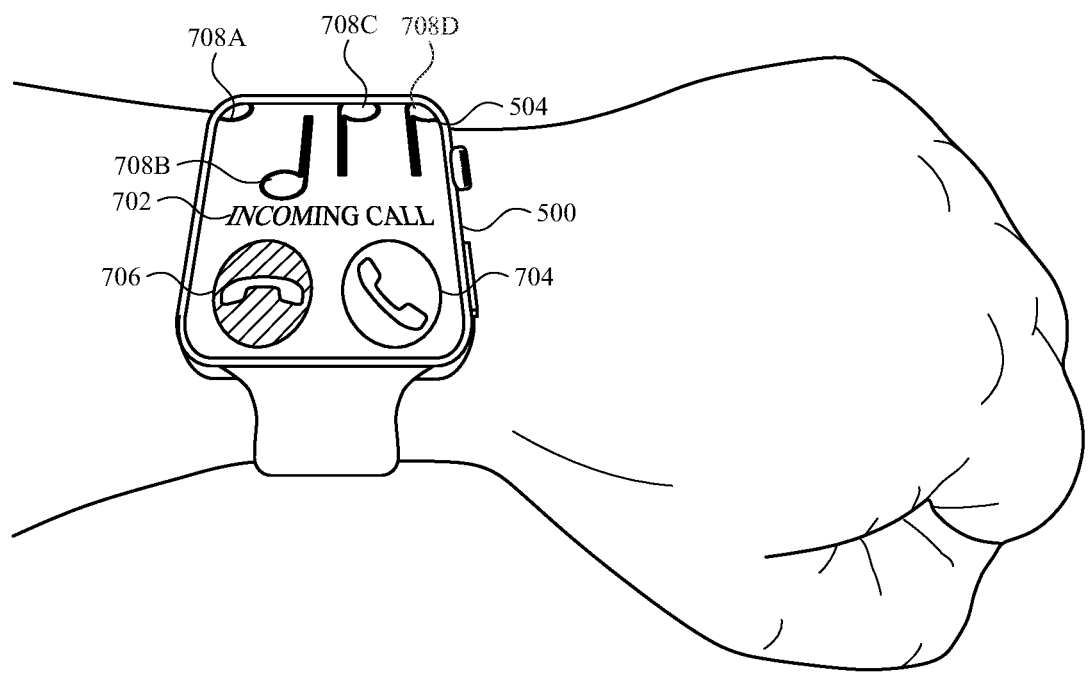
Figure 7P:
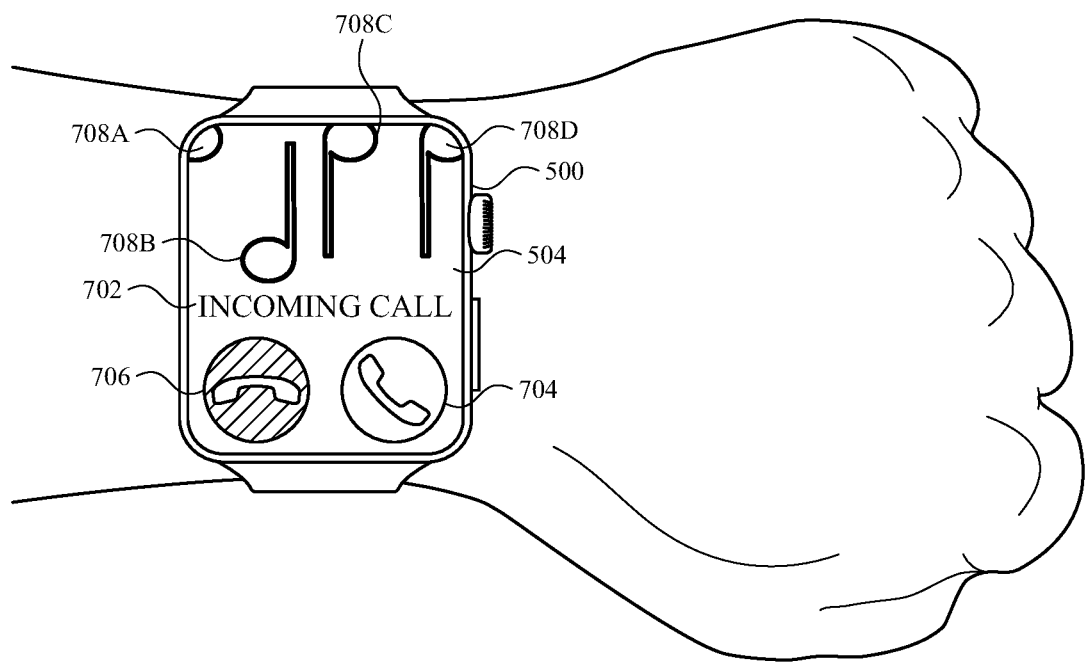

In some embodiments, after the user inputs the sequence of movements corresponding to the movement indicators 708*a*-708*d*, a success notification is displayed on the display screen 504. As shown in FIGS. 7O-7P, the success notification includes an animation of the movement indicators 708*a*-708*d*. The movement indicators 708*a*-708*d* enlarge in size and fade out in appearance to indicate to the user that the sequence of movements inputted by the user satisfy the sequence of movements indicated by the movement indicators 708*a*-708*d*.

In response to the user successfully performing the sequence of movements corresponding to the movement indicators 708*a*-708*d*, a call connecting notification 712 is displayed, as shown in FIG. 7Q. The call connecting notification 712 indicates to the user that an answer call operation has been initiated by electronic device 500. The answer call operation instructs the electronic device 500 or other associated device to answer the incoming telephone call.

If the user fails to input the sequence of movements corresponding to the movement indicators 708*a*-708*d* within a predetermined time, then the electronic device 500 forgoes performing the operation associated with the movement indicators 708*a*-708*d*. For instance, if the user only inputs three out of the four movements indicated by the movement indicators 708*a*-708*d* within the predetermined time, then no operation would be performed by the electronic device 500. In some embodiments, the predetermined time corresponds to a number of times the display of the sequence of movement indicators 708*a*-708*d* is repeated or an amount of time before the incoming telephone call is automatically canceled or forwarded to voicemail.

FIGS. 8A-8BI illustrate exemplary user interfaces for interacting with an electronic device without touching a display screen or other physical input mechanism, in accordance with some embodiments. The user interfaces in these figures are used to illustrate the processes described below, including the processes in FIG. 14.

Figure 8C:
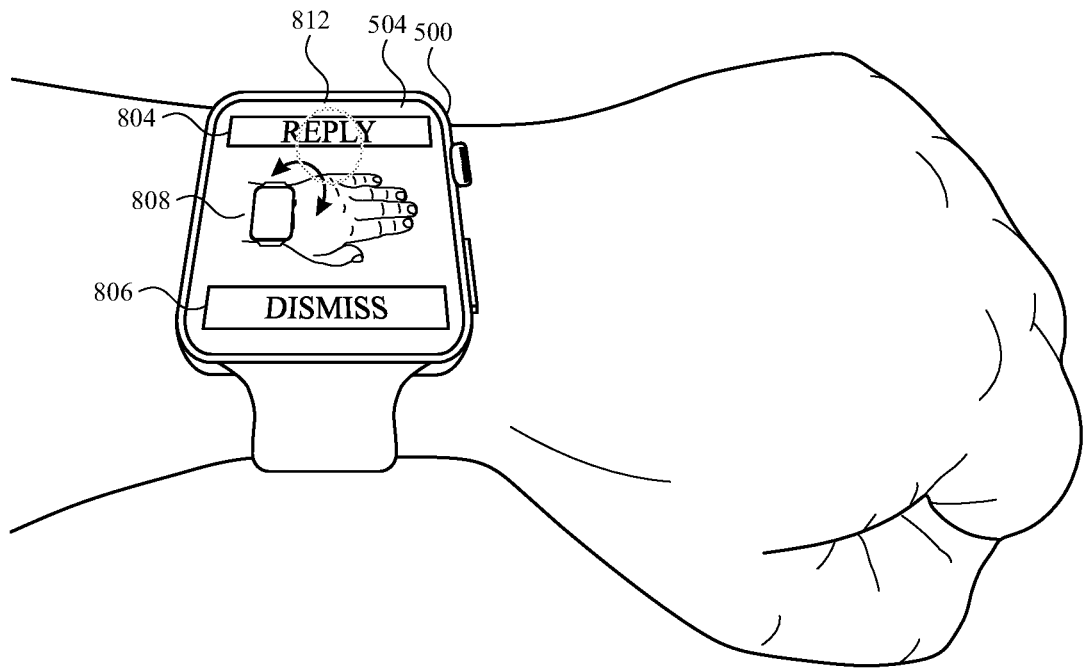
Figure 8D:
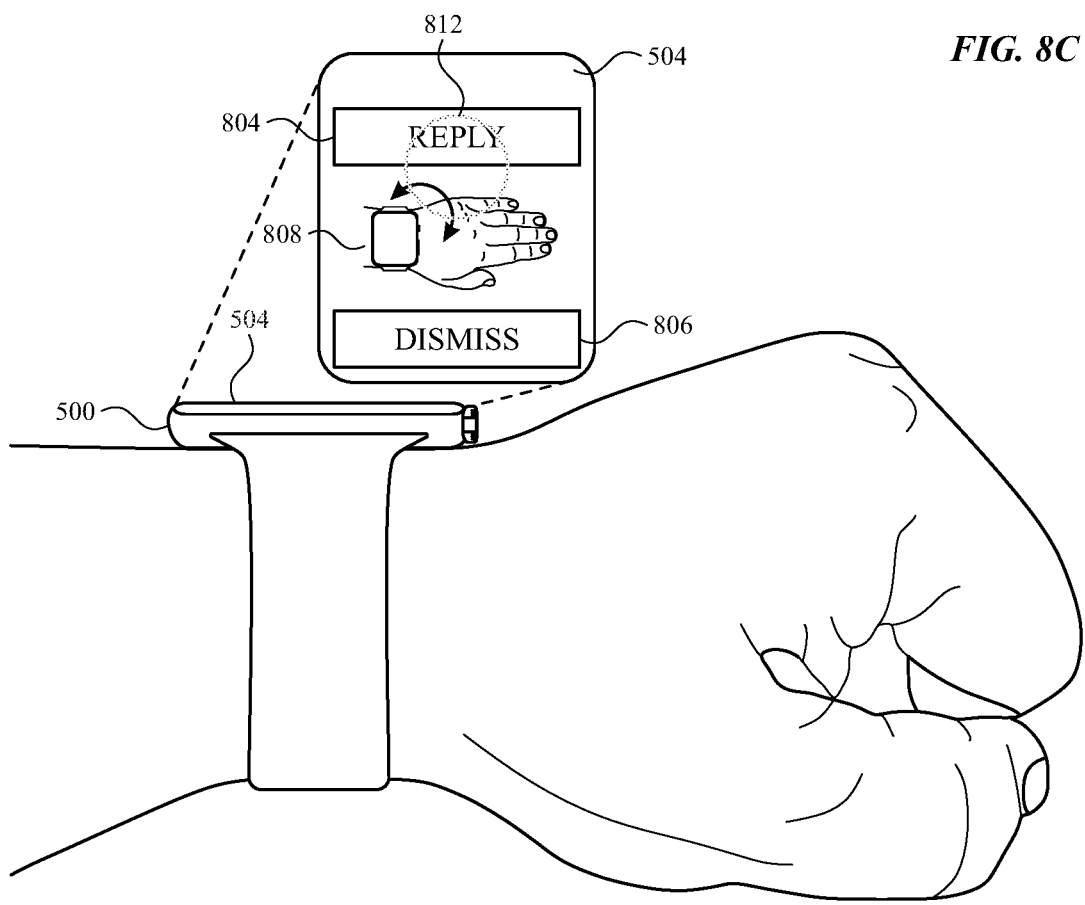
Figure 8E:
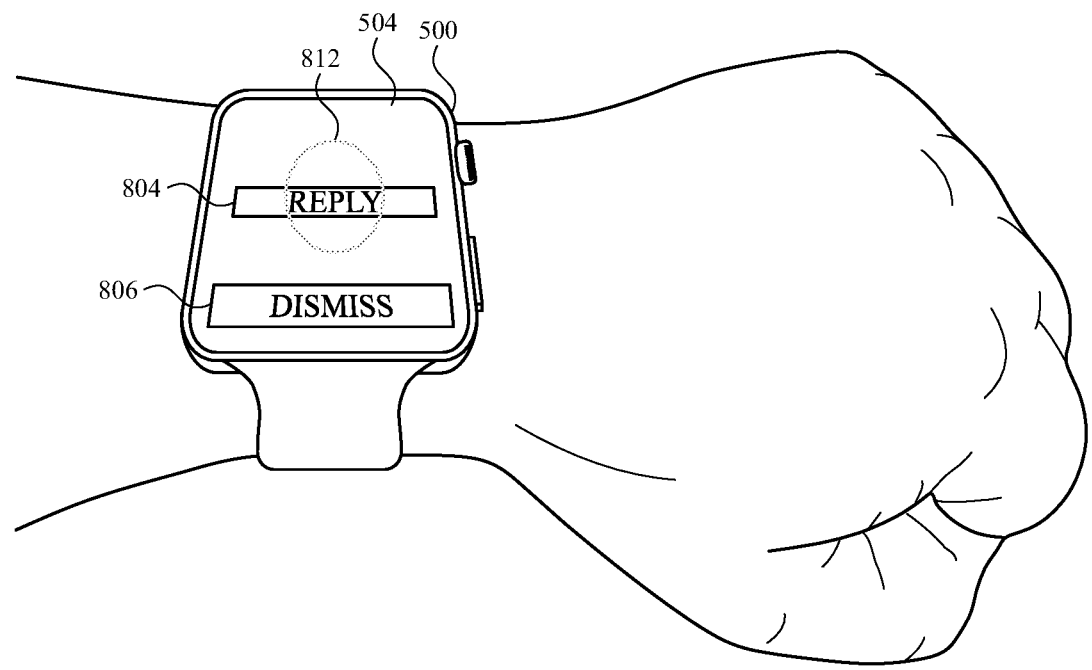
Figure 8F:
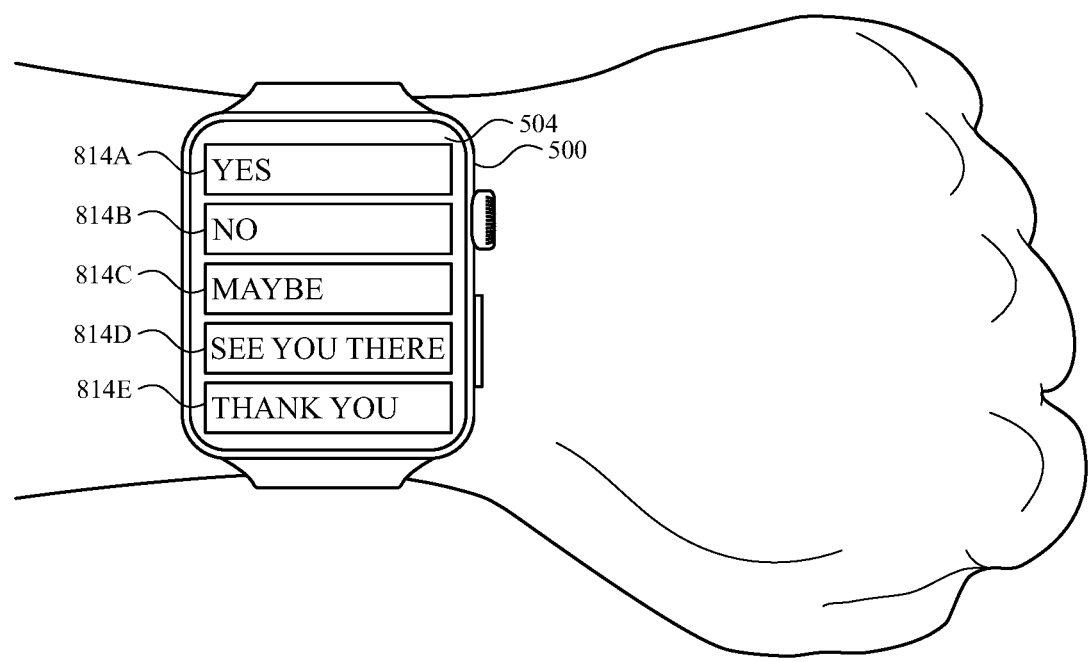
Figure 8G:
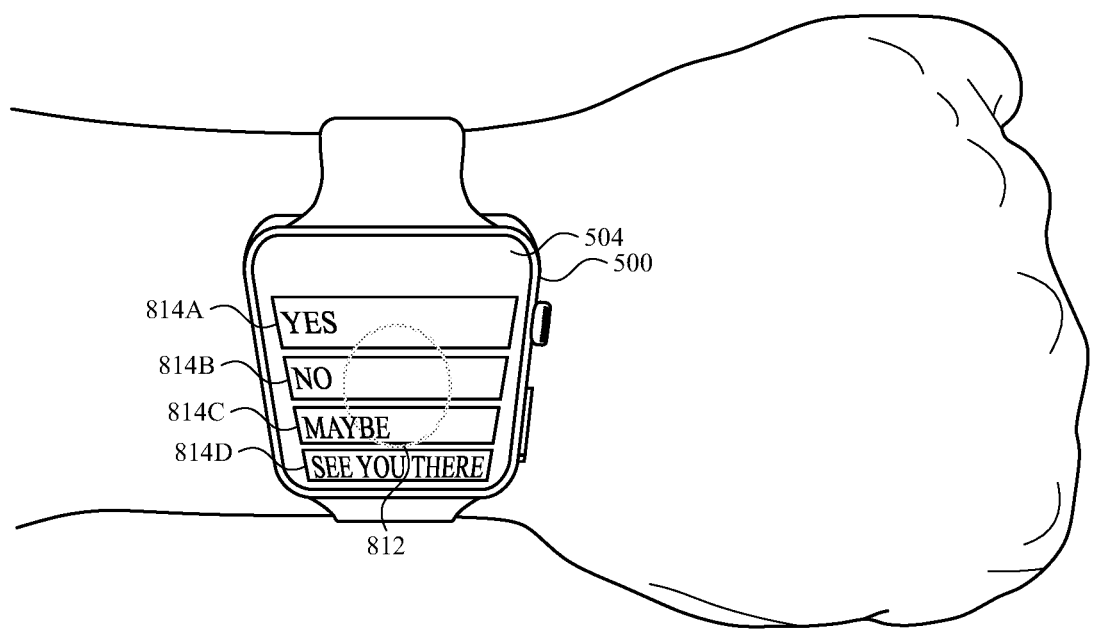
Figure 8H:
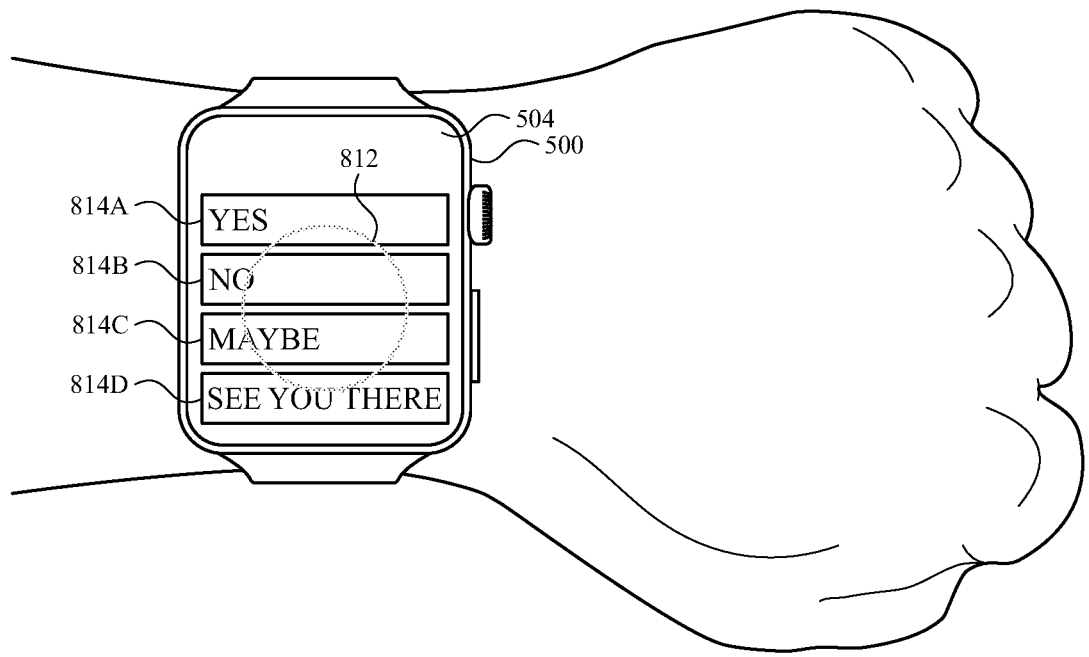
Figure 8I:
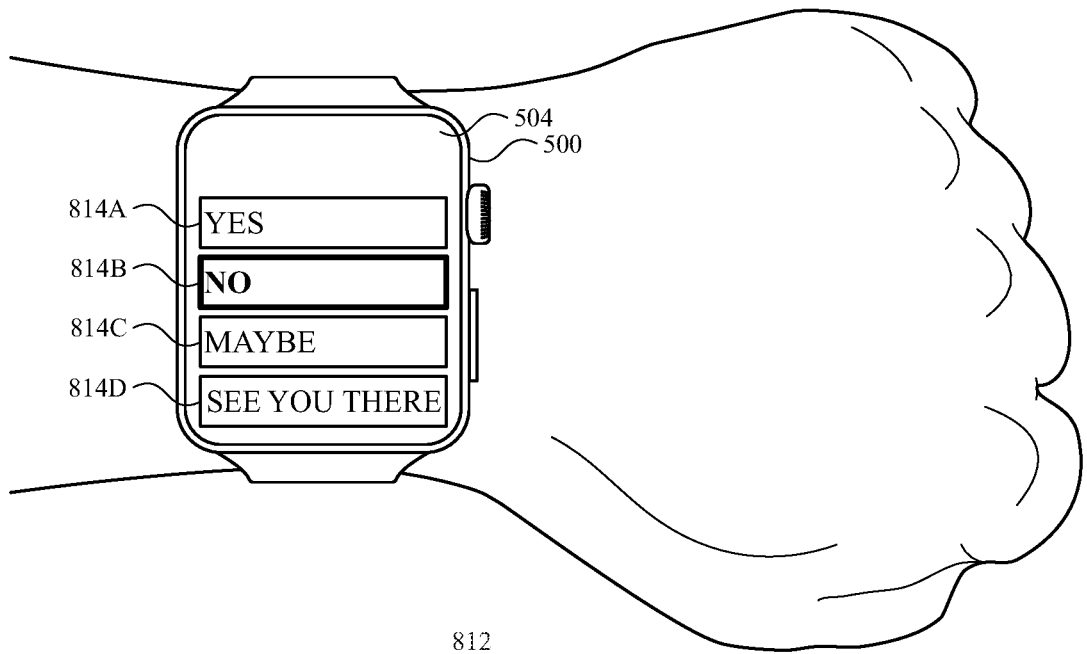
Figure 8J:
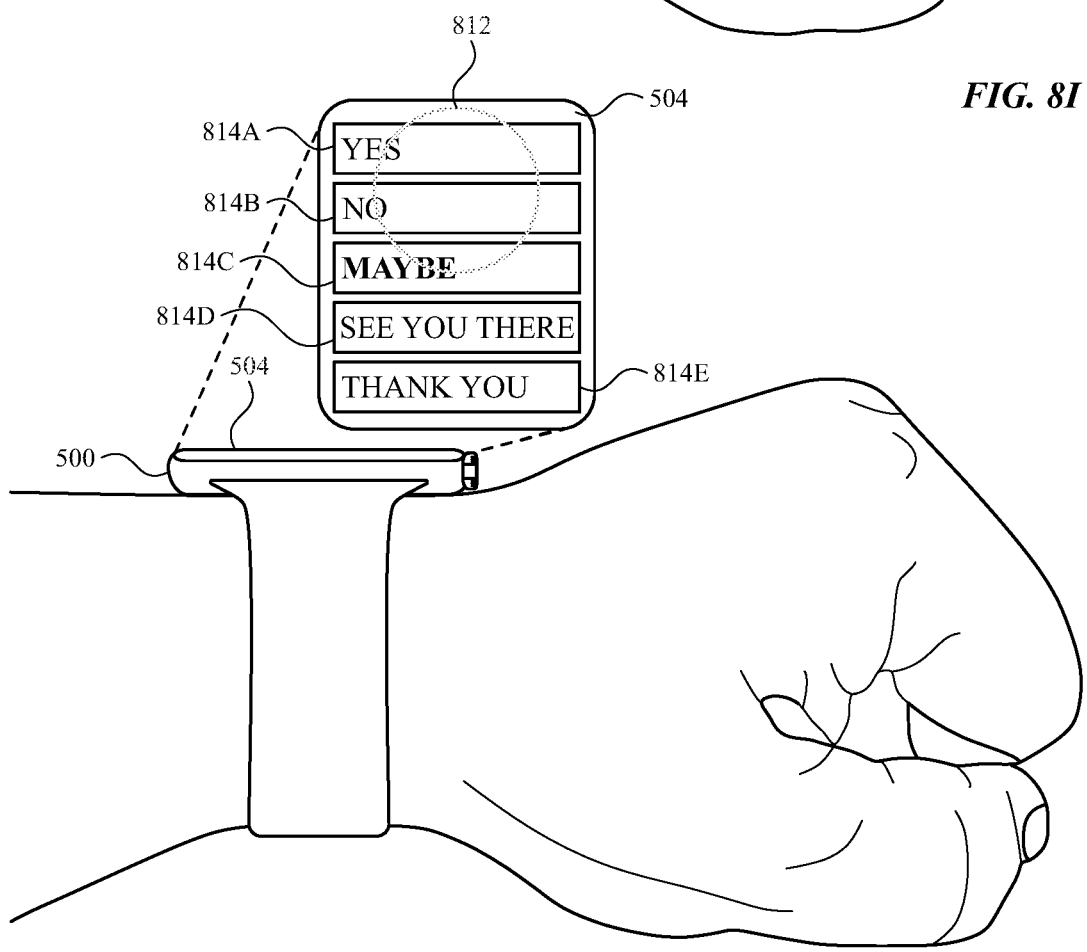
Figure 8K:
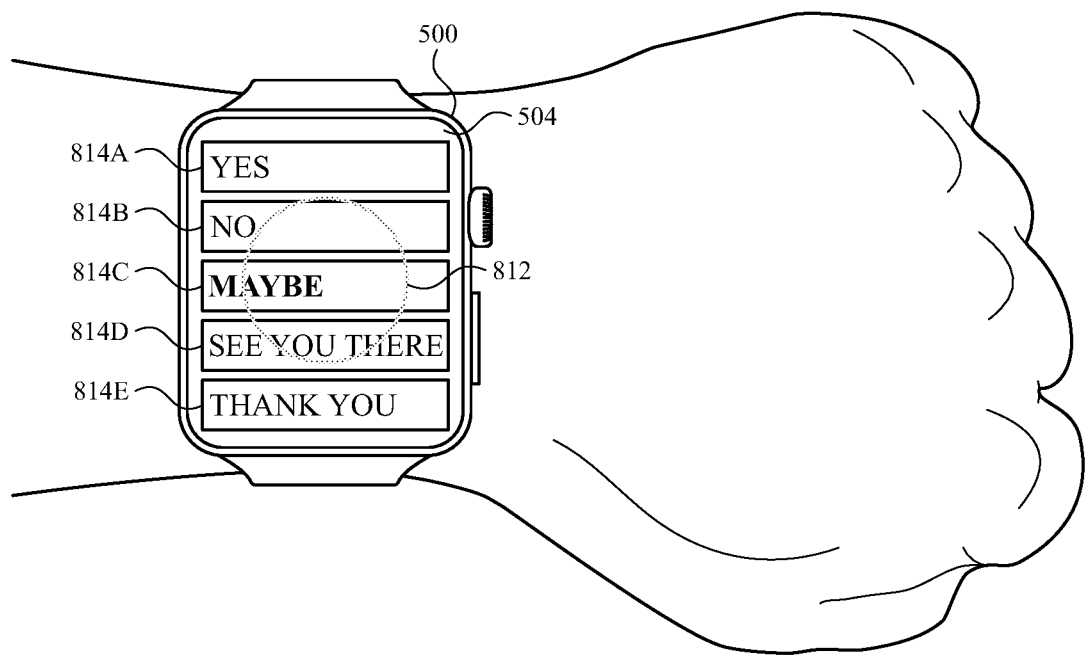
Figure 8L:
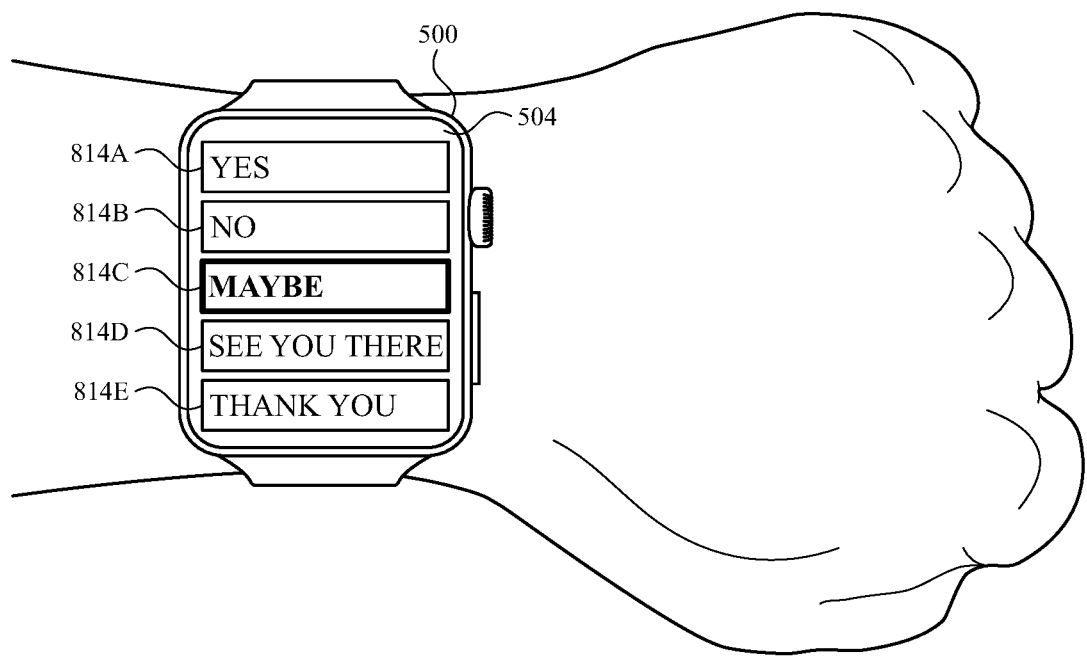
Figure 8M:
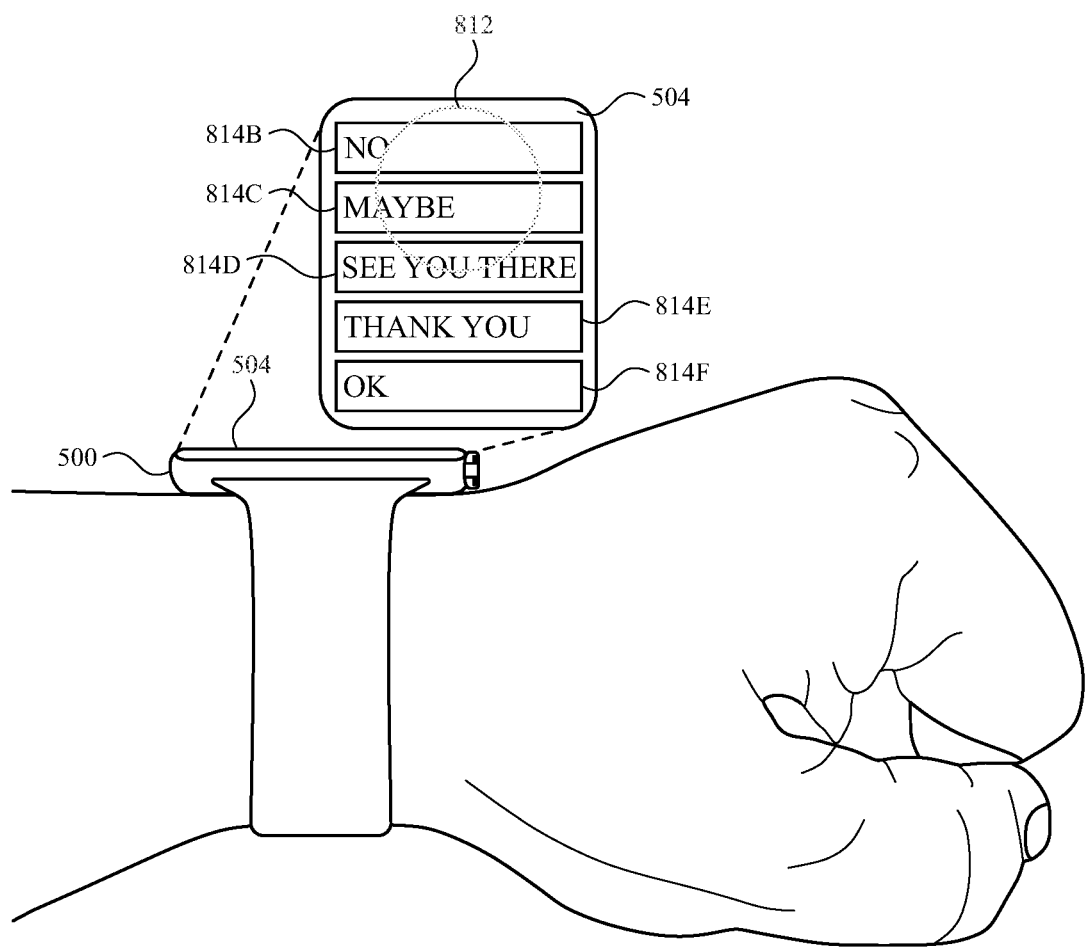
Figure 8N:
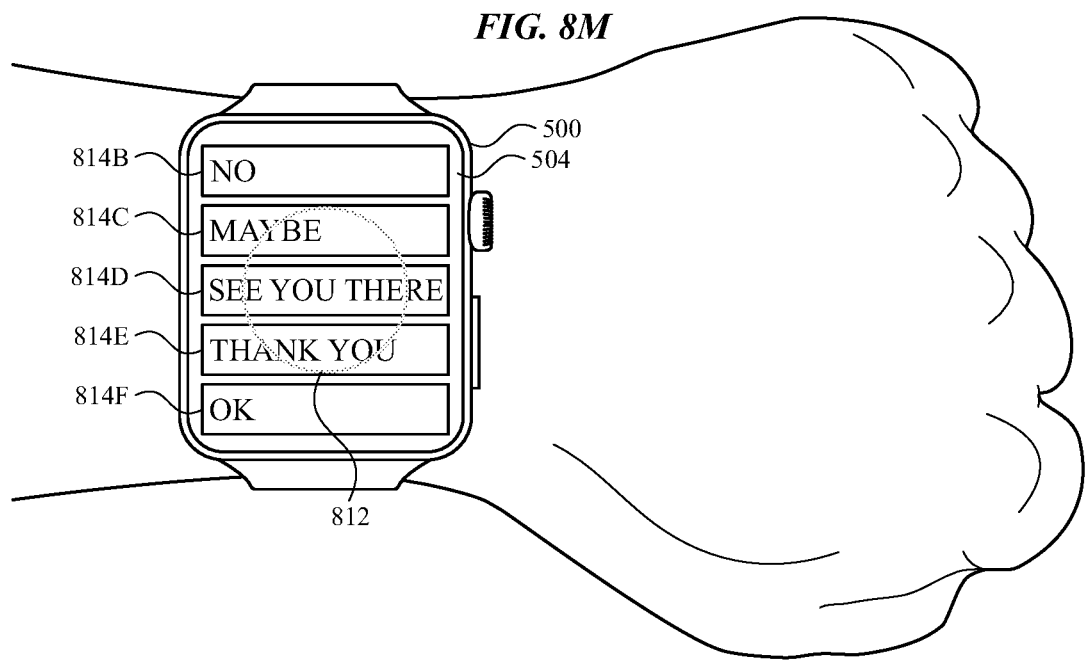
Figure 8O:
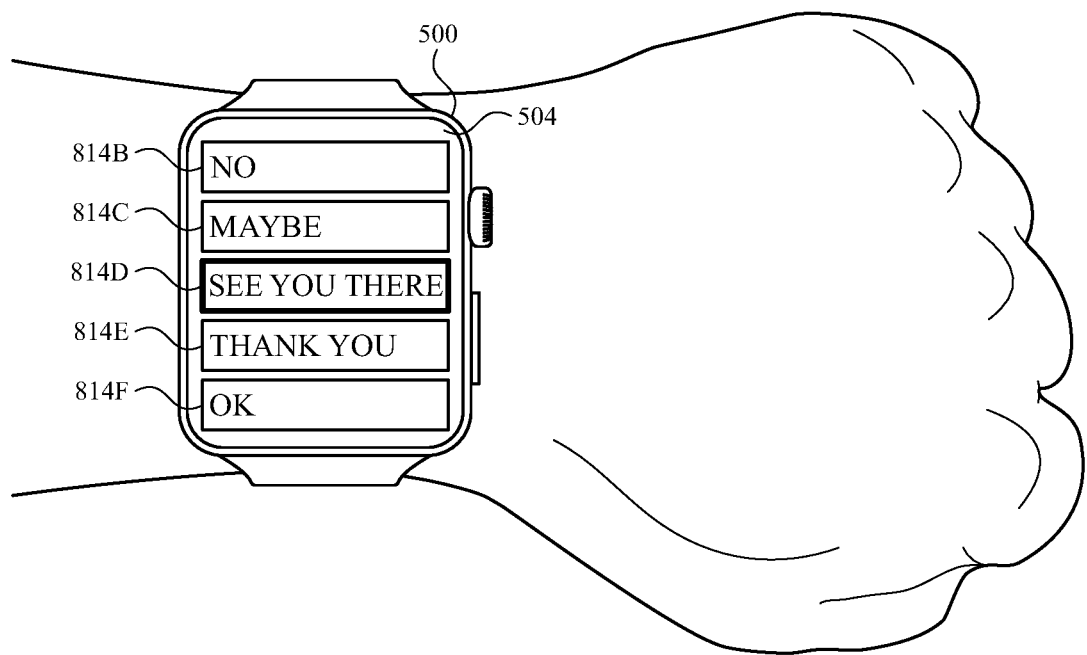
Figure 8P:
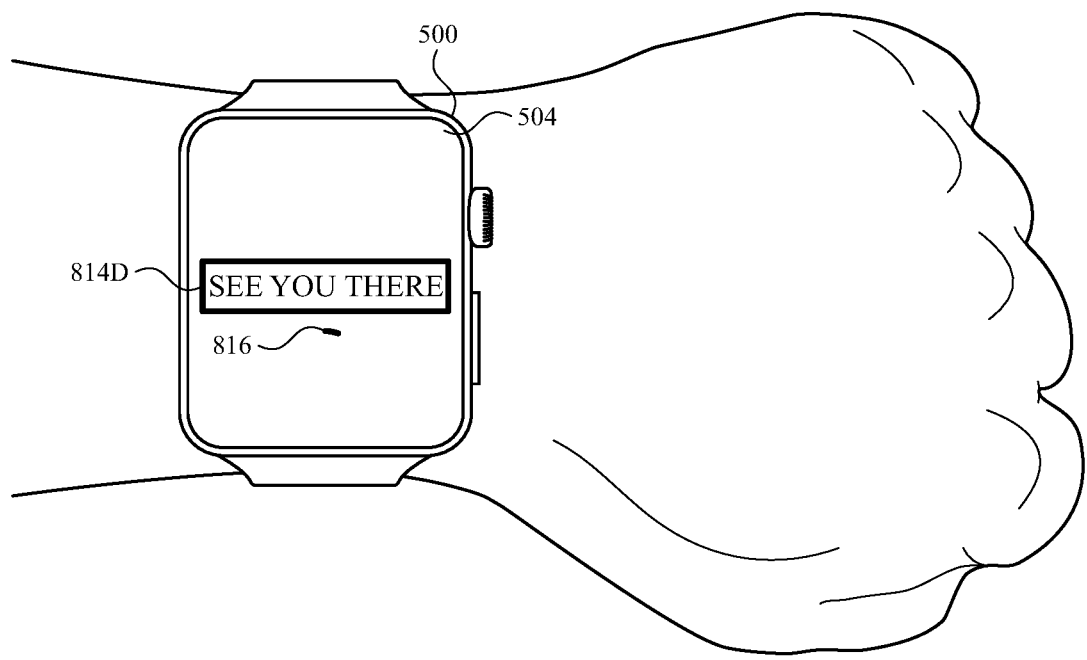
Figure 8Q:
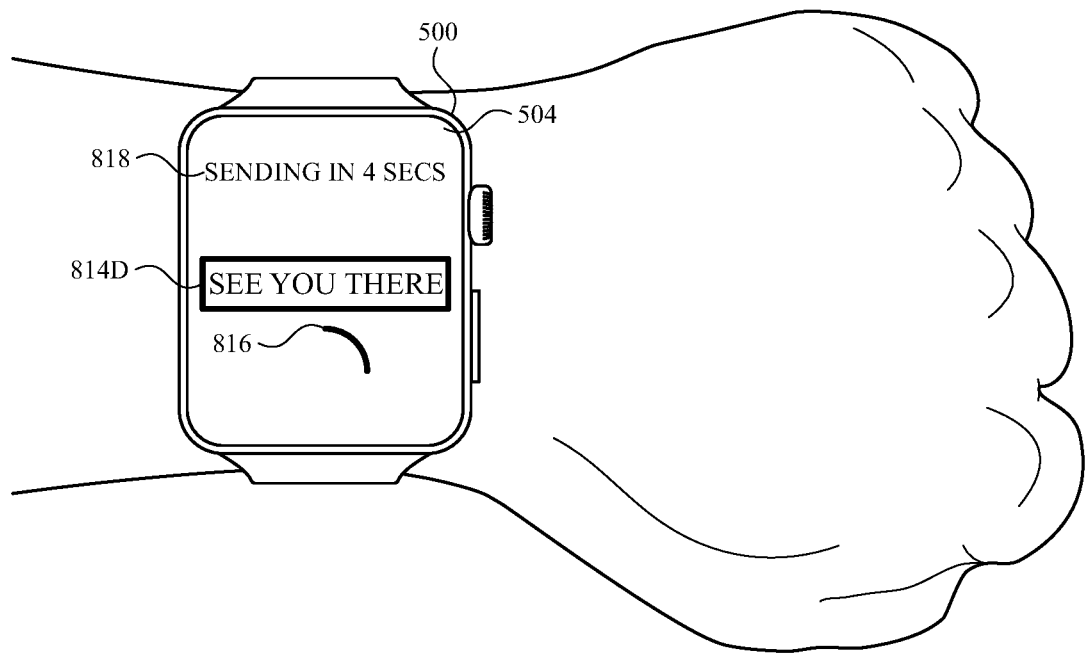
Figure 8R:
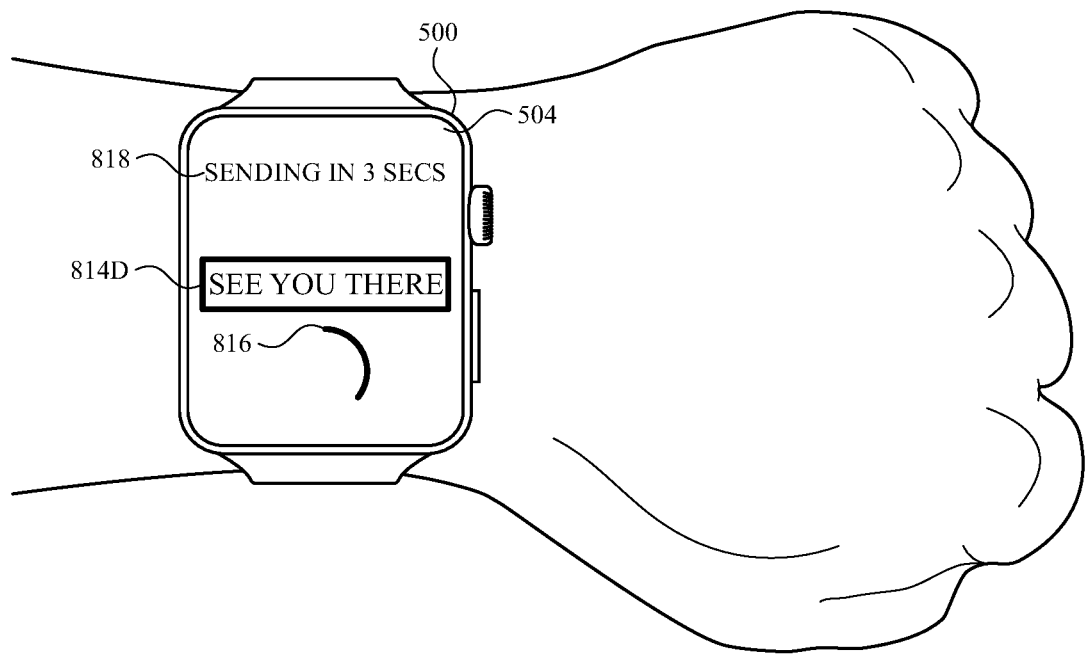
Figure 8S:
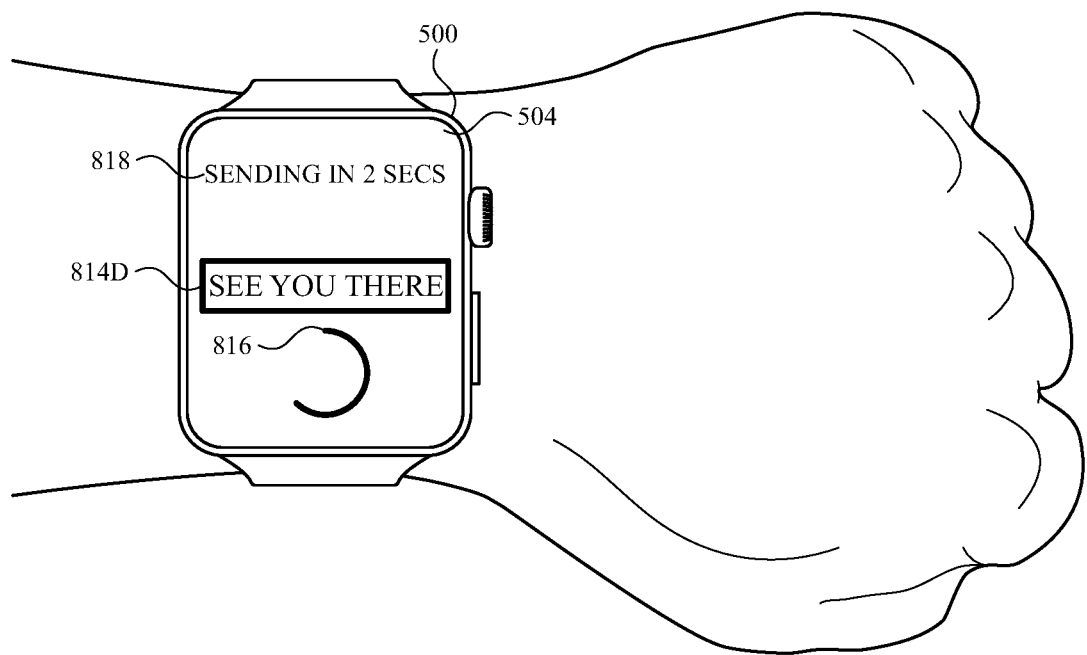
Figure 8T:
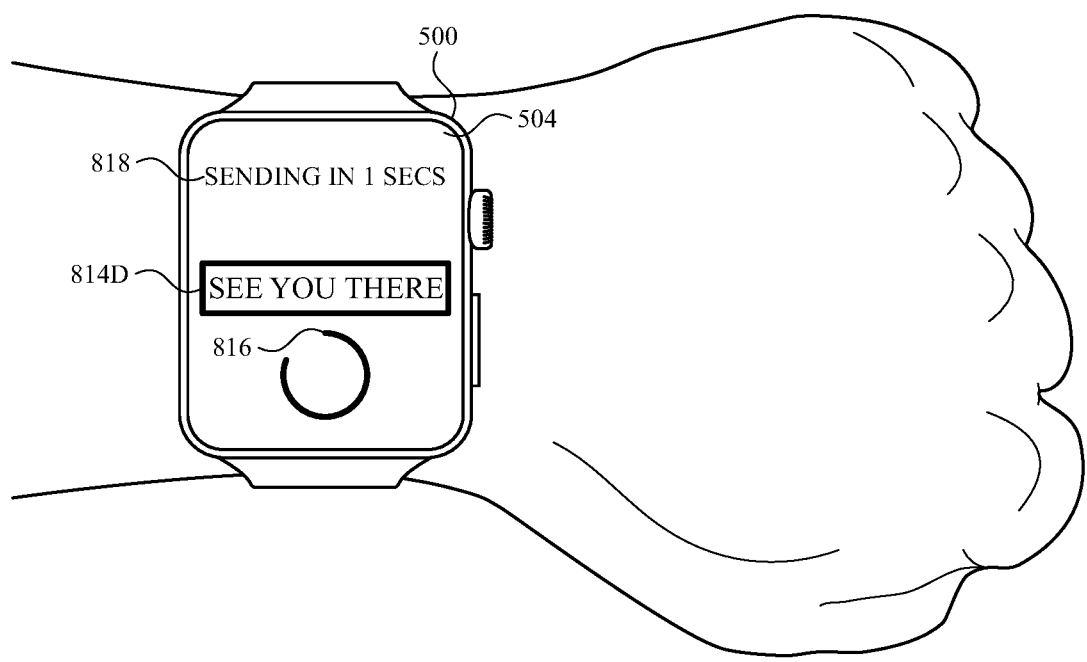
Figure 8U:
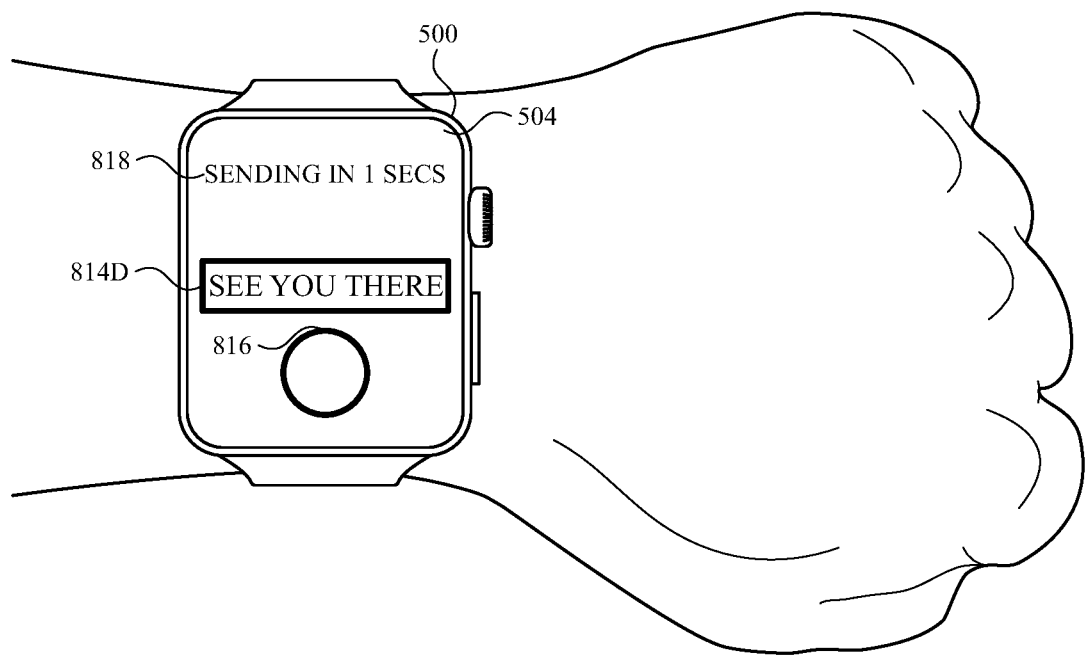
Figure 8V:
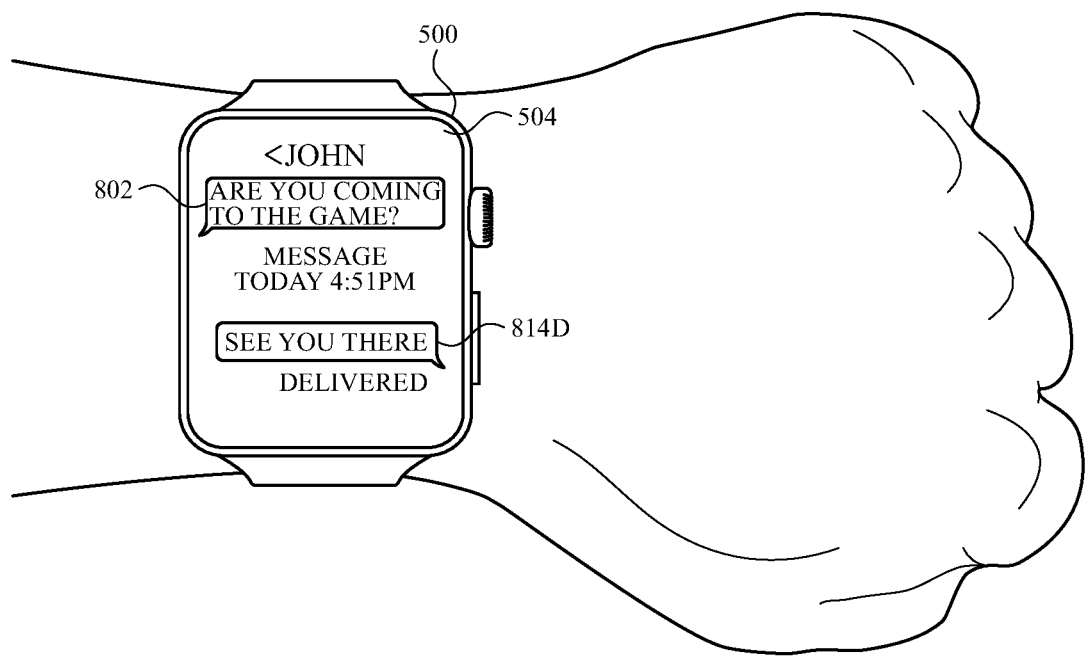
Figure 8W:
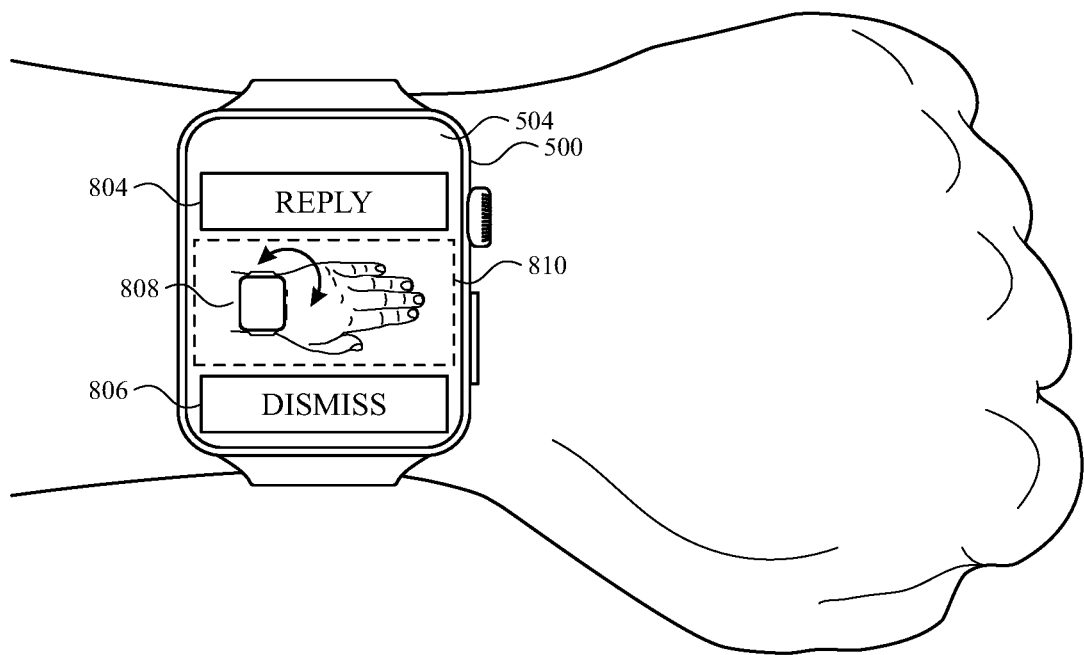
Figure 8X:
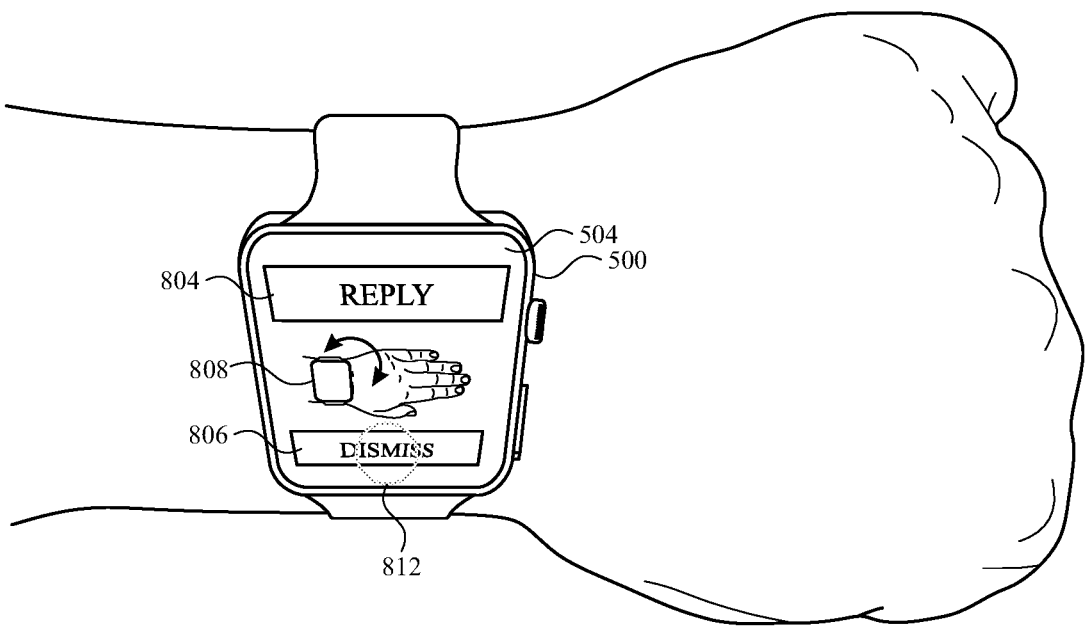
Figure 8Y:
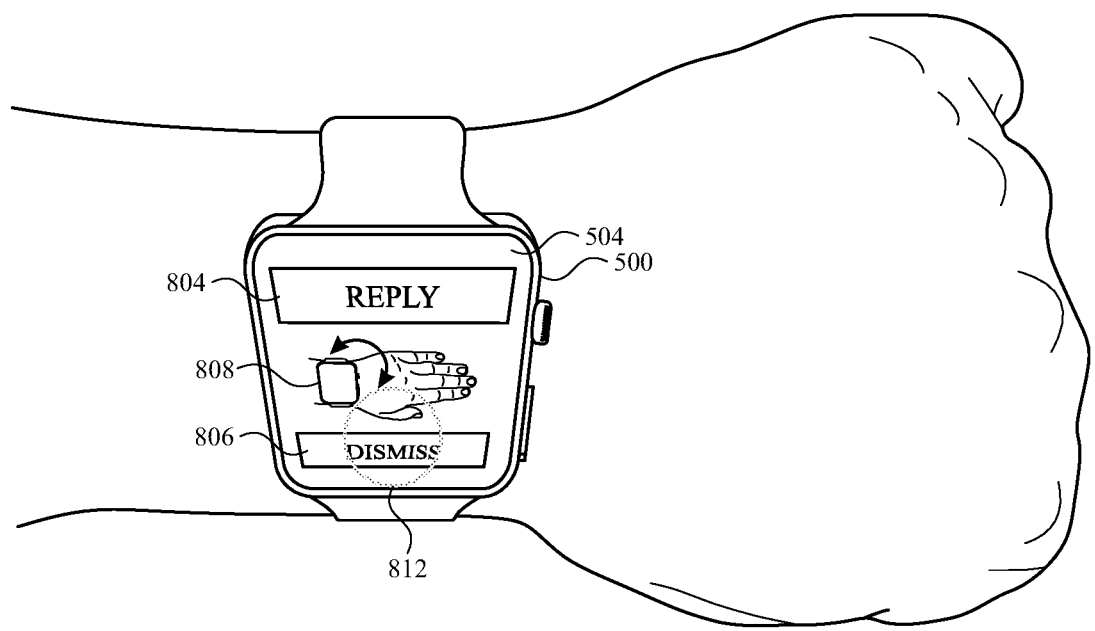
Figure 8Z:
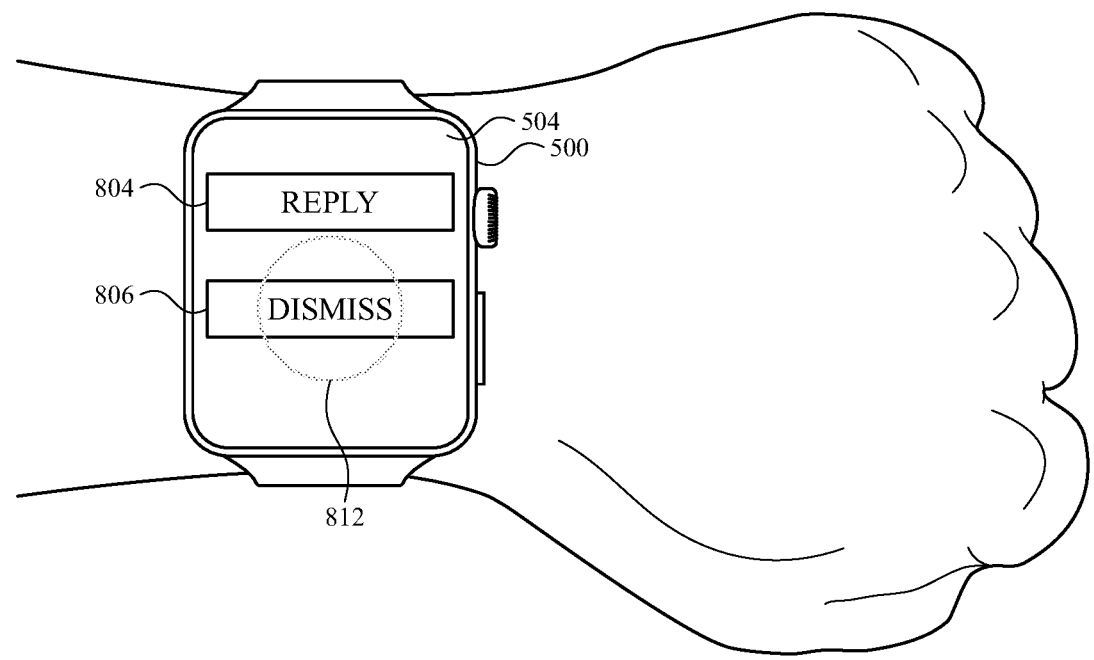
Figure 8A:
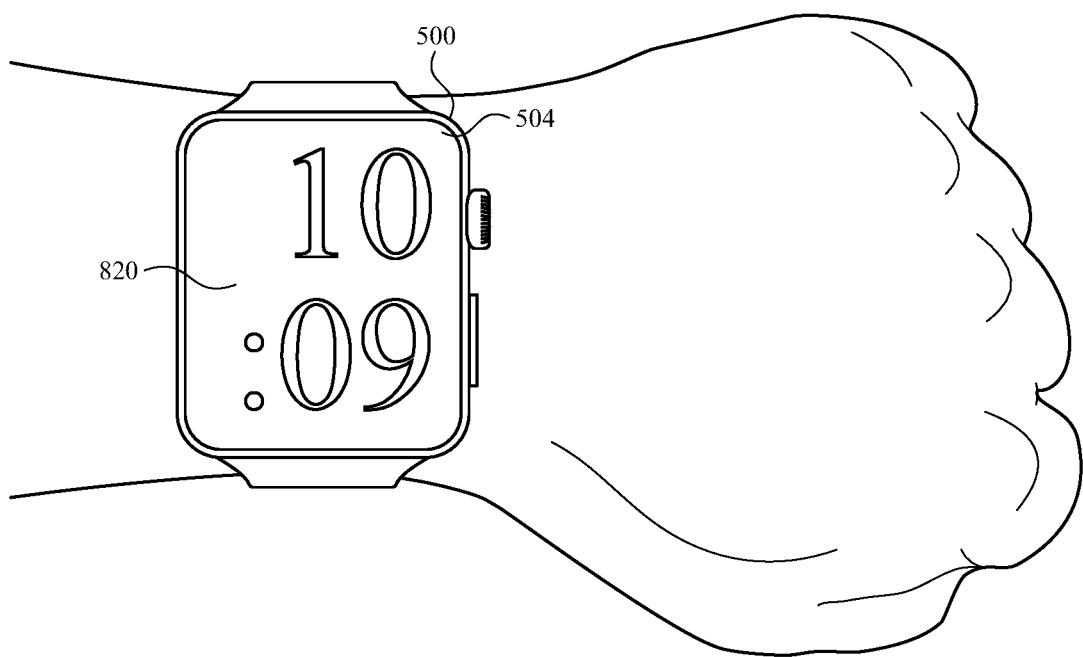
Figure 8A:
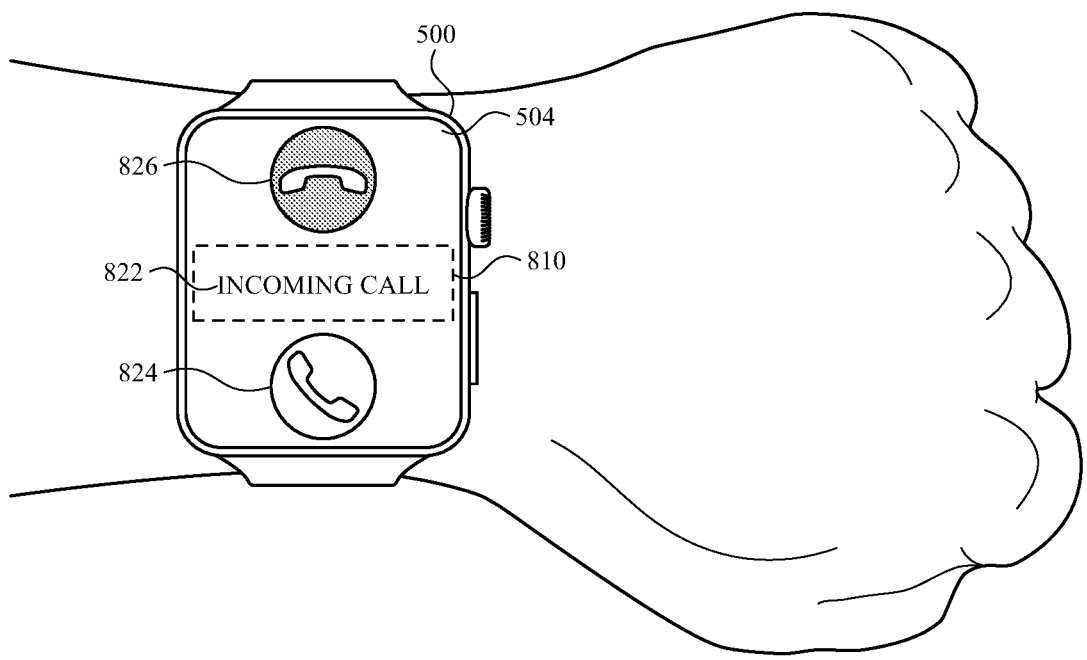
Figure 8A:
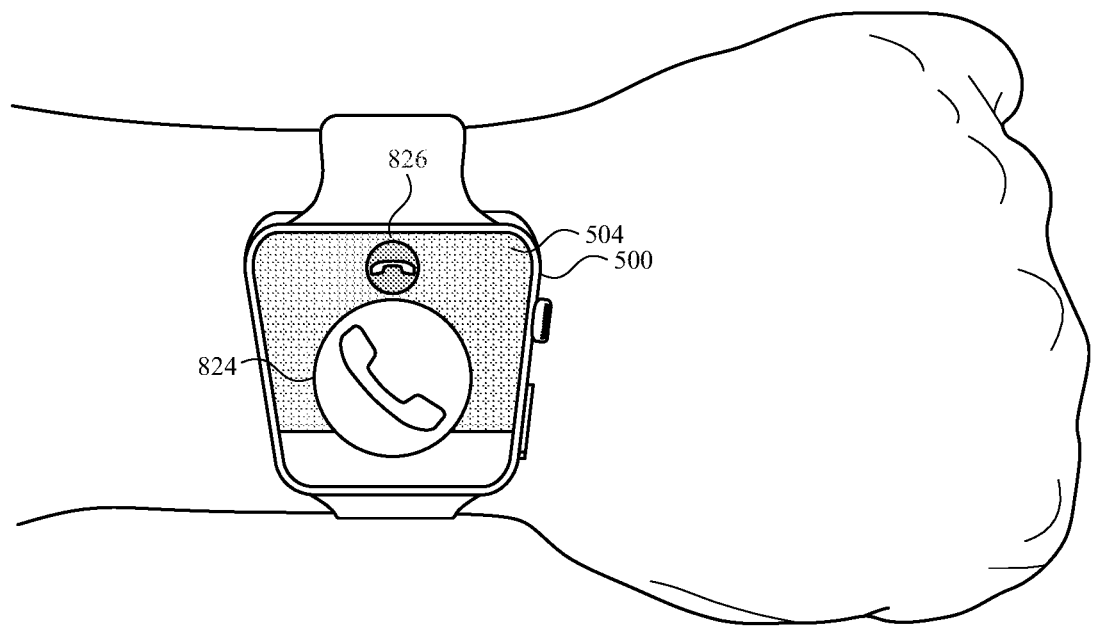
Figure 8A:
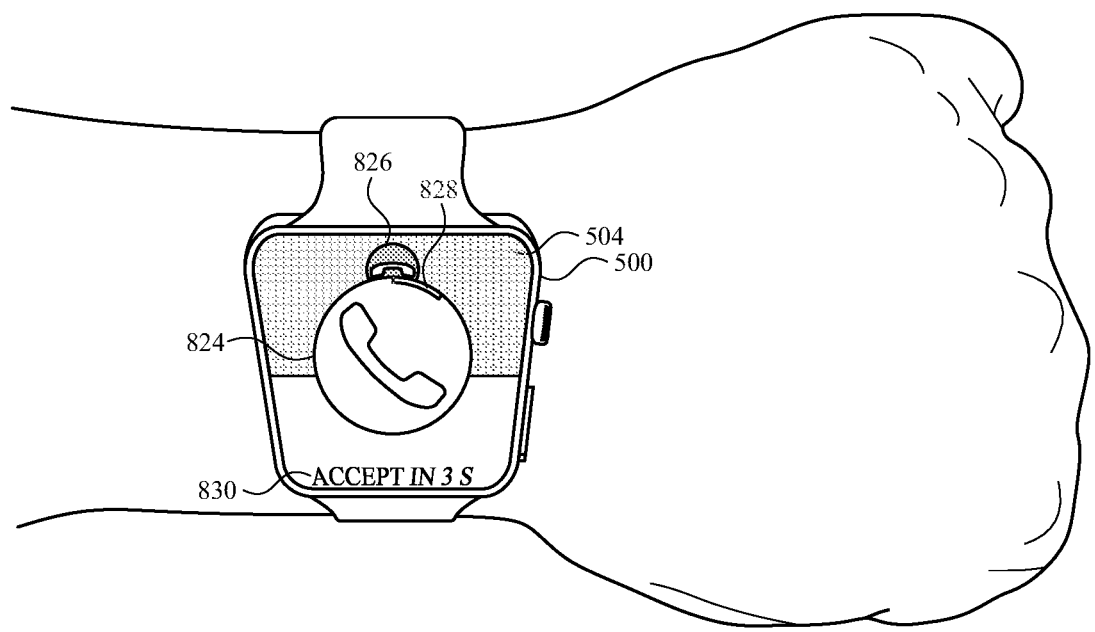
Figure 8A:
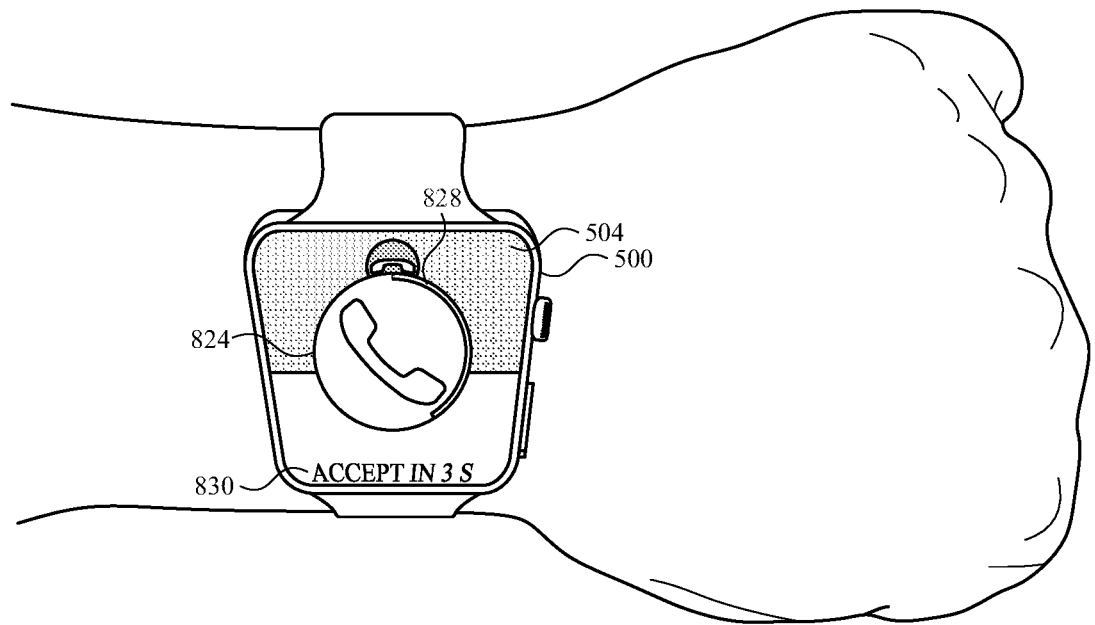
Figure 8A:
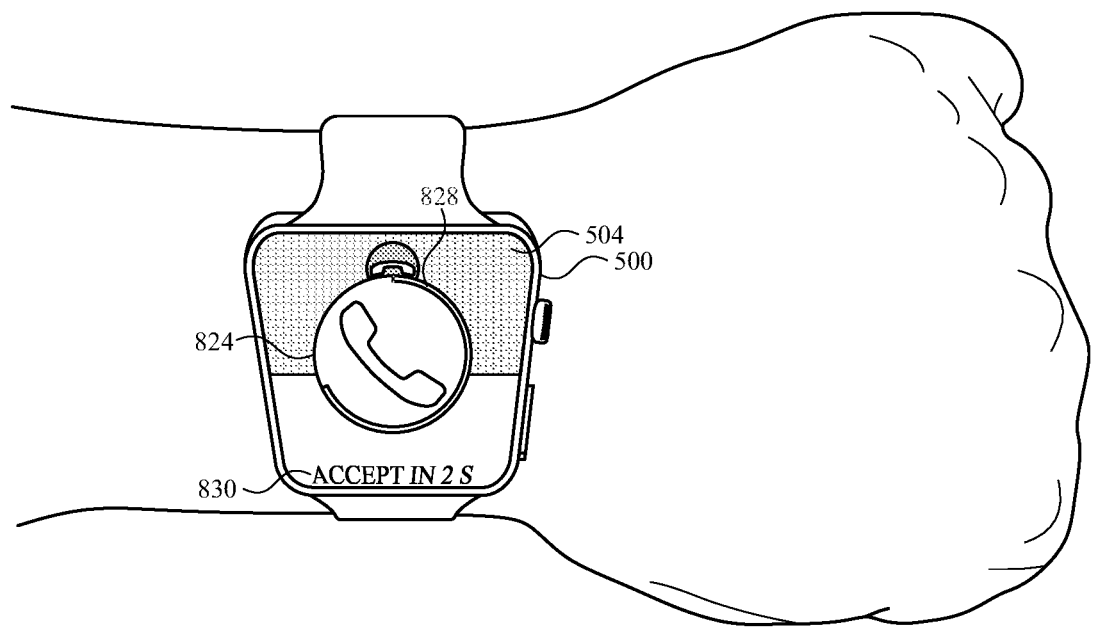
Figure 8A:
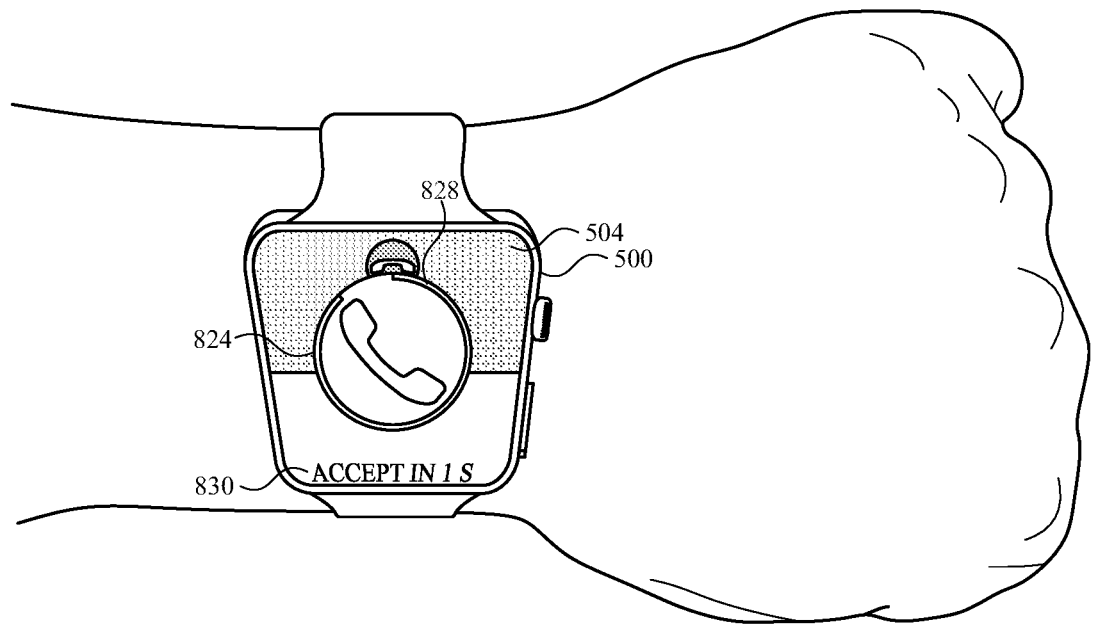
Figure 8A:
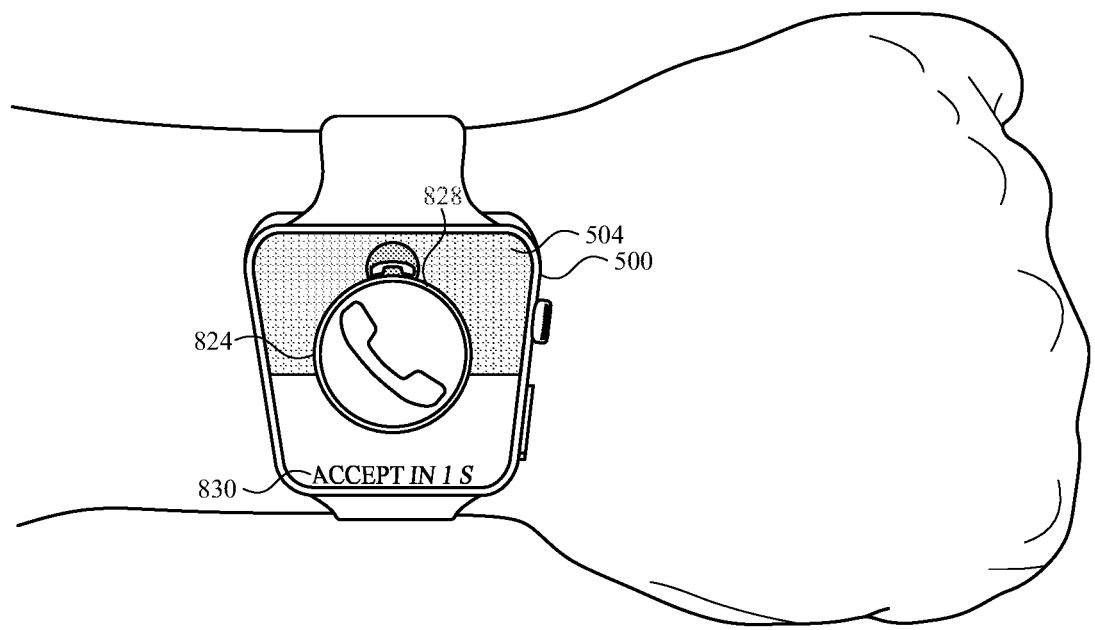
Figure 8A:
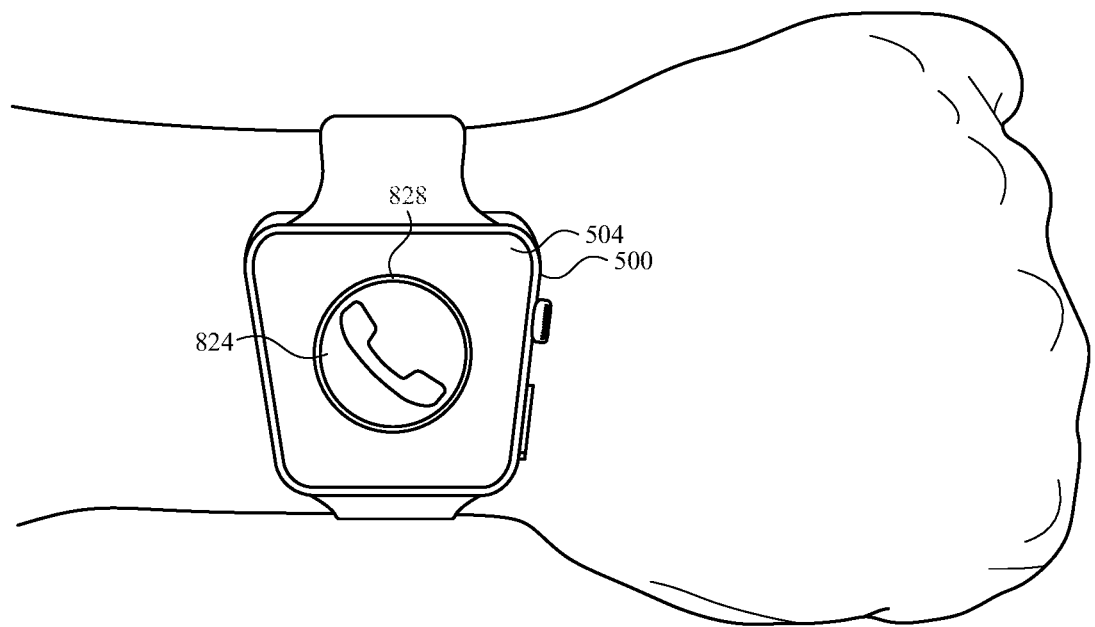
Figure 8A:
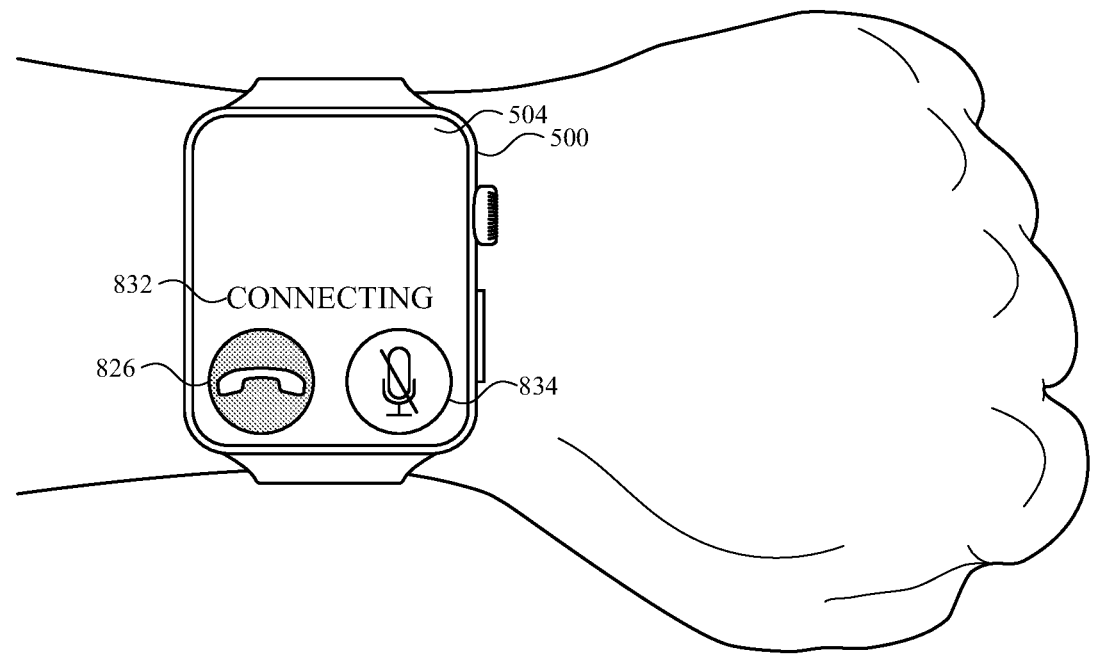
Figure 8A:
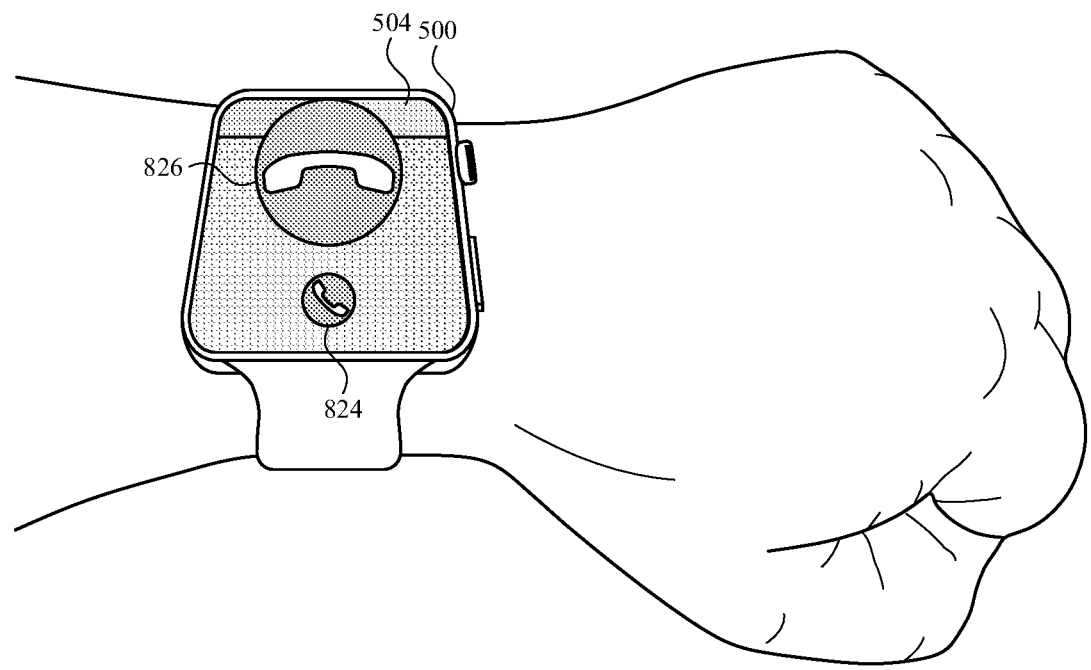
Figure 8A:
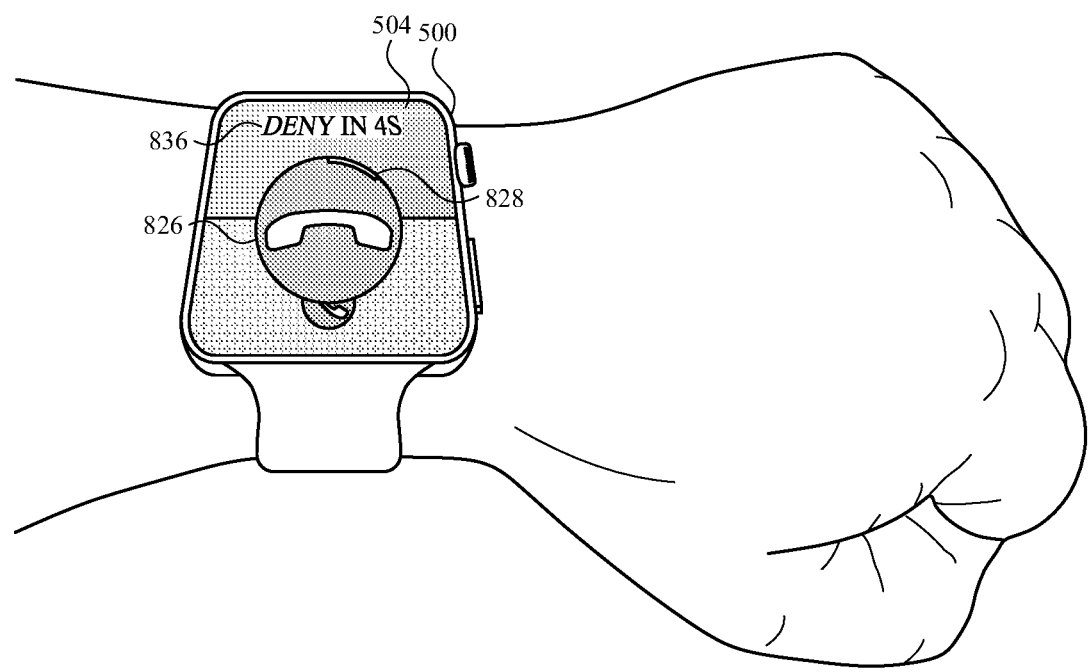
Figure 8A:
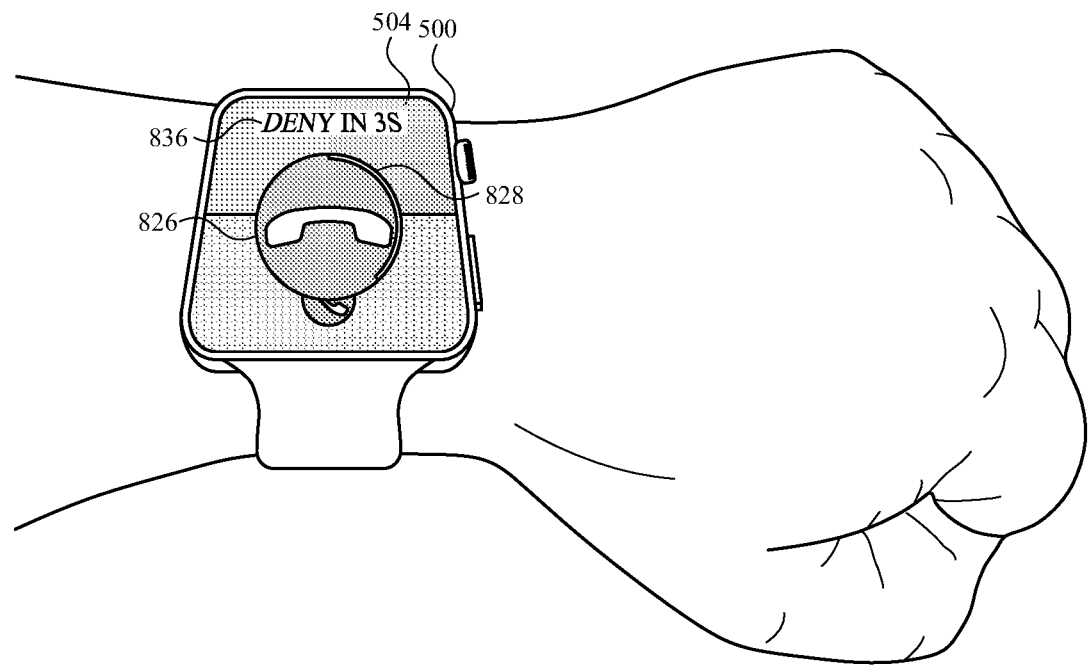
Figure 8A:
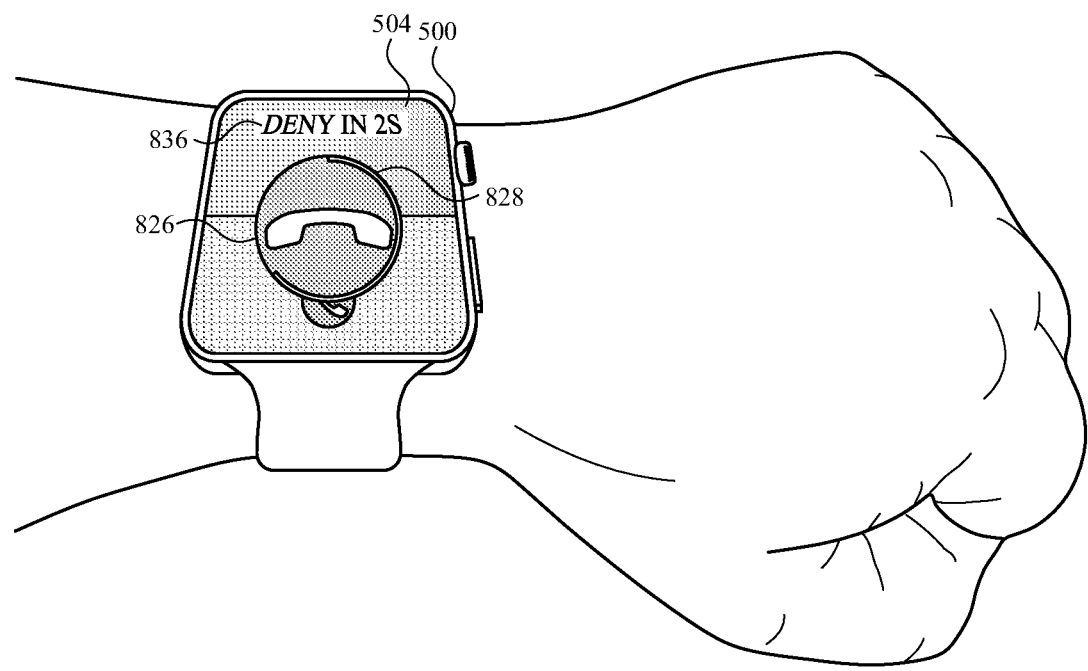
Figure 8A:
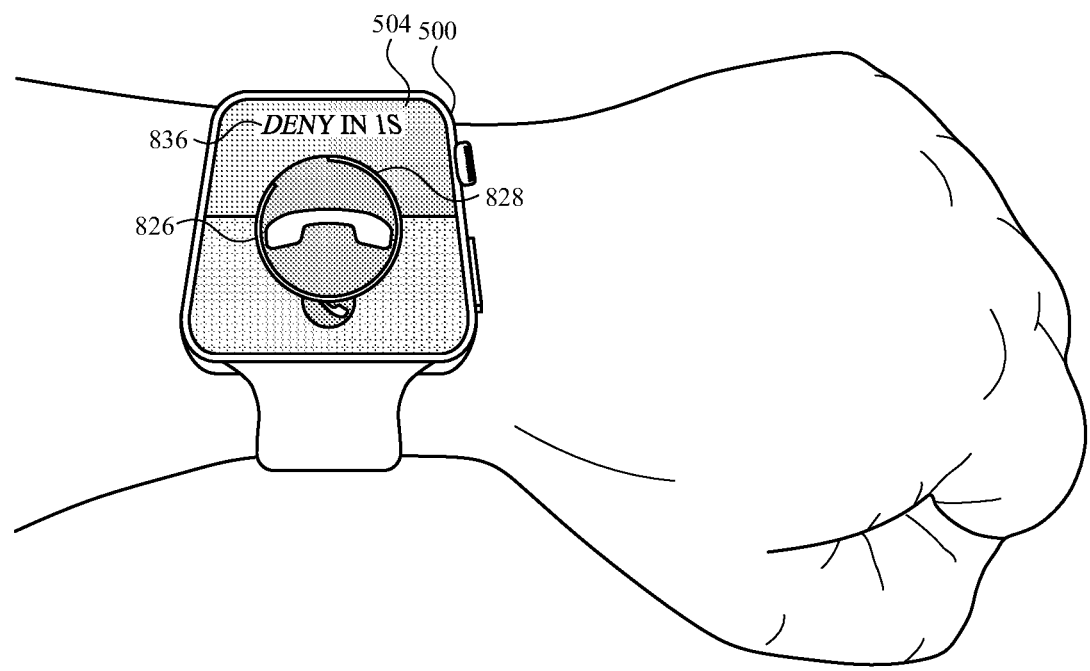
Figure 8A:
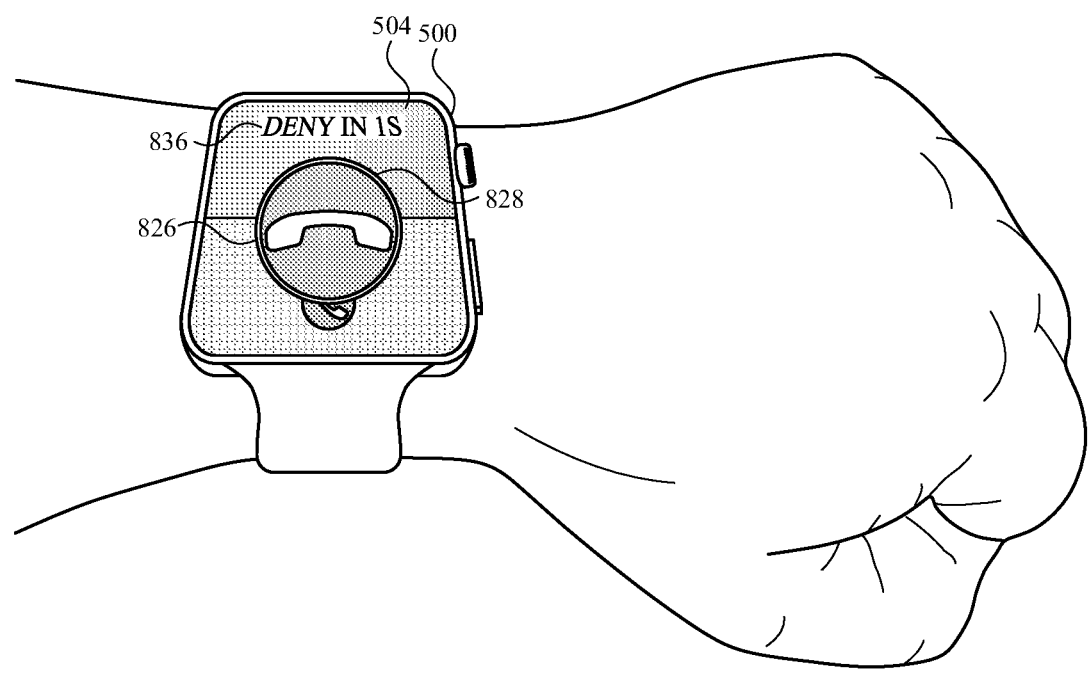
Figure 8A:
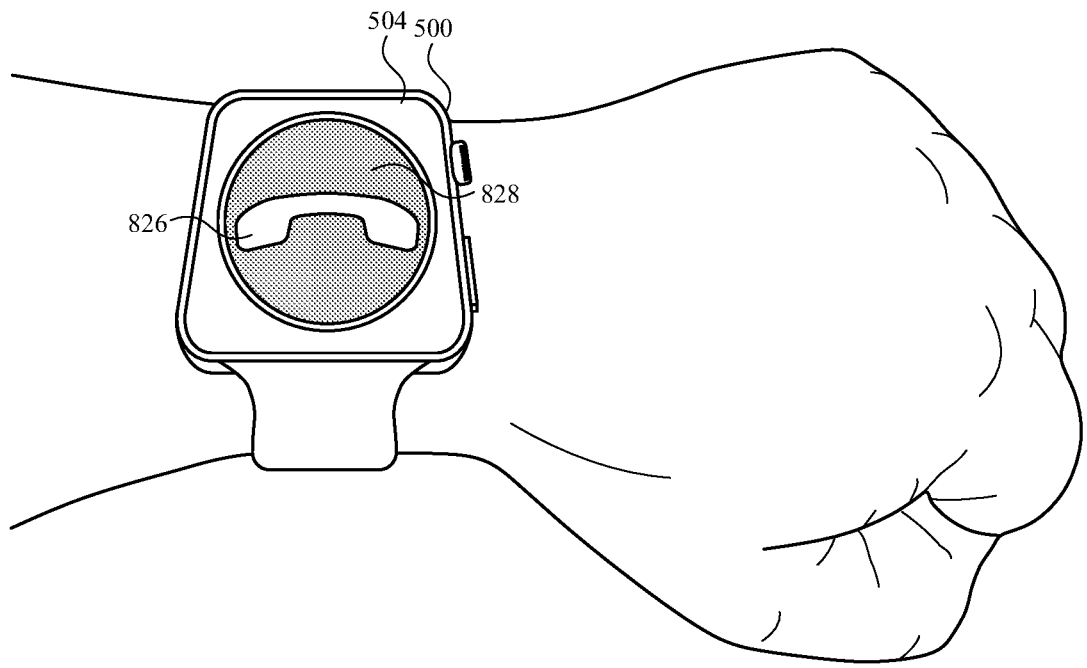
Figure 8A:
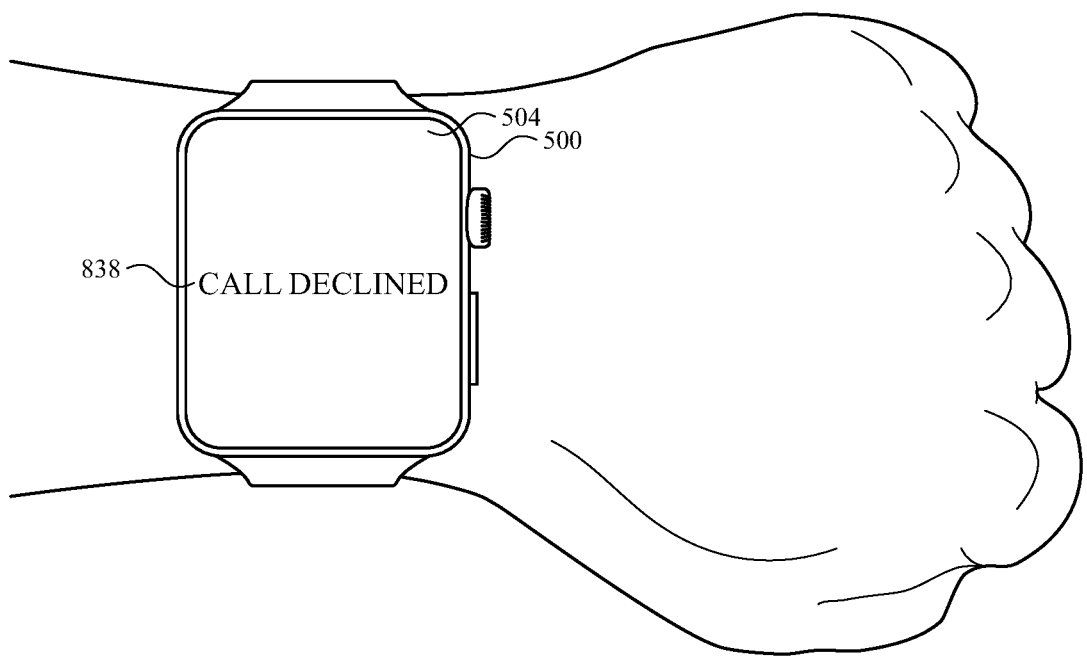
Figure 8A:
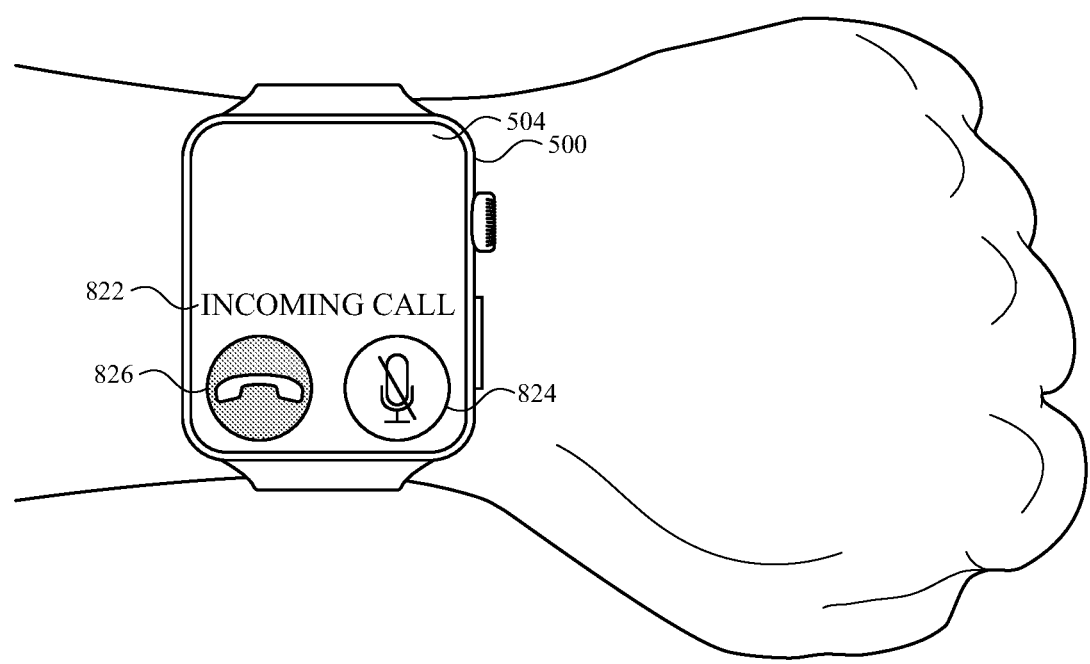
Figure 8A:
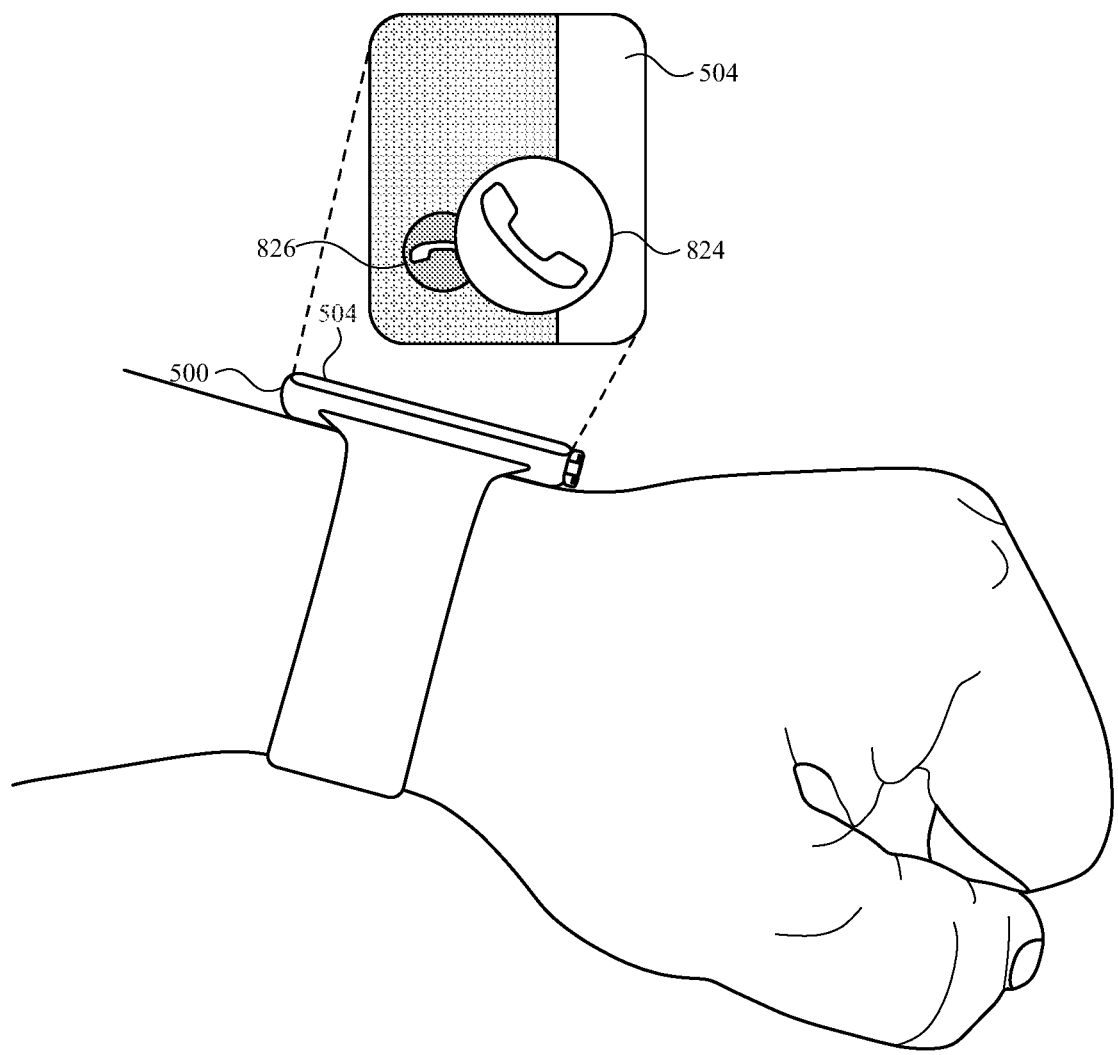
Figure 8A:
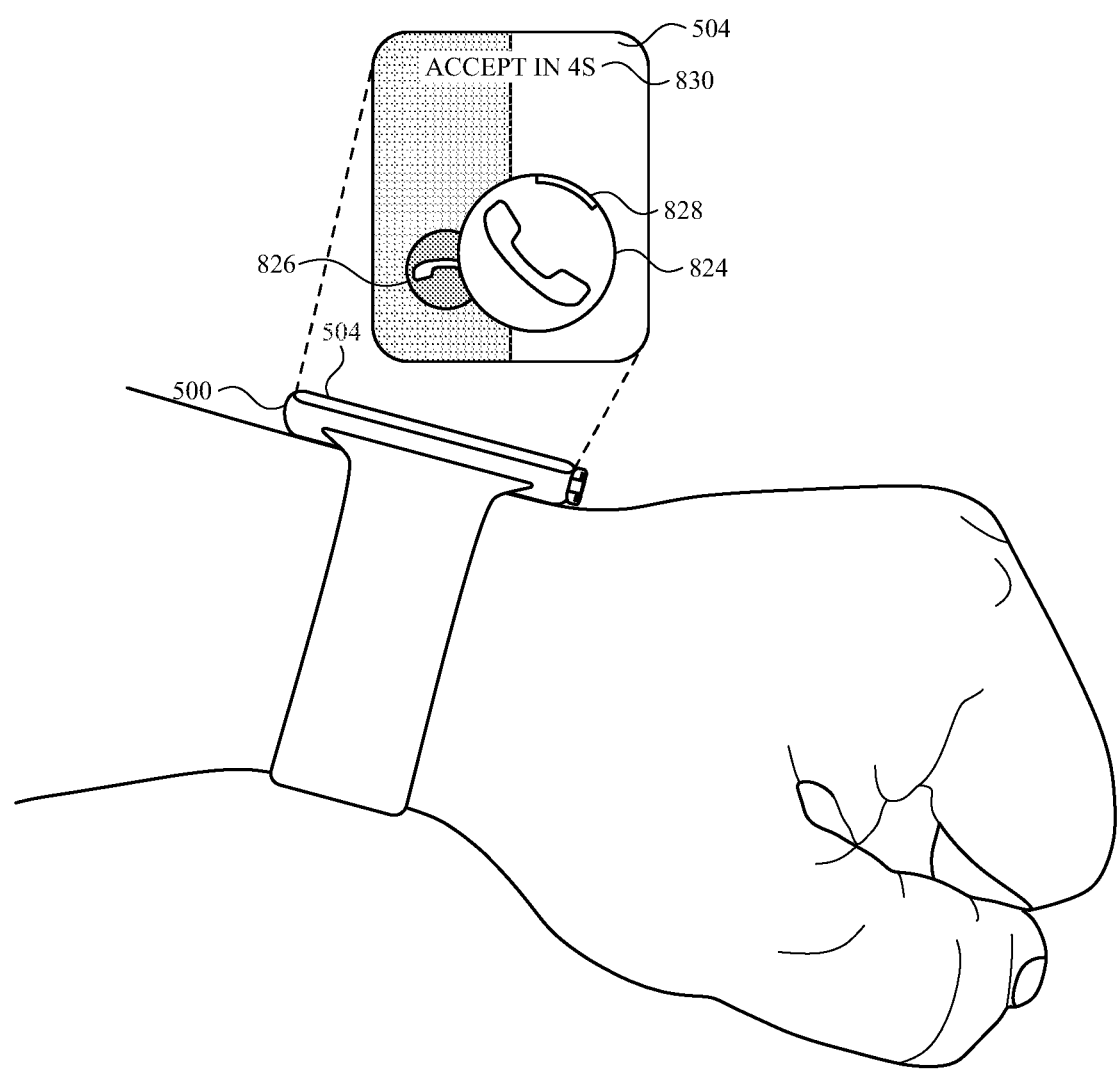
Figure 8A:
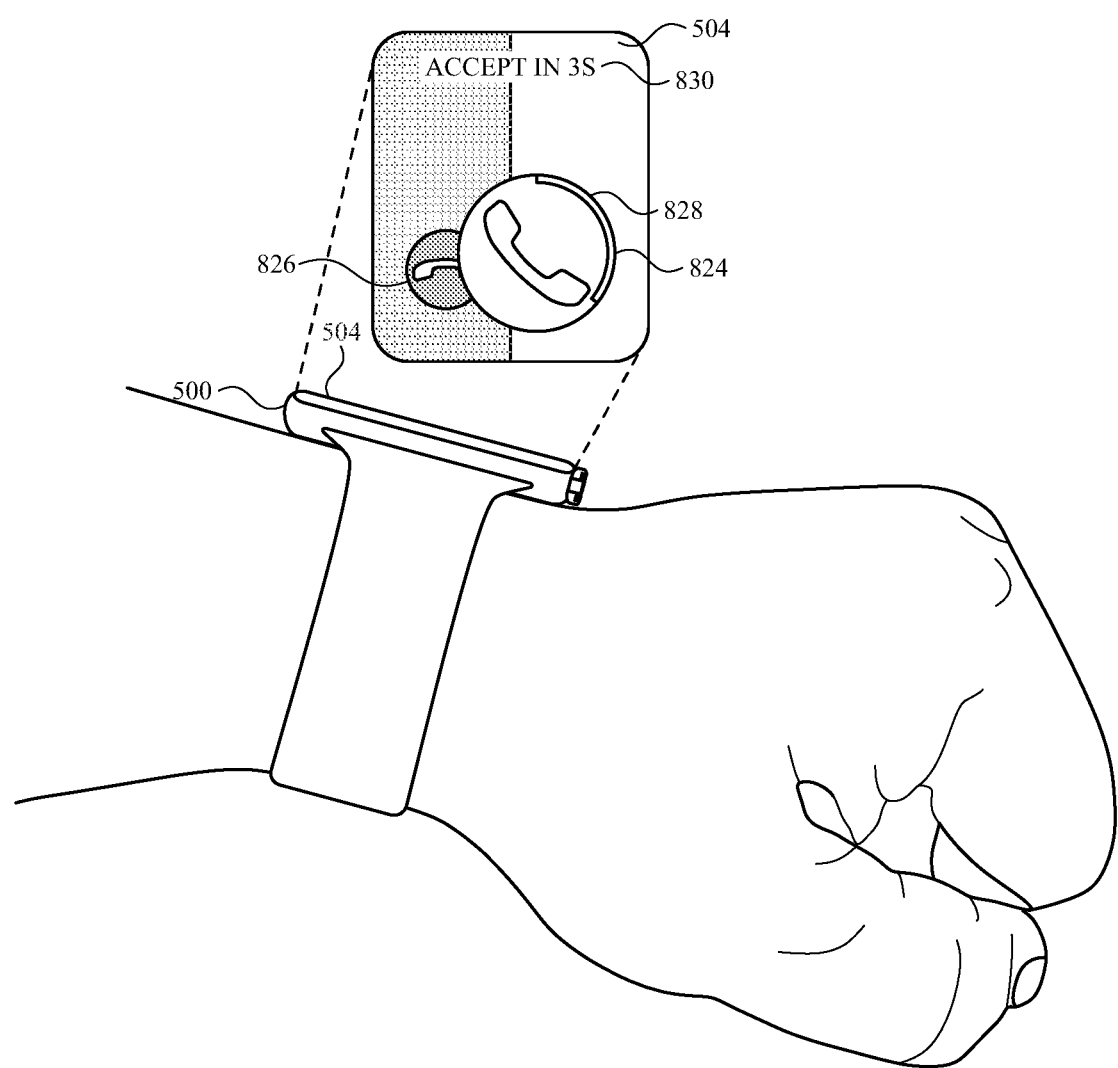
Figure 8A:
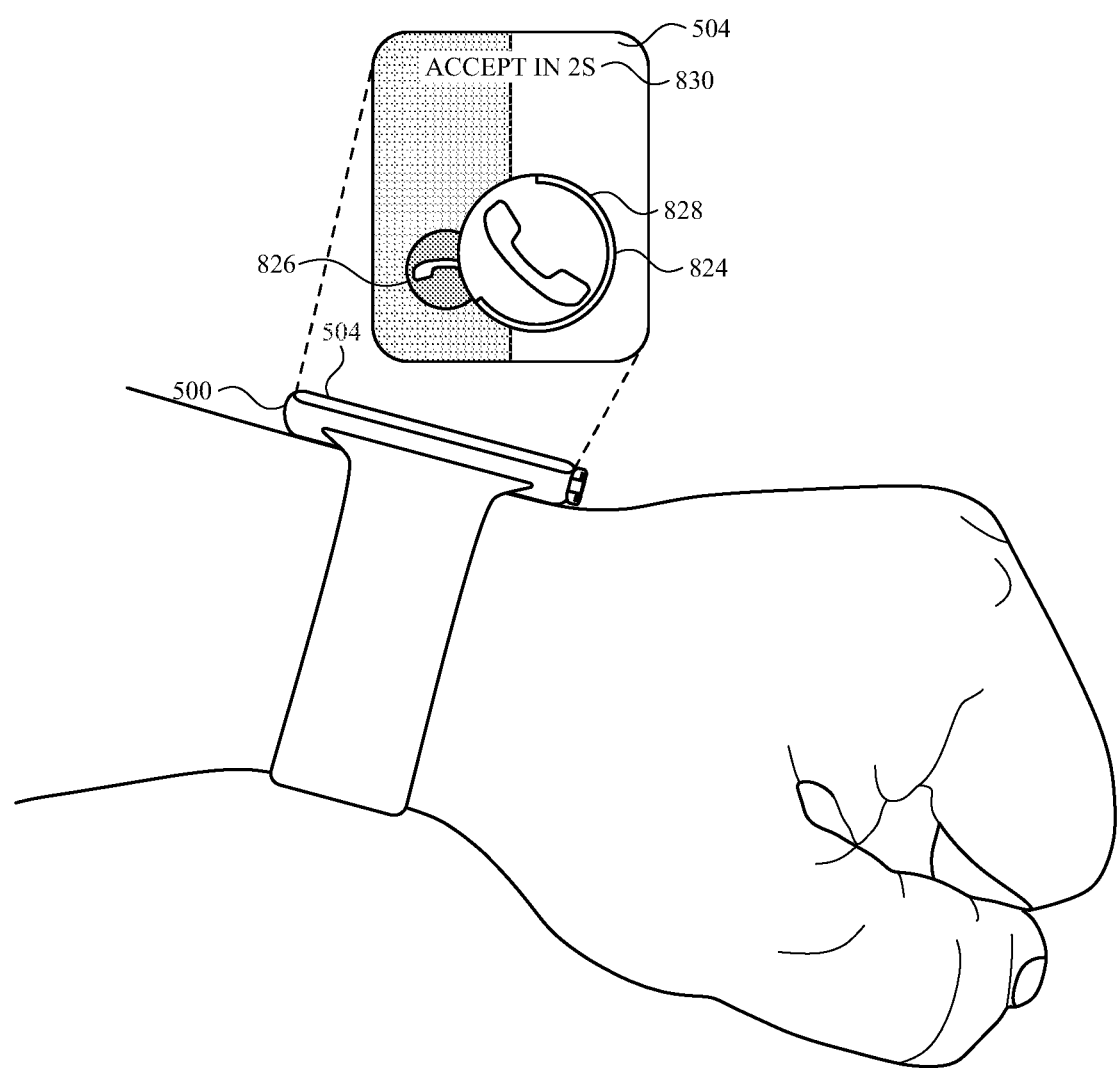
Figure 8A:
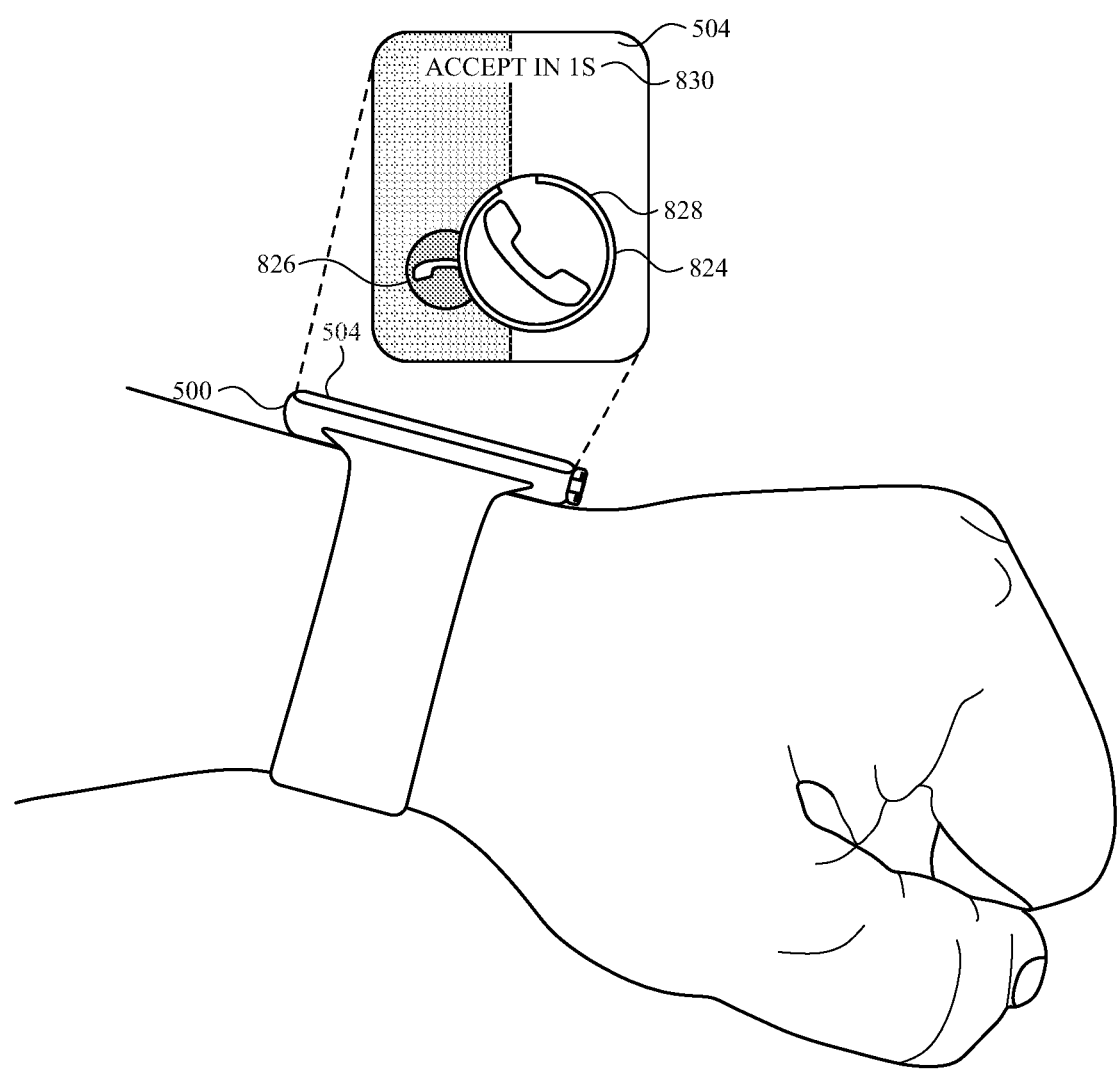
Figure 8A:
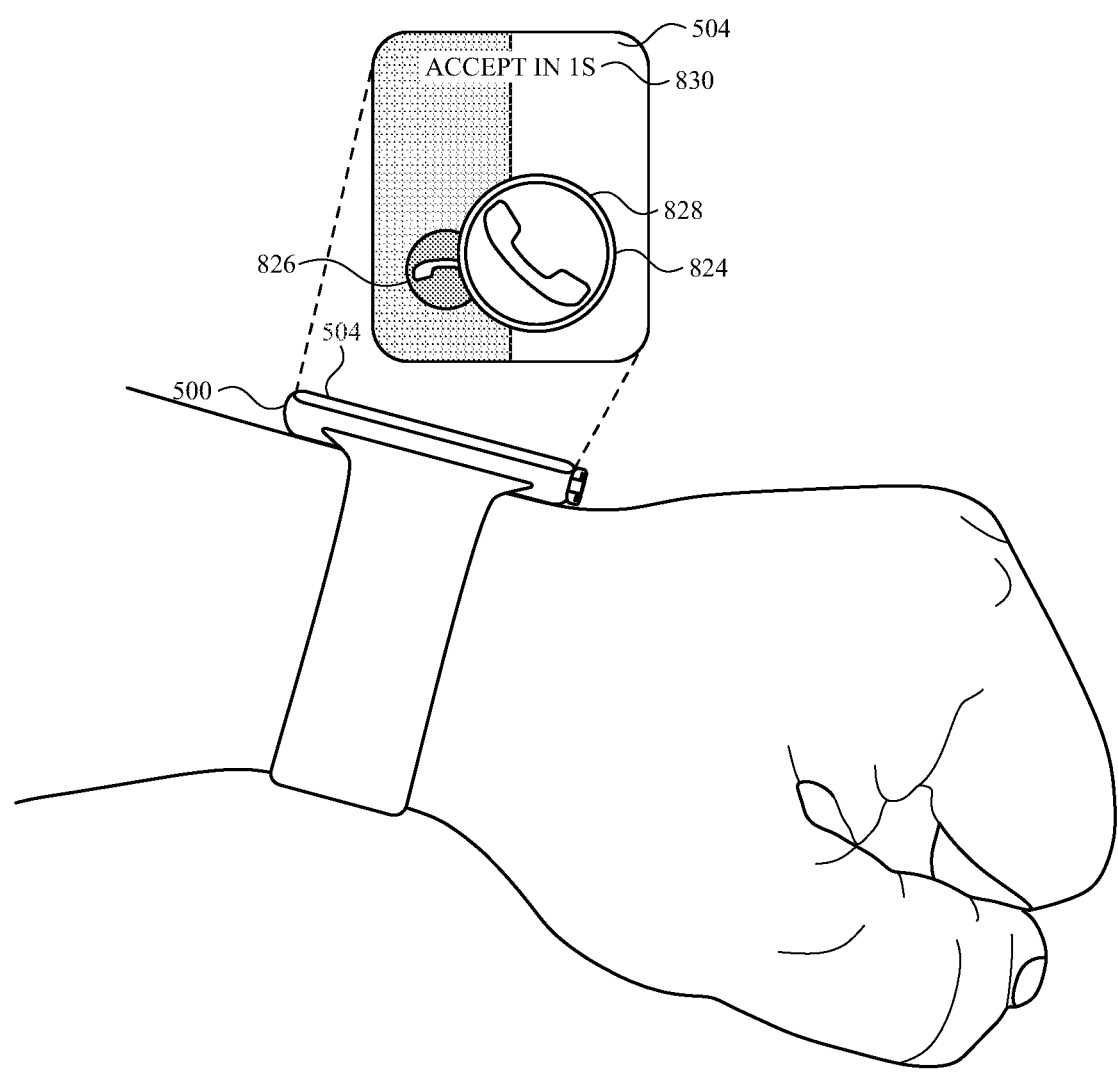
Figure 8A:
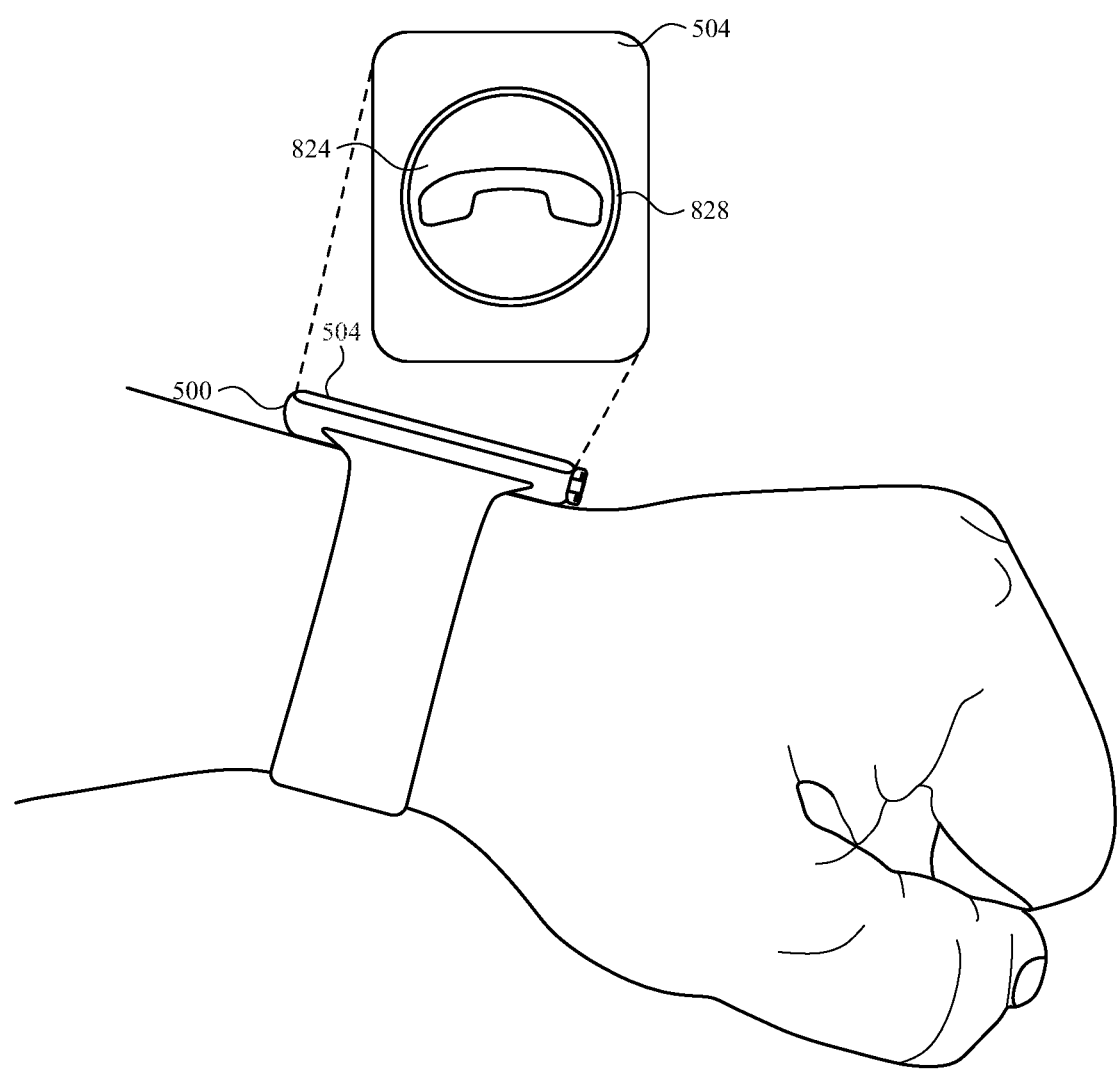
Figure 8B:
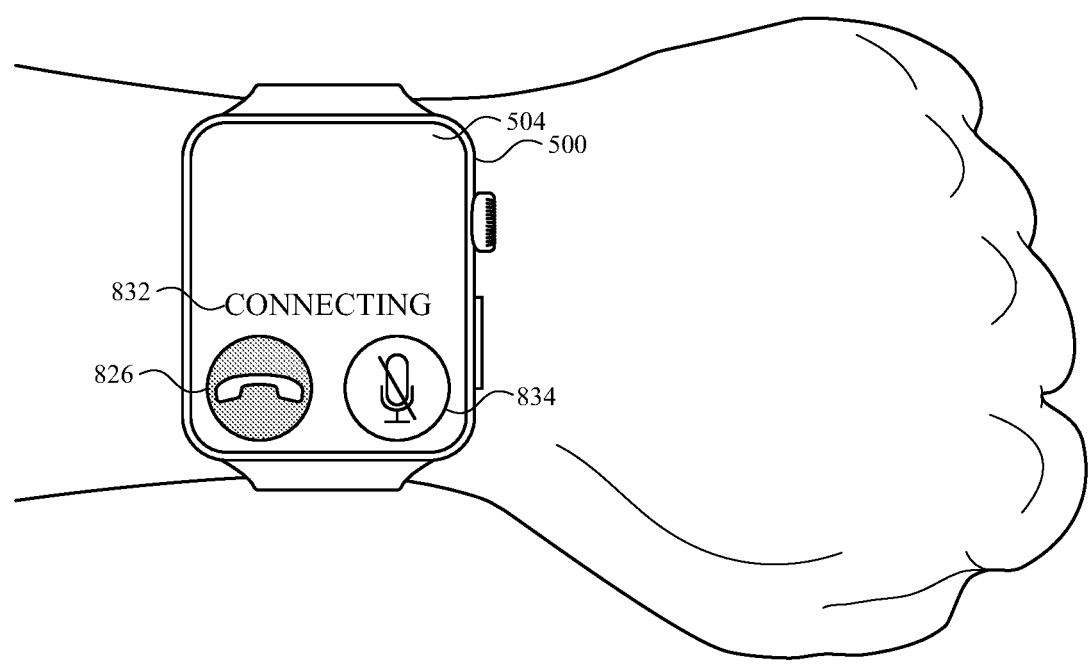
Figure 8B:
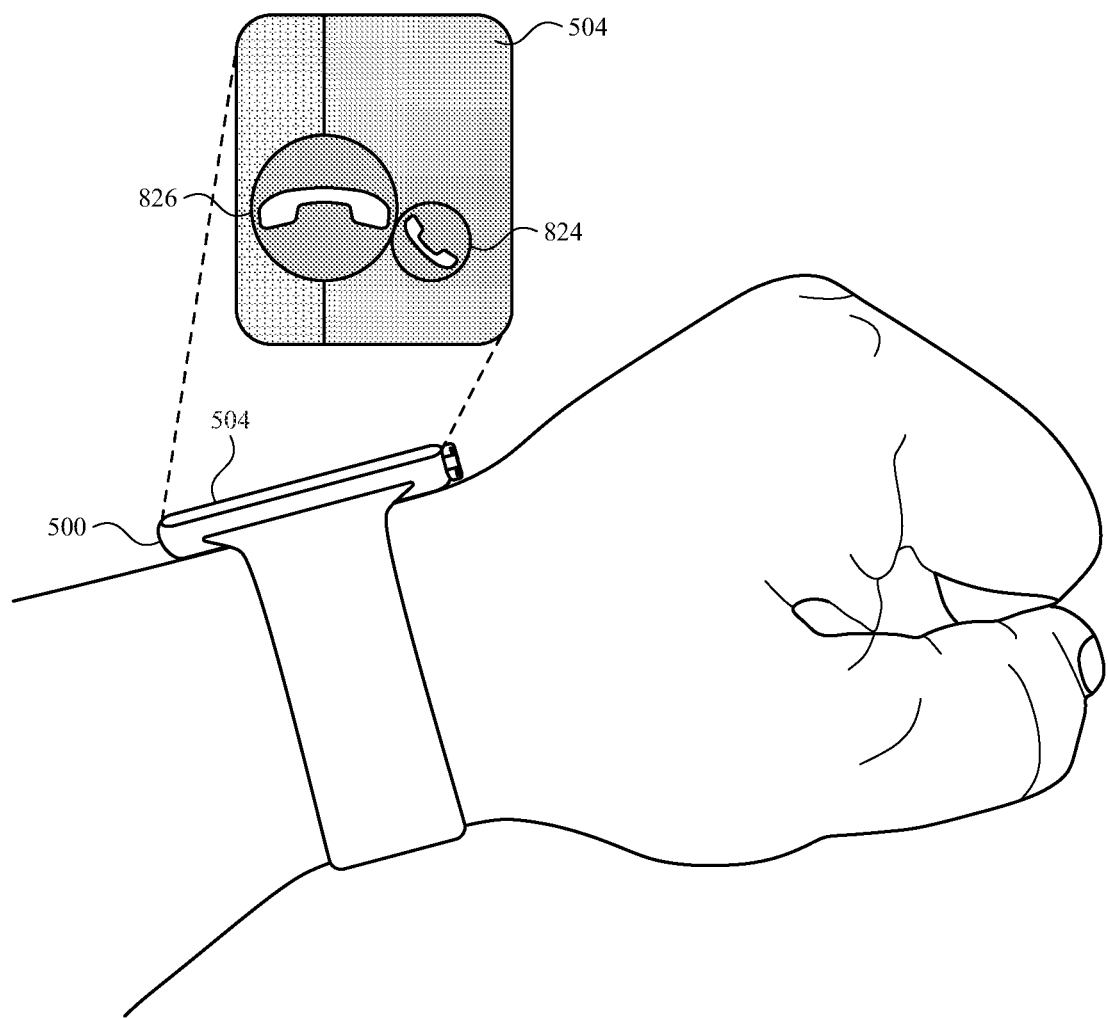
Figure 8B:
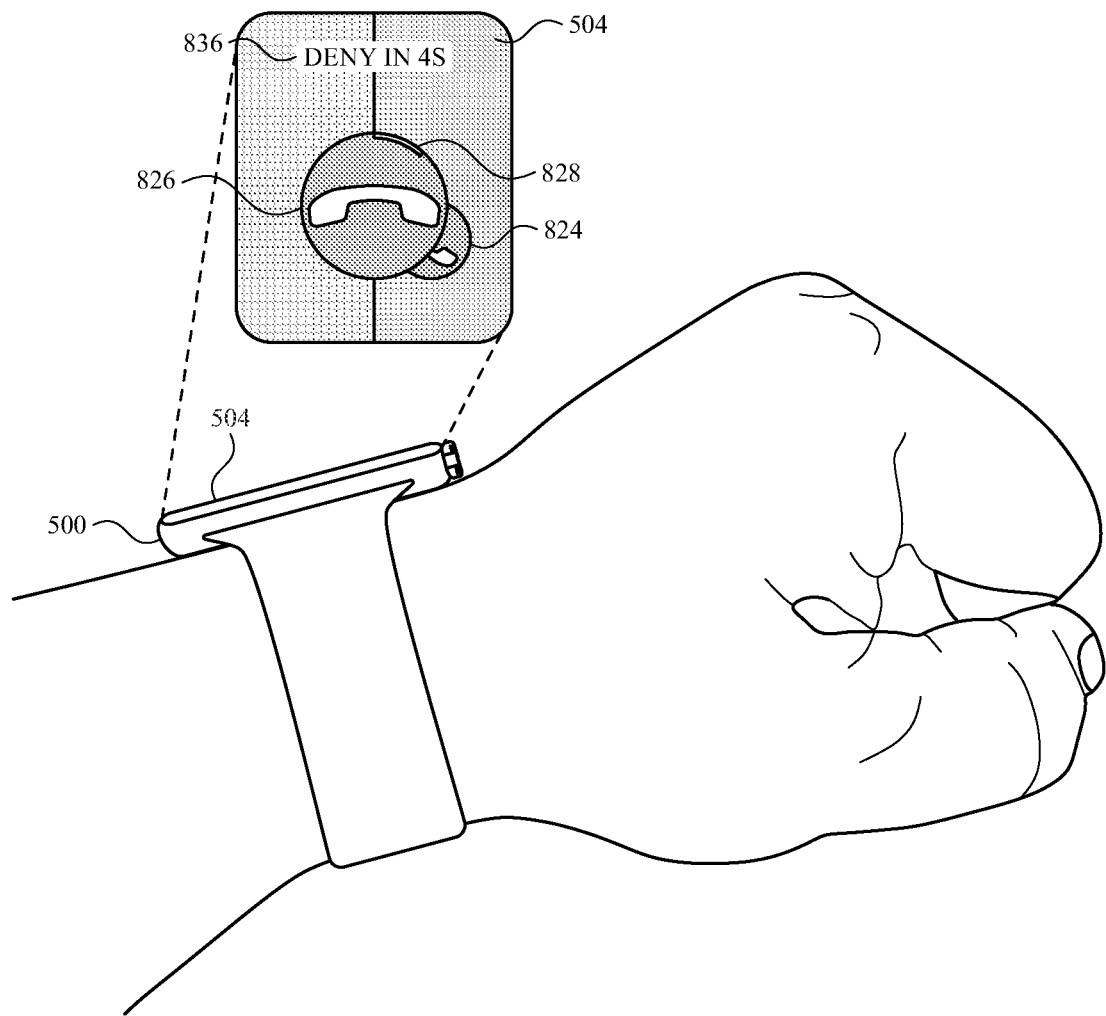
Figure 8B:
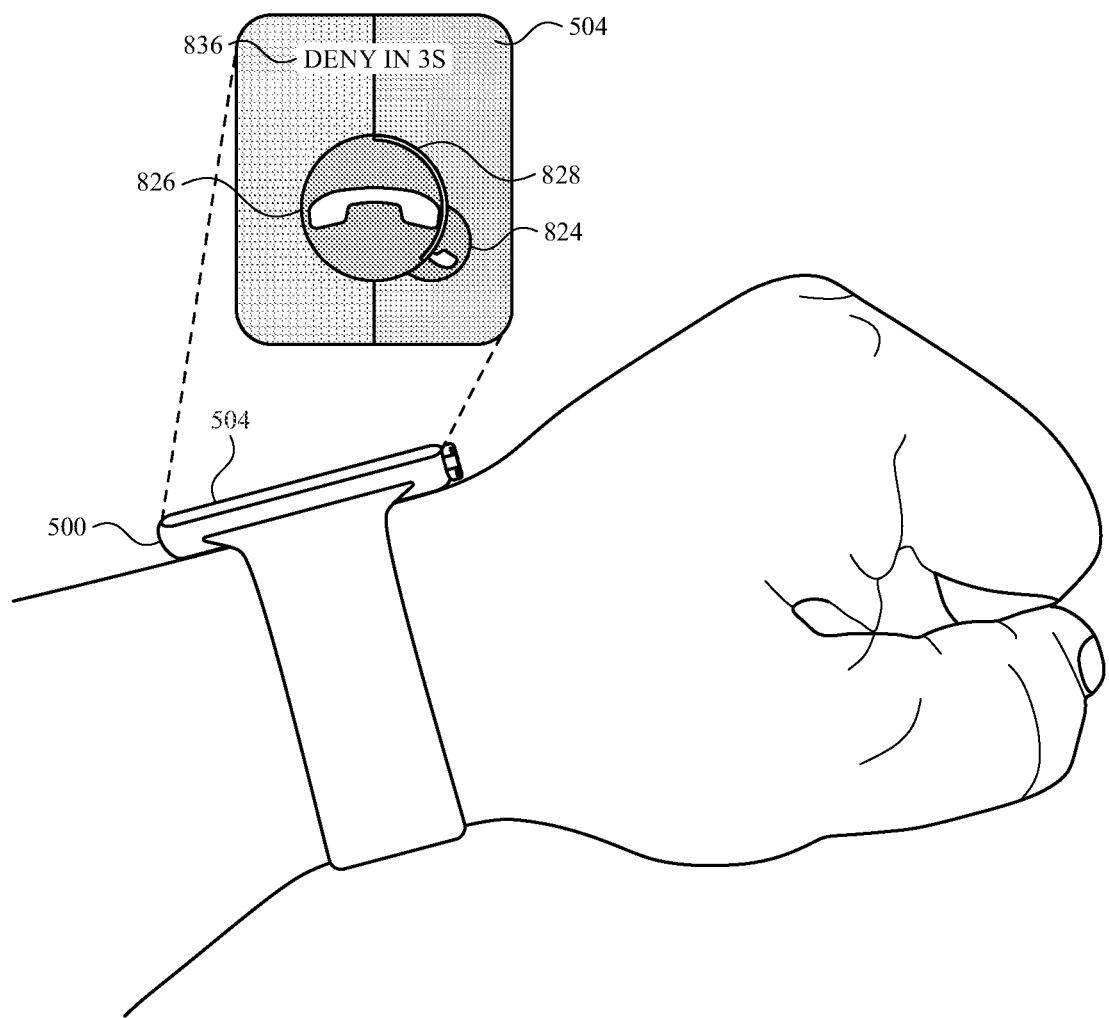
Figure 8B:
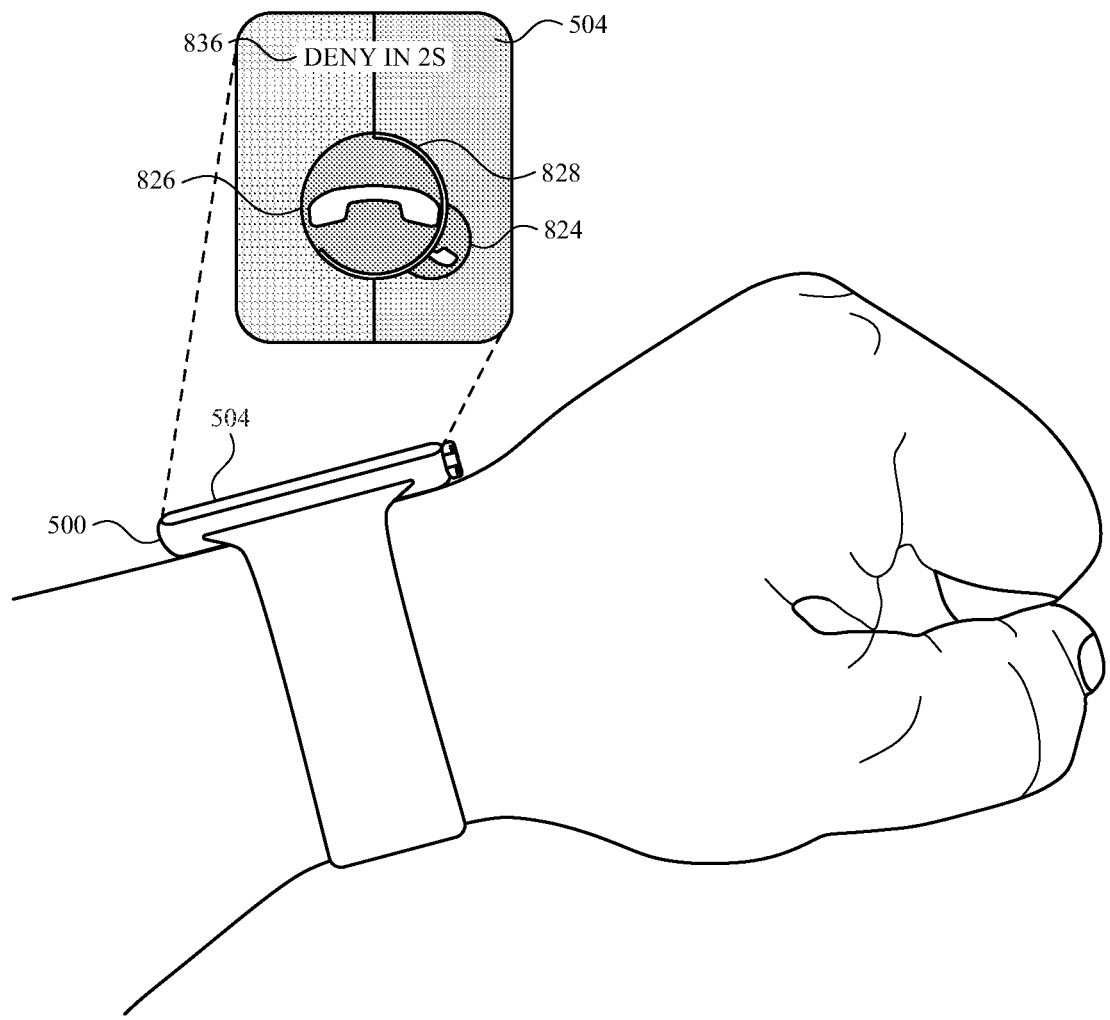
Figure 8B:
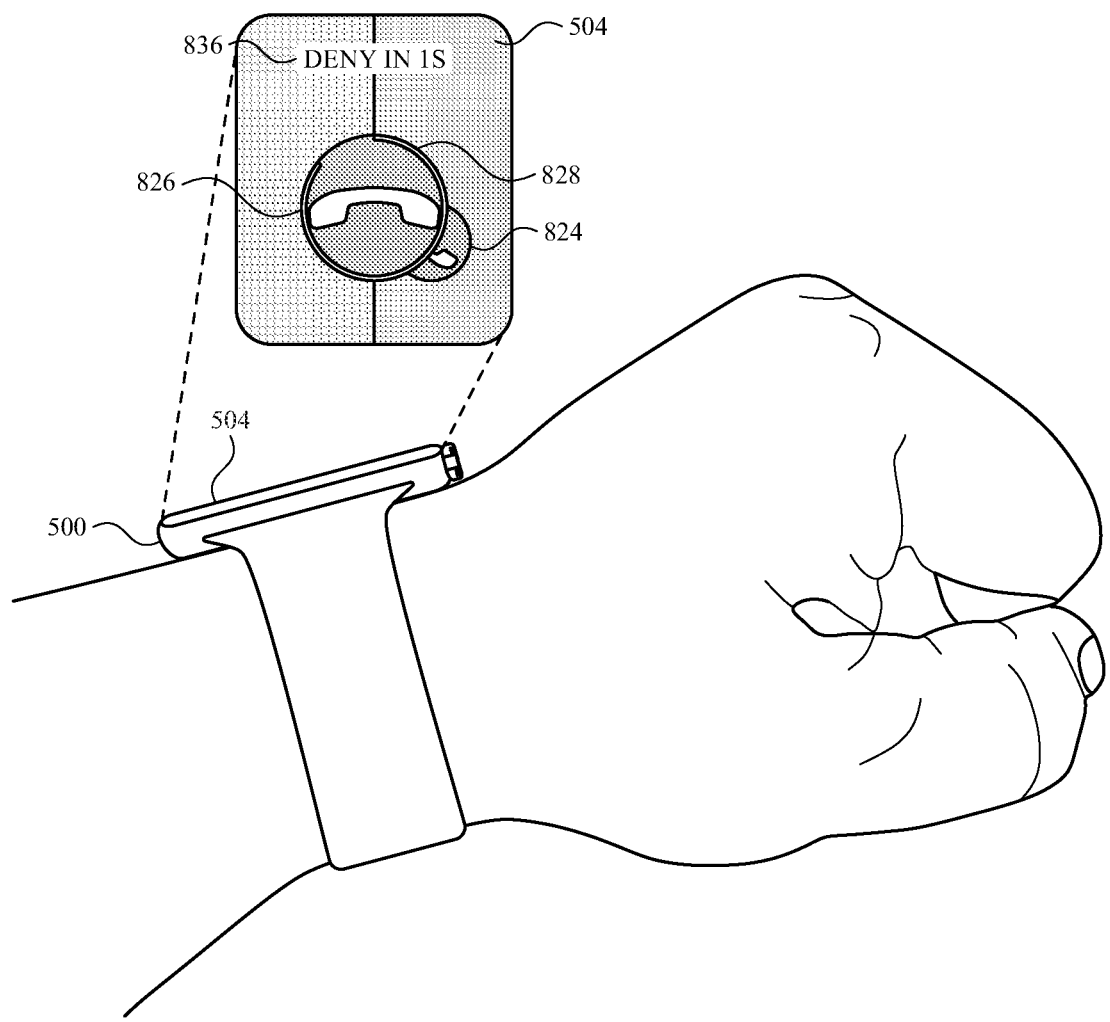
Figure 8B:
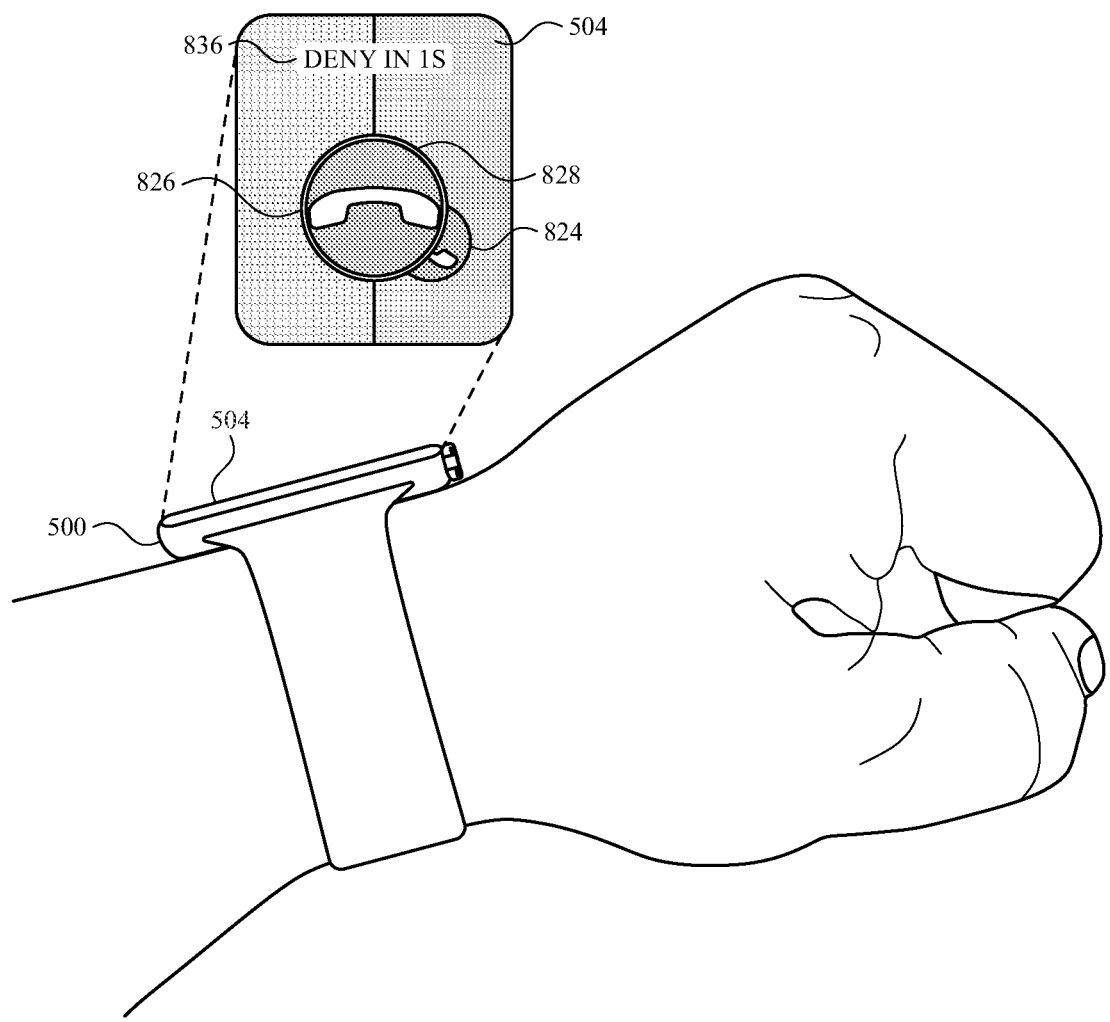
Figure 8B:
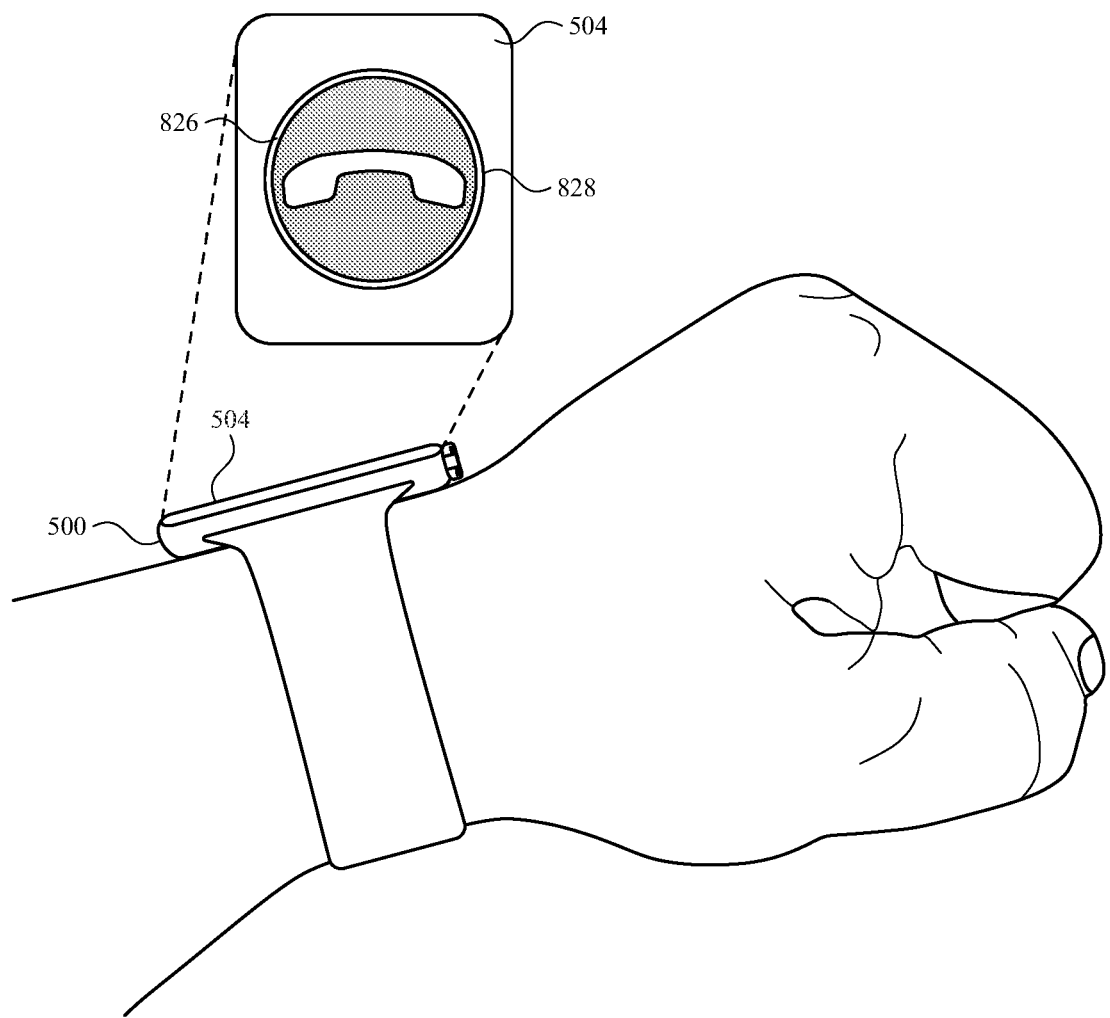
Figure 8B:
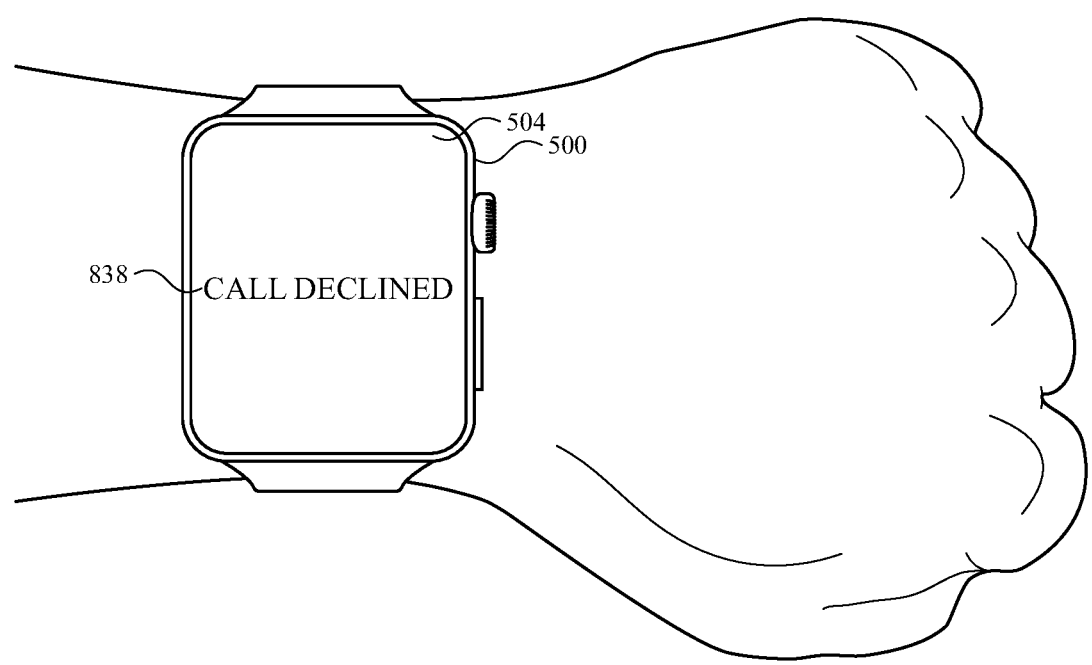

In particular, FIGS. 8A-8Z illustrate exemplary user interfaces for responding to an incoming instant message with an electronic device 500. The electronic device 500 includes a display screen 504 and a tilt sensor, among other elements which can be found above and/or as discussed in reference to FIG. 5A. The display screen 504 can be a touch-sensitive display screen, and the tilt sensor can be an accelerometer 534, directional sensor 540 (e.g., compass), gyroscope 536, motion sensor 538, and/or a combination thereof. In the present example, device 500 is a wearable device on a user's wrist, such as a smart watch. As shown in FIG. 8A, electronic device 500 is worn on the user's left wrist and is being held in a position such that display screen 504 is directly visible to the user's eyes (while being substantially perpendicular to the ground), such as is typical for users when they are checking the time.

As shown in FIG. 8A, an incoming instant message 802 is displayed. In addition, a reply affordance 804 and dismiss affordance 806 are displayed. In some embodiments, the incoming instant message 802 is displayed a predetermined time after the instant message 802 is received and/or in response to a user action. For instance, in some embodiments, the instant message 802 is displayed in response to the user lifting their arm into a raised position where the display screen 504 is visible to the user. Throughout the sequence of interactions shown in FIGS. 8A-8E, the reply affordance 804 or the dismiss affordance 806 can be touched by the user to perform their respective operations with the electronic device 500 (e.g., displaying a reply interface or dismissing the incoming instant message 802, respectively).

As shown in FIG. 8B, the instant message 802 is replaced with an instructional graphic 808 in a center region 810 of the display screen 504. In some embodiments, the instructional graphic 808 is displayed a predetermined time after initially displaying the instant message 802 and/or in response to a user action. For instance, in some embodiments, the instructional graphic 808 is displayed in response to the user lifting their arm into a raised position where the display screen 504 is visible to the user. In addition, the reply affordance 804 is moved to an upper region of the display screen 504 and the dismiss affordance 806 is moved to a lower region of the display screen 504. The instructional graphic 808 indicates movements a user can make with the electronic device 500 to perform the operations associated with the reply affordance 804 and the dismiss affordance 806. In some embodiments, the instructional graphic 808 is animated to demonstrate the movements to the user. The movements include rotating the display screen 504 away from the user's body (e.g., the user rotates their wrist to move the bottom of the display screen 504 upward relative to the top of the display screen 504) or rotating the display screen 504 toward the user's body (e.g., the user rotates their wrist to move the top of the display screen 504 upward relative to the bottom of the display screen 504). In some embodiments, each of the movements indicated by the instructional graphic 808 also include a rotation of the electronic device 500 back toward its original orientation within a predetermined time period (e.g., each movement is a "flicking" motion where the display screen 504 is quickly rotated away/toward the user and then is immediately rotated in the opposite direction). The user can then input one of the movements indicated by the instructional graphic 808, as shown in FIGS. 8C-8E and FIGS. 8X-8Z.

As shown in FIG. 8C, the orientation of the electronic device 500 is changed as a result of the user rotating their wrist away from their body (e.g., the electronic device 500 is tilted up such that the bottom of the display screen 504 is moved upward relative to the top of the display screen 504). This movement corresponds to one of the movements indicated by the instructional graphic 808. In response to the movement of the electronic device 500 to this orientation or a similar orientation, an input indicator 812 is displayed. The input indicator 812 is semi-transparent and is displayed overlapping the other elements on the display screen 504. In some embodiments, the input indicator 812 is displayed when the movement of the electronic device 500 meets a minimum velocity or acceleration threshold. If the minimum velocity or acceleration threshold is not met, then the input indicator 812 is not displayed. In some embodiments, the input indicator 812 is an animated graphic that moves in the direction of movement of the electronic device 504 (e.g., the input indicator 812 moves toward the top of the display screen 504 in response to the user rotating their wrist away from their body).

FIG. 8D illustrates the orientation of the electronic device 500 being further changed as a result of the user further rotating their wrist away from their body (e.g., the electronic device 500 is tilted up further such that the bottom of the display screen 504 is further moved upward relative to the top of the display screen 504). The input indicator 812 is displayed overlapping the reply affordance 804 in the upper region of the display screen 504 to indicate to the user that the movement of the electronic device 500 corresponds to a selection of the reply operation associated with the reply affordance 804. In some embodiments, following the movement of the electronic device 500 into the orientation shown in FIG. 8D or a similar orientation, the electronic device 500 is rotated back toward its original orientation (e.g., the orientation shown in FIG. 8B) within a predetermined time period (e.g., the user makes a "flicking" motion with the electronic device 500, where the display screen 504 is quickly rotated away from the user and then is immediately rotated back toward the user).

As shown in FIG. 8E, following the rotation of the display screen 504 away from the user's body as shown in FIGS. 8C-8D, the reply affordance 804 and overlapping input indicator 812 move toward the center region of the display screen 504. The movement of the reply affordance 804 and overlapping input indicator 812 indicates that the previous movement of the electronic device 500 has resulted in a selection of the reply operation associated with the reply affordance 804.

As shown in FIG. 8F, in response to the reply affordance 804 being selected, a list of predefined responses 814a-814e are displayed. Each of the predefined responses 814a-814e corresponds to a message the user can send to respond to the instant message 802 shown in FIG. 8A. For instance, the predefined responses 814a-814e can include "Yes," "No," "Maybe," "See you there," "Thank you," or other common responses to an instant message. While five predefined responses 814a-814e are shown in FIG. 8E, the number of predefined responses being displayed can vary. Furthermore, in some embodiments, additional predefined responses are displayed by scrolling the list of predefined responses, as discussed in reference to FIGS. 8G-8O.

As shown in FIG. 8G, the orientation of the electronic device 500 is changed as a result of the user rotating their wrist toward their body (e.g., the electronic device 500 is tilted down such that the top of the display screen 504 is moved upward relative to the bottom of the display screen 504). This movement corresponds to one of the movement indicated by the instructional graphic 808 shown in FIG. 8B. In some embodiments, following the movement of the electronic device 500 into the orientation shown in FIG. 8G or a similar orientation, the electronic device 500 is rotated back toward its original orientation (e.g., the orientation shown in FIG. 8F) within a predetermined time period (e.g., the user makes a "flicking" motion with the electronic device 500, where the display screen 504 is quickly rotated toward the user and then is immediately rotated back away from the user).

In response to the movement of the electronic device 500 to the orientation shown in FIG. 8G or a similar orientation, the input indicator 812 is displayed. The input indicator 812 is semi-transparent and is displayed overlapping the other elements on the display screen 504. In some embodiments, the input indicator 812 is displayed when the movement of the electronic device 500 meets a minimum velocity or acceleration threshold. If the minimum velocity or acceleration threshold is not met, then the input indicator 812 is not displayed. In some embodiments, the input indicator 812 is an animated graphic that moves in the direction of movement of the electronic device 504 (e.g., the input indicator 812 moves toward the bottom of the display screen 504 in response to the user rotating their wrist toward their body). In response to this movement of the electronic device 500, the predefined responses 814a-814d are scrolled down such that a predefined response in the upper region of the display screen 504 (e.g., predefined response 814b) is moved toward the center region of the display screen 504 and the predefined response at the bottom of the display screen 504 (e.g., predefined response 814e shown in FIG. 8F) is no longer displayed.

As shown in FIG. 8H, following the rotation of the display screen 504 toward the user's body as shown in FIG. 8G, the predefined response 814b and input indicator 812 are displayed in the center region of the display screen 504 to indicate that the list of predefined responses 814a-814d is no longer being scrolled and the predefined responses 814a-814d will remain in their displayed positions unless additional input is provided by the user.

As shown in FIG. 8I, after the list of predefined responses is scrolled and the predefined response 814b is displayed in the center region of the screen, predefined response 814b is highlighted. If no additional input from the user is received within a predetermined time, then predefined response 814b will be selected after the predetermined time.

As shown in FIG. 8J, before the predetermined time to select predefined response 814b as shown in FIG. 8I has elapsed, the orientation of the electronic device 500 is changed as a result of the user rotating their wrist away from their body (e.g., the electronic device 500 is tilted up such that the bottom of the display screen 504 is moved upward relative to the top of the display screen 504). This movement corresponds to one of the movement indicated by the instructional graphic 808 shown in FIG. 8B. In some embodiments, following the movement of the electronic device 500 into the orientation shown in FIG. 8J or a similar orientation, the electronic device 500 is rotated back toward its original orientation (e.g., the orientation shown in FIG. 8I) within a predetermined time period (e.g., the user makes a "flicking" motion with the electronic device 500, where the display screen 504 is quickly rotated away from the user and then is immediately rotated back toward from the user).

In response to the movement of the electronic device 500 to the orientation shown in FIG. 8J or a similar orientation, the input indicator 812 is displayed. The input indicator 812 is semi-transparent and is displayed overlapping the other elements on the display screen 504. In some embodiments, the input indicator 812 is displayed when the movement of the electronic device 500 meets a minimum velocity or acceleration threshold. If the minimum velocity or acceleration threshold is not met, then the input indicator 812 is not displayed. In some embodiments, the input indicator 812 is an animated graphic that moves in the direction of movement of the electronic device 504 (e.g., the input indicator 812 moves toward the top of the display screen 504 in response to the user rotating their wrist away from their body). In response to this movement of the electronic device 500, the predefined responses 814a-814e are scrolled up such that a predefined response in the lower region of the display screen 504 (e.g., predefined response 814c) is moved toward the center region of the display screen 504. As a result of the upward scroll, the predefined response 814e that had been scrolled off the display screen 504 in FIGS. 8G-8I is displayed again in the bottom region of the display screen.

As shown in FIG. 8K, following the rotation of the display screen 504 away from the user's body as shown in FIG. 8J, the predefined response 814c and input indicator 812 are displayed in the center region of the display screen 504 to indicate that the list of predefined responses 814a-814e is no longer being scrolled and the predefined responses 814a-814e will remain in their displayed positions unless additional input is provided by the user.

As shown in FIG. 8L, after the list of predefined responses is scrolled and the predefined response 814c is displayed in the center region of the screen, the predefined response 814c is highlighted. If no additional input from the user is received within a predetermined time, then predefined response 814c will be selected after the predetermined time.

As shown in FIG. 8M, before the predetermined time to select the predefined response 814c as shown in FIG. 8L has elapsed, the orientation of the electronic device 500 is changed as a result of the user rotating their wrist away from their body again (e.g., the electronic device 500 is tilted up such that the bottom of the display screen 504 is moved upward relative to the top of the display screen 504). This movement corresponds to one of the movement indicated by the instructional graphic 808 shown in FIG. 8B. In some embodiments, following the movement of the electronic device 500 into the orientation shown in FIG. 8M or a similar orientation, the electronic device 500 is rotated back toward its original orientation (e.g., the orientation shown in FIG. 8L) within a predetermined time period (e.g., the user makes a "flicking" motion with the electronic device 500, where the display screen 504 is quickly rotated away from the user and then is immediately rotated back toward from the user).

In response to the movement of the electronic device 500 to the orientation shown in FIG. 8M or a similar orientation, the input indicator 812 is displayed. The input indicator 812 is semi-transparent and is displayed overlapping the other elements on the display screen 504. In some embodiments, the input indicator 812 is displayed when the movement of the electronic device 500 meets a minimum velocity or acceleration threshold. If the minimum velocity or acceleration threshold is not met, then the input indicator 812 is not displayed. In some embodiments, the input indicator 812 is an animated graphic that moves in the direction of movement of the electronic device 504 (e.g., the input indicator 812 moves toward the top of the display screen 504 in response to the user rotating their wrist away from their body). In response to this movement of the electronic device 500, the predefined responses 814a-814e are scrolled up such that a predefined response in the lower region of the display screen 504 (e.g., predefined response 814d) is moved toward the center region of the display screen 504. As a result of the upward scroll, the predefined response at the top of the display screen 504 (e.g., predefined response 814a shown in FIG. 8L) is no longer displayed and a new predefined response 814f is displayed at the bottom of the display screen 504.

As shown in FIG. 8N, following the rotation of the display screen 504 away from the user's body as shown in FIG. 8M, the predefined response 814d and input indicator 812 are displayed in the center region of the display screen 504 to indicate that the list of predefined responses 814a-814e is no longer being scrolled and the predefined responses 814b-814f will remain in their displayed positions unless additional input is provided by the user.

As shown in FIG. 8O, after the list of predefined responses is scrolled and the predefined response 814*d* is displayed in the center region of the screen, the predefined response 814*c* is highlighted. If no additional input from the user is received within a predetermined time, then predefined response 814*d* will be selected after the predetermined time.

As shown in FIGS. 8P-8U, after highlighting the predefined response 814*d*, the other predefined responses are removed from the display screen 504 if no additional input is received from the user within a predetermined time. In addition, a progress ring 816 and a selection notification 818 are displayed to indicate when the highlighted predefined response 814*d* will be sent as a response to the instant message 802 shown in FIG. 8A. The progress ring 816 is a graphical element that forms a circle over a second predetermined period of time. The amount of time that has elapsed in the second predetermined period of time is indicated by the portion of the progress ring 816 that has been displayed. The selection notification 818 notifies the user that the highlighted predefined response 814*d* will be sent once the second predetermined period of time corresponding to the progress ring 816 has elapsed. The sending of the predefined response 814*d* can be canceled by performing a variety of inputs with the electronic device 500. For instance, the user can rapidly and repeatedly rotate their wrist toward and away from their body to cancel the sending of the predefined response 814*d*. Alternatively or in addition, the user can touch the display screen 504 or operate a physical input mechanism on the electronic device to cancel the sending of the predefined response 814*d*. If no cancelation input is received before the predetermined period of time has elapsed, then the electronic device 500 proceeds with sending the predefined response 814*d*, as shown in FIG. 8V.

FIGS. 8W-8Z illustrate the dismiss affordance 806 being selected after the instant message 802 shown in FIG. 8A is received. As shown in FIG. 8W, the instructional graphic 808 is displayed in the center region 810 of the display screen 504, the reply affordance 804 is displayed in an upper region of the display screen 504, and the dismiss affordance 806 is displayed in a lower region of the display screen 504 (same as shown in FIG. 8B).

As shown in FIG. 8X, the orientation of the electronic device 500 is changed as a result of the user rotating their wrist toward their body (e.g., the electronic device 500 is tilted down such that the top of the display screen 504 is moved upward relative to the bottom of the display screen 504). This movement corresponds to one of the movements indicated by the instructional graphic 808. In response to the movement of the electronic device 500 to this orientation or a similar orientation, an input indicator 812 is displayed. The input indicator 812 is semi-transparent and is displayed overlapping the other elements on the display screen 504. In some embodiments, the input indicator 812 is displayed when the movement of the electronic device 500 meets a minimum velocity or acceleration threshold. If the minimum velocity or acceleration threshold is not met, then the input indicator 812 is not displayed. In some embodiments, the input indicator 812 is an animated graphic that moves in the direction of movement of the electronic device 504 (e.g., the input indicator 812 moves toward the bottom of the display screen 504 in response to the user rotating their wrist toward their body).

FIG. 8Y illustrates the orientation of the electronic device 500 being further changed as a result of the user further rotating their wrist away from their body (e.g., the electronic device 500 is tilted down further such that the top of the display screen 504 is further moved upward relative to the bottom of the display screen 504). The input indicator 812 is displayed overlapping the dismiss affordance 806 in the lower region of the display screen 504 to indicate to the user that the movement of the electronic device 500 corresponds to a selection of the dismiss operation associated with the dismiss affordance 806. In some embodiments, following the movement of the electronic device 500 into the orientation shown in FIG. 8Y or a similar orientation, the electronic device 500 is rotated back toward its original orientation (e.g., the orientation shown in FIG. 8W) within a predetermined time period (e.g., the user makes a "flicking" motion with the electronic device 500, where the display screen 504 is quickly rotated toward the user and then is immediately rotated back away from the user).

As shown in FIG. 8Z, following the rotation of the display screen 504 toward the user's body as shown in FIGS. 8X-8Y, the dismiss affordance 806 and overlapping input indicator 812 move toward the center region of the display screen 504. The movement of the dismiss affordance 806 and overlapping input indicator 812 indicates that the previous movement of the electronic device 500 has resulted in a selection of the dismiss operation associated with the dismiss affordance 806. The electronic device 500 then carries out the dismiss operation, which replaces the user interfaces of FIGS. 8A-8Z with a default user interface 820 (e.g. a time display) as shown in FIG. 8AA.

FIGS. 8AB-8AR illustrate exemplary user interfaces for responding to an incoming telephone call with an electronic device 500. The electronic device 500 includes a display screen 504 and a tilt sensor, among other elements which can be found above and/or as discussed in reference to FIG. 5A. The display screen 504 can be a touch-sensitive display screen, and the tilt sensor can be an accelerometer 534, directional sensor 540 (e.g., compass), gyroscope 536, motion sensor 538, and/or a combination thereof. In the present example, device 500 is a wearable device on a user's wrist, such as a smart watch. As shown in FIG. 8AB, electronic device 500 is worn on the user's left wrist and is being held in a position such that display screen 504 is directly visible to the user's eyes (while being substantially perpendicular to the ground), such as is typical for users when they are checking the time.

As shown in FIG. 8AB, an incoming call notification 822 is displayed in a center region 810 of the display screen 504 when the incoming telephone call is received. Alternatively or in addition, an instructional graphic 808 (as shown in FIG. 8B) can be displayed in the center region 810 of the display screen 504. For instance, the center region 810 can alternately display the incoming call notification 822 followed by the instructional graphic 808 while the incoming telephone call is being received. In some embodiments, the incoming call notification 822 and/or instructional graphic 808 are displayed a predetermined time after the incoming telephone call is initially received and/or in response to a user action. For instance, in some embodiments, the incoming call notification 822 and/or instructional graphic 808 are displayed in response to the user lifting their arm into a raised position where the display screen 504 is visible to the user. In addition, an answer call affordance 824 is displayed in a lower region of the display screen 504 and a decline call affordance 826 is displayed in an upper region of the display screen 504. When the incoming telephone call is initially received, the answer call affordance 824 or the decline call affordance 826 can be touched by the user to perform their respective operations with the electronic device 500 (e.g., answering the incoming call or declining the incoming telephone call, respectively).

In addition, the user can change the orientation of the electronic device 500 to perform the operations associated with the answer call affordance 824 and the decline call affordance 826. In some embodiments, the instructional graphic 808 indicates the changes in orientation of the electronic device 500 the user can make to perform the operations associated with the answer call affordance 824 and the decline call affordance 826. In some embodiments, the instructional graphic 808 is animated to demonstrate the changes in orientation to the user. The changes in orientation include rotating the display screen 504 away from the user's body (e.g., the user rotates their wrist to move the bottom of the display screen 504 upward relative to the top of the display screen 504) or rotating the display screen 504 toward the user's body (e.g., the user rotates their wrist to move the top of the display screen 504 upward relative to the bottom of the display screen 504).

As shown in FIG. 8AC, the orientation of the electronic device 500 is changed as a result of the user rotating their wrist toward their body (e.g., the electronic device 500 is tilted down such that the top of the display screen 504 is moved upward relative to the bottom of the display screen 504). In response to the movement of the electronic device 500 to this orientation or a similar orientation, the answer call affordance 824 is enlarged in size and moves toward the center region of the display screen 504. The change in visual appearance and location of the answer call affordance 824 indicates to the user that the answer call operation will be selected as a result of change in orientation of the electronic device 500 shown in FIG. 8AC. In addition, the visual appearance of the decline call affordance 826 can be changed (e.g., darkened in brightness or partially faded) to indicate that the decline call operation will not be selected as a result of change in orientation of the electronic device 500 shown in FIG. 8AC.

As shown in FIGS. 8AD-8AH, the electronic device 500 is held in the same or similar orientation as shown in FIG. 8AC. As a result of the electronic device 500 continuing to be held in this orientation, the answer call affordance 824 is displayed in the center region of the display screen 504 and a progress ring 828 is displayed with the answer call affordance 824. The progress ring 828 indicates a predetermined amount of time the electronic device 500 should be held in this orientation or a similar orientation in order for the answer call operation to be carried out. As shown in FIGS. 8AD-8AH, the progress ring 828 is a graphical element that forms a circle as the predetermined amount of time elapses. The amount of time that has elapsed is indicated by the amount of the progress ring 828 being displayed. In addition, an answer call notification 830 is displayed on the display screen 504. The answer call notification 830 notifies the user that the answer call operation will be carried out once the predetermined amount of time corresponding to the progress ring 828 has elapsed. The answer call operation can be canceled by changing the orientation of the electronic device to a substantially different orientation. If the electronic device continues to be held in the orientation of FIGS. 8AC-8AH or a similar orientation until the predetermined amount of time has elapsed, then the electronic device 500 proceeds with the answer call operation, as shown in FIG. 8AJ.

As shown in FIG. 8AI, if the electronic device 500 is held in the orientation of FIGS. 8AC-8AH or a similar orientation until the predetermined amount of time has elapsed, the progress ring 828 is completed and the answer call affordance 824 and progress ring 828 are enlarged in size. The change in visual appearance of the answer call affordance 824 and progress ring 828 indicates that the electronic device 500 was successfully held in the orientation of FIGS. 8AC-8AH or a similar orientation for the predetermined amount of time, and that the answer call operation is being initiated.

In response to the electronic device 500 being held in the orientation of FIGS. 8AC-8AH or a similar orientation for the predetermined amount of time, a call answering notification 832 is displayed, as shown in FIG. 8AJ. The call answering notification 832 indicates to the user that an answer call operation has been initiated by the electronic device 500. The answer call operation instructs the electronic device 500 or other associated device to answer the incoming telephone call. In addition, the decline call affordance 826 and a mute affordance 834 are displayed while the answer call operation is being carried out and while the telephone call is active.

As shown in FIG. 8AK, the orientation of the electronic device 500 is changed as a result of the user rotating their wrist away from their body (e.g., the electronic device 500 is tilted up such that the bottom of the display screen 504 is moved upward relative to the top of the display screen 504). In response to the movement of the electronic device 500 to this orientation or a similar orientation, the decline call affordance 826 is enlarged in size and moves toward the center region of the display screen 504. The change in visual appearance and location of the decline call affordance 826 indicates to the user that the decline call operation will be selected as a result of change in orientation of the electronic device 500 shown in FIG. 8AK. In addition, the visual appearance of the answer call affordance 824 can be changed (e.g., darkened in brightness or partially faded) to indicate that the decline call operation will not be selected as a result of change in orientation of the electronic device 500 shown in FIG. 8AK.

As shown in FIGS. 8AL-8AP, the electronic device 500 is held in the same or similar orientation as shown in FIG. 8AK. As a result of the electronic device 500 continuing to be held in this orientation, the decline call affordance 826 is displayed in the center region of the display screen 504 and the progress ring 828 is displayed with the decline call affordance 826. The progress ring 828 indicates a predetermined amount of time the electronic device 500 should be held in this orientation or a similar orientation in order for the decline call operation to be carried out. As shown in FIGS. 8AL-8AP, the progress ring 828 is a graphical element that forms a circle as the predetermined amount of time elapses. The amount of time that has elapsed is indicated by the amount of the progress ring 828 being displayed. In addition, a decline call notification 836 is displayed on the display screen 504. The decline call notification 836 notifies the user that the decline call operation will be carried out once the predetermined amount of time corresponding to the progress ring 828 has elapsed. The decline call operation can be canceled by changing the orientation of the electronic device to a substantially different orientation. If the electronic device continues to be held in the orientation of FIGS. 8AK-8P or a similar orientation until the predetermined amount of time has elapsed, then the electronic device 500 proceeds with the decline call operation, as shown in FIG. 8AR.

As shown in FIG. 8AQ, if the electronic device 500 is held in the orientation of FIGS. 8AK-8AP or a similar orientation until the predetermined amount of time has elapsed, the progress ring 828 is completed and the decline call affordance 826 and progress ring 828 are enlarged in size. The change in visual appearance of the decline call affordance 826 and progress ring 828 indicates that the electronic device 500 was successfully held in the orientation of FIGS. 8AK-8AP or a similar orientation for the predetermined amount of time, and that the decline call operation is being initiated.

In response to the electronic device 500 being held in the orientation of FIGS. 8AK-8AP or a similar orientation for the predetermined amount of time, a call ending notification 838 is displayed, as shown in FIG. 8AR. The call ending notification 838 indicates to the user that a decline call operation has been initiated by the electronic device 500. The decline call operation instructs the electronic device 500 or other associated device to decline the incoming telephone call.

FIGS. 8AS-8BI illustrate another exemplary user interface for responding to an incoming telephone call with an electronic device 500. The electronic device 500 includes a display screen 504 and a tilt sensor, among other elements which can be found above and/or as discussed in reference to FIG. 5A. The display screen 504 can be a touch-sensitive display screen, and the tilt sensor can be an accelerometer 534, directional sensor 540 (e.g., compass), gyroscope 536, motion sensor 538, and/or a combination thereof. In the present example, device 500 is a wearable device on a user's wrist, such as a smart watch. As shown in FIG. 8AS, electronic device 500 is worn on the user's left wrist and is being held in a position such that display screen 504 is directly visible to the user's eyes (while being substantially perpendicular to the ground), such as is typical for users when they are checking the time.

As shown in FIG. 8AS, an incoming call notification 822 is displayed on the display screen 504 when the incoming telephone call is received. In some embodiments, the incoming call notification 822 is displayed a predetermined time after the incoming telephone call is initially received and/or in response to a user action. For instance, in some embodiments, the incoming call notification 822 is displayed in response to the user lifting their arm into a raised position where the display screen 504 is visible to the user. In addition, an answer call affordance 824 is displayed in a right region of the display screen 504 and a decline call affordance 826 is displayed in a left region of the display screen 504. When the incoming telephone call is initially received, the answer call affordance 824 or the decline call affordance 826 can be touched by the user to perform their respective operations with the electronic device 500 (e.g., answering the incoming call or declining the incoming telephone call, respectively).

In addition, the user can change the orientation of the electronic device 500 to perform the operations associated with the answer call affordance 824 and the decline call affordance 826. The changes in orientation include tilting the display screen 504 to the right (e.g., the left side of the display screen 504 is moved upward relative to the right side of the display screen 504) or tilting the display screen 504 to the left (e.g., the right side of the display screen 504 is moved upward relative to the left side of the display screen 504).

As shown in FIG. 8AT, the orientation of the electronic device 500 is changed as a result of the user tilting the display screen 504 to the right (e.g., the left side of the display screen 504 is moved upward relative to the right side of the display screen 504). In response to the movement of the electronic device 500 to this orientation or a similar orientation, the answer call affordance 824 is enlarged in size and moves toward the center region of the display screen 504. The change in visual appearance and location of the answer call affordance 824 indicates to the user that the answer call operation will be selected as a result of change in orientation of the electronic device 500 shown in FIG. 8AT. In addition, the visual appearance of the decline call affordance 826 can be changed (e.g., darkened in brightness or partially faded) to indicate that the decline call operation will not be selected as a result of change in orientation of the electronic device 500 shown in FIG. 8AT.

As shown in FIGS. 8AU-8AY, the electronic device 500 is held in the same or similar orientation as shown in FIG. 8AT. As a result of the electronic device 500 continuing to be held in this orientation, the answer call affordance 824 is displayed in the center region of the display screen 504 and a progress ring 828 is displayed with the answer call affordance 824. The progress ring 828 indicates a predetermined amount of time the electronic device 500 should be held in this orientation or a similar orientation in order for the answer call operation to be carried out. As shown in FIGS. 8AU-8AY, the progress ring 828 is a graphical element that forms a circle as the predetermined amount of time elapses. The amount of time that has elapsed is indicated by the amount of the progress ring 828 being displayed. In addition, an answer call notification 830 is displayed on the display screen 504. The answer call notification 830 notifies the user that the answer call operation will be carried out once the predetermined amount of time corresponding to the progress ring 828 has elapsed. The answer call operation can be canceled by changing the orientation of the electronic device to a substantially different orientation. If the electronic device continues to be held in the orientation of FIGS. 8AT-8AY or a similar orientation until the predetermined amount of time has elapsed, then the electronic device 500 proceeds with the answer call operation, as shown in FIG. 8BA.

As shown in FIG. 8AZ, if the electronic device 500 is held in the orientation of FIGS. 8AT-8AY or a similar orientation until the predetermined amount of time has elapsed, the progress ring 828 is completed and the answer call affordance 824 and progress ring 828 are enlarged in size. The change in visual appearance of the answer call affordance 824 and progress ring 828 indicates that the electronic device 500 was successfully held in the orientation of FIGS. 8AT-8AY or a similar orientation for the predetermined amount of time, and that the answer call operation is being initiated.

In response to the electronic device 500 being held in the orientation of FIGS. 8AT-8AY or a similar orientation for the predetermined amount of time, a call answering notification 832 is displayed, as shown in FIG. 8BA. The call answering notification 832 indicates to the user that an answer call operation has been initiated by the electronic device 500. The answer call operation instructs the electronic device 500 or other associated device to answer the incoming telephone call. In addition, the decline call affordance 826 and a mute affordance 834 are displayed while the answer call operation is being carried out and while the telephone call is active.

As shown in FIG. 8BB, the orientation of the electronic device 500 is changed as a result of the user tilting the display screen 504 to the left (e.g., the right side of the display screen 504 is moved upward relative to the left side of the display screen 504). In response to the movement of the electronic device 500 to this orientation or a similar orientation, the decline call affordance 826 is enlarged in size and moves toward the center region of the display screen 504. The change in visual appearance and location of the decline call affordance 826 indicates to the user that the decline call operation will be selected as a result of change in orientation of the electronic device 500 shown in FIG. 8BB. In addition, the visual appearance of the answer call affordance 824 can be changed (e.g., darkened in brightness or partially faded) to indicate that the decline call operation will not be selected as a result of change in orientation of the electronic device 500 shown in FIG. 8BB.

As shown in FIGS. 8BC-8BG, the electronic device 500 is held in the same or similar orientation as shown in FIG. 8BB. As a result of the electronic device 500 continuing to be held in this orientation, the decline call affordance 826 is displayed in the center region of the display screen 504 and the progress ring 828 is displayed with the decline call affordance 826. The progress ring 828 indicates a predetermined amount of time the electronic device 500 should be held in this orientation or a similar orientation in order for the decline call operation to be carried out. As shown in FIGS. 8BC-8BG, the progress ring 828 is a graphical element that forms a circle as the predetermined amount of time elapses. The amount of time that has elapsed is indicated by the amount of the progress ring 828 being displayed. In addition, a decline call notification 836 is displayed on the display screen 504. The decline call notification 836 notifies the user that the decline call operation will be carried out once the predetermined amount of time corresponding to the progress ring 828 has elapsed. The decline call operation can be canceled by changing the orientation of the electronic device to a substantially different orientation. If the electronic device continues to be held in the orientation of FIGS. 8BB-8BG or a similar orientation until the predetermined amount of time has elapsed, then the electronic device 500 proceeds with the decline call operation, as shown in FIG. 8BI.

As shown in FIG. 8BH, if the electronic device 500 is held in the orientation of FIGS. 8BB-8BG or a similar orientation until the predetermined amount of time has elapsed, the progress ring 828 is completed and the decline call affordance 826 and progress ring 828 are enlarged in size. The change in visual appearance of the decline call affordance 826 and progress ring 828 indicates that the electronic device 500 was successfully held in the orientation of FIGS. 8BB-8BG or a similar orientation for the predetermined amount of time, and that the decline call operation is being initiated.

In response to the electronic device 500 being held in the orientation of FIGS. 8BB-8BG or a similar orientation for the predetermined amount of time, a call ending notification 838 is displayed, as shown in FIG. 8BI. The call ending notification 838 indicates to the user that a decline call operation has been initiated by the electronic device 500. The decline call operation instructs the electronic device 500 or other associated device to decline the incoming telephone call.

Figure 9A:
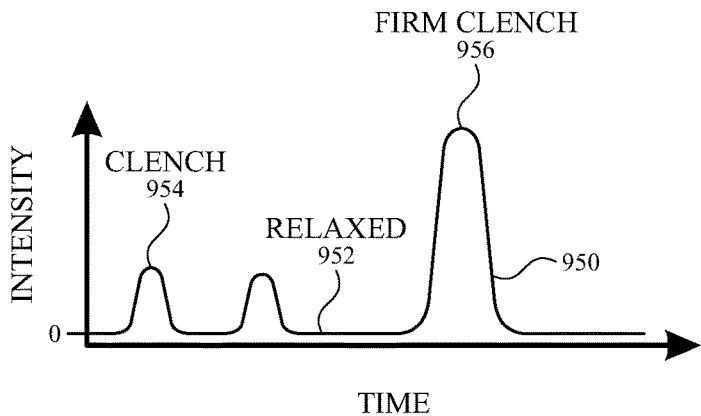
FIG. 9A illustrates an exemplary blood flow pattern associated with a positioning of a user's hand, in accordance with some embodiments.

FIG. 9A illustrates an exemplary blood flow pattern associated with a positioning of a user's hand FIGS. 9B-9H illustrate exemplary user interfaces for interacting with an electronic device based on a blood flow pattern, in accordance with some embodiments. The user interfaces in these figures are used to illustrate the processes described below, including the processes in FIG. 15.

As shown in FIG. 9A, blood flow 950 changes in intensity over time based on a positioning of a user's hand, as measured with a blood flow sensor located on the user's wrist. When the user's hand is a relaxed, open position, the blood flow is at a low intensity, as shown at 952. When the user clenches their hand (e.g., makes a first with their hand), the blood flow increases in intensity, as shown at 954. As the strength of the clench increases (e.g., the user makes a tighter first with their hand), the blood flow intensity also increases, as shown at 956. These different patterns of blood flow intensity can be measured with an electronic device and used to perform operations with the electronic device.

FIGS. 9B-9H illustrate exemplary user interfaces for performing operations with an electronic device 500 based on a positioning of a user's hand. The electronic device 500 includes a display screen 504 and a biological sensor, among other elements which can be found above and/or as discussed in reference to FIG. 5A. The display screen 504 can be a touch-sensitive display screen, and the biological sensor can be an optical sensor positioned in the electronic device to measure blood flow indicative of a clenched hand of the user. In the present example, device 500 is a wearable device on a user's wrist, such as a smart watch.

Figure 9B:
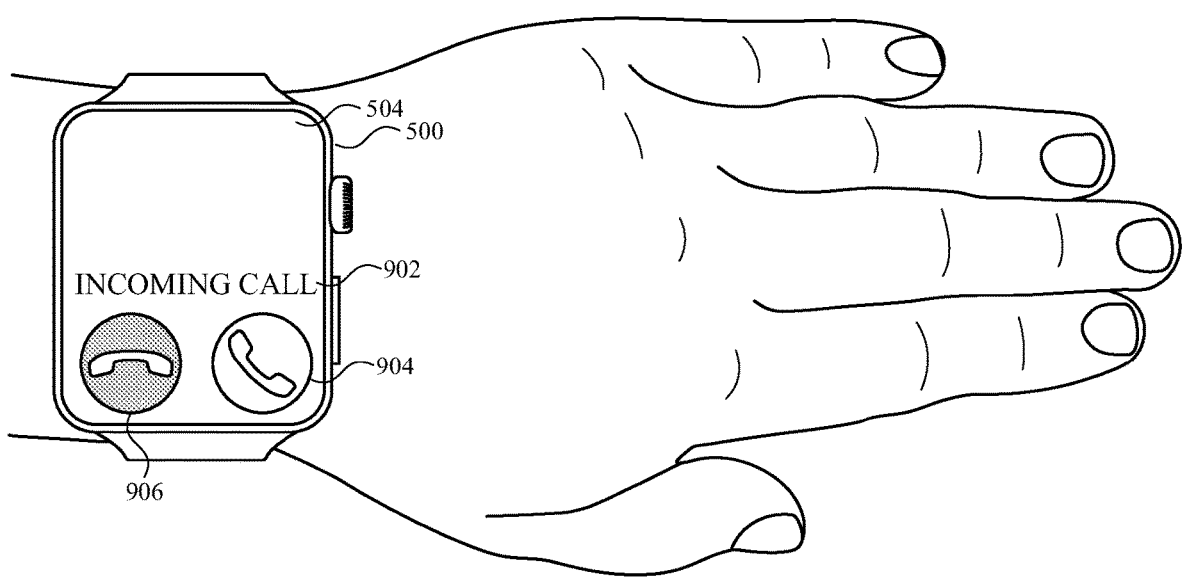
FIGS. 9B-9H illustrate exemplary user interfaces for interacting with an electronic device based on a blood flow pattern, in accordance with some embodiments.

As shown in FIG. 9B, an incoming call notification 902 is displayed when an incoming telephone call is received. In addition, an answer call affordance 904 and a decline call affordance 906 are displayed. In some embodiments, the incoming call notification 902, answer call affordance 904, and decline call affordance 906 are displayed a predetermined time after the incoming telephone call is initially received and/or in response to a user action. For instance, in some embodiments, the incoming call notification 902, answer call affordance 904, and decline call affordance 906 are displayed in response to the user lifting their arm into a raised position where the display screen 504 is visible to the user. Throughout the sequence of interactions shown in FIGS. 9B-9F, the answer call affordance 904 or the decline call affordance 906 can be touched by the user to perform their respective operations with the electronic device 500 (e.g., answering the incoming call or declining the incoming telephone call, respectively). As shown in FIG. 9B, when the incoming call is initially received, the user's hand is in a relaxed, open position.

Figure 9C:
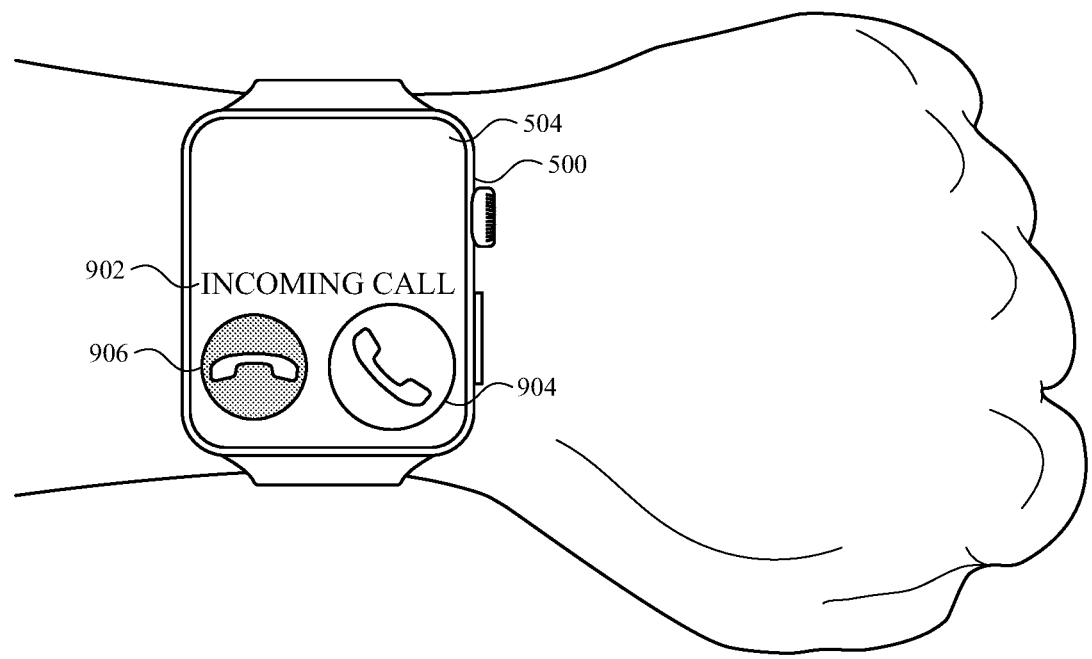
Figure 10A:
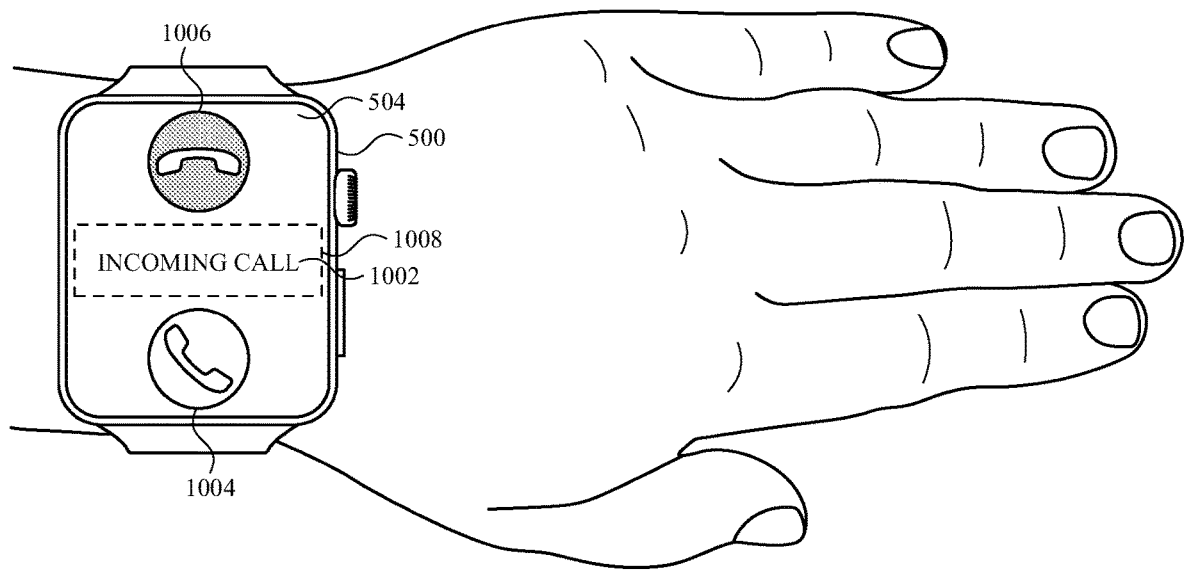
FIGS. 10A-10P illustrate exemplary user interfaces for interacting with an electronic device without touching a display screen or other physical input mechanism, in accordance with some embodiments.

As shown in FIG. 9C, the user has changed the positioning of their hand from the relaxed, open position to a clenched position (e.g., the user makes a first with their hand) In response to the clenched positioning of the user's hand, the answer call affordance 904 is enlarged in size. The change in visual appearance of the answer call affordance indicates to the user that their clenched hand has been detected by the electronic device 500, and the answer call operation will be carried out if the user's hand is held in the clenched position for a predetermined time. In some embodiments, the clenched position of the user's hand is determined by the electronic device 500 by detecting a predefined pattern (e.g., an increase in blood flow intensity as shown in FIG. 9A) for a predetermined time with the biological sensor.

Figure 9D:
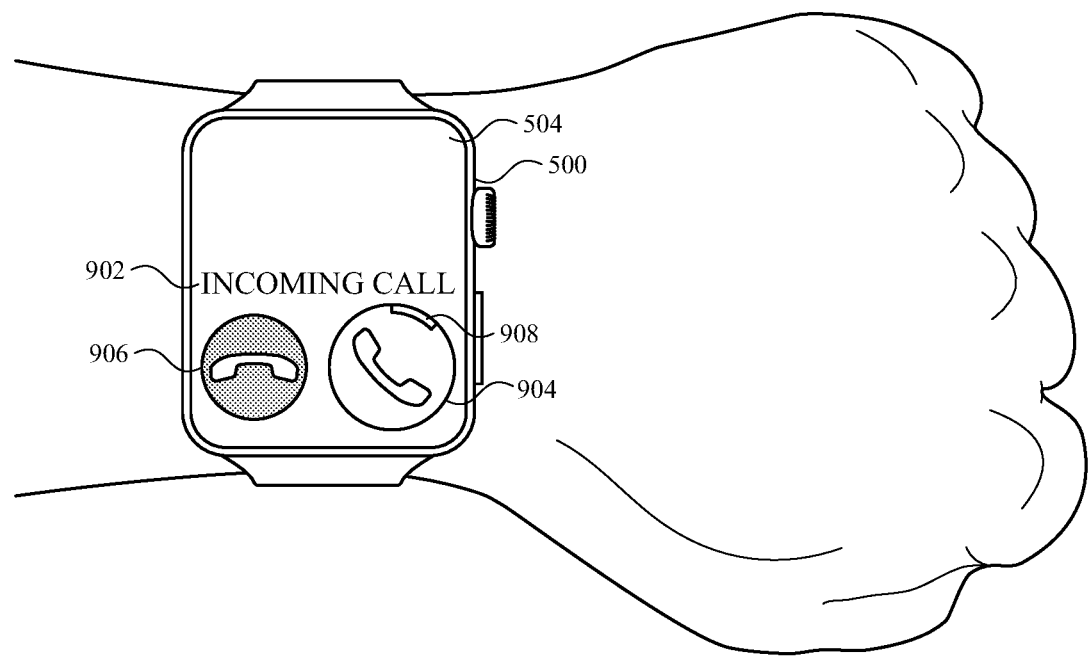
Figure 9E:
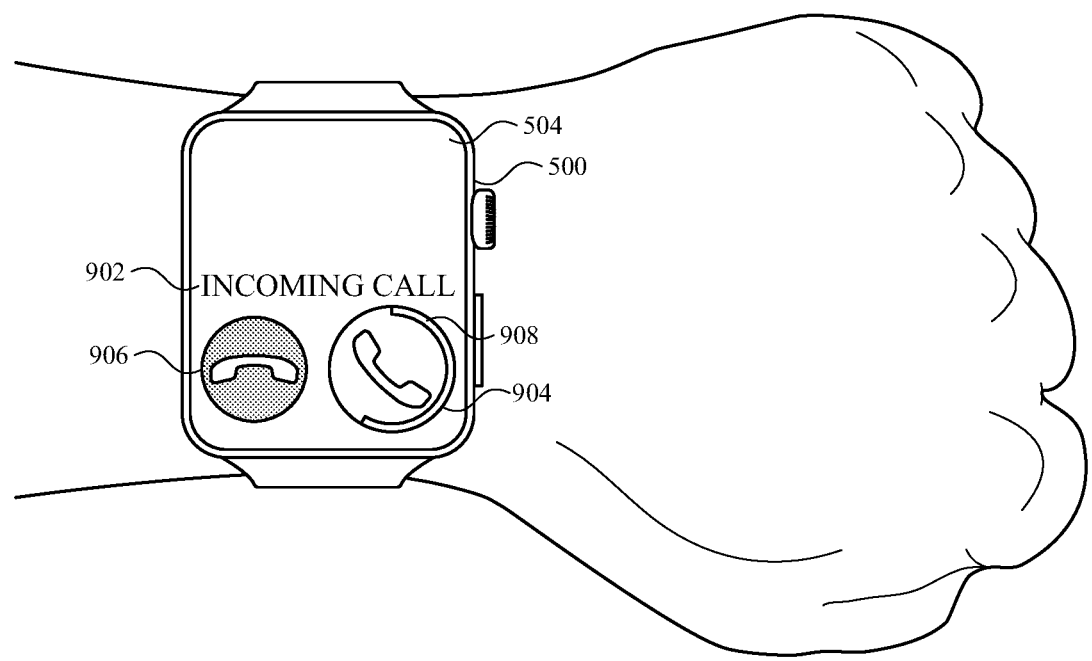
Figure 9F:
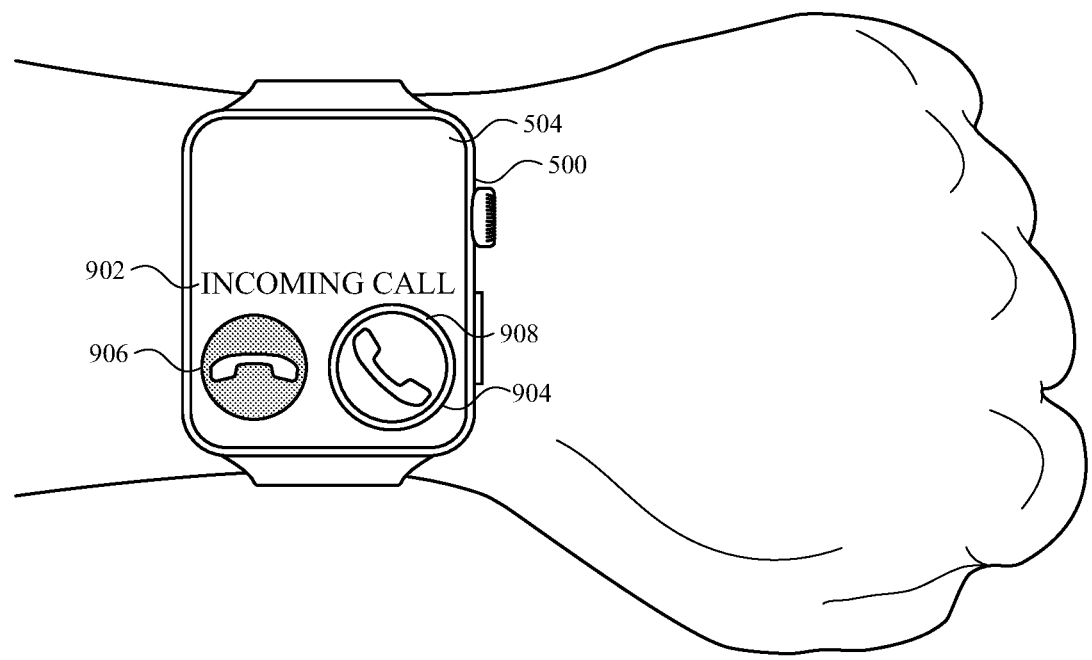

As shown in FIGS. 9D-9F, the user continues to hold their hand in a clenched position as shown in FIG. 9C. As a result of the user continuing to hold their hand in the clenched position, a progress ring 908 is displayed with the answer call affordance 904. The progress ring 908 indicates the predetermined amount of time the user should continue clenching their hand in order for the answer call operation to be carried out. As shown in FIGS. 9D-9F, the progress ring 908 is a graphical element that forms a circle as the predetermined amount of time elapses. The amount of time that has elapsed is indicated by the amount of the progress ring 908 being displayed. If the user stops holding their hand in a clenched position, then the progress ring 908 will stop being displayed and the electronic device 500 will forgo performing the answer call operation unless another input is received from the user before the incoming call stops being received. If the user continues holding their hand in the clenched position until the predetermined amount of time has elapsed, then the electronic device 500 proceeds with the answer call operation, as shown in FIG. 9H.

Figure 9G:
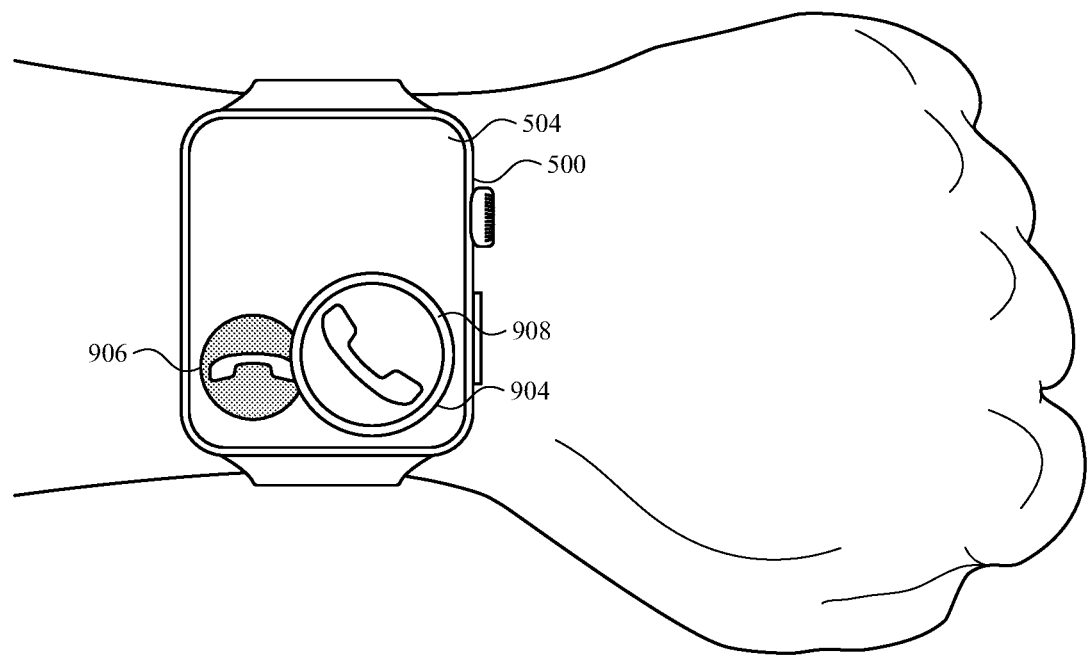

As shown in FIG. 9G, if the user continues holding their hand in the clenched position until the predetermined amount of time has elapsed, then the progress ring 828 is completed and the answer call affordance 904 and progress ring 828 are enlarged in size. The change in visual appearance of the answer call affordance 904 and progress ring 828 indicates that the user successfully held their hand in the clenched position for the predetermined amount of time, and that the answer call operation is being initiated.

Figure 9H:
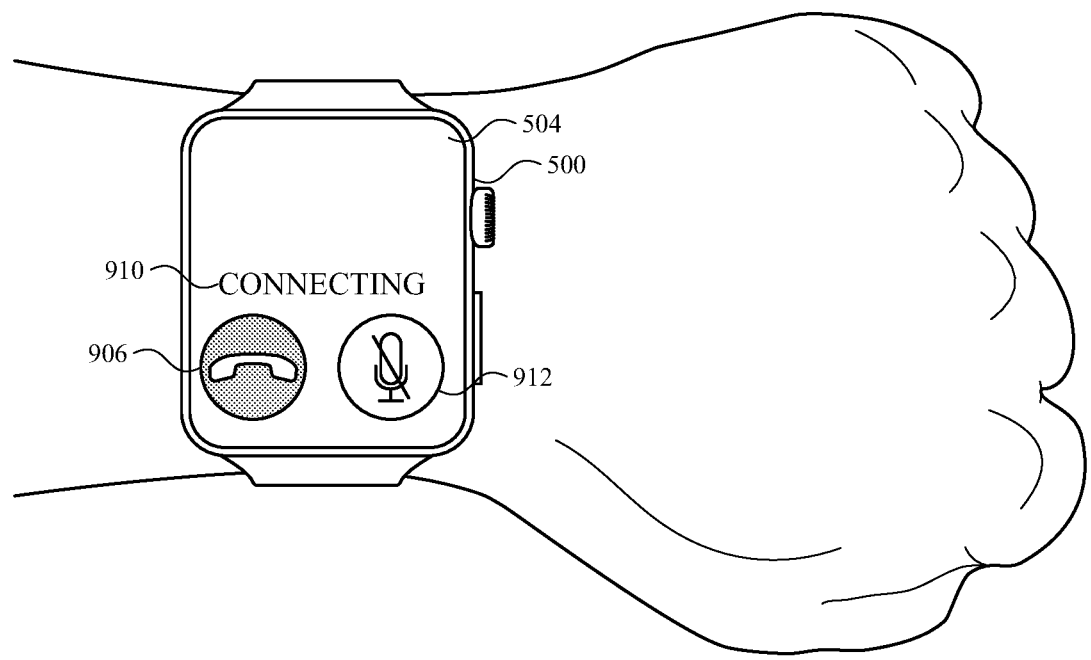

In response to the user holding their hand in the clenched position for the predetermined amount of time, a call answering notification 910 is displayed, as shown in FIG. 9H. The call answering notification 910 indicates to the user that an answer call operation has been initiated by the electronic device 500. The answer call operation instructs the electronic device 500 or other associated device to answer the incoming telephone call. In addition, the decline call affordance 906 and a mute affordance 912 are displayed while the answer call operation is being carried out and while the telephone call is active.

FIGS. 10A-10P illustrate exemplary user interfaces for interacting with an electronic device without touching a display screen or other physical input mechanism, in accordance with some embodiments. The user interfaces in these figures are used to illustrate the processes described below, including the processes in FIGS. 16A-16B.

In particular, FIGS. 10A-10P illustrate exemplary user interfaces for performing operations with an electronic device 500 based on a positioning of a user's hand and an orientation of the electronic device. The electronic device 500 includes a display screen 504, a tilt sensor, and a biological sensor, among other elements which can be found above and/or as discussed in reference to FIG. 5A. The display screen 504 can be a touch-sensitive display screen. The biological sensor can be an optical sensor positioned in the electronic device to measure blood flow indicative of a clenched hand of the user. The tilt sensor can be an accelerometer 534, directional sensor 540 (e.g., compass), gyroscope 536, motion sensor 538, and/or a combination thereof. In the present example, device 500 is a wearable device on a user's wrist, such as a smart watch.

As shown in FIG. 10A, an incoming call notification 1002 is displayed in a center region 1008 of the display screen 504 when an incoming telephone call is received. In addition, an answer call affordance 1004 and a decline call affordance 1006 are displayed. In some embodiments, the incoming call notification 1002, answer call affordance 1004, and decline call affordance 1006 are displayed a predetermined time after the incoming telephone call is initially received and/or in response to a user action. For instance, in some embodiments, the incoming call notification 1002, answer call affordance 1004, and decline call affordance 1006 are displayed in response to the user lifting their arm into a raised position where the display screen 504 is visible to the user. Throughout the sequence of interactions shown in FIGS. 10A-10D and 10G-10H, the answer call affordance 1004 or the decline call affordance 1006 can be touched by the user to perform their respective operations with the electronic device 500 (e.g., answering the incoming call or declining the incoming telephone call, respectively). As shown in FIG. 10A, when the incoming call is initially received, the user's hand is in a relaxed, open position.

Figure 10B:
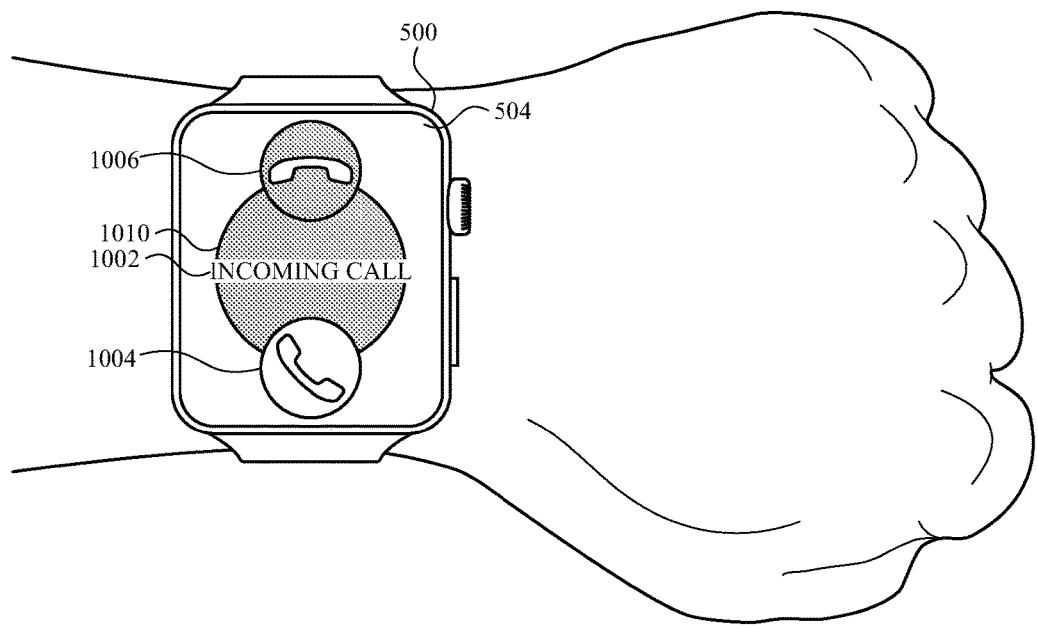

As shown in FIG. 10B, the user has changed the positioning of their hand from the relaxed, open position to a clenched position (e.g., the user makes a first with their hand) In response to the clenched position of the user's hand, a clenching indicator 1010 is displayed. In some embodiments, the clenched position of the user's hand is determined by the electronic device 500 by detecting a predefined pattern (e.g., an increase in blood flow intensity as shown in FIG. 9A) for a predetermined time with the biological sensor. The clenching indicator 1010 is semi-transparent and is displayed overlapping the other elements on the display screen 504. In some embodiments, the clenching indicator 1010 is an animated graphic that enlarges in size based on the strength of the clench of the user's hand (e.g., the user makes a tighter first with their hand and the blood flow intensity increases as shown in FIG. 9A). The clenching indicator 1010 indicates to the user that their clenched hand has been detected by the electronic device 500, and that additional input can be provided to the electronic device 500. As shown in FIG. 10B, the electronic device 500 is worn on the user's left wrist and is being held in a position such that display screen 504 is directly visible to the user's eyes (while being substantially perpendicular to the ground), such as is typical for users when they are checking the time.

While the user's hand is clenched as shown in FIG. 10B, the user can change the orientation of the electronic device 500 to perform the operations associated with the answer call affordance 1004 or the decline call affordance 1006. The changes in orientation include rotating the display screen 504 away from the user's body (e.g., the user rotates their wrist to move the bottom of the display screen 504 upward relative to the top of the display screen 504) or rotating the display screen 504 toward the user's body (e.g., the user rotates their wrist to move the top of the display screen 504 upward relative to the bottom of the display screen 504). In some embodiments, the operations are performed when the movement of the electronic device 500 meets a minimum velocity or acceleration threshold. If the minimum velocity or acceleration threshold is not met, then the operations are not performed.

Figure 10C:
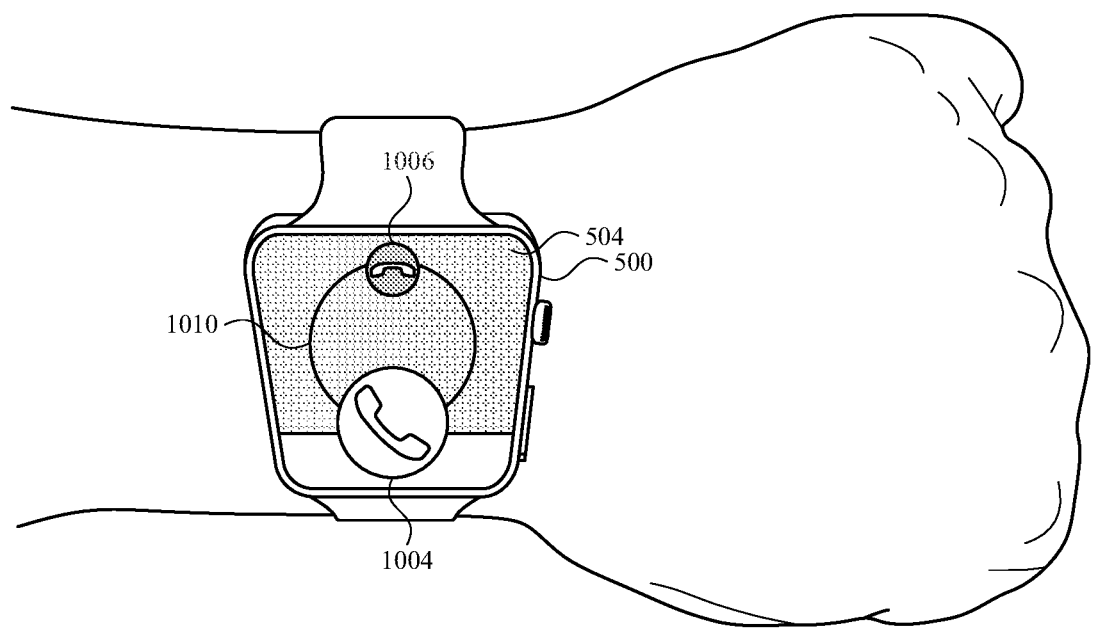
Figure 10D:
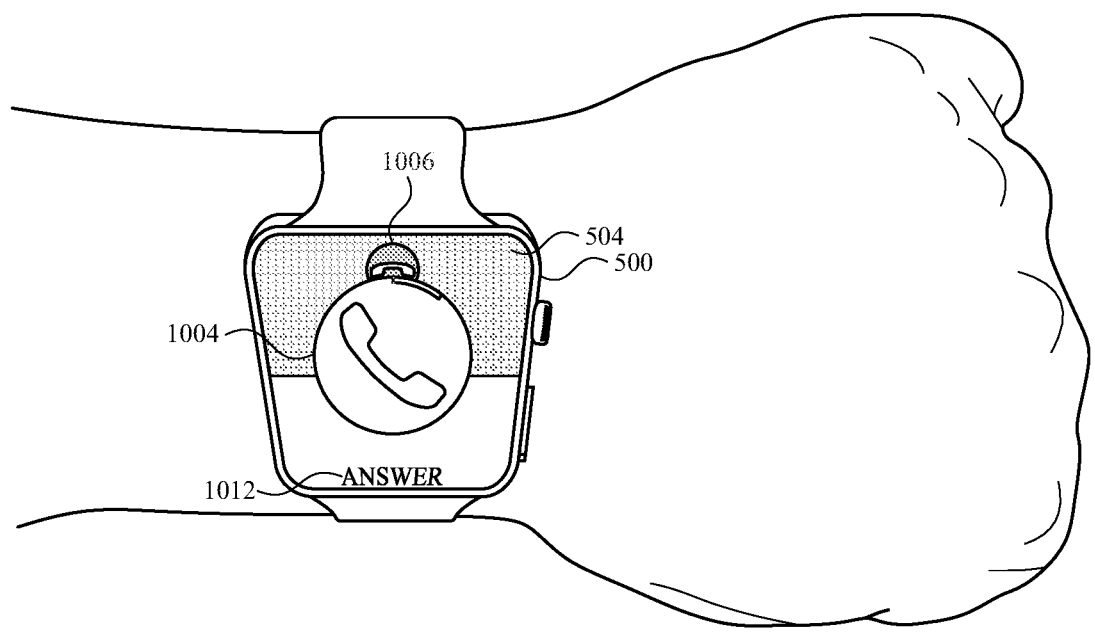

As shown in FIG. 10C, after the user clenches their hand, the orientation of the electronic device 500 is changed into a downward orientation as a result of the user rotating their wrist toward their body (e.g., the electronic device 500 is tilted down such that the top of the display screen 504 is moved upward relative to the bottom of the display screen 504). In response to the movement of the electronic device 500 to this orientation or a similar orientation, the answer call affordance 1004 is enlarged in size and moves toward the center region of the display screen 504, as shown in FIG. 10D. The change in visual appearance and location of the answer call affordance 1004 indicates to the user that the answer call operation will be selected as a result of this change in orientation of the electronic device 500 while the user's hand is in the clenched position. In addition, the visual appearance of the decline call affordance 1006 can be changed (e.g., darkened in brightness or partially faded) to indicate that the decline call operation will not be selected as a result of this change in orientation of the electronic device 500 while the user's hand is in the clenched position.

As shown in FIG. 10D, the electronic device 500 is held in the same or similar downward orientation as shown in FIG. 10C. Alternatively, in some embodiments, the orientation of the electronic device 500 is further changed into a further downward orientation as a result of the user further rotating their wrist toward their body (e.g., the electronic device 500 is tilted down further such that the top of the display screen 504 is further moved upward relative to the bottom of the display screen 504). As a result of the electronic device 500 being held in this downward orientation, the answer call affordance 1004 is displayed in the center region of the display screen 504. In addition, an answer call notification 1012 is displayed on the display screen 504. The answer call notification 1012 notifies the user that the answer call operation will be carried out in response the user clenching their hand and moving the electronic device 500 into the downward orientation. The answer call operation can be canceled if the user changes the orientation of the electronic device 500 to a substantially different orientation or if the user stops holding their hand in the clenched position. If the user continues holding their hand in the clenched position and holding the electronic device 500 in the downward orientation, then the electronic device 500 proceeds with the answer call operation, as shown in FIG. 10F.

Figure 10E:
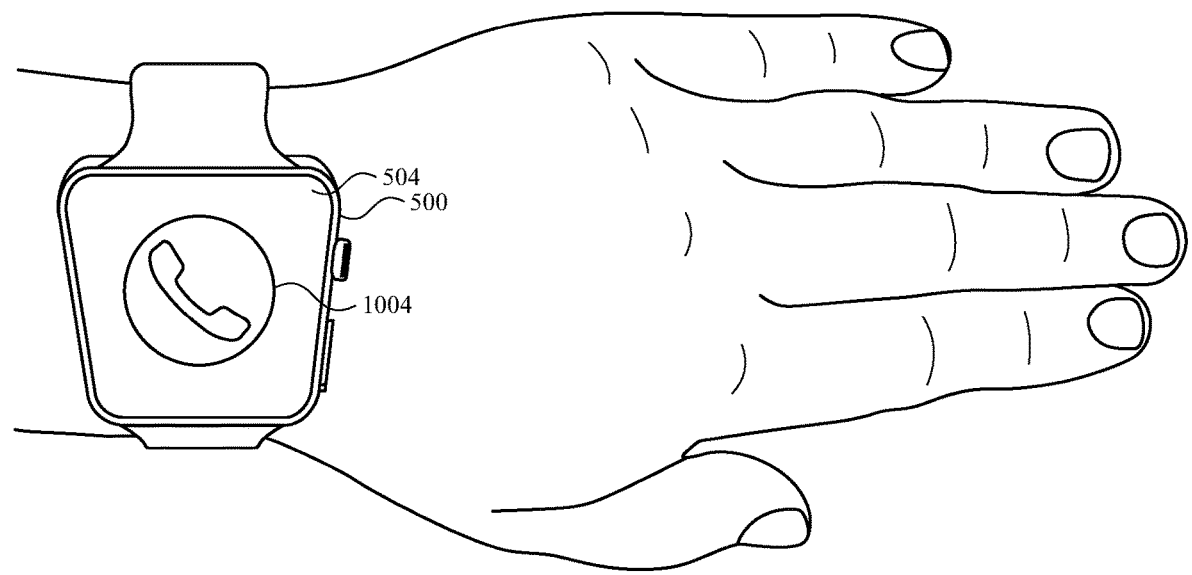

As shown in FIG. 10E, the user releases their hand from the clenched position (e.g., the user moves their hand to a relaxed, open position) while continuing to hold the electronic device 500 in the downward orientation. In response to the user releasing their hand from the clenched position, the answer call affordance 1004 is further enlarged in size. The change in appearance of the answer call affordance 1004 indicates that as a result of the user releasing their hand from the clenched position while holding the electronic device 500 in the downward orientation, the answer call operation is being initiated. Alternatively, in some embodiments, the answer call operation is initiated if the user holds their hand in the clenched position and holds the electronic device 500 in the downward orientation for a predetermined amount of time.

Figure 10F:
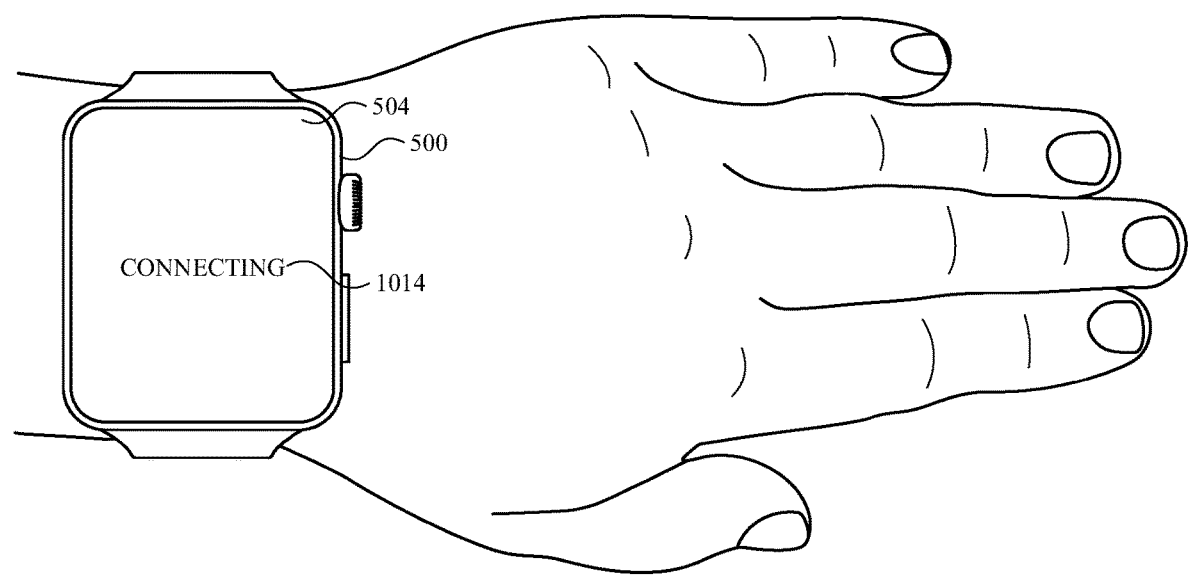

In response to the user releasing their hand from the clenched position while holding the electronic device 500 in the downward orientation, a call answering notification 1014 is displayed, as shown in FIG. 10F. Alternatively, in some embodiments, the call answering notification 1014 is displayed in response to the user holding their hand in the clenched position and holding the electronic device 500 in the downward orientation for a predetermined amount of time. The call answering notification 1014 indicates to the user that an answer call operation has been initiated by the electronic device 500. The answer call operation instructs the electronic device 500 or other associated device to answer the incoming telephone call.

Figure 10G:
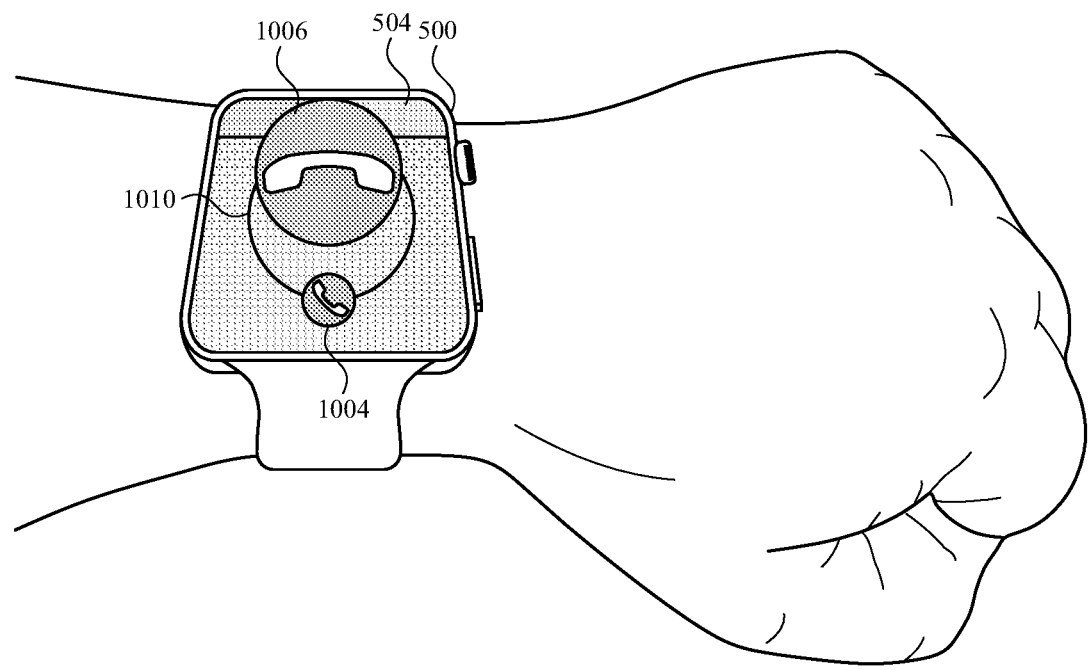
Figure 10H:
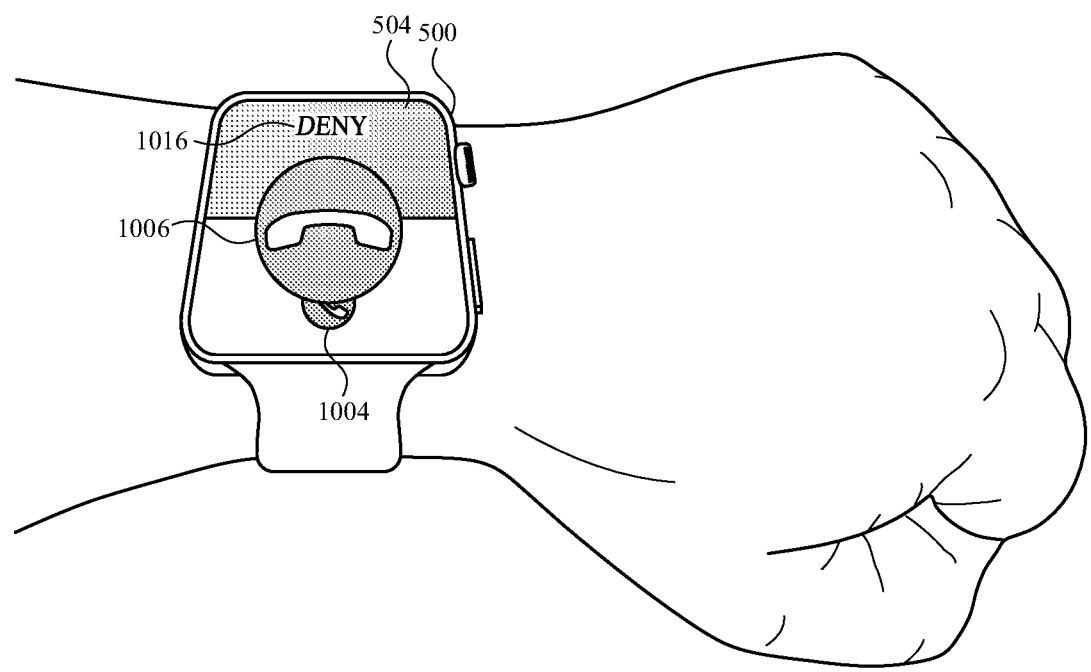

As shown in FIG. 10G, after the user clenches their hand, the orientation of the electronic device 500 is changed into a upward orientation as a result of the user rotating their wrist away from their body (e.g., the electronic device 500 is tilted up such that the bottom of the display screen 504 is moved upward relative to the top of the display screen 504). In response to the movement of the electronic device 500 to this orientation or a similar orientation, the decline call affordance 1006 is enlarged in size and moves toward the center region of the display screen 504, as shown in FIG. 10H. The change in visual appearance and location of the decline call affordance 1006 indicates to the user that the decline call operation will be selected as a result of this change in orientation of the electronic device 500 while the user's hand is in the clenched position. In addition, the visual appearance of the answer call affordance 1004 can be changed (e.g., darkened in brightness or partially faded) to indicate that the answer call operation will not be selected as a result of this change in orientation of the electronic device 500 while the user's hand is in the clenched position.

As shown in FIG. 10H, the electronic device 500 is held in the same or similar upward orientation as shown in FIG. 10G. Alternatively, in some embodiments, the orientation of the electronic device 500 is further changed into a further upward orientation as a result of the user further rotating their wrist away from their body (e.g., the electronic device 500 is tilted up further such that the bottom of the display screen 504 is further moved upward relative to the top of the display screen 504). As a result of the electronic device 500 being held in this upward orientation, the decline call affordance 1006 is displayed in the center region of the display screen 504. In addition, a decline call notification 1016 is displayed on the display screen 504. The decline call notification 1016 notifies the user that the decline call operation will be carried out in response the user clenching their hand and moving the electronic device 500 into the upward orientation. The decline call operation can be canceled if the user changes the orientation of the electronic device 500 to a substantially different orientation or if the user stops holding their hand in the clenched position. If the user continues holding their hand in the clenched position and holding the electronic device 500 in the upward orientation, then the electronic device 500 proceeds with the decline call operation, as shown in FIG. 10J.

Figure 10I:
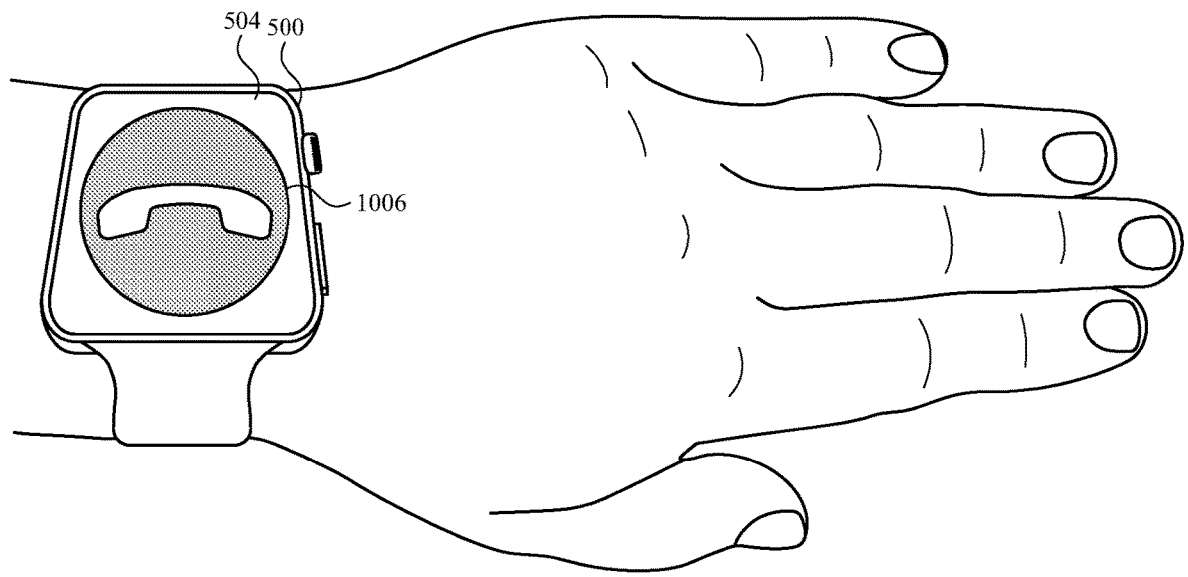

As shown in FIG. 10I, the user releases their hand from the clenched position (e.g., the user moves their hand to a relaxed, open position) while continuing to hold the electronic device 500 in the upward orientation. In response to the user releasing their hand from the clenched position, the decline call affordance 1006 is further enlarged in size. The change in appearance of the decline call affordance 1006 indicates that as a result of the user releasing their hand from the clenched position while holding the electronic device 500 in the upward orientation, the decline call operation is being initiated. Alternatively, in some embodiments, the decline call operation is initiated if the user holds their hand in the clenched position and holds the electronic device 500 in the upward orientation for a predetermined amount of time.

Figure 10J:
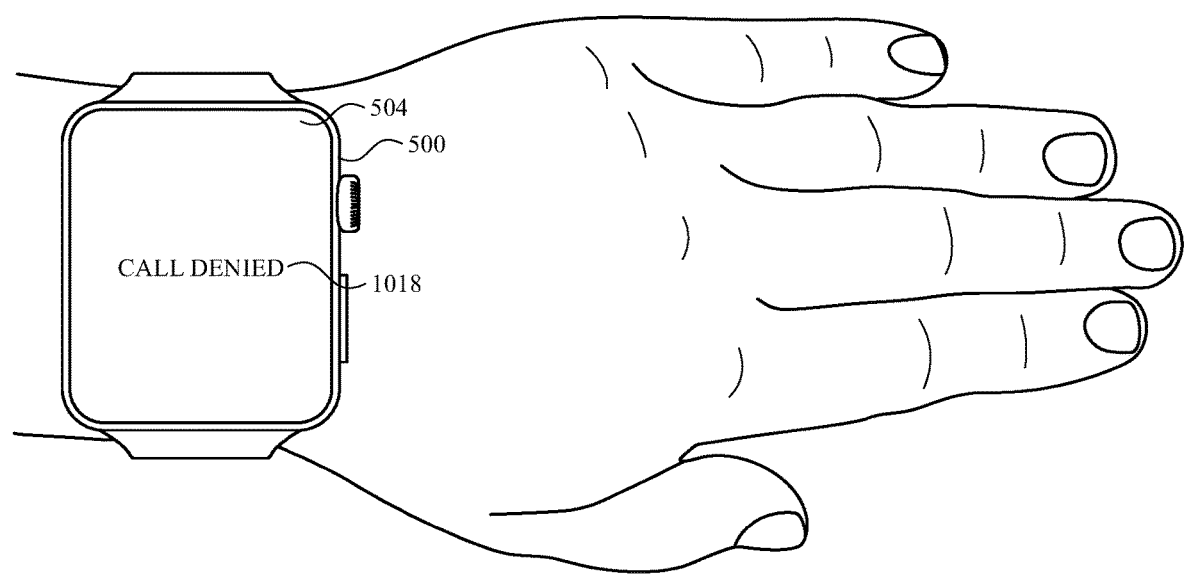

In response to the user releasing their hand from the clenched position while holding the electronic device 500 in the upward orientation, a call ending notification 1018 is displayed, as shown in FIG. 10J. Alternatively, in some embodiments, the call ending notification 1018 is displayed in response to the user holding their hand in the clenched position and holding the electronic device 500 in the upward orientation for a predetermined amount of time. The call ending notification 1018 indicates to the user that a decline call operation has been initiated by the electronic device 500. The decline call operation instructs the electronic device 500 or other associated device to decline the incoming telephone call.

Figure 10K:
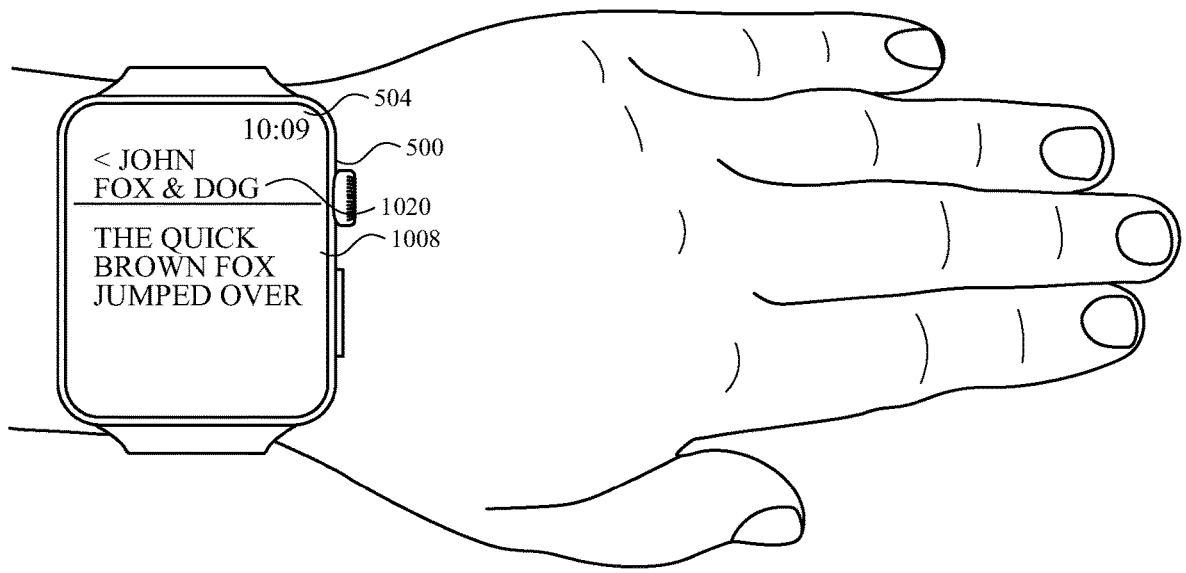

As shown in FIG. 10K, a portion of an electronic document 1020 is displayed on the display screen 504. The electronic document 1020 can be a portion of any type of graphical content, such as a website, email, book, photograph, or message. As shown in FIG. 10K, when the portion of the electronic document 1020 initially displayed, the user's hand is in a relaxed, open position.

Figure 10L:
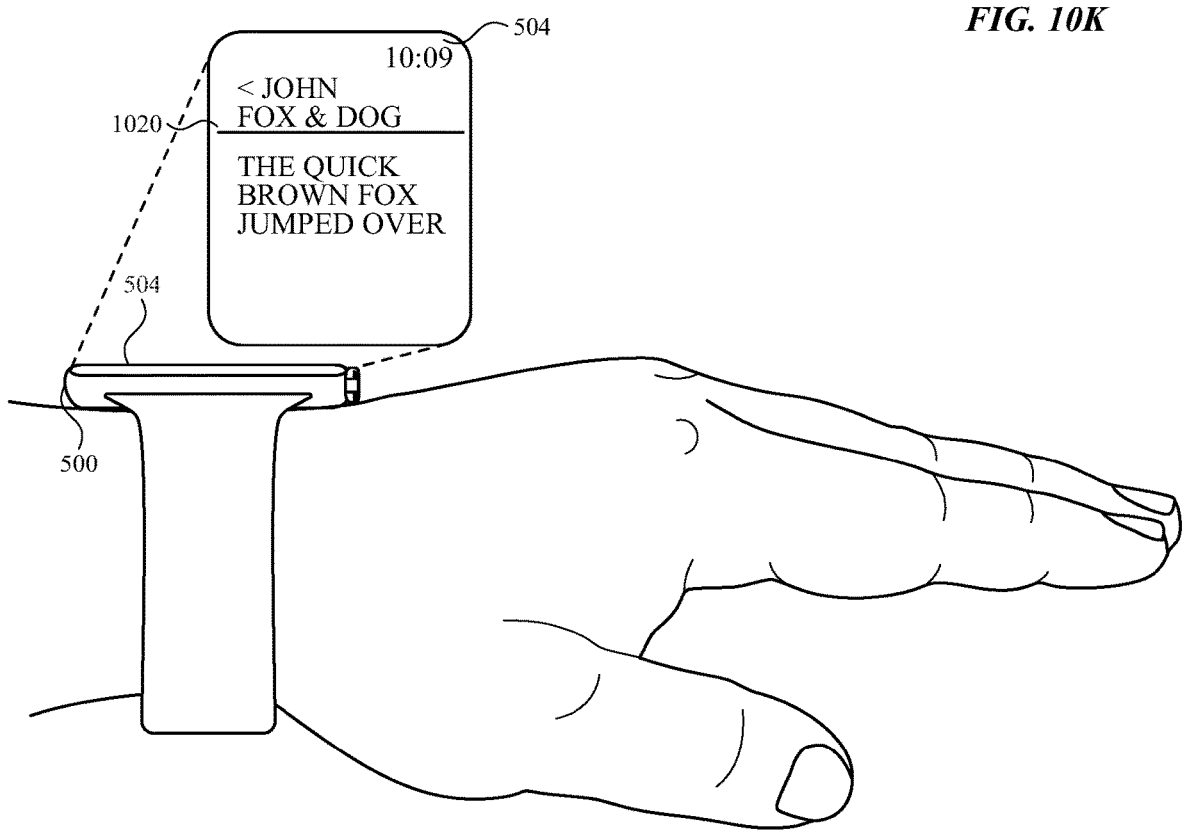

As shown in FIG. 10L, the orientation of the electronic device 500 is changed as a result of the user rotating their wrist away from their body (e.g., the electronic device 500 is tilted up such that the bottom of the display screen 504 is moved upward relative to the top of the display screen 504). Because the user's hand remains in the relaxed, open position, the portion of the electronic document 1020 being displayed does not change in response to this change in orientation of the electronic device 500.

Figure 10M:
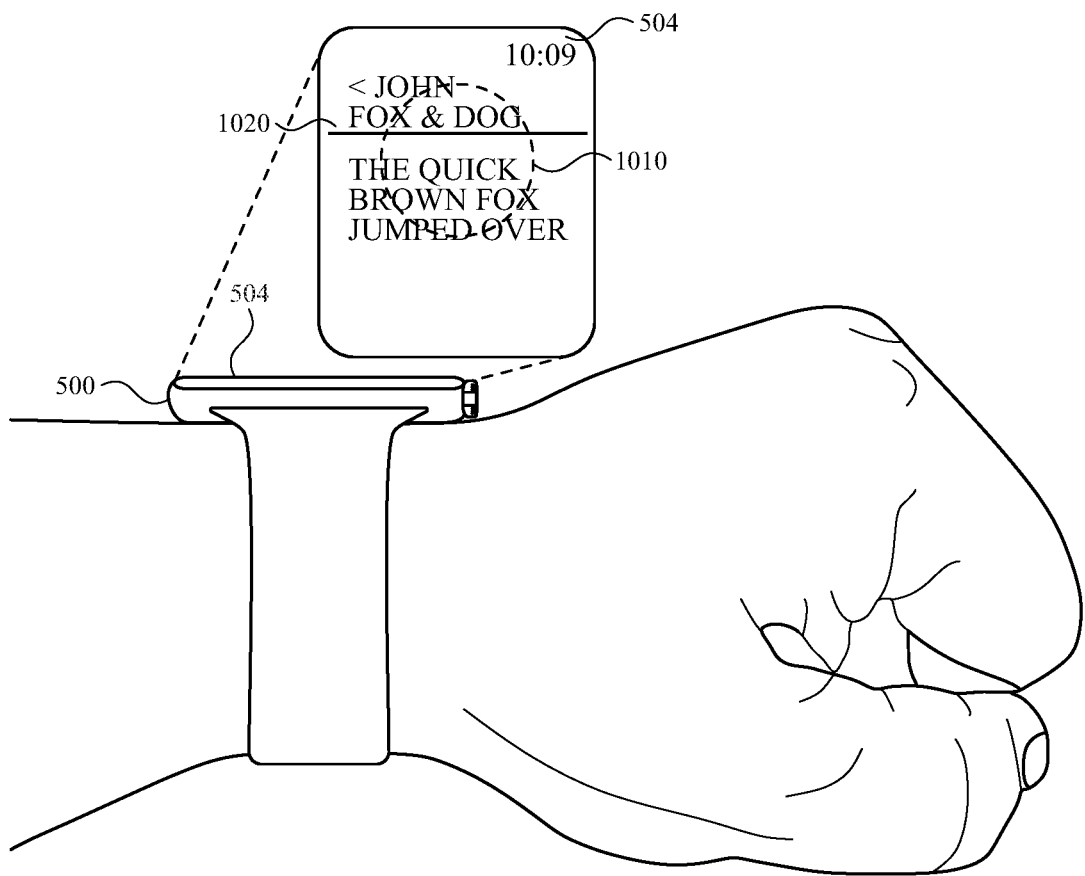

As shown in FIG. 10M, the user has changed the positioning of their hand from the relaxed, open position to a clenched position (e.g., the user makes a first with their hand) In response to the clenched position of the user's hand, a clenching indicator 1010 is displayed. In some embodiments, the clenched position of the user's hand is determined by the electronic device 500 by detecting a predefined pattern (e.g., an increase in blood flow intensity as shown in FIG. 9A) for a predetermined time with the biological sensor. The clenching indicator 1010 is semi-transparent and is displayed overlapping the other elements on the display screen 504. In some embodiments, the clenching indicator 1010 is an animated graphic that enlarges in size based on the strength of the clench of the user's hand (e.g., the user makes a tighter first with their hand and the blood flow intensity increases as shown in FIG. 9A). The clenching indicator 1010 indicates to the user that their clenched hand has been detected by the electronic device 500, and that additional input can be provided to the electronic device 500.

While the user's hand is clenched, the user can change the orientation of the electronic device 500 to scroll the portion of the electronic document 1020 being displayed. The changes in orientation include rotating the display screen 504 away from the user's body to scroll upward (e.g., the user rotates their wrist to move the bottom of the display screen 504 upward relative to the top of the display screen 504) or rotating the display screen 504 toward the user's body to scroll downward (e.g., the user rotates their wrist to move the top of the display screen 504 upward relative to the bottom of the display screen 504).

Figure 10N:
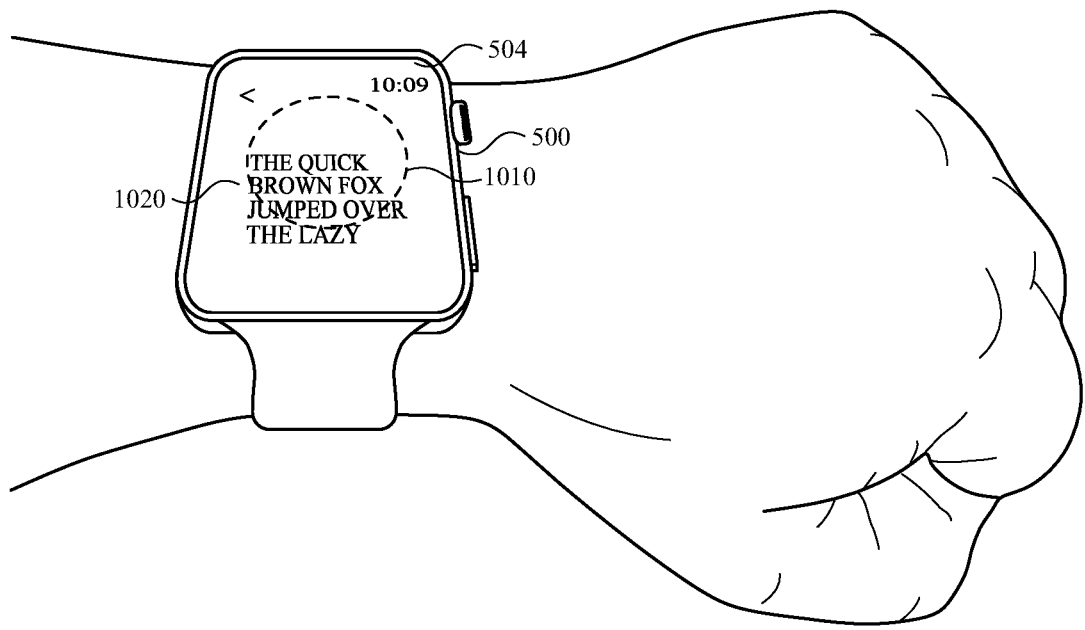

As shown in FIG. 10N, after the user clenches their hand, the orientation of the electronic device 500 is changed into a downward orientation as a result of the user rotating their wrist toward their body (e.g., the electronic device 500 is tilted down such that the top of the display screen 504 is moved upward relative to the bottom of the display screen 504). In response to the movement of the electronic device 500 to this orientation or a similar orientation, the electronic document 1020 is scrolled downward so that a different portion of the electronic document 1020 is displayed on the display screen 504, as shown in FIG. 10N. The clenching indicator 1010 continues to be displayed while the user's hand is clenched.

Similarly, the electronic document 1020 can be scrolled upward by the user clenching their hand and rotating their wrist away from their body to change the orientation of the electronic device 500 into an upward orientation (e.g., the electronic device 500 is tilted up such that the bottom of the display screen 504 is moved upward relative to the top of the display screen 504).

Figure 10O:
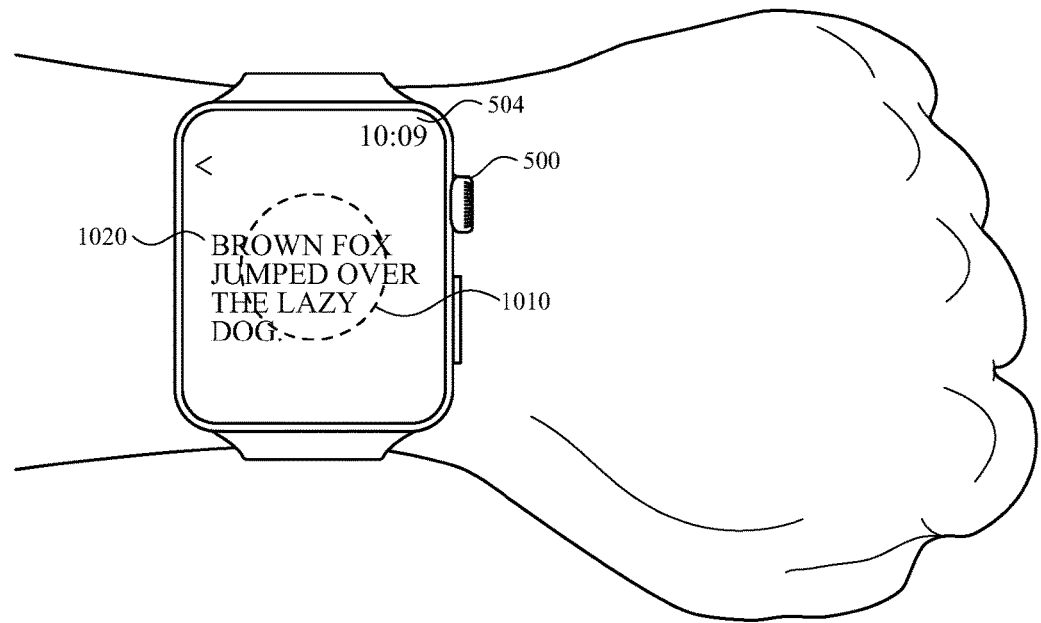
Figure 10P:
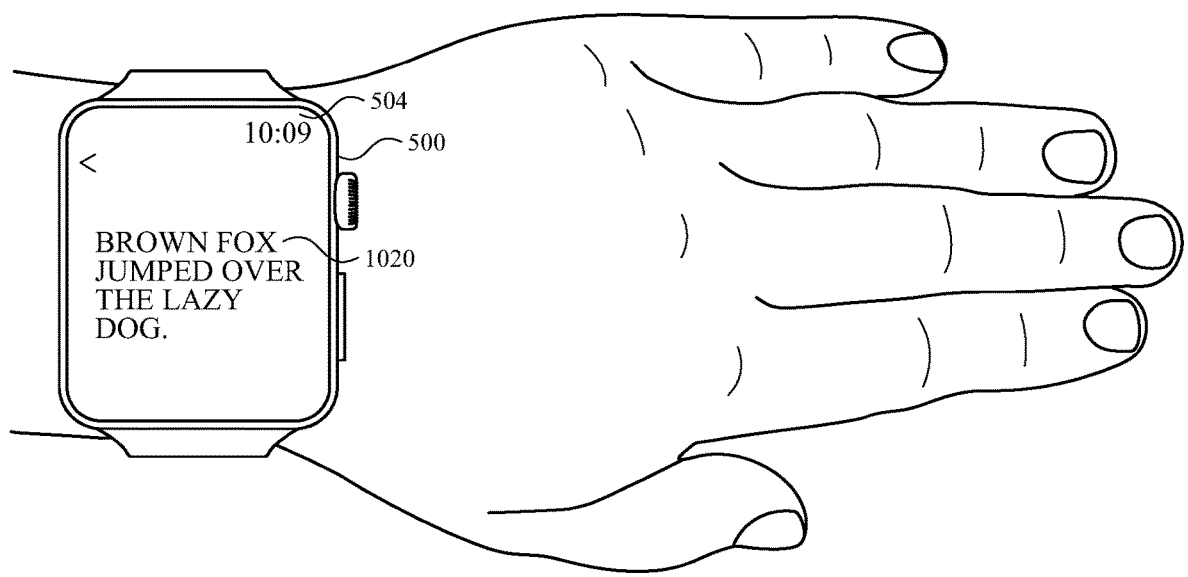

As shown in FIG. 10O, the orientation of the electronic device 500 is further changed into a further downward orientation as a result of the user further rotating their wrist toward their body (e.g., the electronic device 500 is tilted down further such that the top of the display screen 504 is further moved upward relative to the bottom of the display screen 504). As a result of the electronic device 500 being held in this downward orientation, the electronic document 1020 is scrolled further downward so that a different portion of the electronic document 1020 is displayed on the display screen 504, as shown in FIG. 10O. The clenching indicator 1010 continues to be displayed while the user's hand is clenched. In some embodiments, if the user continues holding their hand in the clenched position and holding the electronic device 500 in the downward orientation, then the electronic device 500 continues to scroll the electronic document downward.

Similarly, in some embodiments, if the user continues holding their hand in the clenched position and holding the electronic device 500 in the upward orientation (e.g., by rotating their wrist away from their body), then the electronic device 500 continues to scroll the electronic document upward.

As shown in FIG. 10P, the user releases their hand from the clenched position and holds their hand in a relaxed, open position. In response to the user moving their hand to the relaxed, open position, the clenching indicator 1010 is removed from the display. In addition, the electronic document 1020 stops being scrolled regardless of the orientation of the electronic device 500.

FIGS. 11A-11D illustrate exemplary user interfaces for interacting with an electronic device without touching a display screen or other physical input mechanism, in accordance with some embodiments. The user interfaces in these figures are used to illustrate the processes described below, including the processes in FIGS. 17A-17B.

In particular, FIGS. 11A-11D illustrate exemplary user interfaces for performing operations with an electronic device 500 based on an orientation of the electronic device. The electronic device 500 includes a display screen 504, a tilt sensor, and a biological sensor, among other elements which can be found above and/or as discussed in reference to FIG. 5A. The display screen 504 can be a touch-sensitive display screen. The biological sensor can be an optical sensor positioned in the electronic device to measure blood flow indicative of a clenched hand of the user. The tilt sensor can be an accelerometer 534, directional sensor 540 (e.g., compass), gyroscope 536, motion sensor 538, and/or a combination thereof. In the present example, device 500 is a wearable device on a user's wrist, such as a smart watch.

Figure 11A:
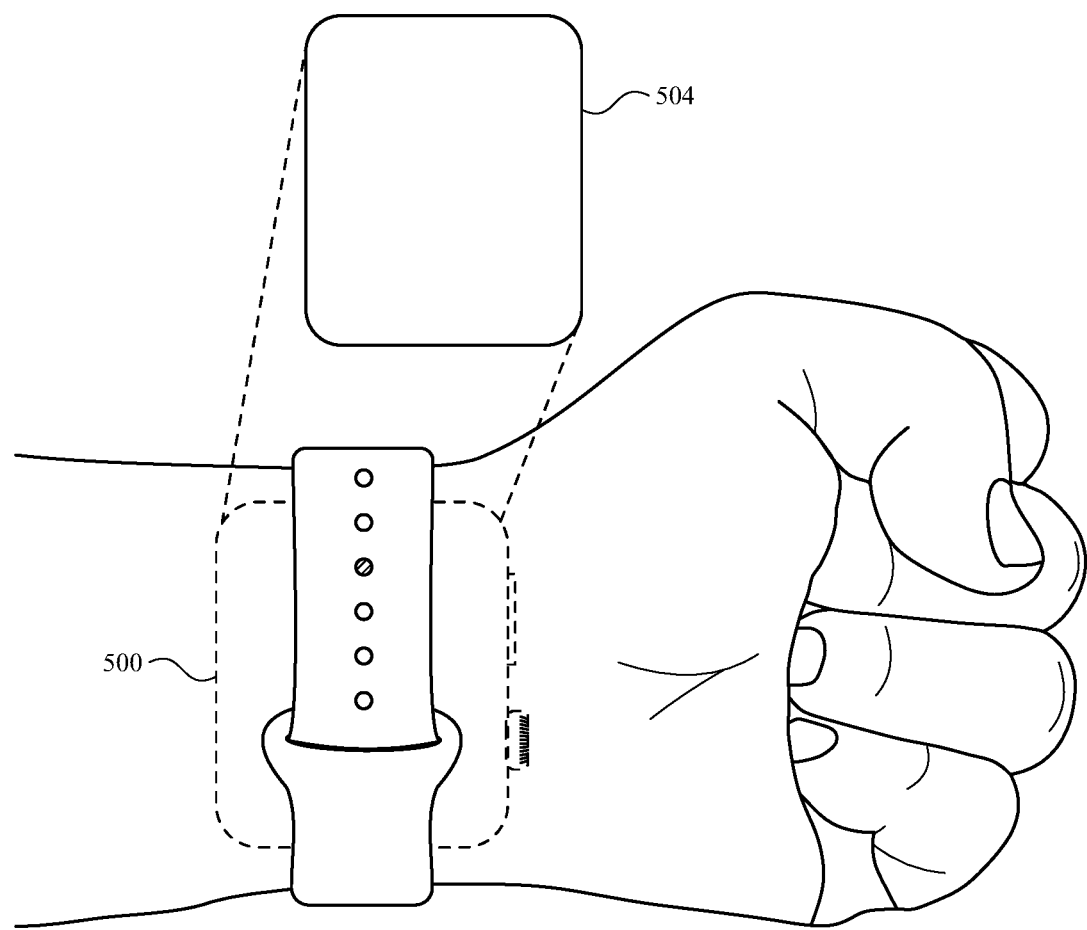
FIGS. 11A-11D illustrate exemplary user interfaces for interacting with an electronic device without touching a display screen or other physical input mechanism, in accordance with some embodiments.

As shown in FIG. 11A, the electronic device 500 is initially in an orientation where the display screen 504 is not visible to the user and/or the display screen 504 is in a passive mode. For instance, the user's arm can be to side of the user's body. Alternatively, in some embodiments, the display screen 504 of the electronic device 500 is visible to user but in the passive mode (e.g., the display screen 504 is off or displaying passive information, such as a time).

Figure 11B:
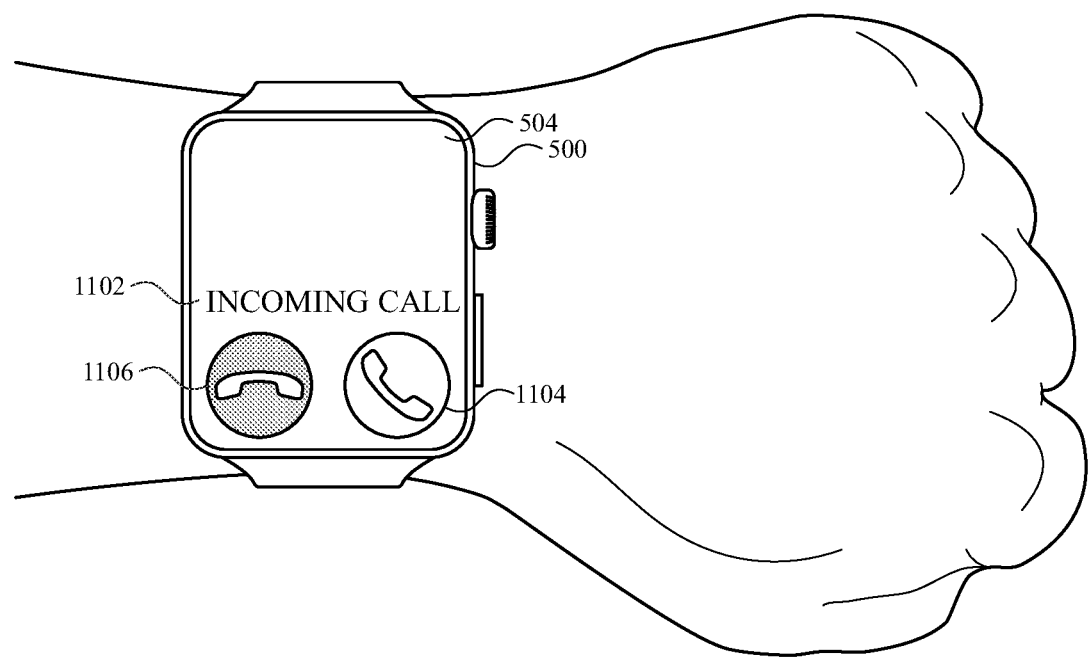

As shown in FIG. 11B, an incoming call notification 1102, answer call affordance 1104, and decline call affordance 1106 are displayed on the display screen 504 (similar to FIGS. 6A, 7A, 8AS, and 9B). When an incoming telephone call is being received, the incoming call notification 1102, answer call affordance 1104, and decline call affordance 1106 are displayed in response to the user changing the orientation of the electronic device 500 such that the display screen 504 is visible to the user. In some embodiments, the change in orientation is the result of the user lifting their arm and/or rotating their wrist. For example, as shown in FIG. 11B, the electronic device 500 is worn on the user's left wrist and is being held in a position such that display screen 504 is directly visible to the user's eyes (while being substantially perpendicular to the ground), such as is typical for users when they are checking the time. Throughout the sequence of interactions described in reference to FIGS. 11B-11C, the answer call affordance 1004 or the decline call affordance 1006 can be touched by the user to perform their respective operations with the electronic device 500 (e.g., answering the incoming call or declining the incoming telephone call, respectively).

When the incoming call notification 1102, answer call affordance 1104, and decline call affordance 1106 are displayed in response to the user changing the orientation of the electronic device 500, the electronic device 500 enters an active mode where the user can provide additional input to perform an operation (e.g., answering the incoming call or declining the incoming telephone call). In some embodiments, the additional input includes changing the positioning of the user's hand to a clenched position, as described in reference to FIGS. 9A-9H. Alternatively or in addition, in some embodiments, the additional input includes further changing the orientation of the electronic device 500 (e.g., tilting the electronic device 500 to the left or right), as described in reference to FIGS. 8AS-8BI). Alternatively or in addition, in some embodiments, prior to receiving the additional input from the user, the electronic device 500 displays additional movement indicators (e.g., the incoming call track 608 of FIG. 6B or the movement indicators 708a-708d of FIGS. 7B-7E). After the additional movement indicators are displayed, additional input is received from the user, which includes further changing the orientation of the electronic device 500 (e.g., tilting the electronic device 500), as described in reference to FIG. 6C-6I or 7G-7Q.

In some embodiments, if the electronic device 500 does not first enter the active mode before receiving additional input from the user, then the electronic device 500 forgoes performing the operations when the additional input is received. For instance, if the user does not first change the orientation of the electronic device 500 such that the display screen 504 is visible to the user, then the user clenching their hand will not perform an answer call operation.

Figure 11C:
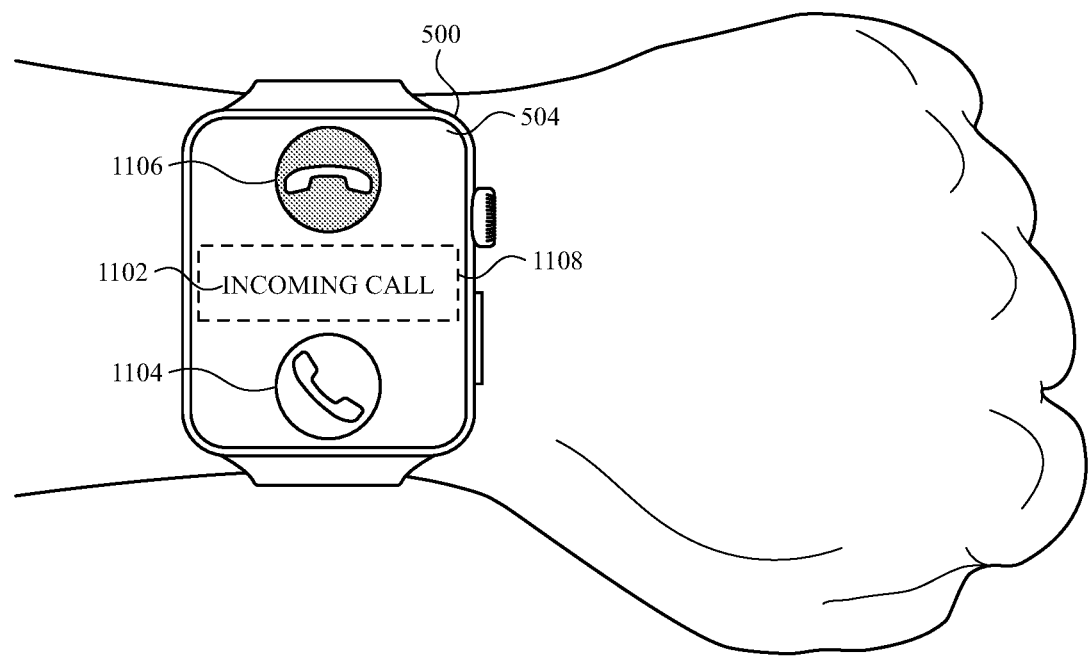

As shown in FIG. 11C, the answer call affordance 1104 is displayed in a lower region of the display screen 504 and the decline call affordance 1106 is displayed in an upper region of the display screen 504 (similar to FIG. 8AB). The incoming call notification 1102 is displayed in a center region 1108 of the display screen 504. Similar to as described in reference to FIG. 11B, when an incoming telephone call is being received, the incoming call notification 1102, answer call affordance 1104, and decline call affordance 1106 are displayed in response to the user changing the orientation of the electronic device 500 such that the display screen 504 is visible to the user, which also results in the electronic device 500 entering an active mode where the user can provide additional input to perform an operation (e.g., answering the incoming call or declining the incoming telephone call). In some embodiments, the additional input includes further changing the orientation of the electronic device 500 (e.g., rotating the display screen 504 away from or toward the user), as described in reference to FIGS. 8AB-8AR).

In some embodiments, if the electronic device 500 does not first enter the active mode before receiving additional input from the user, then the electronic device 500 forgoes performing the operations when the additional input is received. For instance, if the user does not first change the orientation of the electronic device 500 such that the display screen 504 is visible to the user, then the user rotating the display screen 504 will not perform an answer call or decline call operation.

Figure 11D:
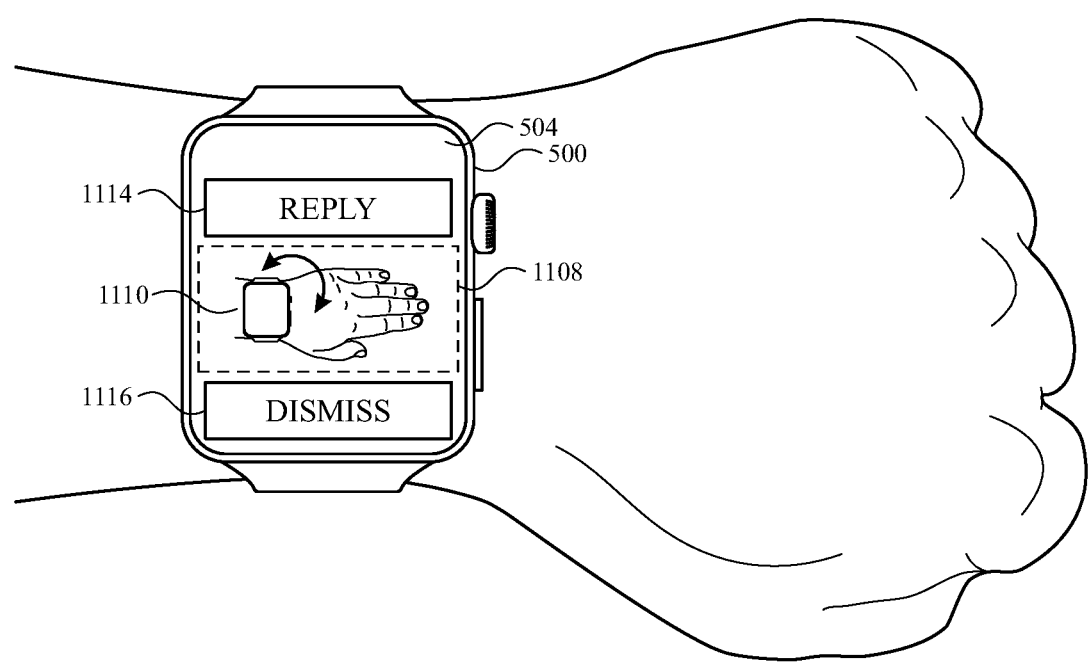

As shown in FIG. 11D, a reply affordance 1114 is displayed in an upper region of the display screen 504 and a dismiss affordance 1116 is displayed in a lower region of the display screen (similar to FIG. 8B). In addition, an instructional graphic 1110 can be displayed in the center region 1108 of the display screen. Similar to as described in reference to FIG. 11B, after an instant message is received, the reply affordance 1114 and dismiss affordance 1116 are displayed in response to the user changing the orientation of the electronic device 500 such that the display screen 504 is visible to the user, which also results in the electronic device 500 entering an active mode where the user can provide additional input to perform an operation (e.g., answering the incoming call or declining the incoming telephone call). In some embodiments, the additional input includes further changing the orientation of the electronic device 500 (e.g., rotating the display screen 504 away from or toward the user), as described in reference to FIGS. 8B-8E and 8W-8Z).

In some embodiments, if the electronic device 500 does not first enter the active mode before receiving additional input from the user, then the electronic device 500 forgoes performing the operations when the additional input is received. For instance, if the user does not first change the orientation of the electronic device 500 such that the display screen 504 is visible to the user, then the user rotating the display screen 504 will not perform a reply or dismiss operation.

In some embodiments, if the electronic device 500 enters the active mode and no additional input is received from the user, then the display screen 504 is activated and displays a time or a default "home" interface.

FIGS. 12A-12B are flow diagrams illustrating a method 1200 for performing one or more operations with an electronic device, in accordance with some embodiments. Method 1200 can be performed at a device (e.g., 100, 300, 500) with a display screen and a tilt sensor. In some examples, the tilt sensor includes an accelerometer, directional sensor (e.g., compass), gyroscope, motion sensor, and/or a combination thereof. Some operations in method 1200 are, optionally, combined, the order of some operations are, optionally, changed, and some operations are, optionally, omitted.

As described below, method 1200 provides an intuitive way for interacting with the device. In some cases, the device performs an operation in response to the user's hand, arm, and/or wrist movement. Performing an operation in response to the user's hand, arm, and/or wrist movement enhances the operability of the device by enabling the user to interact with the device without touching the display screen or other physical input mechanisms. This also allows operations to be performed more quickly and efficiently with the device.

As shown in method 1200, in some embodiments, the device (1202) displays a first graphical element at a first location on the display screen (e.g., graphical object 614 of FIG. 6B). The device also (1204) displays a second graphical element at a second location on the display screen (e.g., answer call affordance 604 of FIG. 6B). The second graphical element is associated with a first operation (e.g., answering an incoming telephone call). In some examples, the device displays a graphical indication of a path for simulated movement of the first graphical element (e.g., displays incoming call track 608 of FIG. 6B).

As shown in method 1200, in some embodiments, the device (1206) receives a tilt sensor input associated with movement of the electronic device (e.g., the orientation of the electronic device 500 is changed as a result of the user moving their arm/wrist/hand as shown in FIGS. 6C-6G). The device (1220) can optionally, while receiving the tilt sensor input, display the first graphical element at locations on the display screen based on the tilt sensor input (e.g., graphical object 614 is displayed at intermediate locations along the incoming call track 608 as shown in FIGS. 6C-6F).

As shown in method 1200, in some embodiments, in accordance with a determination that the tilt sensor input satisfies a first predefined tilt sensor condition (e.g., the tilt sensor input results in the graphical object 614 moving to the answer call affordance 604 as shown in FIG. 6G), the device (1208) displays the first graphical element proximate to the second location on the display screen (e.g., graphical object 614 is displayed at the end of the right track segment 610 as shown in FIG. 6G). Furthermore, in accordance with the determination that the tilt sensor input satisfies the first predefined tilt sensor condition, the device also (1210) performs the first operation associated with the second graphical element (e.g., answers an incoming telephone call as shown in FIGS. 6I-6K). Performing the first operation in response to the determination that the tilt sensor input satisfies the first predefined tilt sensor condition allows the first operation to be performed with fewer physical inputs from the user (e.g. finger touches on the display screen). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the first predefined tilt sensor condition includes simulated physical movement of a virtual object (having virtual mass) corresponding to the first graphical element (e.g., the acceleration and velocity of the graphical object 614 as it moves along the incoming call track 608 is representative of how a physical ball would roll along a physical track being held in the same orientation as the electronic device 500 as shown in FIGS. 6C-6F). In some examples, the simulated physical movement of the virtual object is based at least in part on a tilt angle of the device over a period of time. In some examples, the predefined tilt sensor condition is satisfied when the simulated physical movement of the virtual object results in the virtual object being moved proximate to the second location on the display screen (e.g., graphical object 614 is moved to the end of the right track segment 610 as shown in FIG. 6G). In some examples, the device includes a haptic feedback mechanism, and, further in accordance with the determination that the tilt sensor input satisfies the first predefined tilt sensor condition, the device provides a haptic feedback via the haptic feedback mechanism. In some examples, the first operation includes answering an incoming telephone call or declining an incoming telephone call.

In some examples, the device (1214) optionally displays a third graphical element at a fourth location on the display screen (e.g., decline call affordance 606 of FIG. 6B). The third graphical element is associated with a second operation (e.g., declining an incoming telephone call). In some examples, the second graphical element is an affordance associated with the first operation (e.g., answer call affordance 604 of FIG. 6B) and the third graphical element is an affordance associated with the second operation (e.g., decline call affordance 606 of FIG. 6B). In accordance with a determination that the tilt sensor input satisfies a second predefined tilt sensor condition (e.g., the tilt sensor input results in the ball rolling to the decline call affordance), the device (1216) displays the first graphical element proximate to the fourth location on the display screen (e.g., graphical object 614 is displayed at the end of the left track segment 612 of FIG. 6G) and (1218) performs the second operation associated with the third graphical element (e.g., declines the incoming telephone call).

As shown in method 1200, in some embodiments, in accordance with a determination that the tilt sensor input fails to satisfy the first or second predefined tilt sensor conditions (e.g., the tilt sensor input does not result in the graphical object 614 moving to the answer call affordance 604 or the decline call affordance 606 as shown in FIG. 6G), the device (1212) displays the first graphical element at a third location on the display screen based on the tilt sensor input (e.g., graphical object 614 is displayed at its initial location on the incoming call track 608 as shown in FIG. 6B or at intermediate locations along the incoming call track 608 as shown in FIGS. 6C-6F). In some examples, the third location is the same as the first location (e.g., graphical object 614 is displayed at its initial location on the incoming call track 608 as shown in FIG. 6B). In some examples, the predefined tilt sensor condition is not satisfied when the simulated physical movement of the virtual object does not result in the virtual object being moved proximate to the second location on the display screen (e.g., graphical object 614 is moved to its initial location on the incoming call track 608 as shown in FIG. 6B or moved to intermediate locations along the incoming call track 608 as shown in FIGS. 6C-6F).

Note that details of the processes described above with respect to method 1200 (e.g., FIGS. 12A-12B) are also applicable in an analogous manner to other methods described herein. For example, method 1700 optionally includes one or more of the characteristics of the various methods described above with reference to method 1200. For example, the mode change criteria of method 1700 can be satisfied prior to receiving the tilt sensor input of method 1200 (e.g., the display screen is held in view of a user for a predetermined time as a precondition to pto receiving the tilt sensor input). For brevity, these details are not repeated below.

FIGS. 13A-13B are flow diagrams illustrating a method 1300 for performing one or more operations with an electronic device, in accordance with some embodiments. Method 1300 is performed at a device (e.g., 100, 300, 500) with a display screen and a tilt sensor. In some examples, the tilt sensor includes an accelerometer, directional sensor (e.g., compass), gyroscope, motion sensor, and/or a combination thereof. Some operations in method 1300 are, optionally, combined, the order of some operations are, optionally, changed, and some operations are, optionally, omitted.

As described below, method 1300 provides an intuitive way for interacting with the device. In some cases, the device performs an operation in response to the user's hand, arm, and/or wrist movement. Performing an operation in response to the user's hand, arm, and/or wrist movement enhances the operability of the device by enabling the user to interact with the device without touching the display screen or other physical input mechanisms. This also allows operations to be performed more quickly and efficiently with the device.

As shown in method 1300, in some embodiments, the device (1302) displays a first plurality of graphical elements (e.g., movement indicators 708a-708d of FIGS. 7B-7E) indicating a predefined sequence of movements associated with an operation (e.g., answering an incoming telephone call). The first plurality of graphical elements include a first graphical element indicating a first movement (e.g., a "high" musical note as shown in FIG. 7B) and a second graphical element indicating a second movement (e.g., a "low" musical note as shown in FIG. 7C). The first movement includes rotation of the device in a first direction around a central axis from a neutral position to a first position and back toward the neutral position within a first predetermined time (e.g., the user makes a "flicking" motion with the device, where the display screen is quickly rotated away from the user and then is immediately rotated back toward the user). The second movement comprises a rotation of the electronic device in a second direction opposite the first direction around the central axis from the neutral position to a second position and back toward the neutral position within a second predetermined time (e.g., the user makes a "flicking" motion with the device, where the display screen is quickly rotated toward the user and then is immediately rotated back away from the user). In some examples, the central axis corresponds to an axis of rotation of a user's wrist. In some examples, the first or second movement includes rotation of the device at a velocity greater than a predetermined minimum velocity. In some examples, the first or second movement includes rotation of the electronic device with an acceleration greater than a predetermined minimum acceleration.

As shown in method 1300, in some embodiments, the device (1304) receives a plurality of tilt sensor inputs associated with movements of the electronic device (e.g., the orientation of the device is changed as shown in FIGS. 7G-7N). In some examples, while receiving the plurality of tilt sensor inputs, the device (1310) optionally displays a second plurality of graphical elements indicating movements of the electronic device (e.g., movement indicators 708a-708d of FIGS. 7G-7N). In some examples, while receiving the plurality of tilt sensor inputs, the device (1312) optionally displays an indicator that indicates the direction of rotation of the electronic device (e.g., input indicator 710 of FIGS. 7G-7N).

As shown in method 1300, in some embodiments, in accordance with a determination that the plurality of tilt sensor inputs corresponds to the predefined sequence of movements indicated by the first plurality of graphical elements (e.g., the tilt sensor input corresponds to the movement indicators 708a-708d shown in FIGS. 7B-7E), the device (1306) performs the operation associated with the predefined sequence of movements. In some examples, the operation includes answering an incoming telephone call or declining the incoming telephone call. Performing the operation in response to the determination that the plurality of tilt sensor inputs corresponds to the predefined sequence of movements indicated by the first plurality of graphical elements allows the first operation to be performed with fewer physical inputs from the user (e.g. finger touches on the display screen). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

As shown in method 1300, in some embodiments, in accordance with a determination that the plurality of tilt sensor inputs does not correspond to the predefined sequence of movements indicated by the first plurality of graphical elements (e.g., the tilt sensor input does not correspond to the movement indicators 708a-708d shown in FIGS. 7B-7E), the device (1308) forgoes performing the operation associated with the predefined sequence of movements. In some examples, in accordance with a determination that at least one of the plurality of tilt sensor inputs is not greater than a predetermined minimum velocity, the device (1314) optionally forgoes performing the operation associated with the predefined sequence of movements. In some examples, in accordance with a determination that at least one of the plurality of tilt sensor inputs is not greater than a predetermined minimum acceleration, the device (1316) optionally forgoes performing the operation associated with the predefined sequence of movements.

Note that details of the processes described above with respect to method 1300 (e.g., FIGS. 13A-13B) are also applicable in an analogous manner to other methods described herein. For example, method 1700 optionally includes one or more of the characteristics of the various methods described above with reference to method 1300. For example, the mode change criteria of method 1700 can be satisfied prior to receiving the tilt sensor inputs of method 1300 (e.g., the display screen is held in view of a user for a predetermined time as a precondition to receiving the tilt sensor inputs). For brevity, these details are not repeated below.

FIG. 14 is a flow diagram illustrating a method 1400 for performing one or more operations with an electronic device, in accordance with some embodiments. Method 1400 is performed at a device (e.g., 100, 300, 500) with a display screen and a tilt sensor. In some examples, the tilt sensor includes an accelerometer, directional sensor (e.g., compass), gyroscope, motion sensor, and/or a combination thereof. Some operations in method 1400 are, optionally, combined, the order of some operations are, optionally, changed, and some operations are, optionally, omitted.

As described below, method 1400 provides an intuitive way for interacting with the device. In some cases, the device performs an operation in response to the user's hand, arm, and/or wrist movement. Performing an operation in response to the user's hand, arm, and/or wrist movement enhances the operability of the device by enabling the user to interact with the device without touching the display screen or other physical input mechanisms. This also allows operations to be performed more quickly and efficiently with the device.

As shown in method 1400, in some embodiments, the device (1402) displays a first item (e.g., reply affordance 804 of FIG. 8B, a predefined response 814a-814e of FIG. 8E, or decline call affordance 826 of FIG. 8AB or 8AS) at a first position on the display screen and a second item (e.g., dismiss affordance 806 of FIG. 8B, a predefined response 814a-814e of FIG. 8E, or answer call affordance 824 of FIG. 8AB or 8AS) at a second position on the display screen. The first position and second position correspond to positions along a line substantially perpendicular to an axis of rotation of the electronic device (e.g., items are positioned vertically or horizontally on the display screen so that rotation of the device is toward one item or the other, such as shown in FIG. 8B, 8F, 8AB, or 8AS). In some examples, the axis of rotation of the device corresponds to an axis of rotation of a user's wrist. In some examples, the first position is in an upper half of the display screen and the second position is in a lower half of the display screen. In some examples, the first or second item is a reply command for a received text message, a dismiss command for a received text message, a predefined response to a received text message, an answer command for a telephone call, or a decline command for a telephone call.

As shown in method 1400, in some embodiments, the device (1404) receives a tilt sensor input associated with movement of the electronic device (e.g., the orientation of the device is changed as shown in FIG. 8C-8E, 8G, 8J, 8M, 8X-8Y, 8AC-8AI, 8AK-8AQ, 8AT-8AZ, or 8BB-8BH). In some examples, the device (1412) optionally displays an indicator that indicates the direction of rotation of the electronic device (e.g., input indicator 812 of FIG. 8C-8D, 8G, 8J, 8M, or 8X-8Y). In some examples, the tilt sensor input corresponds to rotation of the device in the first or second direction at a velocity greater than a predetermined minimum velocity. In some examples, the tilt sensor input corresponds to rotation of the device in the first or second direction with an acceleration greater than a predetermined minimum acceleration.

As shown in method 1400, in some embodiments, in accordance with a determination that the tilt sensor input corresponds to a rotation of the electronic device in a first direction around the axis of rotation from a neutral position to a first position (e.g., the orientation of the device is changed as shown in FIG. 8C-8E, 8J, 8M, 8AK-8AQ, or 8BB-8BH), the device (1406) moves the first item from the first position on the display screen to a third position along the line substantially perpendicular to the axis of rotation (e.g., reply affordance 804, a predefined response 814a-814e, or decline call affordance 826 is moved toward a center region of the display screen, as shown in FIG. 8C-8E, 8J, 8M, 8AK-8AQ, or 8BB-8BH). In some examples, the tilt sensor input corresponds to a rotation of the electronic device in the first direction around the axis of rotation from the neutral position to the first position and from the first position back toward the neutral position within a first predetermined time (e.g., the user makes a "flicking" motion with the device, where the display screen is quickly rotated away from the user and then is immediately rotated back toward the user).

As shown in method 1400, in some embodiments, in accordance with a determination that the tilt sensor input corresponds to a rotation of the electronic device in a second direction opposite the first direction around the axis of rotation from the neutral position to a second position (e.g., the orientation of the device is changed as shown in FIG. 8G, 8X-8Y, 8AC-8AI, or 8AT-8AZ), the device (1408) moves the second item from the second position on the display screen to a fourth position along the line substantially perpendicular to the axis of rotation (e.g., dismiss affordance 806, a predefined response 814a-814e, or answer call affordance 824 is moved toward a center region of the display, as shown in FIG. 8G, 8X-8Y, 8AC-8AI, or 8AT-8AZ). In some examples, the tilt sensor input corresponds to a rotation of the electronic device in the second direction opposite the first direction around the axis of rotation from the neutral position to the second position and from the second position back toward the neutral position within a second predetermined time (e.g., the user makes a "flicking" motion with the device, where the display screen is quickly rotated toward the user and then is immediately rotated back away from the user).

Moving the first or second items to different positions on the display screen in response to the determination that the tilt sensor input corresponds to a rotation of the device allows the device to be operated with fewer physical inputs from the user (e.g. finger touches on the display screen). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the third and fourth positions are in a center region of the display screen. In some examples, the device includes a haptic feedback mechanism (e.g., vibration mechanism), and, in accordance with the determination that the tilt sensor input corresponds to rotation of the device in the first or second direction, the device provides a haptic feedback, via the haptic feedback mechanism. In some examples, in accordance with a determination that the tilt sensor input is not greater than a predetermined minimum velocity, the device forgoes moving the first or second item. In some examples, in accordance with a determination that the tilt sensor input is not greater than a predetermined minimum acceleration, the device forgoes moving the first or second item.

In some examples, after moving the first or second item, and in accordance with a determination that no additional tilt sensor input above a threshold value is received within a predetermined time, the device (1410) optionally selects the moved item (e.g., the reply affordance 804 is selected as shown in FIG. 8E, the predefined response 814d is selected as shown in FIG. 8U, the dismiss affordance 806 is selected as shown in FIG. 8Z, the answer call affordance 824 is selected as shown in FIG. 8AI or 8AZ, or the decline call affordance is selected as shown in FIG. 8AQ or 8BH). In some examples, displaying a countdown indicator corresponding to the predetermined time (e.g., progress ring 816 of FIG. 8P-8U or progress ring 828 of FIG. 8AD-8AI, 8AL-8AQ, 8AU-8AZ, or 8BC-8BH). In some examples, the device includes a haptic feedback mechanism (e.g., vibration mechanism), and, in accordance with the determination that no additional tilt sensor input above the threshold value is received within the predetermined time, the device provides a haptic feedback, via the haptic feedback mechanism.

Note that details of the processes described above with respect to method 1400 (e.g., FIG. 14) are also applicable in an analogous manner to other methods described herein. For example, method 1700 optionally includes one or more of the characteristics of the various methods described above with reference to method 1400. For example, the mode change criteria of method 1700 can be satisfied prior to receiving the tilt sensor input of method 1400 (e.g., the display screen is held in view of a user for a predetermined time as a precondition to receiving the tilt sensor input). For brevity, these details are not repeated below.

FIG. 15 is a flow diagram illustrating a method 1500 for performing an operation with an electronic device, in accordance with some embodiments. Method 1500 is performed at a device (e.g., 100, 300, 500) with a display screen and a biological sensor. In some examples, the biological sensor is an optical sensor positioned in the device to measure blood flow indicative of a clenched hand of the user. Some operations in method 1500 are, optionally, combined, the order of some operations are, optionally, changed, and some operations are, optionally, omitted.

As described below, method 1500 provides an intuitive way for interacting with the device. In some cases, the device performs an operation in response to a positioning of a user's hand Performing an operation in response to the positioning of the user's hand enhances the operability of the device by enabling the user to interact with the device without touching the display screen or other physical input mechanisms. This also allows operations to be performed more quickly and efficiently with the device.

As shown in method 1500, in some embodiments, the device (1502) displays an affordance on the display screen (e.g., answer call affordance 904 of FIG. 9B).

As shown in method 1500, in some embodiments, the device (1504) receives biological sensor input associated with a positioning of a user's hand (e.g., the user changes the positioning of their hand to a clenched position as shown in FIG. 9C).

As shown in method 1500, in some embodiments, in accordance with a determination that the biological sensor input corresponds to a predefined pattern for a predetermined time, the predefined pattern being associated with the positioning of the user's hand (e.g., the user continues to hold their hand in the clenched position for a predetermined amount of time as shown in FIGS. 9D-9G), the device (1506) displays an indication that the biological sensor input corresponds to the predefined pattern for the predetermined time (e.g., the answer call affordance 904 is enlarged in size and a progress ring 908 is displayed, as shown in FIGS. 9D-9G). In some examples, the device (1512) optionally modifies a visual appearance of the affordance (e.g., the answer call affordance 904 is enlarged in size as shown in FIGS. 9D-9G). In some examples, the device (1514) optionally displays a graphical element indicating the predetermined time (e.g., progress ring 908 of FIGS. 9D-9G). In some examples, the device includes a haptic feedback mechanism (e.g., vibration mechanism), and, further in accordance with the determination that the biological sensor input corresponds to the predefined pattern, the device provides a haptic feedback, via the haptic feedback mechanism (e.g., the device vibrates when the user clenches their hand).

The device then (1508) performs an operation associated with the affordance. In some examples, the operation includes answering a telephone call. Performing the operation in response to the determination that the biological sensor input corresponds to the predefined pattern for the predetermined time allows the operation to be performed with fewer physical inputs from the user (e.g. finger touches on the display screen). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

As shown in method 1500, in some embodiments, in accordance with a determination that the sensor input does not correspond to the predefined pattern for the predetermined time (e.g., the user stops holding their hand in a clenched position), the device (1510) forgoes performing the operation associated with the affordance (e.g., the incoming telephone call is not answered).

Note that details of the processes described above with respect to method 1500 (e.g., FIG. 15) are also applicable in an analogous manner to other methods described herein. For example, method 1700 optionally includes one or more of the characteristics of the various methods described above with reference to method 1500. For example, the mode change criteria of method 1700 can be satisfied prior to receiving the biological sensor input of method 1500 (e.g., the display screen is held in view of a user for a predetermined time as a precondition to receiving the biological sensor input). For brevity, these details are not repeated below.

FIGS. 16A-16B are flow diagrams illustrating a method 1600 for performing an operation with an electronic device, in accordance with some embodiments. Method 1600 is performed at a device (e.g., 100, 300, 500) with a display screen, a biological sensor, and a tilt sensor. In some examples, the biological sensor is an optical sensor positioned in the device to measure blood flow indicative of a clenched hand of the user. In some examples, the tilt sensor includes an accelerometer, directional sensor (e.g., compass), gyroscope, motion sensor, and/or a combination thereof. Some operations in method 1600 are, optionally, combined, the order of some operations are, optionally, changed, and some operations are, optionally, omitted.

As described below, method 1600 provides an intuitive way for interacting with the device. In some cases, the device performs an operation in response to a positioning of a user's hand and an orientation of the device. Performing an operation in response to the positioning of the user's hand and the orientation of the device enhances the operability of the device by enabling the user to interact with the device without touching the display screen or other physical input mechanisms. This also allows operations to be performed more quickly and efficiently with the device.

As shown in method 1600, in some embodiments, the device (1602) displays a user interface on the display screen (e.g., an incoming telephone call interface as shown in FIG. 10A or an electronic document 1020 as shown in FIG. 10K). The user interface is responsive to at least a first operation and a second operation associated with movement of the device (e.g., an answer call operation, a decline call operation, a scroll up operation, or a scroll down operation). In some examples, the user interface includes a first graphical element associated with the first operation and a second graphical element associated with the second operation. In some examples, the first graphical element is a first affordance associated with an answer call operation (e.g., answer call affordance 1004 of FIG. 10A), and the second graphical element is a second affordance associated with a decline call operation (e.g., decline call affordance 1006 of FIG. 10A). In some examples, the user interface includes a portion of an electronic document (e.g., electronic document 1020 of FIG. 10K).

As shown in method 1600, in some embodiments, the device (1604) receives biological sensor input associated with positioning of a user's hand (e.g., the user changes the positioning of their hand to a clenched position as shown in FIGS. 10B and 10M).

As shown in method 1600, in some embodiments, in accordance with a determination that the biological sensor input corresponds to a predefined pattern for a predetermined time, the predefined pattern being associated with the positioning of the user's hand (e.g., the user holds their hand in the clenched position as shown in FIG. 10B-10D, 10G-10H, or 10M-10O), the device (1606) displays an indication in the user interface that the sensor input corresponds to the predefined pattern (e.g., clenching indicator 1010 of FIG. 10B-10C, 10G, or 10M-10O). In some examples, the device includes a haptic feedback mechanism (e.g., vibration mechanism), and, further in accordance with the determination that the biological sensor input corresponds to the predefined pattern, providing a haptic feedback, via the haptic feedback mechanism.

As shown in method 1600, in some embodiments, while the biological sensor input corresponds to the predefined pattern (e.g., while the user's hand is in the clenched position as shown in FIG. 10B-10D, 10G-10H, or 10M-10O), the device (1608) receives a tilt sensor input associated with movement of the electronic device (e.g., the orientation of the device is changed as shown in FIG. 10C-10E, 10G-10I, or 10N-10O).

As shown in method 1600, in some embodiments, in accordance with a determination that the tilt sensor input corresponds to movement of a first type (e.g., the orientation of the device is changed as shown in FIG. 10C-10E or 10N-10O), the device (1610) performs the first operation (e.g., answers the incoming telephone call as shown in FIG. 10F or scrolls the electronic document 1020 in a downward direction as shown in FIGS. 10N-10O). In some examples, in accordance with the determination that the tilt sensor input corresponds to movement of the first type, the device (1614) optionally modifies a visual appearance of the first graphical element (e.g., enlarges the size of the answer call affordance 1004 as shown in FIGS. 10D-10E). In some examples, the first operation includes scrolling the electronic document in a first direction (e.g., electronic document 1020 of FIG. 10K is scrolled downward). In some examples, the movement of the first type includes a rotation of the device in a first direction around a central axis from a neutral position to a first position (e.g., the orientation of the device is changed as shown in FIG. 10C-10E or 10N-10O). In some examples, the movement of the first type further comprises rotation from the first position back toward the neutral position within a first predetermined time (e.g., the user makes a "flicking" motion with the device, where the display screen is quickly rotated toward the user and then is immediately rotated back away from the user). In some examples, after receiving the tilt sensor input and prior to performing the first operation, the device (1624) determines the biological sensor input ceases to correspond to the predefined pattern (e.g., the user releases their hand from the clenched position), and in response, the device (1610) performs the first operation (e.g., releasing the clenched hand initiates the answer call operation as shown in FIG. 10E).

As shown in method 1600, in some embodiments, in accordance with a determination that the tilt sensor input corresponds to movement of a second type (e.g., the orientation of the device is changed as shown in FIGS. 10G-10I), the device (1612) performs the second operation (e.g., declines the incoming telephone call as shown in FIG. 10J or scrolls the electronic document 1020 in an upward direction). In some examples, in accordance with the determination that the tilt sensor input corresponds to movement of the second type, the device (1616) optionally modifies a visual appearance of the second graphical element (e.g., enlarges the size of the decline call affordance 1006 as shown in FIGS. 10G-10I). In some examples, the second operation including scrolling the electronic document in a second direction (e.g., electronic document 1020 of FIG. 10K is scrolled upward). In some examples, the movement of the second type includes a rotation of the electronic device in a second direction around a central axis from a neutral position to a second position (e.g., the orientation of the device is changed as shown in FIGS. 10G-10I). In some examples, the movement of the second type further includes rotation from the second position back toward the neutral position within a second predetermined time (e.g., the user makes a "flicking" motion with the device, where the display screen is quickly rotated away from the user and then is immediately rotated back toward the user). In some examples, after receiving the tilt sensor input and prior to performing the second operation, the device (1626) determines the biological sensor input ceases to correspond to the predefined pattern (e.g., the user releases their hand from the clenched position), and in response, the device (1612) performs the second operation (e.g., releasing the clenched hand initiates the decline call operation as shown in FIG. 10I).

Performing the first or second operations based on tilt sensor input and biological sensor input allows the device to be operated with fewer physical inputs from the user (e.g. finger touches on the display screen). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

In some examples, the central axis corresponds to an axis of rotation of a user's wrist. In some examples, the movement of the first or second type corresponds to movement of the electronic device at a velocity greater than a predetermined minimum velocity. In some examples, in accordance with a determination that the tilt sensor input is not greater than a predetermined minimum velocity, the device forgoes performing the first or second operations. In some examples, the movement of the first or second type corresponds to movement of the electronic device with an acceleration greater than a predetermined minimum acceleration. In some examples, in accordance with a determination that the tilt sensor input is not greater than a predetermined minimum acceleration, the device forgoes performing the first or second operations.

In some examples, the device (1618) optionally determines that the biological sensor input does not correspond to the predefined pattern for the predetermined time (e.g., the user releases their hand from the clenched position). In some examples, while the biological sensor input does not correspond to the predefined pattern (e.g., while the user's hand is not clenched), the device (1620) receives the tilt sensor input associated with movement of the electronic device and (1622) optionally forgoes performing the first or second operations.

Note that details of the processes described above with respect to method 1600 (e.g., FIGS. 16A-16B) are also applicable in an analogous manner to other methods described herein. For example, method 1700 optionally includes one or more of the characteristics of the various methods described above with reference to method 1600. For example, the mode change criteria of method 1700 can be satisfied prior to receiving the biological sensor input of method 1600 (e.g., the display screen is held in view of a user for a predetermined time as a precondition to receiving the biological sensor input). For brevity, these details are not repeated below.

FIGS. 17A-17B are flow diagrams illustrating a method 1700 for performing an operation with an electronic device, in accordance with some embodiments. Method 1700 is performed at a device (e.g., 100, 300, 500) with a display screen and a sensor. In some examples, the sensor includes a tilt sensor. In some examples, the tilt sensor is an accelerometer, directional sensor (e.g., compass), gyroscope, motion sensor, and/or a combination thereof. In some examples, the sensor includes a biological sensor. In some examples, the biological sensor is an optical sensor positioned in the device to measure blood flow indicative of a clenched hand of the user. Some operations in method 1700 are, optionally, combined, the order of some operations are, optionally, changed, and some operations are, optionally, omitted.

As described below, method 1700 provides an intuitive way for interacting with the device. In some cases, the device performs an operation in response to an orientation of the device. Performing an operation in response to the orientation of the device enhances the operability of the device by enabling the user to interact with the device without touching the display screen or other physical input mechanisms. This also allows operations to be performed more quickly and efficiently with the device.

As shown in method 1700, in some embodiments, the device (1702) receives, via the sensor, a sensor input (e.g., the orientation of the device is changed as a result of the user lifting their arm and or rotating their wrist, as described in reference to FIGS. 11A-11B).

As shown in method 1700, in some embodiments, in response to receiving the sensor input, the device (1704) determines whether the device satisfies a mode change criteria, the mode change criteria including an orientation criterion satisfied based on an orientation of the electronic device (e.g., the orientation of the device is changed such that the display screen is visible to the user, as described in reference to FIGS. 11A-11B). In some examples, the mode change criteria further includes a time criterion that is satisfied based on maintaining the orientation of the device for a predetermined time (e.g., device is held for a predetermined time in an orientation where the display screen is visible to the user). In some examples, the mode change criteria further include, prior to satisfying the orientation criterion, a movement criterion that is satisfied when the sensor input corresponds to a predetermined pattern indicative of a particular movement of the device (e.g., upward movement of the user's arm). In some examples, the orientation of the device that satisfies the orientation criterion corresponds to a raised position of the device.

As shown in method 1700, in some embodiments, in accordance with a determination that the mode change criteria is satisfied, the device (1706) transitions the device to a first mode (e.g., active mode as described in reference to FIGS. 11A-11B). The device (1708) also modifies the user interface to indicate that the device is in the first mode (e.g., displays the answer call affordance 1104 and decline call affordance 1106 of FIG. 11B or 11C, or displays the reply affordance 1114 and dismiss affordance 1116 of FIG. 11D). In some examples, the user interface includes a first graphical element associated with a first operation (e.g., answer call affordance 1104 of FIG. 11B or 11C or dismiss affordance 1116 of FIG. 11D), and a second graphical element associated with a second operation (e.g., decline call affordance 1106 of FIG. 11B or 11C or reply affordance 1114 of FIG. 11D). In some examples, the device includes a haptic feedback mechanism (e.g., vibration mechanism), and, further in accordance with the determination that the mode change criteria is satisfied, the device provides a haptic feedback, via the haptic feedback mechanism.

As shown in method 1700, in some embodiments, in accordance with a determination that the mode change criteria is not satisfied, the device (1710) forgoes transitioning the device to the first mode (e.g., the orientation of the device is not changed such that the display screen is visible to the user, as described in reference to FIGS. 11B-11D).

As shown in method 1700, in some embodiments, subsequent to receiving the sensor input, the device (1712) receives a user input (e.g., user input changing the positioning of the user's hand to a clenched position, as described in reference to FIG. 9A-9H, or user input further changing the orientation of the device, as described in reference to FIG. 6C-6I, 7G-7Q, 8B-8E, 8W-8Z, or 8AB-8BI). In some examples, the user input includes receiving a tilt sensor input associated with movement of the electronic device. In some examples, the user input is detected via the sensor.

As shown in method 1700, in some embodiments, in response to the user input and in accordance with a determination that the device satisfies a first operation criteria (e.g., user input results in graphical object 614 being displayed at the end of the right track segment 610 as shown in FIG. 6G, user input corresponds to the movement indicators 708a-708d shown in FIGS. 7B-7E, user input further changes the orientation of the device as described in references to FIG. 8C-8E, 8G, 8J, 8M, 8X-8Y, 8AC-8AI, 8AK-8AQ, 8AT-8AZ, or 8BB-8BH, and/or user input changes the positioning of the user's hand to a clenched position as shown in FIG. 9C), the first operation criteria including a mode criterion that is satisfied when the device is in the first mode, the device (1714) performs a first operation (e.g., answers an incoming telephone call, declines the incoming call, displays a reply interface for a received instant message, or dismisses the received instant message). In some examples, the first operation criteria further includes a first tilt criterion that is satisfied when the device is rotated in a first direction around a central axis from a neutral position to a first position (e.g., the display screen is rotated away from or toward the user). In some examples, the first tilt criterion further includes a rotation criterion that is satisfied when the device is rotated from the first position back toward the neutral position within a predetermined time (e.g., the user makes a "flicking" motion with the device, where the display screen is quickly rotated in a first direction and then is immediately rotated back in the opposite direction). In some examples, the central axis corresponds to an axis of rotation of a user's wrist. In some examples, the first operation criteria further includes a hand position criterion that is satisfied when the user input corresponds to a predefined pattern for a predetermined time, the predefined pattern being associated with positioning of the user's hand (e.g., the user holds their hand in a clenched position for a predetermined amount of time such as shown in FIGS. 9C-9G). In some examples, in accordance with the determination that the device satisfies the first operation criteria, the device (1720) optionally modifies a visual appearance of the first graphical element (e.g., the first graphical element is enlarged in size, the first graphical element moves toward a center region of the display screen, and/or a progress ring is displayed). In some examples, the first graphical element is a first affordance associated with an answer call operation (e.g., answer call affordance 1104 of FIG. 11B or 11C).

In some examples, in response to the user input and in accordance with a determination that the device satisfies a second operation criteria, the second operation criteria including a criterion that is satisfied when the device is in the first mode, the device (1718) optionally performs a second operation (e.g., answers an incoming telephone call, declines the incoming call, displays a reply interface for a received instant message, or dismisses the received instant message). The second operation criteria is different than the first operation criteria and the second operation is different than the first operation. In some examples, the second operation criteria includes a second tilt criterion that is satisfied when the electronic device is rotated in a second direction around a central axis from a neutral position to a second position (e.g., the display screen is rotated away from or toward the user). In some examples, the second tilt criterion further includes rotation from the second position back toward the neutral position within a predetermined time (e.g., the user makes a "flicking" motion with the device, where the display screen is quickly rotated in a first direction and then is immediately rotated back in the opposite direction). In some examples, the central axis corresponds to an axis of rotation of a user's wrist. In some examples, in accordance with the determination that the device satisfies the second operation criteria, the device (1722) optionally modifies a visual appearance of the second graphical element (e.g., the second graphical element is enlarged in size, the second graphical element moves toward a center region of the display screen, and/or a progress ring is displayed). In some examples, the second graphical element is a second affordance associated with a decline call operation (e.g., decline call affordance 1106 of FIG. 11B or 11C).

Performing the first or second operations in response to receiving a user input after an orientation criterion is satisfied allows the device to be operated with fewer physical inputs from the user (e.g. finger touches on the display screen). Reducing the number of inputs needed to perform an operation enhances the operability of the device and makes the user-device interface more efficient (e.g., by helping the user to provide proper inputs and reducing user mistakes when operating/interacting with the device) which, additionally, reduces power usage and improves battery life of the device by enabling the user to use the device more quickly and efficiently.

As shown in method 1700, in some embodiments, in accordance with a determination that the device does not satisfy the first operation criteria (e.g., user input does not result in graphical object 614 being displayed at the end of the right track segment 610 as shown in FIG. 6G, user input does not correspond to the movement indicators 708a-708d shown in FIGS. 7B-7E, user input does not change the orientation of the device as described in references to FIG. 8C-8E, 8G, 8J, 8M, 8X-8Y, 8AC-8AI, 8AK-8AQ, 8AT-8AZ, or 8BB-8BH, and/or user input does not change the positioning of the user's hand to a clenched position as shown in FIG. 9C), the device (1716) forgoes performing the first operation.

In some examples, in response to the user input and in accordance with a determination that the device does not satisfy the first operation criteria, performing a third operation, wherein the third operation is different than the first operation and the second operation (e.g., the device displays a time or a default "home" interface).

Note that details of the processes described above with respect to method 1700 (e.g., FIG. 17A-17B) are also applicable in an analogous manner to other methods described herein. For example, method 1700 optionally includes one or more of the characteristics of the various methods described above with reference to methods 1200, 1300, 1400, 1500, or 1600. For example, the mode change criteria of method 1700 can be satisfied prior to receiving the biological sensor input of method 1500 (e.g., the display screen is held in view of a user for a predetermined time as a precondition to receiving the biological sensor input). For brevity, these details are not repeated above.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

What is claimed is:

1. An electronic device, comprising:
   a display;
   a sensor;
   one or more processors; and
   memory storing one or more programs configured to be executed by the one or more processors, the one or more programs including instructions for:
   displaying an affordance via the display;
   receiving sensor input, via the sensor, associated with a positioning of a user's hand; and
   in response to receiving the sensor input:
      in accordance with a determination that the sensor input corresponds to a predefined pattern for a threshold amount of time, the predefined pattern being associated with the positioning of the user's hand:
         displaying, concurrently with the affordance, an indication that the sensor input corresponds to the predefined pattern for the threshold amount of time; and
         performing the operation associated with the affordance; and
      in accordance with a determination that the sensor input does not correspond to the predefined pattern for the threshold amount of time, forgoing performing the operation associated with the affordance.

2. The electronic device of claim 1, wherein the one or more programs further include instructions for:
   in accordance with the determination that the sensor input corresponds to the predefined pattern for the threshold amount of time, modifying a visual appearance of the affordance.

3. The electronic device of claim 1, wherein the one or more programs further include instructions for:
   in response to receiving the sensor input and in accordance with a determination that the sensor input corresponds to the predefined pattern, displaying a graphical element indicating the threshold amount of time.

4. The electronic device of claim 1, wherein the electronic device further comprises a haptic feedback mechanism, and wherein the one or more programs further include instructions for:
   in response to receiving the sensor input and in accordance with a determination that the sensor input corresponds to the predefined pattern, providing a haptic feedback, via the haptic feedback mechanism.

5. The electronic device of claim 1, wherein the operation comprises answering a telephone call.

6. The electronic device of claim 1, wherein the sensor comprises an optical sensor positioned in the electronic device to measure blood flow indicative of a clenched hand of the user.

7. A method, comprising:
   at an electronic device with a display and a sensor:
      displaying an affordance via the display;
      receiving sensor input, via the sensor, associated with a positioning of a user's hand; and
      in response to receiving the sensor input:
         in accordance with a determination that the sensor input corresponds to a predefined pattern for a threshold amount of time, the predefined pattern being associated with the positioning of the user's hand:
  displaying, concurrently with the affordance, an indication that the sensor input corresponds to the predefined pattern for the threshold amount of time; and
  performing the operation associated with the affordance; and
in accordance with a determination that the sensor input does not correspond to the predefined pattern for the threshold amount of time, forgoing performing the operation associated with the affordance.

8. The method of claim 7, further comprising:
in accordance with the determination that the sensor input corresponds to the predefined pattern for the threshold amount of time, modifying a visual appearance of the affordance.

9. The method of claim 7, further comprising:
in response to receiving the sensor input and in accordance with a determination that the sensor input corresponds to the predefined pattern, displaying a graphical element indicating the threshold amount of time.

10. The method of claim 7, wherein the electronic device includes a haptic feedback mechanism, the method further comprising:
  in response to receiving the sensor input and in accordance with a determination that the sensor input corresponds to the predefined pattern, providing a haptic feedback, via the haptic feedback mechanism.

11. The method of claim 7, wherein the operation comprises answering a telephone call.

12. The method of claim 7, wherein the sensor comprises an optical sensor positioned in the electronic device to measure blood flow indicative of a clenched hand of the user.

13. A non-transitory computer-readable storage medium storing one or more programs configured to be executed by one or more processors of an electronic device with a display and a sensor, the one or more programs including instructions for:
  displaying an affordance via the display;
  receiving sensor input, via the sensor, associated with a positioning of a user's hand; and
  in response to receiving the sensor input:
    in accordance with a determination that the sensor input corresponds to a predefined pattern for a threshold amount of time, the predefined pattern being associated with the positioning of the user's hand;
      displaying, concurrently with the affordance, an indication that the sensor input corresponds to the predefined pattern for the threshold amount of time; and
      performing the operation associated with the affordance; and
    in accordance with a determination that the sensor input does not correspond to the predefined pattern for the threshold amount of time, forgoing performing the operation associated with the affordance.

14. The non-transitory computer-readable storage medium of claim 13, wherein the one or more programs further include instructions for:
  in accordance with the determination that the sensor input corresponds to the predefined pattern for the threshold amount of time, modifying a visual appearance of the affordance.

15. The non-transitory computer-readable storage medium of claim 13, wherein the one or more programs further include instructions for:
  in response to receiving the sensor input and in accordance with a determination that the sensor input corresponds to the predefined pattern, displaying a graphical element indicating the threshold amount of time.

16. The non-transitory computer-readable storage medium of claim 13, wherein the electronic device includes a haptic feedback mechanism, and wherein the one or more programs further include instructions for:
  in response to receiving the sensor input and in accordance with a determination that the sensor input corresponds to the predefined pattern, providing a haptic feedback, via the haptic feedback mechanism.

17. The non-transitory computer-readable storage medium of claim 13, wherein the operation comprises answering a telephone call.

18. The non-transitory computer-readable storage medium of claim 13, wherein the sensor comprises an optical sensor positioned in the electronic device to measure blood flow indicative of a clenched hand of the user.

* * * * *